US009090679B2

(12) United States Patent
Yokoseki et al.

(10) Patent No.: US 9,090,679 B2
(45) Date of Patent: Jul. 28, 2015

(54) ANTIBODIES THAT SPECIFICALLY BIND TO A BETA OLIGOMERS AND USE THEREOF

(75) Inventors: Tatsuki Yokoseki, Kanagawa (JP); Yasuhide Okamoto, Kanagawa (JP); Makoto Umeda, Kanagawa (JP); Toshiyuki Ito, Kanagawa (JP); Yukiho Imai, Kanagawa (JP); Shinobu Fujii, Kanagawa (JP); Naofumi Takamatsu, Kanagawa (JP)

(73) Assignee: Immunas Pharma, Inc., Kanagawa (JP)

( * ) Notice: Subject to any disclaimer, the term of this patent is extended or adjusted under 35 U.S.C. 154(b) by 852 days.

(21) Appl. No.: 13/264,671

(22) PCT Filed: Apr. 16, 2010

(86) PCT No.: PCT/JP2010/002771
§ 371 (c)(1),
(2), (4) Date: Dec. 21, 2011

(87) PCT Pub. No.: WO2010/119704
PCT Pub. Date: Oct. 21, 2010

(65) Prior Publication Data
US 2012/0082667 A1    Apr. 5, 2012

Related U.S. Application Data

(60) Provisional application No. 61/212,986, filed on Apr. 17, 2009, provisional application No. 61/282,549, filed on Feb. 26, 2010.

(51) Int. Cl.
C07K 16/00 (2006.01)
C07K 16/18 (2006.01)
G01N 33/68 (2006.01)

(52) U.S. Cl.
CPC ............ *C07K 16/18* (2013.01); *G01N 33/6896* (2013.01); *C07K 2317/33* (2013.01); *C07K 2317/76* (2013.01); *C07K 2317/92* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS

| 5,530,101 | A * | 6/1996 | Queen et al. ............... 530/387.3 |
| 6,218,506 | B1 | 4/2001 | Krafft et al. |
| 6,706,487 | B1 | 3/2004 | Abdel-Meguid et al. |
| 7,339,035 | B2 | 3/2008 | Yanagisawa et al. |
| 7,638,283 | B2 | 12/2009 | Krafft et al. |
| 7,741,448 | B2 | 6/2010 | Yanagisawa et al. |
| 8,378,081 | B2 | 2/2013 | Matsubara et al. |
| 2003/0068316 | A1 | 4/2003 | Klein et al. |
| 2006/0228349 | A1 | 10/2006 | Acton et al. |
| 2006/0257396 | A1 | 11/2006 | Jacobsen |
| 2007/0081998 | A1 | 4/2007 | Kinney et al. |
| 2007/0098721 | A1 | 5/2007 | Hillen et al. |
| 2007/0218499 | A1 | 9/2007 | Lambert et al. |
| 2010/0028357 | A1 | 2/2010 | Matsubara et al. |
| 2010/0183611 | A1 | 7/2010 | Imboden et al. |
| 2010/0260783 | A1 | 10/2010 | Matsubara et al. |
| 2010/0291071 | A1 | 11/2010 | Matsubara et al. |
| 2011/0097319 | A1 | 4/2011 | Matsubara et al. |
| 2012/0141477 | A1 | 6/2012 | Matsubara et al. |
| 2012/0156193 | A1 | 6/2012 | Yokoseki et al. |
| 2012/0177664 | A1 | 7/2012 | Yokoseki et al. |

FOREIGN PATENT DOCUMENTS

| CN | 101137394 A | 3/2008 |
| JP | 3512815 B2 | 1/2004 |
| JP | 2006-509721 A | 3/2006 |
| JP | 2008-520553 A | 6/2008 |
| JP | 2008-527005 A | 7/2008 |
| JP | 5599454 B2 | 8/2014 |
| WO | WO 00/56771 A1 | 9/2000 |
| WO | WO 03/004056 A1 | 1/2003 |
| WO | WO 03/014162 A1 | 2/2003 |
| WO | WO 03/077858 A2 | 9/2003 |
| WO | WO 03/104437 A2 | 12/2003 |
| WO | WO 2006/047254 A1 | 5/2006 |
| WO | WO 2006/055178 A2 | 5/2006 |
| WO | WO 2006/081171 A1 | 8/2006 |
| WO | WO 2006/083533 A2 | 8/2006 |
| WO | WO 2006/094724 A2 | 9/2006 |
| WO | WO 2006/137354 A1 | 12/2006 |
| WO | WO 2007/010040 A1 | 1/2007 |
| WO | WO 2007/108756 A1 | 9/2007 |
| WO | WO 2008/150946 A1 | 12/2008 |
| WO | WO 2009/051220 A1 | 4/2009 |
| WO | WO 2009/085200 A2 | 7/2009 |

(Continued)

OTHER PUBLICATIONS

Wang et al. (FEBS Letters, vol. 583, pp. 579-584, 2009).*
Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*

(Continued)

*Primary Examiner* — Laura B Goddard
*Assistant Examiner* — Meera Natarajan
(74) *Attorney, Agent, or Firm* — Sterne, Kessler, Goldstein & Fox PLLC

(57) ABSTRACT

The present inventors successfully produced monoclonal antibodies that are specific to only soluble A beta oligomers, but do not recognize soluble A beta monomers, which are physiological molecules. It was demonstrated that the antibodies are useful as diagnostic/therapeutic monoclonal antibodies for Alzheimer's disease.

13 Claims, 7 Drawing Sheets

(56) References Cited

FOREIGN PATENT DOCUMENTS

| WO | WO 2009/099176 A1 | 8/2009 |
| WO | WO 2010/012004 A2 | 1/2010 |

OTHER PUBLICATIONS

Padlan et al. (PNAS 1989, 86:5938-5942).*
Lamminmaki et al. (JBC 2001, 276:36687-36694).*
Wang et. al. (FEBS Letters, vol. 583, pp. 579-584, Jan. 2009).*
Co-pending U.S. Appl. No. 13/760,936, inventors Matsubara, E., et al., filed Feb. 6, 2013 (Not Yet Published).
Bussière, T. et al., "Animal Model: Morphological Characterization of Thioflavin-S-Positive Amyloid Plaques in Transgenic Alzheimer Mice and Effect of Passive Aβ Immunotherapy on Their Clearance," *Am. J. Pathol. 165*:987-995, American Society for Investigative Pathology (2004).
Quereurth, H.W. and LaFerla, F.M., "Mechanisms of Disease: Alzheimer's Disease," *N. Engl. J. Med. 362*:329-344, Massachusetts Medical Society (2010).
Office Action mailed Aug. 29, 2012, in U.S. Appl. No. 12/762,878, inventors Matsubara, E., et al., filed Apr. 19, 2010, U.S. Patent and Trademark Office, Alexandria, VA.
Haass, C., et al., "Soluble protein oligomers in neurodegeneration: lessons from the Alzheimer's amyloid β-peptide," *Nat. Rev. Mol. Cell Bio. 8*:101-112, Nature Publishing Group, England (2007).
Kayed, R., et al., "Common Structure of Soluble Amyloid Oligomers Implies Common Mechanism of Pathogenesis," *Science 300*:486-489, American Association for the Advancement of Science, United States (2003).
Kayed, R., et al., "Fibril specific, conformation dependent antibodies recognize a generic epitope common to amyloid fibrils and fibrillar oligomers that is absent in prefibrillar oligomers," *Mol. Neurodegener. 2*:18, BioMed Central Ltd., England (2007).
Klein, W. L., et al., "Targeting small Aβ oligomers: the solution disease conundrum?" *Trends Neurosci. 24(4)*:219-224, Elsevier Inc., England (2001).
Lambert, M. P., et al., "Vaccination with soluble Aβ oligomers generates toxicity-neutralizing antibodies," *J. Neurochem. 79*:595-605, International Neurochemisty, England (2001).
Lambert, M. P., et al., "Monoclonal antibodies that target pathological assemblies of Aβ," *J. Neurochem. 100*:23-35, International Society for Neurochemistry, England (2007).
Lee, E. B., et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice," *J. Biol. Chem. 281*:4292-4299, American Society for Biochemistry and Molecular Biology, United States (2006).
Lesné, S., et al., "A specific amyloid-β protein assembly in the brain impairs memory," *Nature 440*:352-357, Nature Publishing Group, England (2006).
Matsubara, E., et al., "Development of diagnosing system for Alzheimer's disease using anti-Aβ oligomer antibodies," Abstract 1-2-9, The 46th Annual Meeting of Japanese Society of Neurology, Kagoshima, Japan, May 25-27, 2005.
Matsubara, Etsuro, "Aβ oligomers," *Dementia Japan 21*:253-259, Japan (2007).
Matsubara, Etsuro, "Immunotherapy targeting Aβ oligomers for Alzheimer's disease," Abstracts S31-2 and presentation, 8th Asia/Oceania Regional Congress of Gerontology and Geriatrics, Beijing, China, Oct. 22, 2007.
Matsubara, Etsuro, "Passive immunotherapy Aβ oligomers in Alzheimer's disease," Abstract S38-4, 128th Annual Meeting of the Pharmaceutical Society of Japan, Yokohama, Japan, Mar. 26-28, 2008.
Matsubara, Etsuro, "The Aβ-oligomer specific passive immunization in Alzheimer's disease," 128th Annual Meeting of the Pharmaceutical Society of Japan, Yokohama, Japan, Feb. 1, 2007.
Matsubara, Etsuro, "Neurotoxic Aβ oligomer being the basis of developmental pathology of Alzheimer's disease," Abstract SY-2-2, The 49th Annual Meeting of Japanese Society of Neurology, Yokohama, Japan, Apr. 25, 2008.
Matsubara, Etsuro, "The Aβ-oligomer specific passive immunization in Alzheimer's disease," The 49th Annual Meeting of Japanese Society of Neurology, Yokohama, Japan, May 16, 2008.
Moretto, N., et al., "Conformation-sensitive Antibodies against Alzheimer Amyloid-β by Immunization with a Thioredoxin-constrained B-cell Epitope Peptide," *J. Biol. Chem. 282*: 11436-11445, American Society for Biochemistry and Molecular Biology, United States (2007).
Selkoe, Dennis J., "Alzheimer's Disease Is a Synaptic Failure," *Science 298*:789-791, American Association for the Advancement of Science, United States (2002).
Shoji, M., et al., "Investigtion on pathogenicity of Aβ peptide and development of pathogenic Aβ oligomer removal therapy," Health and Labour Sciences ResearchA Grants (Research on specified diseases), pp. 68-72 (2004).
Shoji, M., et al., "Antibody therapy for Alzheimer's disease," Health and Labour Sciences Research Grants, Study and research group on amyloidosis, pp. 76-78 (2008).
Sun, H., et al., "Characterization of therapeutic antibody against Aβ oligomers for Alzheimer's disease," *Dementia Japan 21*: 183, Abstract P2-261, Japan (2007).
Sun, H., et al., "Characterization of therapeutic antibody against Aβ oligomers for Alzheimer's disease," The 26th Annual Meeting of Japan Society for Dementia Research, Oct. 17-18, 2007.
Sun, H., et al., "Characterization of therapeutic antibody against Aβ oligomers for Alzheimer's disease," Abstract, Neuroscience 2007, San Diego, United States, Aug. 16, 2007.
Sun, H., et al., "Characterization of therapeutic antibody against Aβ oligomers for Alzheimer's disease," Poster 485.15/W10, Neuroscience 2007, San Diego, United States, Nov. 5, 2007.
Unverified English language translation of Matsubara, E., et al., "Development of a diagnosing system for Alzheimer's disease using anti-Aβ oligomer antibodies," Abstract 1-2-9, The 46th Annual Meeting of Japanese Society of Neurology, Kagoshima, Japan, May 25-27, 2005.
Unverified English language translation of Abstract of Matsubara, Etsuro, "Aβ oligomers," *Dementia Japan 21*: 253-259, Japan (2007).
Unverified English language translation of Matsubara, Etsuro, "Passive immunotherapy Aβ oligomer in Alzheimer's disease," Abstract S38-4, 128th Annual Meeting of the Pharmaceutical Society of Japan, Yokohama, Japan, Mar. 26-28, 2008.
Unverified English language translation of Matsubara, Etsuro, "The Aβ-oligomer specific passive immunization on Alzheimer's disease," 128th Annual Meeting of the Pharmaceutical Society of Japan, Yokohama, Japan, Mar. 28, 2008.
Unverified English language translation of Matsubara, Etsuro, "Neurotoxic Aβ oligomer being the basis of developmental pathology of Alzheimer's disease," Abstract SY-2-2, The 49th Annual Meeting of Japanese Society of Neurology, Yokohama, Japan, May 15-17, 2008.
Unverified English language translation of Matsubara, Etsuro, "The Aβ-oligomer specific passive immunization in Alzheimer's disease," The 49th Annual Meeting of Japanese Society of Neurology, Yokohama, Japan, May 16, 2008.
Unverified English language translation of Shoji, M., et al., "Investigation on pathogenicity of Aβ peptide and development of pathogenic Aβ oligomer removal therapy," Health and Labour Sciences ResearchA Grants (Research on specified diseases), pp. 68-72 (2004).
Unverified English language translation of Shoji, M., et al., "Antibody therapy for Alzheimer's disease," Health and Labour Sciences Research Grants, Study and research group on amyloidosis, pp. 76-78 (2008).
Office Action mailed Apr. 13, 2011, in U.S. Appl. No. 12/533,294, inventors Matsubara, E., et al., filed Jul. 31, 2009, U.S. Patent and Trademark Office, Alexandria, VA.
Office Action mailed Jan. 19, 2012, in U.S. Appl. No. 12/762,878, inventors Matsubara, E., et al., filed Apr. 19, 2010, U.S. Patent and Trademark Office, Alexandria, VA.

(56) References Cited

OTHER PUBLICATIONS

Co-pending Application, U.S. Appl. No. 13/389,228, inventors Yokoseki, T., et al., Int'l Filing Date: Aug. 5, 2010 (Not Yet Published).

Co-pending Application, U.S. Appl. No. 13/389,229, inventors Yokoseki, T., et al., Int'l Filing Date: Aug. 5, 2010 (Not Yet Published).

Brookmeyer, R., et al., "Forecasting the global burden of Alzheimer's disease," *Alzheimer's & Dementia 3*:186-191, The Alzheimer's Association (2007).

Ma, Q.-L. et al., "Antibodies Against β-Amyloid Reduce Aβ Oligomers, Glycogen Synthase Kinase-3β Activation and τ Phosphorylation In Vivo and In Vitro," *J. Neurosci. Res. 83*:374-384, Wiley-Liss, Inc. (2006).

Wang, X.-p. et al., "Conformation-dependent single-chain variable fragment antibodies specifically recognize beta-amyloid oligomers," *FEBS Letts. 583*:579-584, Elsevier B.V. (2009).

Kayed, R. and Glabe, C.G., "Conformation-Dependent Anti-Amyloid Oligomer Antibodies," *Methods Enzymol. 413*:326-344, Elsevier Inc. (2006).

Klein, W.L., "Aβ toxicity in Alzheimer's disease: globular oligomers (ADDLs) as new vaccine and drug targets," *Neurochemistry International 41*:345-352, Elsevier Science Ltd. (2002).

Casset, F., et al., "A peptide mimetic of an anti-CD4 monoclonal antibody by rational design," *Biochem. Biophys. Res. Commun. 307*:198-205, Elsevier Science, United States (2003).

MacCallum, R.M., et al. "Antibody-antigen Interactions: Contact Analysis and Binding Site Topography," *J. Mol. Biol. 262*:732-745, Academic Press Limited, Netherlands (1996).

Padlan, E.A., et al., "Structure of an antibody-antigen complex: Crystal structure of the HyHEL-10 Fab-lysozyme complex," *Proc. Natl. Acad. Sci. USA 86*:5938-5942, National Academy of Science, United States (Aug. 1989).

Paul, W.E., ed., *Fundamental Immunology, Third Edition*, pp. 292-295, Raven Press, Ltd., New York, United States (1993).

Rudikoff, S., et al. "Single amino acid substitution altering antigen-binding specificity," *Proc. Natl. Acad. Sci. USA 79*:1979-1983, National Academy of Science, United States (Mar. 1982).

Terryberry, J.W., et al., "Autoantibodies in Neurodegenerative Diseases: Antigen-Specific Frequencies and Intrathecal Analysis," *Neurobiol. Aging 19(3)*:205-216, Elsevier Science Inc., United States (1998).

Vajdos, F. F., et al. "Comprehensive Functional Maps of the Antigen-binding Site of an Anti-ErbB2 Antibody Obtained with Shotgun Scanning Mutagenesis," *J. Mol. Biol. 320*:415-428, Elsevier Science Ltd., United States (2002).

International Search Report for International Application No. PCT/JP2010/002771, Japan Patent Office, Japan, mailed on Jul. 20, 2010.

Co-pending U.S. Appl. No. 13/369,807, inventors Matsubara E., et al., filed Feb. 9, 2012.

Office Action mailed Apr. 12, 2011, in U.S. Appl. No. 12/533,348, inventors Matsubara, E., et al., filed Jul. 31, 2009, U.S. Patent and Trademark Office, Alexandria, VA.

\* cited by examiner

Fig. 1

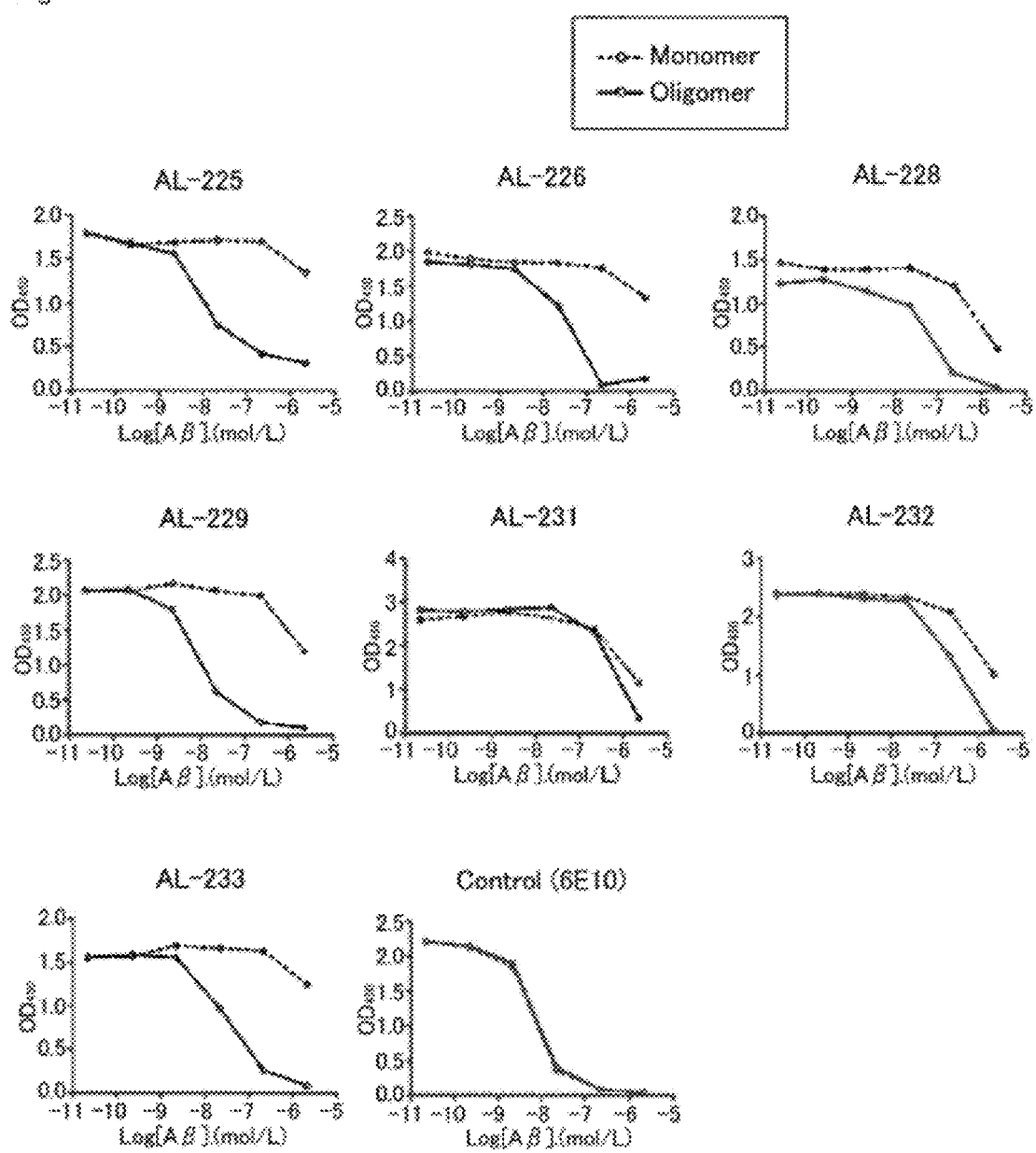

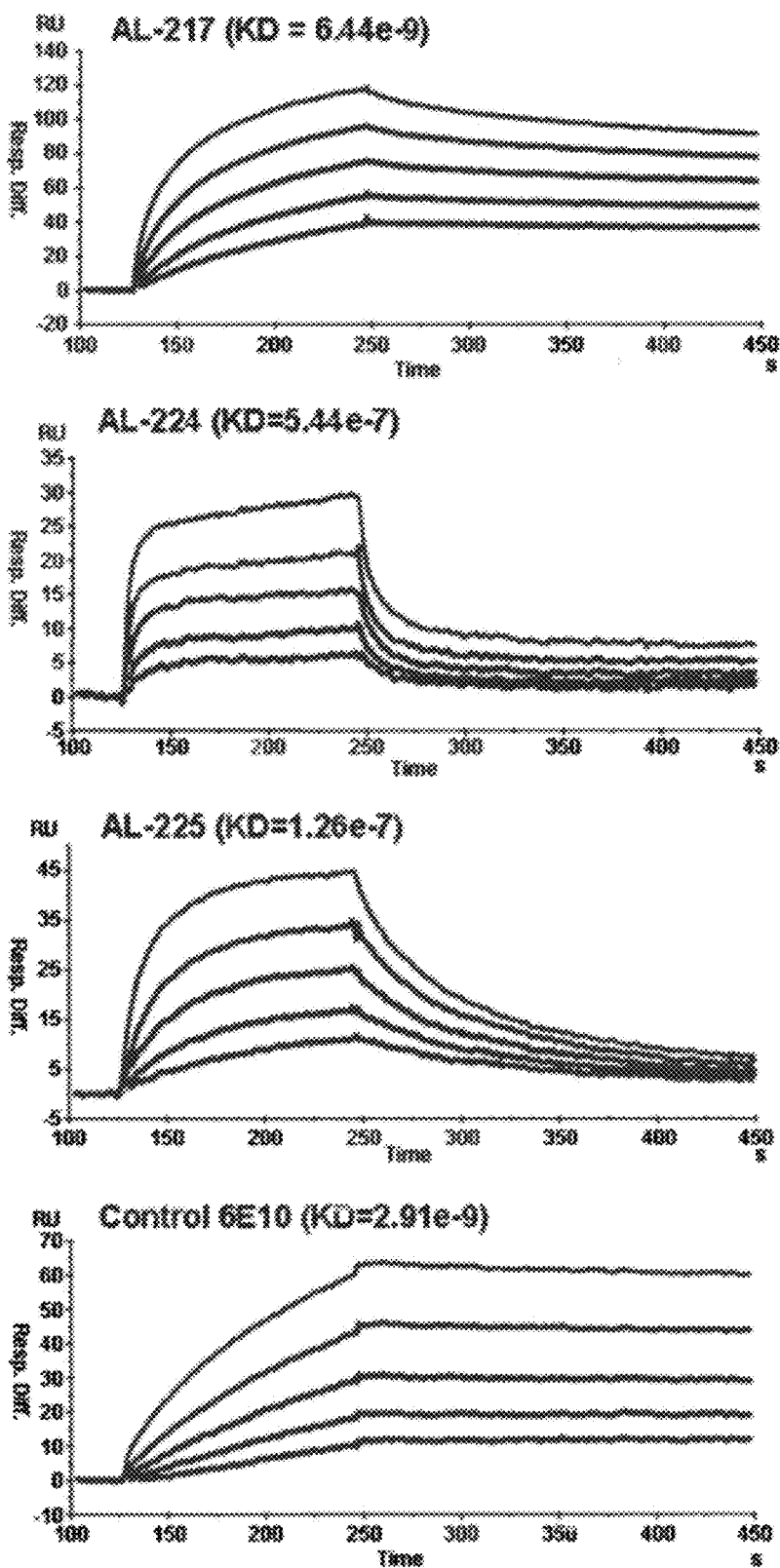

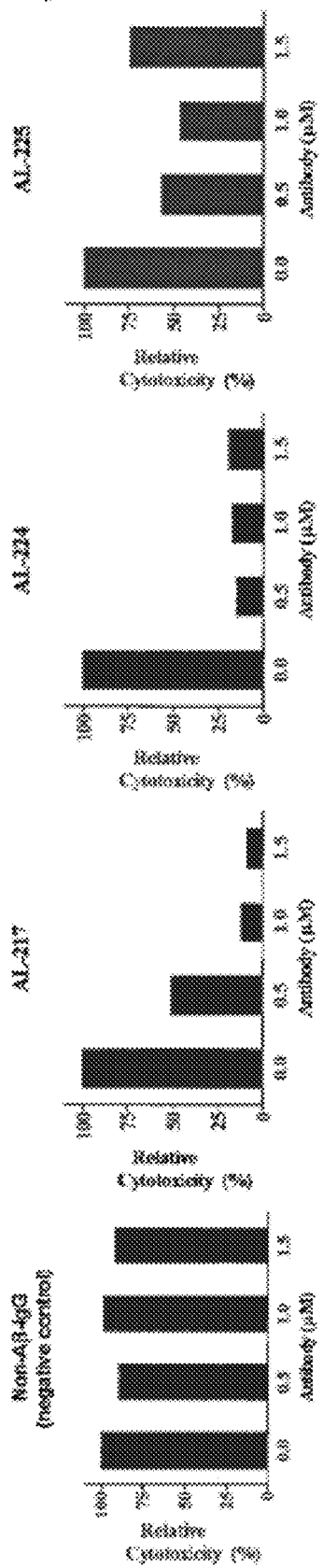

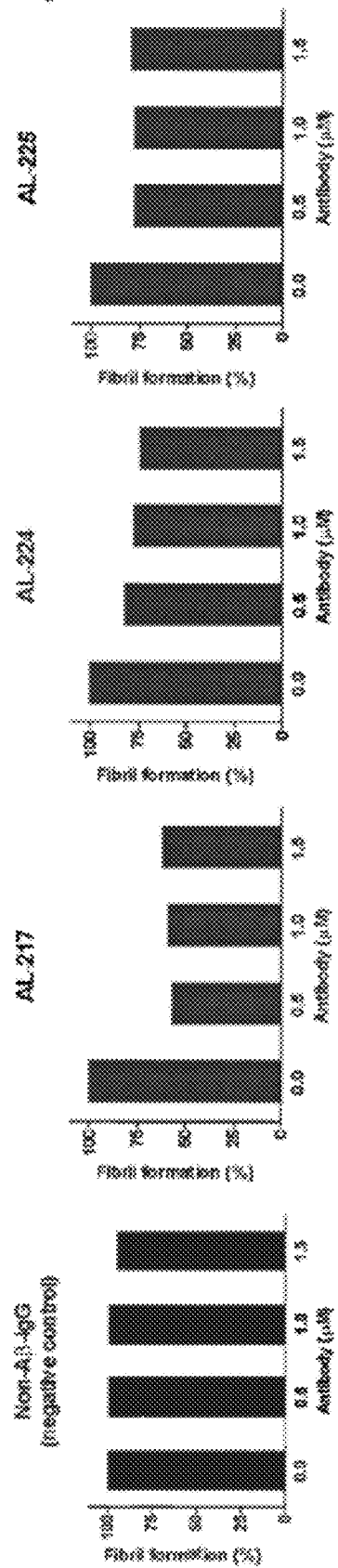

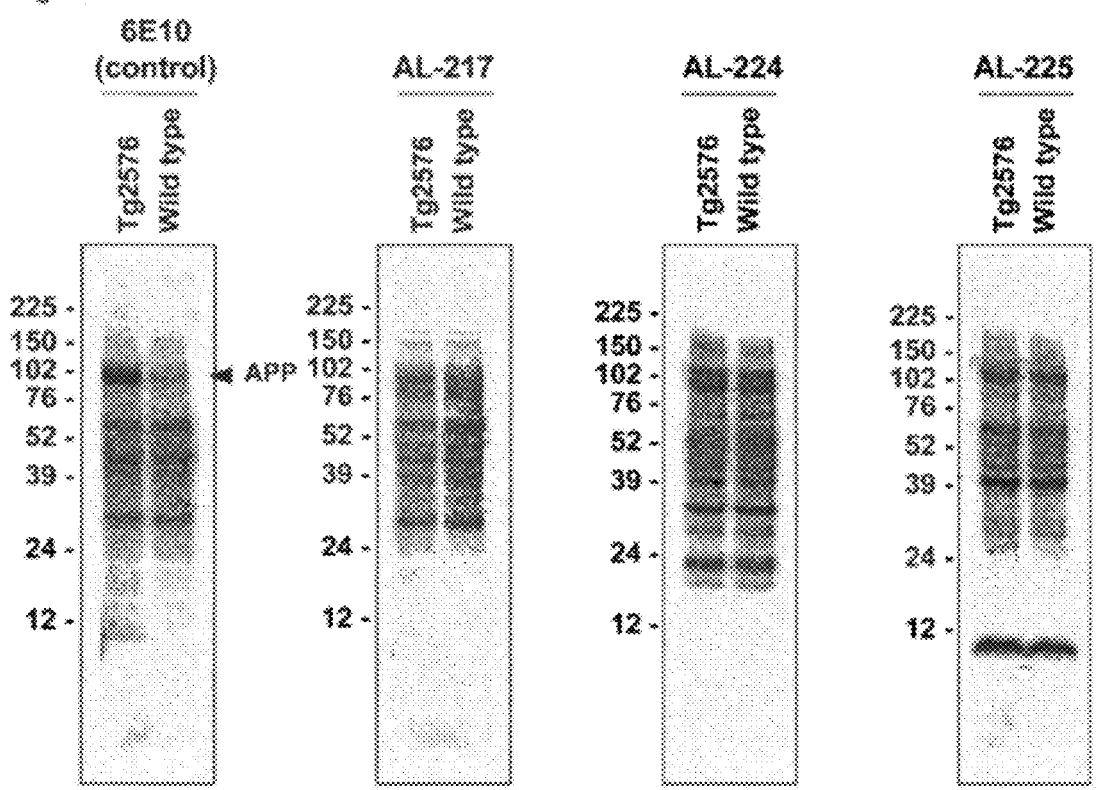

ANTIBODIES THAT SPECIFICALLY BIND TO A BETA OLIGOMERS AND USE THEREOF

The present application claims the benefit of U.S. Provisional Application No. 61/212,986, filed on Apr. 17, 2009, and U.S. Provisional Application No. 61/282,549, filed on Feb. 26, 2010, the entire contents of which are incorporated by reference herein.

TECHNICAL FIELD

The present invention relates to antibodies that specifically bind to Abeta oligomers and uses thereof.

BACKGROUND ART

The number of Alzheimer's disease (AD) patients is more than about 26 million worldwide in 2006, and it is predicted to continue increasing in an aging society (Non-Patent Document 1). However, there is no curative therapeutic agent that arrests or reverses the progression of Alzheimer's disease, although therapeutic agents that retard the progression of the disease are commercially available.

Various evidence has shown that deterioration of memory arises from synaptic dysfunction triggered by soluble amyloid beta (A beta) oligomers (see Non-Patent Documents 2 and 3). Excessive accumulation and deposition of A beta oligomers may be the trigger for a series of pathological cascades that lead to Alzheimer's disease. Therefore, therapeutic intervention targeting A beta oligomers may be effective for blocking these cascades (see Non-Patent Documents 4 and 5).

Recently, antibody pharmaceuticals that target A beta are being developed. However, previously-reported anti-A beta oligomer antibodies do not specifically bind to A beta oligomers, but bind to all of the three forms, i.e., A beta monomers, oligomers, and fibrils. Thus, even if they are administered in vivo, it is thought that the amount of antibodies that bind to A beta oligomers would be relatively low, and the dosage may need to be increased to obtain effect. Moreover, since A beta monomers are present in the brain of healthy individuals, side effects may be cause by the binding of the antibodies to A beta monomers.

Furthermore, the amount of A beta oligomer could be an index of Alzheimer's disease; however, it was difficult to measure A beta oligomers alone using conventional anti-A beta antibodies.

Prior art information related to the present invention is shown below.

CITATION LIST

Non Patent Literature

[NPL 1] Brookmeyer R et al., Alzheimers Dement. July; 3(3):186-91, 2007
[NPL 2] Klein W L, Trends Neurosci. 24: 219-224, 2001
[NPL 3] Selkoe D J, Science 298: 789-791, 2002
[NPL 4] Haass C et al.: Nat Rev Mol Cell Biol. 8: 101-12, 2007
[NPL 5] Lee E B, et al.: J. Biol. Chem. 281: 4292-4299, 2006

SUMMARY OF INVENTION

Technical Problem

The present invention was achieved in view of the above circumstances. An objective of the present invention is to provide antibodies that bind specifically to A beta oligomers, and uses thereof. More specifically, the present invention provides antibodies that bind specifically to A beta oligomers, methods for detecting A beta oligomers using the antibodies, methods for diagnosing Alzheimer's disease using the antibodies, pharmaceutical compositions and agents comprising the antibodies, agents and kits for detecting A beta oligomers, and agents and kits for diagnosing Alzheimer's disease.

Solution to Problem

The present inventors successfully produced multiple monoclonal antibodies that are specific to only soluble amyloid beta (A beta) oligomers and do not recognize soluble A beta monomers which are physiological molecules, using an isolated A beta tetramer as an antigen.

Thus, the present inventors disclose that the multiple antibodies are promising candidates for therapeutic antibodies for treating/preventing Alzheimer's disease, or for diagnostic antibodies for diagnosing Alzheimer's disease.

More specifically, the present invention provides the following:

[1] An antibody that recognizes an isolated A beta tetramer as an antigen, wherein the antibody does not bind to an A beta monomer.
[2] The antibody of [1], which is any one of (1) to (99) below:
(1) an antibody that comprises an H chain having CDR1, CDR2, and CDR3, which are identified in VH comprising the amino acid sequence of SEQ ID NO: 530;
(2) an antibody that comprises an L chain having. CDR1, CDR2, and CDR3, which are identified in VL comprising the amino acid sequence of SEQ ID NO: 532;
(3) an antibody that comprises the H chain of (1) and the L chain of (2);
(4) an antibody that comprises an H chain having CDR1, CDR2, and CDR3, which are identified in VH comprising the amino acid sequence of SEQ ID NO: 534;
(5) an antibody that comprises an L chain having CDR1, CDR2, and CDR3, which are identified in VL comprising the amino acid sequence of SEQ ID NO: 536;
(6) an antibody that comprises the H chain of (4) and the L chain of (5);
(7) an antibody that comprises an H chain having CDR1, CDR2, and CDR3, which are identified in VH comprising the amino acid sequence of SEQ ID NO: 538;
(8) an antibody that comprises an L chain having CDR1, CDR2, and CDR3, which are identified in VL comprising the amino acid sequence of SEQ ID NO: 540;
(9) an antibody that comprises the H chain of (7) and the L chain of (8);
(10) an antibody that comprises an H chain having CDR1, CDR2, and CDR3, which are identified in VH comprising the amino acid sequence of SEQ ID NO: 542;
(11) an antibody that comprises an L chain having CDR1, CDR2, and CDR3, which are identified in VL comprising the amino acid sequence of SEQ ID NO: 544;
(12) an antibody that comprises the H chain of (10) and the L chain of (11);
(13) an antibody that comprises an H chain having CDR1, CDR2, and CDR3, which are identified in VH comprising the amino acid sequence of SEQ ID NO: 546;
(14) an antibody that comprises an L chain having CDR1, CDR2, and CDR3, which are identified in VL comprising the amino acid sequence of SEQ ID NO: 548;
(15) an antibody that comprises the H chain of (13) and the L chain of (14);

(16) an antibody that comprises an H chain having CDR1, CDR2, and CDR3, which are identified in VH comprising the amino acid sequence of SEQ ID NO: 550;
(17) an antibody that comprises an L chain having CDR1, CDR2, and CDR3, which are identified in VL comprising the amino acid sequence of SEQ ID NO: 552;
(18) an antibody that comprises the H chain of (16) and the L chain of (17);
(19) an antibody that comprises an H chain having CDR1, CDR2, and CDR3, which are identified in VH comprising the amino acid sequence of SEQ ID NO: 554;
(20) an antibody that comprises an L chain having CDR1, CDR2, and CDR3, which are identified in VL comprising the amino acid sequence of SEQ ID NO: 556;
(21) an antibody that comprises the H chain of (19) and the L chain of (20);
(22) an antibody that comprises an H chain having CDR1, CDR2, and CDR3, which are identified in VH comprising the amino acid sequence of SEQ ID NO: 558;
(23) an antibody that comprises an L chain having CDR1, CDR2, and CDR3, which are identified in VL comprising the amino acid sequence of SEQ ID NO: 560;
(24) an antibody that comprises the H chain of (22) and the L chain of (23);
(25) an antibody that comprises an H chain having CDR1, CDR2, and CDR3, which are identified in VH comprising the amino acid sequence of SEQ ID NO: 562;
(26) an antibody that comprises an L chain having CDR1, CDR2, and CDR3, which are identified in VL comprising the amino acid sequence of SEQ ID NO: 564;
(27) an antibody that comprises the H chain of (25) and the L chain of (26);
(28) an antibody that comprises an H chain having CDR1, CDR2, and CDR3, which are identified in VH comprising the amino acid sequence of SEQ ID NO: 566;
(29) an antibody that comprises an L chain having CDR1, CDR2, and CDR3, which are identified in VL comprising the amino acid sequence of SEQ ID NO: 568;
(30) an antibody that comprises the H chain of (28) and the L chain of (29);
(31) an antibody that comprises an H chain having CDR1, CDR2, and CDR3, which are identified in VH comprising the amino acid sequence of SEQ ID NO: 570;
(32) an antibody that comprises an L chain having CDR1, CDR2, and CDR3, which are identified in VL comprising the amino acid sequence of SEQ ID NO: 572;
(33) an antibody that comprises the H chain of (31) and the L chain of (32);
(34) an antibody that comprises an H chain having CDR1, CDR2, and CDR3, which are identified in VH comprising the amino acid sequence of SEQ ID NO: 574;
(35) an antibody that comprises an L chain having CDR1, CDR2, and CDR3, which are identified in VL comprising the amino acid sequence of SEQ ID NO: 576;
(36) an antibody that comprises the H chain of (34) and the L chain of (35);
(37) an antibody that comprises an H chain having CDR1, CDR2, and CDR3, which are identified in VH comprising the amino acid sequence of SEQ ID NO: 578;
(38) an antibody that comprises an L chain having CDR1, CDR2, and CDR3, which are identified in VL comprising the amino acid sequence of SEQ ID NO: 580;
(39) an antibody that comprises the H chain of (37) and the L chain of (38);
(40) an antibody that comprises an H chain having CDR1, CDR2, and CDR3, which are identified in VH comprising the amino acid sequence of SEQ ID NO: 582;
(41) an antibody that comprises an L chain having CDR1, CDR2, and CDR3, which are identified in VL comprising the amino acid sequence of SEQ ID NO: 584;
(42) an antibody that comprises the H chain of (40) and the L chain of (41);
(43) an antibody that comprises an H chain having CDR1, CDR2, and CDR3, which are identified in VH comprising the amino acid sequence of SEQ ID NO: 586;
(44) an antibody that comprises an L chain having CDR1, CDR2, and CDR3, which are identified in VL comprising the amino acid sequence of SEQ ID NO: 588;
(45) an antibody that comprises the H chain of (43) and the L chain of (44);
(46) an antibody that comprises an H chain having CDR1, CDR2, and CDR3, which are identified in VH comprising the amino acid sequence of SEQ ID NO: 590;
(47) an antibody that comprises an L chain having CDR1, CDR2, and CDR3, which are identified in VL comprising the amino acid sequence of SEQ ID NO: 592;
(48) an antibody that comprises the H chain of (46) and the L chain of (47);
(49) an antibody that comprises an H chain having CDR1, CDR2, and CDR3, which are identified in VH comprising the amino acid sequence of SEQ ID NO: 594;
(50) an antibody that comprises an L chain having CDR1, CDR2, and CDR3, which are identified in VL comprising the amino acid sequence of SEQ ID NO: 596;
(51) an antibody that comprises the H chain of (49) and the L chain of (50);
(52) an antibody that comprises an H chain having CDR1, CDR2, and CDR3, which are identified in VH comprising the amino acid sequence of SEQ ID NO: 598;
(53) an antibody that comprises an L chain having CDR1, CDR2, and CDR3, which are identified in VL comprising the amino acid sequence of SEQ ID NO: 600;
(54) an antibody that comprises the H chain of (52) and the L chain of (53);
(55) an antibody that comprises an H chain having CDR1, CDR2, and CDR3, which are identified in VH comprising the amino acid sequence of SEQ ID NO: 602;
(56) an antibody that comprises an L chain having CDR1, CDR2, and CDR3, which are identified in VL comprising the amino acid sequence of SEQ ID NO: 604;
(57) an antibody that comprises the H chain of (55) and the L chain of (56);
(58) an antibody that comprises an H chain having CDR1, CDR2, and CDR3, which are identified in VH comprising the amino acid sequence of SEQ ID NO: 606;
(59) an antibody that comprises an L chain having CDR1, CDR2, and CDR3, which are identified in VL comprising the amino acid sequence of SEQ ID NO: 608;
(60) an antibody that comprises the H chain of (58) and the L chain of (59);
(61) an antibody that comprises, an H chain having CDR1, CDR2, and CDR3, which are identified in VH comprising the amino acid sequence of SEQ ID NO: 610;
(62) an antibody that comprises an L chain having CDR1, CDR2, and CDR3, which are identified in VL comprising the amino acid sequence of SEQ ID NO: 612;
(63) an antibody that comprises the H chain of (61) and the L chain of (62);
(64) an antibody that comprises an H chain having CDR1, CDR2, and CDR3, which are identified in VH comprising the amino acid sequence of SEQ ID NO: 614;
(65) an antibody that comprises an L chain having CDR1, CDR2, and CDR3, which are identified in VL comprising the amino acid sequence of SEQ ID NO: 616;

(66) an antibody that comprises the H chain of (64) and the L chain of (65);
(67) an antibody that comprises an H chain having CDR1, CDR2, and CDR3, which are identified in VH comprising the amino acid sequence of SEQ ID NO: 618;
(68) an antibody that comprises an L chain having CDR1, CDR2, and CDR3, which are identified in VL comprising the amino acid sequence of SEQ ID NO: 620;
(69) an antibody that comprises the H chain of (67) and the L chain of (68);
(70) an antibody that comprises an H chain having CDR1, CDR2, and CDR3, which are identified in VH comprising the amino acid sequence of SEQ ID NO: 622;
(71) an antibody that comprises an L chain having CDR1, CDR2, and CDR3, which are identified in VL comprising the amino acid sequence of SEQ ID NO: 624;
(72) an antibody that comprises the H chain of (70) and the L chain of (71);
(73) an antibody that comprises an H chain having CDR1, CDR2, and CDR3, which are identified in VH comprising the amino acid sequence of SEQ ID NO: 626;
(74) an antibody that comprises an L chain having CDR1, CDR2, and CDR3, which are identified in VL comprising the amino acid sequence of SEQ ID NO: 628;
(75) an antibody that comprises the H chain of (73) and the L chain of (74);
(76) an antibody that comprises an H chain having CDR1, CDR2, and CDR3, which are identified in VH comprising the amino acid sequence of SEQ ID NO: 630;
(77) an antibody that comprises an L chain having CDR1, CDR2, and CDR3, which are identified in VL comprising the amino acid sequence of SEQ ID NO: 632;
(78) an antibody that comprises the H chain of (76) and the L chain of (77);
(79) an antibody that comprises an H chain having CDR1, CDR2, and CDR3, which are identified in VH comprising the amino acid sequence of SEQ ID NO: 634;
(80) an antibody that comprises an L chain having CDR1, CDR2, and CDR3, which are identified in VL comprising the amino acid sequence of SEQ ID NO: 636;
(81) an antibody that comprises the H chain of (79) and the L chain of (80);
(82) an antibody that comprises an H chain having CDR1, CDR2, and CDR3, which are identified in VH comprising the amino acid sequence of SEQ ID NO: 638;
(83) an antibody that comprises an L chain having CDR1, CDR2, and CDR3, which are identified in VL comprising the amino acid sequence of SEQ ID NO: 640;
(84) an antibody that comprises the H chain of (82) and the L chain of (83);
(85) an antibody that comprises an H chain having CDR1, CDR2, and CDR3, which are identified in VH comprising the amino acid sequence of SEQ ID NO: 642;
(86) an antibody that comprises an L chain having CDR1, CDR2, and CDR3, which are identified in VL comprising the amino acid sequence of SEQ ID NO: 644;
(87) an antibody that comprises the H chain of (85) and the L chain of (86);
(88) an antibody that comprises an H chain having CDR1, CDR2, and CDR3, which are identified in VH comprising the amino acid sequence of SEQ ID NO: 646;
(89) an antibody that comprises an L chain having CDR1, CDR2, and CDR3, which are identified in VL comprising the amino acid sequence of SEQ ID NO: 648;
(90) an antibody that comprises the H chain of (88) and the L chain of (89);
(91) an antibody that comprises an H chain having CDR1, CDR2, and CDR3, which are identified in VH comprising the amino acid sequence of SEQ ID NO: 650;
(92) an antibody that comprises an L chain having CDR1, CDR2, and CDR3, which are identified in VL comprising the amino acid sequence of SEQ ID NO: 652;
(93) an antibody that comprises the H chain of (91) and the L chain of (92);
(94) an antibody that comprises an H chain having CDR1, CDR2, and CDR3, which are identified in VH comprising the amino acid sequence of SEQ ID NO: 654;
(95) an antibody that comprises an L chain having CDR1, CDR2, and CDR3, which are identified in VL comprising the amino acid sequence of SEQ ID NO: 656;
(96) an antibody that comprises the H chain of (94) and the L chain of (95);
(97) an antibody that comprises an H chain having CDR1, CDR2, and CDR3, which are identified in VH comprising the amino acid sequence of SEQ ID NO: 658;
(98) an antibody that comprises an L chain having CDR1, CDR2, and CDR3, which are identified in VL comprising the amino acid sequence of SEQ ID NO: 660; and
(99) an antibody that comprises the H chain of (97) and the L chain of (98).
[3] The antibody of [1], which is any one of (1) to (200) below:
(1) an antibody that comprises an H chain having the amino acid sequence of SEQ ID NO: 6 as CDR1, the amino acid sequence of SEQ ID NO: 8 as CDR2, and the amino acid sequence of SEQ ID NO: 10 as CDR3;
(2) an antibody that comprises an L chain having the amino acid sequence of SEQ ID NO: 12 as CDR1, the amino acid sequence of SEQ ID NO: 14 as CDR2, and the amino acid sequence of SEQ ID NO: 16 as CDR3;
(3) an antibody that comprises the H chain of (1) and the L chain of (2);
(4) an antibody that comprises an H chain having the amino acid sequence of SEQ ID NO: 530 as VH;
(5) an antibody that comprises an L chain having the amino acid sequence of SEQ ID NO: 532 as VL;
(6) an antibody that comprises the H chain of (4) and the L chain of (5);
(7) an antibody that comprises an H chain having the amino acid sequence of SEQ ID NO: 22 as CDR1, the amino acid sequence of SEQ ID NO: 24 as CDR2, and the amino acid sequence of SEQ ID NO: 26 as CDR3;
(8) an antibody that comprises an L chain having the amino acid sequence of SEQ ID NO: 28 as CDR1, the amino acid sequence of SEQ ID NO: 30 as CDR2, and the amino acid sequence of SEQ ID NO: 32 as CDR3;
(9) an antibody that comprises the H chain of (7) and the L chain of (8);
(10) an antibody that comprises an H chain having the amino acid sequence of SEQ ID NO: 534 as VH;
(11) an antibody that comprises an L chain having the amino acid sequence of SEQ ID NO: 536 as VL;
(12) an antibody that comprises the H chain of (10) and the L chain of (11);
(13) an antibody that comprises an H chain having the amino acid sequence of SEQ ID NO: 38 as CDR1, the amino acid sequence of SEQ ID NO: 40 as CDR2, and the amino acid sequence of SEQ ID NO: 42 as CDR3;
(14) an antibody that comprises an L chain having the amino acid sequence of SEQ ID NO: 44 as CDR1, the amino acid sequence of SEQ ID NO: 46 as CDR2, and the amino acid sequence of SEQ ID NO: 48 as CDR3;

(15) an antibody that comprises the H chain of (13) and the L chain of (14);
(16) an antibody that comprises an H chain having the amino acid sequence of SEQ ID NO: 538 as VH;
(17) an antibody that comprises an L chain having the amino acid sequence of SEQ ID NO: 540 as VL;
(18) an antibody that comprises the H chain of (16) and the L chain of (17);
(19) an antibody that comprises an H chain having the amino acid sequence of SEQ ID NO: 54 as CDR1, the amino acid sequence of SEQ ID NO: 56 as CDR2, and the amino acid sequence of SEQ ID NO: 58 as CDR3;
(20) an antibody that comprises an L chain having the amino acid sequence of SEQ ID NO: 60 as CDR1, the amino acid sequence of SEQ ID NO: 62 as CDR2, and the amino acid sequence of SEQ ID NO: 64 as CDR3;
(21) an antibody that comprises the H chain of (19) and the L chain of (20);
(22) an antibody that comprises an H chain having the amino acid sequence of SEQ ID NO: 542 as VH;
(23) an antibody that comprises an L chain having the amino acid sequence of SEQ ID NO: 544 as VL;
(24) an antibody that comprises the H chain of (22) and the L chain of (23);
(25) an antibody that comprises an H chain having the amino acid sequence of SEQ ID NO: 70 as CDR1, the amino acid sequence of SEQ ID NO: 72 as CDR2, and the amino acid sequence of SEQ ID NO: 74 as CDR3;
(26) an antibody that comprises an L chain having the amino acid sequence of SEQ ID NO: 76 as CDR1, the amino acid sequence of SEQ ID NO: 78 as CDR2, and the amino acid sequence of SEQ ID NO: 80 as CDR3;
(27) an antibody that comprises the H chain of (25) and the L chain of (26);
(28) an antibody that comprises an H chain having the amino acid sequence of SEQ ID NO: 546 as VH;
(29) an antibody that comprises an L chain having the amino acid sequence of SEQ ID NO: 548 as VL;
(30) an antibody that comprises the H chain of (28) and the L chain of (29);
(31) an antibody that comprises an H chain having the amino acid sequence of SEQ ID NO: 86 as CDR1, the amino acid sequence of SEQ ID NO: 88 as CDR2, and the amino acid sequence of SEQ ID NO: 90 as CDR3;
(32) an antibody that comprises an L chain having the amino acid sequence of SEQ ID NO: 92 as CDR1, the amino acid sequence of SEQ ID NO: 94 as CDR2, and the amino acid sequence of SEQ ID NO: 96 as CDR3;
(33) an antibody that comprises the H chain of (31) and the L chain of (32);
(34) an antibody that comprises an H chain having the amino acid sequence of SEQ ID NO: 550 as VH;
(35) an antibody that comprises an L chain having the amino acid sequence of SEQ ID NO: 552 as VL;
(36) an antibody that comprises the H chain of (34) and the L chain of (35);
(37) an antibody that comprises an H chain having the amino acid sequence of SEQ ID NO: 102 as CDR1, the amino acid sequence of SEQ ID NO: 104 as CDR2, and the amino acid sequence of SEQ ID NO: 106 as CDR3;
(38) an antibody that comprises an L chain having the amino acid sequence of SEQ ID NO: 108 as CDR1, the amino acid sequence of SEQ ID NO: 110 as CDR2, and the amino acid sequence of SEQ ID NO: 112 as CDR3;
(39) an antibody that comprises the H chain of (37) and the L chain of (38);
(40) an antibody that comprises an H chain having the amino acid sequence of SEQ ID NO: 554 as VH;
(41) an antibody that comprises an L chain having the amino acid sequence of SEQ ID NO: 556 as VL;
(42) an antibody that comprises the H chain of (40) and the L chain of (41);
(43) an antibody that comprises an H chain having the amino acid sequence of SEQ ID NO: 118 as CDR1, the amino acid sequence of SEQ ID NO: 120 as CDR2, and the amino acid sequence of SEQ ID NO: 122 as CDR3;
(44) an antibody that comprises an L chain having the amino acid sequence of SEQ ID NO: 124 as CDR1, the amino acid sequence of SEQ ID NO: 126 as CDR2, and the amino acid sequence of SEQ ID NO: 128 as CDR3;
(45) an antibody that comprises the H chain of (43) and the L chain of (44);
(46) an antibody that comprises an H chain having the amino acid sequence of SEQ ID NO: 558 as VH;
(47) an antibody that comprises an L chain having the amino acid sequence of SEQ ID NO: 560 as VL;
(48) an antibody that comprises the H chain of (46) and the L chain of (47);
(49) an antibody that comprises an H chain having the amino acid sequence of SEQ ID NO: 134 as CDR1, the amino acid sequence of SEQ ID NO: 136 as CDR2, and the amino acid sequence of SEQ ID NO: 138 as CDR3;
(50) an antibody that comprises an L chain having the amino acid sequence of SEQ ID NO: 140 as CDR1, the amino acid sequence of SEQ ID NO: 142 as CDR2, and the amino acid sequence of SEQ ID NO: 144 as CDR3;
(51) an antibody that comprises the H chain of (49) and the L chain of (50);
(52) an antibody that comprises an H chain having the amino acid sequence of SEQ ID NO: 562 as VH;
(53) an antibody that comprises an L chain having the amino acid sequence of SEQ ID NO: 564 as VL;
(54) an antibody that comprises the H chain of (52) and the L chain of (53);
(55) an antibody that comprises an H chain having the amino acid sequence of SEQ ID NO: 150 as CDR1, the amino acid sequence of SEQ ID NO: 152 as CDR2, and the amino acid sequence of SEQ ID NO: 154 as CDR3;
(56) an antibody that comprises an L chain having the amino acid sequence of SEQ ID NO: 156 as CDR1, the amino acid sequence of SEQ ID NO: 158 as CDR2, and the amino acid sequence of SEQ ID NO: 160 as CDR3;
(57) an antibody that comprises the H chain of (55) and the L chain of (56);
(58) an antibody that comprises an H chain having the amino acid sequence of SEQ ID NO: 566 as VH;
(59) an antibody that comprises an L chain having the amino acid sequence of SEQ ID NO: 568 as VL;
(60) an antibody that comprises the H chain of (58) and the L chain of (59);
(61) an antibody that comprises an H chain having the amino acid sequence of SEQ ID NO: 166 as CDR1, the amino acid sequence of SEQ ID NO: 168 as CDR2, and the amino acid sequence of SEQ ID NO: 170 as CDR3;
(62) an antibody that comprises an L chain having the amino acid sequence of SEQ ID NO: 172 as CDR1, the amino acid sequence of SEQ ID NO: 174 as CDR2, and the amino acid sequence of SEQ ID NO: 176 as CDR3;
(63) an antibody that comprises the H chain of (61) and the L chain of (62);
(64) an antibody that comprises an H chain having the amino acid sequence of SEQ ID NO: 570 as VH;

(65) an antibody that comprises an L chain having the amino acid sequence of SEQ ID NO: 572 as VL;
(66) an antibody that comprises the H chain of (64) and the L chain of (65);
(67) an antibody that comprises an H chain having the amino acid sequence of SEQ ID NO: 182 as CDR1, the amino acid sequence of SEQ ID NO: 184 as CDR2, and the amino acid sequence of SEQ ID NO: 186 as CDR3;
(68) an antibody that comprises an L chain having the amino acid sequence of SEQ ID NO: 188 as CDR1, the amino acid sequence of SEQ ID NO: 190 as CDR2, and the amino acid sequence of SEQ ID NO: 192 as CDR3;
(69) an antibody that comprises the H chain of (67) and the L chain of (68);
(70) an antibody that comprises an H chain having the amino acid sequence of SEQ ID NO: 574 as VH;
(71) an antibody that comprises an L chain having the amino acid sequence of SEQ ID NO: 576 as VL;
(72) an antibody that comprises the H chain of (70) and the L chain of (71);
(73) an antibody that comprises an H chain having the amino acid sequence of SEQ ID NO: 198 as CDR1, the amino acid sequence of SEQ ID NO: 200 as CDR2, and the amino acid sequence of SEQ ID NO: 202 as CDR3;
(74) an antibody that comprises an L chain having the amino acid sequence of SEQ ID NO: 204 as CDR1, the amino acid sequence of SEQ ID NO: 206 as CDR2, and the amino acid sequence of SEQ ID NO: 208 as CDR3;
(75) an antibody that comprises the H chain of (73) and the L chain of (74);
(76) an antibody that comprises an H chain having the amino acid sequence of SEQ ID. NO: 578 as VH;
(77) an antibody that comprises an L chain having the amino acid sequence of SEQ ID NO: 580 as VL;
(78) an antibody that comprises the H chain of (75) and the L chain of (76);
(79) an antibody that comprises an H chain having the amino acid sequence of SEQ ID NO: 214 as CDR1, the amino acid sequence of SEQ ID NO: 216 as CDR2, and the amino acid sequence of SEQ ID NO: 218 as CDR3;
(80) an antibody that comprises an L chain having the amino acid sequence of SEQ ID NO: 220 as CDR1, the amino acid sequence of SEQ ID NO: 222 as CDR2, and the amino acid sequence of SEQ ID NO: 224 as CDR3;
(81) an antibody that comprises the H chain of (79) and the L chain of (80);
(82) an antibody that comprises an H chain having the amino acid sequence of SEQ ID NO: 582 as VH;
(83) an antibody that comprises an L chain having the amino acid sequence of SEQ ID NO: 584 as VL;
(84) an antibody that comprises the H chain of (82) and the L chain of (83);
(85) an antibody that comprises an H chain having the amino acid sequence of SEQ ID NO: 230 as CDR1, the amino acid sequence of SEQ ID NO: 232 as CDR2, and the amino acid sequence of SEQ ID NO: 234 as CDR3;
(86) an antibody that comprises an L chain having the amino acid sequence of SEQ ID NO: 236 as CDR1, the amino acid sequence of SEQ ID NO: 238 as CDR2, and the amino acid sequence of SEQ ID NO: 240 as CDR3;
(87) an antibody that comprises the H chain of (85) and the L chain of (86);
(88) an antibody that comprises an H chain having the amino acid sequence of SEQ ID NO: 586 as VH;
(89) an antibody that comprises an L chain having the amino acid sequence of SEQ ID NO: 588 as VL;
(90) an antibody that comprises the H chain of (88) and the L chain of (89);
(91) an antibody that comprises an H chain having the amino acid sequence of SEQ ID NO: 246 as CDR1, the amino acid sequence of SEQ ID NO: 248 as CDR2, and the amino acid sequence of SEQ ID NO: 250 as CDR3;
(92) an antibody that comprises an L chain having the amino acid sequence of SEQ ID NO: 252 as CDR1, the amino acid sequence of SEQ ID NO: 254 as CDR2, and the amino acid sequence of SEQ ID NO: 256 as CDR3;
(93) an antibody that comprises the H chain of (91) and the L chain of (92);
(94) an antibody that comprises an H chain having the amino acid sequence of SEQ ID NO: 590 as VH;
(95) an antibody that comprises an L chain having the amino acid sequence of SEQ ID NO: 592 as VL;
(96) an antibody that comprises the H chain of (94) and the L chain of (95);
(97) an antibody that comprises an H chain having the amino acid sequence of SEQ ID NO: 262 as CDR1, the amino acid sequence of SEQ ID NO: 264 as CDR2, and the amino acid sequence of SEQ ID NO: 266 as CDR3;
(98) an antibody that comprises an L chain having the amino acid sequence of SEQ ID NO: 268 as CDR1, the amino acid sequence of SEQ ID NO: 270 as CDR2, and the amino acid sequence of SEQ ID NO: 272 as CDR3;
(99) an antibody that comprises the H chain of (97) and the L chain of (98);
(100) an antibody that comprises an H chain having the amino acid sequence of SEQ ID NO: 594 as VH;
(101) an antibody that comprises an L chain having the amino acid sequence of SEQ ID NO: 596 as VL;
(102) an antibody that comprises the H chain of (100) and the L chain of (101);
(103) an antibody that comprises an H chain having the amino acid sequence of SEQ ID NO: 278 as CDR1, the amino acid sequence of SEQ ID NO: 280 as CDR2, and the amino acid sequence of SEQ ID NO: 282 as CDR3;
(104) an antibody that comprises an L chain having the amino acid sequence of SEQ ID NO: 284 as CDR1, the amino acid sequence of SEQ ID NO: 286 as CDR2, and the amino acid sequence of SEQ ID NO: 288 as CDR3;
(105) an antibody that comprises the H chain of (103) and the L chain of (104);
(106) an antibody that comprises an H chain having the amino acid sequence of SEQ ID NO: 598 as VH;
(107) an antibody that comprises an L chain having the amino acid sequence of SEQ ID NO: 600 as VL;
(108) an antibody that comprises the H chain of (106) and the L chain of (107);
(109) an antibody that comprises an H chain having the amino acid sequence of SEQ ID NO: 294 as CDR1, the amino acid sequence of SEQ ID NO: 296 as CDR2, and the amino acid sequence of SEQ ID NO: 298 as CDR3;
(110) an antibody that comprises an L chain having the amino acid sequence of SEQ ID NO: 300 as CDR1, the amino acid sequence of SEQ ID NO: 302 as CDR2, and the amino acid sequence of SEQ ID NO: 304 as CDR3;
(111) an antibody that comprises the H chain of (109) and the L chain of (110);
(112) an antibody that comprises an H chain having the amino acid sequence of SEQ ID NO: 602 as VH;
(113) an antibody that comprises an L chain having the amino acid sequence of SEQ ID NO: 604 as VL;
(114) an antibody that comprises the H chain of (112) and the L chain of (113);

(115) an antibody that comprises an H chain having the amino acid sequence of SEQ ID NO: 310 as CDR1, the amino acid sequence of SEQ ID NO: 312 as CDR2, and the amino acid sequence of SEQ ID NO: 314 as CDR3;
(116) an antibody that comprises an L chain having the amino acid sequence of SEQ ID NO: 316 as CDR1, the amino acid sequence of SEQ ID NO: 318 as CDR2, and the amino acid sequence of SEQ ID NO: 320 as CDR3;
(117) an antibody that comprises the H chain of (115) and the L chain of (116);
(118) an antibody that comprises an H chain having the amino acid sequence of SEQ ID NO: 606 as VH;
(119) an antibody that comprises an L chain having the amino acid sequence of SEQ ID NO: 608 as VL;
(120) an antibody that comprises the H chain of (118) and the L chain of (119);
(121) an antibody that comprises an H chain having the amino acid sequence of SEQ ID NO: 326 as CDR1, the amino acid sequence of SEQ ID NO: 328 as CDR2, and the amino acid sequence of SEQ ID NO: 330 as CDR3;
(122) an antibody that comprises an L chain having the amino acid sequence of SEQ ID NO: 332 as CDR1, the amino acid sequence of SEQ ID NO: 334 as CDR2, and the amino acid sequence of SEQ ID NO: 336 as CDR3;
(123) an antibody that comprises the H chain of (121) and the L chain of (122);
(124) an antibody that comprises an H chain having the amino acid sequence of SEQ ID NO: 610 as VH;
(125) an antibody that comprises an L chain having the amino acid sequence of SEQ ID NO: 612 as VL;
(126) an antibody that comprises the H chain of (124) and the L chain of (125);
(127) an antibody that comprises an H chain having the amino acid sequence of SEQ ID NO: 342 as CDR1, the amino acid sequence of SEQ ID NO: 344 as CDR2, and the amino acid sequence of SEQ ID NO: 346 as CDR3;
(128) an antibody that comprises an L chain having the amino acid sequence of SEQ ID NO: 348 as CDR1, the amino acid sequence of SEQ ID NO: 350 as CDR2, and the amino acid sequence of SEQ ID NO: 352 as CDR3;
(129) an antibody that comprises the H chain of (127) and the L chain of (128);
(130) an antibody that comprises an H chain having the amino acid sequence of SEQ ID NO: 614 as VH;
(131) an antibody that comprises an L chain having the amino acid sequence of SEQ ID NO: 616 as VL;
(132) an antibody that comprises the H chain of (130) and the L chain of (131);
(133) an antibody that comprises an H chain having the amino acid sequence of SEQ ID NO: 358 as CDR1, the amino acid sequence of SEQ ID NO: 360 as CDR2, and the amino acid sequence of SEQ ID NO: 362 as CDR3;
(134) an antibody that comprises an L chain having the amino acid sequence of SEQ ID NO: 364 as CDR1, the amino acid sequence of SEQ ID NO: 366 as CDR2, and the amino acid sequence of SEQ ID NO: 368 as CDR3;
(135) an antibody that comprises the H chain of (133) and the L chain of (134);
(136) an antibody that comprises an H chain having the amino acid sequence of SEQ ID NO: 618 as VH;
(137) an antibody that comprises an L chain having the amino acid sequence of SEQ ID NO: 620 as VL;
(138) an antibody that comprises the H chain of (136) and the L chain of (137);
(139) an antibody that comprises an H chain having the amino acid sequence of SEQ ID NO: 374 as CDR1, the amino acid sequence of SEQ ID NO: 376 as CDR2, and the amino acid sequence of SEQ ID NO: 378 as CDR3;
(140) an antibody that comprises an L chain having the amino acid sequence of SEQ ID NO: 380 as CDR1, the amino acid sequence of SEQ ID NO: 382 as CDR2, and the amino acid sequence of SEQ ID NO: 384 as CDR3;
(141) an antibody that comprises the H chain of (139) and the L chain of (140);
(142) an antibody that comprises an H chain having the amino acid sequence of SEQ ID NO: 622 as VH;
(143) an antibody that comprises an L chain having the amino acid sequence of SEQ ID NO: 624 as VL;
(144) an antibody that comprises the H chain of (142) and the L chain of (143);
(145) an antibody that comprises an H chain having the amino acid sequence of SEQ ID NO: 390 as CDR1, the amino acid sequence of SEQ ID NO: 392 as CDR2, and the amino acid sequence of SEQ ID NO: 394 as CDR3;
(146) an antibody that comprises an L chain having the amino acid sequence of SEQ ID NO: 396 as CDR1, the amino acid sequence of SEQ ID NO: 398 as CDR2, and the amino acid sequence of SEQ ID NO: 400 as CDR3;
(147) an antibody that comprises the H chain of (145) and the L chain of (146);
(148) an antibody that comprises an H chain having the amino acid sequence of SEQ ID NO: 626 as VH;
(149) an antibody that comprises an L chain having the amino acid sequence of SEQ ID NO: 628 as VL;
(150) an antibody that comprises the H chain of (148) and the L chain of (149);
(151) an antibody that comprises an H chain having the amino acid sequence of SEQ ID NO: 406 as CDR1, the amino acid sequence of SEQ ID NO: 408 as CDR2, and the amino acid sequence of SEQ ID NO: 410 as CDR3;
(152) an antibody that comprises an L chain having the amino acid sequence of SEQ ID NO: 412 as CDR1, the amino acid sequence of SEQ ID NO: 414 as CDR2, and the amino acid sequence of SEQ ID NO: 416 as CDR3;
(153) an antibody that comprises the H chain of (151) and the L chain of (152);
(154) an antibody that comprises an H chain having the amino acid sequence of SEQ ID NO: 630 as VH;
(155) an antibody that comprises an L chain having the amino acid sequence of SEQ ID NO: 632 as VL;
(156) an antibody that comprises the H chain of (154) and the L chain of (155);
(157) an antibody that comprises an H chain having the amino acid sequence of SEQ ID NO: 422 as CDR1, the amino acid sequence of SEQ ID NO: 424 as CDR2, and the amino acid sequence of SEQ ID NO: 426 as CDR3;
(158) an antibody that comprises an L chain having the amino acid sequence of SEQ ID NO: 428 as CDR1, the amino acid sequence of SEQ ID NO: 430 as CDR2, and the amino acid sequence of SEQ ID NO: 432 as CDR3;
(159) an antibody that comprises the H chain of (157) and the L chain of (158);
(160) an antibody that comprises an H chain having the amino acid sequence of SEQ ID NO: 634 as VH;
(161) an antibody that comprises an L chain having the amino acid sequence of SEQ ID NO: 636 as VL;
(162) an antibody that comprises the H chain of (160) and the L chain of (161);
(163) an antibody that comprises an H chain having the amino acid sequence of SEQ ID NO: 438 as CDR1, the amino acid sequence of SEQ ID NO: 440 as CDR2, and the amino acid sequence of SEQ ID NO: 442 as CDR3;

(164) an antibody that comprises an L chain having the amino acid sequence of SEQ ID NO: 444 as CDR1, the amino acid sequence of SEQ ID NO: 446 as CDR2, and the amino acid sequence of SEQ ID NO: 448 as CDR3;
(165) an antibody that comprises the H chain of (163) and the L chain of (164);
(166) an antibody that comprises an H chain having the amino acid sequence of SEQ ID NO: 638 as VH;
(167) an antibody that comprises an L chain having the amino acid sequence of SEQ ID NO: 640 as VL;
(168) an antibody that comprises the H chain of (166) and the L chain of (167);
(169) an antibody that comprises an H chain having the amino acid sequence of SEQ ID NO: 454 as CDR1, the amino acid sequence of SEQ ID NO: 456 as CDR2, and the amino acid sequence of SEQ ID NO: 458 as CDR3;
(170) an antibody that comprises an L chain having the amino acid sequence of SEQ ID NO: 460 as CDR1, the amino acid sequence of SEQ ID NO: 462 as CDR2, and the amino acid sequence of SEQ ID NO: 464 as CDR3;
(171) an antibody that comprises the H chain of (169) and the L chain of (170);
(172) an antibody that comprises an H chain having the amino acid sequence of SEQ ID NO: 642 as VH;
(173) an antibody that comprises an L chain having the amino acid sequence of SEQ ID NO: 644 as VL;
(174) an antibody that comprises the H chain of (172) and the L chain of (173);
(175) an antibody that comprises an H chain having the amino acid sequence of SEQ ID NO: 470 as CDR1, the amino acid sequence of SEQ ID NO: 472 as CDR2, and the amino acid sequence of SEQ ID NO: 474 as CDR3;
(176) an antibody that comprises an L chain having the amino acid sequence of SEQ ID NO: 476 as CDR1, the amino acid sequence of SEQ ID NO: 478 as CDR2, and the amino acid sequence of SEQ ID NO: 480 as CDR3;
(177) an antibody that comprises the H chain of (175) and the L chain of (176);
(178) an antibody that comprises an H chain having the amino acid sequence of SEQ ID NO: 646 as VH;
(179) an antibody that comprises an L chain having the amino acid sequence of SEQ ID NO: 648 as VL;
(180) an antibody that comprises the H chain of (178) and the L chain of (179);
(181) an antibody that comprises an H chain having the amino acid sequence of SEQ ID NO: 486 as CDR1, the amino acid sequence of SEQ ID NO: 488 as CDR2, and the amino acid sequence of SEQ ID NO: 490 as CDR3;
(182) an antibody that comprises an L chain having the amino acid sequence of SEQ ID NO: 492 as CDR1, the amino acid sequence of SEQ ID NO: 494 as CDR2, and the amino acid sequence of SEQ ID NO: 496 as CDR3;
(183) an antibody that comprises the H chain of (181) and the L chain of (182);
(184) an antibody that comprises an H chain having the amino acid sequence of SEQ ID NO: 650 as VH;
(185) an antibody that comprises an L chain having the amino acid sequence of SEQ ID NO: 652 as VL;
(186) an antibody that comprises the H chain of (184) and the L chain of (185);
(187) an antibody that comprises an H chain having the amino acid sequence of SEQ ID NO: 502 as CDR1, the amino acid sequence of SEQ ID NO: 504 as CDR2, and the amino acid sequence of SEQ ID NO: 506 as CDR3;
(188) an antibody that comprises an L chain having the amino acid sequence of SEQ ID NO: 508 as CDR1, the amino acid sequence of SEQ ID NO: 510 as CDR2, and the amino acid sequence of SEQ ID NO: 512 as CDR3;
(189) an antibody that comprises the H chain of (187) and the L chain of (188);
(190) an antibody that comprises an H chain having the amino acid sequence of SEQ ID NO: 654 as VH;
(191) an antibody that comprises an L chain having the amino acid sequence of SEQ ID NO: 656 as VL;
(192) an antibody that comprises the H chain of (190) and the L chain of (191);
(193) an antibody that comprises an H chain having the amino acid sequence of SEQ ID NO: 518 as CDR1, the amino acid sequence of SEQ ID NO: 520 as CDR2, and the amino acid sequence of SEQ ID NO: 522 as CDR3;
(194) an antibody that comprises an L chain having the amino acid sequence of SEQ ID NO: 524 as CDR1, the amino acid sequence of SEQ ID NO: 526 as CDR2, and the amino acid sequence of SEQ ID NO: 528 as CDR3;
(195) an antibody that comprises the H chain of (193) and the L chain of (194);
(196) an antibody that comprises an H chain having the amino acid sequence of SEQ ID NO: 658 as VH;
(197) an antibody that comprises an L chain having the amino acid sequence of SEQ ID NO: 660 as VL;
(198) an antibody that comprises the H chain of (196) and the L chain of (197);
(199) an antibody that comprises one or more amino acid substitutions, deletions, additions, and/or insertions in the antibody of any one of (1) to (198), which has equivalent activity to the antibody of any one of (1) to (198); and
(200) an antibody that binds to the epitope bound by the antibody of any one of (1) to (198).

[4] The antibody of any one of [1] to [3], wherein the antibody is a chimeric antibody or a humanized antibody.

[5] An antigen-binding fragment of the antibody of any one of [1] to [4].

[6] A pharmaceutical composition comprising the antibody of any one of [1] to [4] or the antigen-binding fragment of [5], and a pharmaceutically acceptable carrier.

[7] The composition of [6], which comprises an agent against cognitive impairment, a therapeutic agent for Alzheimer's disease, an agent for suppressing the progression of Alzheimer's disease, an agent for suppressing senile plaque formation, an agent for suppressing A beta accumulation, an anti-neurotoxic agent, an agent for inhibiting A beta amyloid fibril formation, or an agent against synaptic toxicity.

[8] A method for detecting an A beta oligomer, which comprises the step of detecting an A beta oligomer contained in a sample using the antibody of any one of [1] to [4] or the antigen-binding fragment of [5].

[9] A method of diagnosing whether or not a subject is a possible Alzheimer's disease patient, which comprises using the antibody of any one of [1] to [4] or the antigen-binding fragment of [5], to detect an A beta oligomer in a sample collected from a subject.

[10] A method of diagnosing whether or not a subject is a possible Alzheimer's disease patient, which comprises the steps of:
(a) contacting a sample collected from a subject with the antibody of any one of [1] to [4] or the antigen-binding fragment of [5]; and
(b) measuring the amount of A beta oligomer in the sample, wherein the subject is determined to be a possible Alzheimer's disease patient, when the amount measured in step (b) is higher than that of a healthy individual.

[11] A method of diagnosing whether or not a subject is a possible Alzheimer's disease patient, which comprises the steps of:
(a) contacting a sample collected from a subject with the antibody of any one of [1] to [4] or the antigen-binding fragment of [5], and an antibody that binds to an A beta monomer; and
(b) measuring the ratio of A beta oligomer to A beta monomer in the sample,
wherein the subject is determined to be a possible Alzheimer's disease patient, when the ratio measured in step (b) is higher than that of a healthy individual.
[12] The method of any one of [8] to [11], wherein the sample is blood or cerebrospinal fluid.
[13] A pharmaceutical agent for use in the method of any one of [8] to [12].
[14] A kit for use in the method of any one of [8] to [12]. Furthermore, the present invention provides the following:
[15] Use of the antibody of any one of [1] to [4] or the antigen-binding fragment of [5] in the production of an agent against cognitive impairment, a therapeutic agent for Alzheimer's disease, an agent for suppressing the progression of Alzheimer's disease, an agent for suppressing senile plaque formation, an agent for suppressing A beta accumulation, an anti-neurotoxic agent, an agent for inhibiting A beta amyloid fibril formation, or an agent against synaptic toxicity.
[16] The antibody of any one of [1] to [4] or the antigen-binding fragment of [5] for use in preventing and/or treating cognitive impairment.
[17] The antibody of any one of [1] to [4] or the antigen-binding fragment of [5] for use in preventing and/or treating Alzheimer's disease.
[18] The antibody of any one of [1] to [4] or the antigen-binding fragment of [5] for use in suppressing the progression of Alzheimer's disease.
[19] The antibody of any one of [1] to [4] or the antigen-binding fragment of [5] for use in suppressing senile plaque formation.
[20] The antibody of any one of [1] to [4] or the antigen-binding fragment of [5] for use in suppressing A beta accumulation.
[21] The antibody of any one of [1] to [4] or the antigen-binding fragment of [5] for use in neutralizing (suppressing) neurotoxicity.
[22] The antibody of any one of [1] to [4] or the antigen-binding fragment of [5] for use in inhibiting A beta amyloid fibril formation.
[23] The antibody of any one of [1] to [4] or the antigen-binding fragment of [5] for use in neutralizing (suppressing) synaptic toxicity.
[24] A method for preventing and/or treating cognitive impairment, which comprises the step of administering the antibody of any one of [1] to [4] or the antigen-binding fragment of [5] as an active ingredient.
[25] A method for preventing and/or treating Alzheimer's disease, which comprises the step of administering the antibody of any one of [1] to [4] or the antigen-binding fragment of [5] as an active ingredient.
[26] A method for suppressing the progression of Alzheimer's disease, which comprises the step of administering the antibody of any one of [1] to [4] or the antigen-binding fragment of [5] as an active ingredient.
[27] A method for suppressing senile plaque formation, which comprises the step of administering the antibody of any one of [1] to [4] or the antigen-binding fragment of [5] as an active ingredient.
[28] A method for suppressing A beta accumulation, which comprises the step of administering the antibody of any one of [1] to [4] or the antigen-binding fragment of [5] as an active ingredient.
[29] A method for neutralizing neurotoxicity, which comprises the step of administering the antibody of any one of [1] to [4] or the antigen-binding fragment of [5] as an active ingredient.
[30] A method for inhibiting A beta amyloid fibril formation, which comprises the step of administering the antibody of any one of [1] to [4] or the antigen-binding fragment of [5] as an active ingredient.
[31] A method for neutralizing synaptic toxicity, which comprises the step of administering the antibody of any one of [1] to [4] or the antigen-binding fragment of [5] as an active ingredient.
[32] Use of the antibody of any one of [1] to [4] or the antigen-binding fragment of [5] for preventing and/or treating cognitive impairment.
[33] Use of the antibody of any one of [1] to [4] or the antigen-binding fragment of [5] for preventing and/or treating Alzheimer's disease.
[34] Use of the antibody of any one of [1] to [4] or the antigen-binding fragment of [5] for suppressing the progression of Alzheimer's disease.
[35] Use of the antibody of any one of [1] to [4] or the antigen-binding fragment of [5] for suppressing senile plaque formation.
[36] Use of the antibody of any one of [1] to [4] or the antigen-binding fragment of [5] for suppressing A beta accumulation.
[37] Use of the antibody of any one of [1] to [4] or the antigen-binding fragment of [5] for neutralizing neurotoxicity.
[38] Use of the antibody of any one of [1] to [4] or the antigen-binding fragment of [5] for inhibiting A beta amyloid fibril formation.
[39] Use of the antibody of any one of [1] to [4] or the antigen-binding fragment of [5] for neutralizing (suppressing) synaptic toxicity.

Advantageous Effects of Invention

The antibodies provided by the present invention are expected to contribute to the establishment of preventive/therapeutic methods selective to molecules responsible for evoking pathological conditions of Alzheimer's disease, and the establishment of early diagnostic markers for Alzheimer's disease.

BRIEF DESCRIPTION OF DRAWINGS

FIG. 3 shows the results of analysis of the affinity of the three antibodies, whose selectivity was higher in the competitive ELISA, to A beta oligomers, by Biacore 3000.

FIG. 4 shows the results of neutralization assay against A beta-induced cytotoxicity using the three anti-A beta oligomer antibodies (AL-217, AL-224 and AL-225).

FIG. 5 shows the results of inhibition assay against A beta fibril formation using the three anti-A beta oligomer antibodies (AL-217, and AL224 and AL-225).

FIG. 6 shows the results of immunoblotting assay to assess whether the three anti-A beta oligomer antibodies (AL-217, AL-224 and AL-225) bind to APP. APP was detected in the result of Tg2576 using the control antibody 6E10 (marked by arrow head).

DESCRIPTION OF EMBODIMENTS

Figures 1, 2:
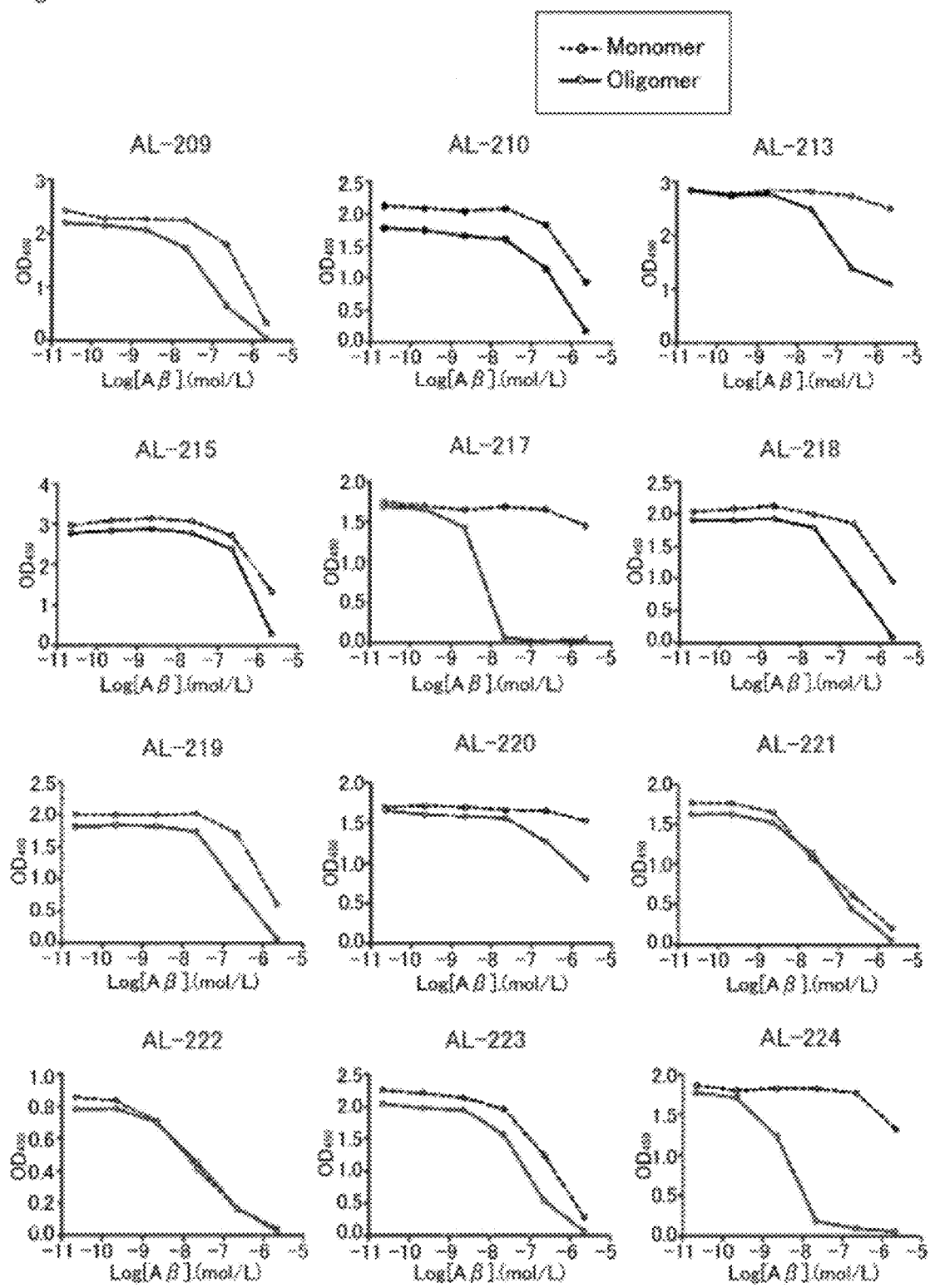
FIG. 1 presents photographs of dot-blot analysis results on each of the AL-201 to AL-233 antibodies.
FIG. 2 presents competitive ELISA results on the 19 antibodies. The vertical axis shows the absorbance at a wavelength of 450 nm, and horizontal axis shows the concentration of A beta oligomer or monomer used as an inhibitor. The dotted lines of each graph show the antigen binding activity when the A beta oligomer was used as an inhibitor. The solid lines of each graph show the antigen binding activity when the A beta monomer was used as an inhibitor. The molar concentration (mol/L) of A beta oligomer was calculated by converting the molar number of A beta oligomer into that of A beta monomer.

The present invention will be described more specifically below.

As described above, the present inventors succeeded in obtaining antibodies that bind specifically to A beta oligomers but not to A beta monomers. That is, the present invention provides antibodies that bind to A beta oligomers but not to A beta monomers. The antibodies are preferably isolated or purified.

The terms "isolated" and "purified" used for substances (antibodies and such) of the present invention indicate that the substances do not substantially include at least one other substance that may be contained in the natural source. Therefore, "isolated antibodies" and "purified antibodies" refer to antibodies that do not substantially include cell materials such as hydrocarbons, lipids, or other contaminant proteins from the cell or tissue source from which the antibodies (proteins) are derived. When the antibodies are chemically synthesized, the terms refer to antibodies that do not substantially include chemical precursor substances or other chemical substances. In a preferred embodiment, the antibodies of the present invention are isolated or purified.

"Antibodies" refers to glycoproteins that have the same structural characteristics. Antibodies show binding specificity towards specific antigens. Herein, "antigens" refers to proteins that have the ability to bind to the corresponding antibodies, and induce antigen-antibody reactions in vivo.

Herein, the antibody heavy chain may be denoted as "H chain", the antibody light chain may be denoted as "L chain", the heavy chain variable region may be denoted as "VH", the light chain variable region may be denoted as "VL", the heavy chain constant region may be denoted as "CH", the light chain constant region may be denoted as "CL", the framework region may be denoted as "FR", and the complementarity-determining region may be denoted as "CDR".

A beta proteins, which are the major constituents of amyloids, are peptides consisting of 40 to 42 amino acids, and are known to be produced from precursor proteins called amyloid precursor proteins (APPs) by the action of proteases. Besides amyloid fibrils collected in ultracentrifuged sediment fractions, the amyloid molecules produced from APPs include oligomeric non-fibrous assemblies in addition to soluble monomers. "A beta oligomers" of the present invention refer to non-fibrous assemblies. The degree of A beta polymerization of "A beta oligomer" of the present invention is not particularly limited, but is typically 2 to 150. The "A beta oligomers" of the present invention include, for example, A beta40 (A beta 1-40) oligomers, A beta42 (A beta 1-42) oligomers, and A beta40/A beta42 oligomers (in which A beta40 and A beta42 are polymerized). For example, "A beta oligomers" of the present invention are, typically, molecules showing a molecular weight of 45 to 160 kDa in SDS-PAGE, and 22.5 to 1,035 kDa in Blue Native PAGE. Using molecular sieves, the molecules are collected mainly in the >100 kDa retention solution. When observed under an atomic force microscope, the molecules show mixed morphologies of granular, bead-shaped, and ring-shaped molecules having a height of 1.5 to 3.1 nm. There is no limitation on the origin and form of the antibodies used in the present invention as long as they bind to A beta oligomers but not to A beta monomers.

The antibodies of the present invention are featured by the characteristics that they bind to A beta oligomers but not to A beta monomers. Preferably, these antibodies have the following characteristics.

In dot-blot analysis, they react with A beta40 oligomers and A beta42 oligomers, but not with A beta40 monomers.

In competitive ELISA assay using immobilized A beta oligomers, the 50%-inhibition concentration (IC50) of A beta monomer for the binding of the antibodies to the immobilized A beta oligomers is higher than that of A beta oligomer.

In competitive ELISA assay using immobilized A beta oligomers, IC50 of A beta monomer is 500 nmol/L or more, preferably 1000 nmol/L or more, more preferably 1500 nmol/L or more, or more preferably 2000 nmol/L or more.

In competitive ELISA assay using immobilized A beta oligomers, IC50 of A beta oligomer is 100 nmol/L or less, preferably 50 nmol/L or less, more preferably 25 nmol/L or less, or more preferably 20 nmol/L or less.

In competitive ELISA assay using immobilized A beta oligomers, the antigen selectivity shown by IC50 of A beta monomer versus A beta oligomer for the binding of the antibodies to the immobilized A beta oligomers, i.e., IC50 of A beta monomer/IC50 of A beta oligomer, is 50 or more, preferably 100 or more, more preferably 150 or more, or more preferably 200 or more.

In the affinity analysis for A beta oligomers using Biacore (Biacore 3000), the binding rate constant (ka) is $1.0E+04$ $M^{-1}S^{-1}$ or more, preferably $2.0E+04$ $M^{-1}S^{-1}$ or more, more preferably $5.0E+04$ $M^{-1}S^{-1}$ or more, more preferably $1.0E+05$ $M^{-1}S^{-1}$ or more, or more preferably $1.5E+05$ $M^{-1}S^{-1}$ or more.

In the affinity analysis for A beta oligomers using Biacore (Biacore 3000), the dissociation rate constant (kd) is $0.5$ $S^{-1}$ or less, preferably $0.2$ $S^{-1}$ or less, more preferably $0.1$ $S^{-1}$ or less, more preferably $0.05$ $S^{-1}$ or less, more preferably $0.01$ $S^{-1}$ or less, or more preferably $6.0E-03$ $S^{-1}$ or less.

In the affinity analysis for A beta oligomers using Biacore (Biacore 3000), the dissociation constant (KD) is $5.0E-06$ M or less, preferably $1.0E-06$ M or less, more preferably $7.0E-07$ M or less, more preferably $1.0E-07$ M or less, or more preferably $5.0E-08$ M or less.

The antibodies of the present invention may be featured by at least one of the above characteristics. Furthermore, the antibodies may be featured by two or more of the above characteristics.

"Antibodies" of the present invention include both monoclonal and polyclonal antibodies. The antibodies of the present invention also include any type of antibodies such as non-human animal antibodies, humanized antibodies, chimeric antibodies, human antibodies, the later-described minibodies, amino acid sequence-modified antibodies, modified antibodies conjugated to other molecules (for example, polymers such as polyethylene glycol), and sugar chain-modified antibodies.

Herein, the term "monoclonal antibodies" refers to antibodies that are obtained from a substantially homogeneous population of antibodies. That is, the individual antibodies constituting the population are identical with the exception of possible natural mutants that may be present in a trace amount. Monoclonal antibodies are highly specific and recognize a single antigenic site. Each of the monoclonal antibodies recognizes a single determinant of the antigen, in contrast to conventional (polyclonal) antibody preparations that typically contain different antibodies against different antigenic determinants (epitopes).

In addition to the above-mentioned specificity, monoclonal antibodies have the advantage that they can be synthesized from a hybridoma culture that is not contaminated with other immunoglobulins. Therefore, "monoclonal" indicates the characteristics of antibodies that can be obtained from a substantially homogeneous antibody population. This term does not indicate the requirement for any specific method for antibody production.

Basically, monoclonal antibodies can be produced by using known techniques. For example, they may be produced by the hybridoma method first described by Kohler and Milstein (Nature 256: 495-7, 1975), or by the recombinant DNA method (Cabilly et al., Proc. Natl. Acad. Sci. USA 81:3273-7, 1984), but the methods are not limited thereto. For example, when using the hybridoma method, an A beta oligomer (for example, the A beta tetramer described in the Examples) is used as a sensitizing antigen, and immunization is carried out according to a conventional immunization method. The obtained immune cells are fused with known parent cells by a conventional cell fusion method, and monoclonal antibody-producing cells can be screened and isolated using a conventional screening method.

The monoclonal antibodies of the present invention can be produced, for example, as follows. First, synthetic A beta 1-42 (Peptide Institute, Inc., Osaka) is dissolved in distilled deionized water or a 10 mM phosphate buffer solution, and this is incubated at 37 degrees C. for 18 hours. Then, the peptides are separated by 4-12% SDS-PAGE, and visualized by CBB staining, and the portion of the A beta 1-42 tetramer alone which is not contaminated with the A beta 1-42 monomer is cut out. Next, BALB/c mice are immunized at their foot pad with 2.5 micro g of the A beta 1-42 tetramer emulsified using complete Freund's adjuvant. Subsequently, booster immunizations are carried out six times. Hybridomas are produced from the inguinal lymph node by fusion with Sp2/O—Ag14 cells using Polyethylene Glycol 1500.

In the present invention, the animals immunized with sensitizing antigens are not particularly limited, but are preferably selected considering the compatibility with parent cells used for cell fusion. Generally, rodents, lagomorphs, or primates are used. Rodents include, for example, mice, rats, and hamsters. Lagomorphs include, for example, rabbits. Primates include, for example, Catarrhini (old-world) monkeys such as *Macaca fascicularis, Macaca mulatta, hamadryas, and chimpanzees.*

Animals are immunized with sensitizing antigens according to known methods. For example, as a standard method, immunization is performed by intraperitoneal or subcutaneous injection of a sensitizing antigen into mammals.

An example of the parent cells fused with the aforementioned immunocytes is the Sp2/O—Ag14 cell, which will be described below in the Examples. However, various other known cell lines can be used.

Cell fusion between the aforementioned immunocyte and a myeloma cell can be carried out basically according to known methods including the method by Kohler and Milstein (Kohler G. and Milstein C., Methods Enzymol. (1981) 73, 3-46).

Hybridomas obtained in this manner are selected by culturing them in a conventional selection culture medium such as a HAT culture medium, which contains hypoxanthine, aminopterin, and thymidine. Culturing in the above-mentioned HAT culture medium is generally continued for several days to several weeks for an adequate time for killing cells other than the desired hybridomas (non-fused cells). Next, a conventional limiting dilution method is performed for screening and singly-cloning of a hybridoma that produces the desired antibody.

Thereafter, the obtained hybridoma is transplanted into the abdominal cavity of a mouse, and ascitic fluid containing the desired monoclonal antibodies is extracted. For example, the antibodies can be purified from the ascitic fluid by conventional protein separation and/or purification methods such as a selected combination of column chromatography including, but not limited to, affinity chromatography, filtration, ultrafiltration, salt precipitation, dialysis, SDS polyacrylamide gel electrophoresis, and isoelectric focusing (Antibodies: A Laboratory manual, Harlow and David, Lane (edit), Cold Spring Harbor Laboratory, 1988).

Protein A columns and Protein G columns can be used for affinity columns. Examples of the Protein A columns used include Hyper D, POROS, and Sepharose F.F. (Pharmacia).

Chromatography (excluding affinity chromatography) includes ion exchange chromatography, hydrophobic chromatography, gel filtration, reverse-phase chromatography, and adsorption chromatography ("Strategies for Protein Purification and Characterization: A Laboratory Course Manual", Daniel R Marshak et al., Cold Spring Harbor Laboratory Press, 1996). When chromatography is carried out, liquid-phase chromatography methods such as HPLC and FPLC can be used.

Monoclonal antibody-producing hybridomas prepared in this manner can be sub-cultured in a conventional culture medium, and they can be stored for a long time in liquid nitrogen.

Any mammal can be immunized using an immunogen for antibody production. However, when preparing monoclonal antibodies by producing hybridomas, the compatibility with parent cells used in cell fusion for hybridoma production is preferably considered.

Generally, rodents, lagomorphs, or primates are used for the immunization. Rodents include, for example, mice, rats, and hamsters. Lagomorphs include, for example, rabbits. Primates include, for example, Catarrhini (old-world) monkeys such as *Macaca fascicularis, Macaca mulatta, hamadryas, and chimpanzees.*

The use of transgenic animals that have a human antibody gene repertoire is known in the art (Ishida I, et al., Cloning and Stem Cells 4: 91-102, 2002). As with other animals, to obtain human monoclonal antibodies, the transgenic animals are immunized, then antibody-producing cells are collected from the animals and fused with myeloma cells to produce hybridomas, and anti-protein human antibodies can be prepared from these hybridomas (see International Publication Nos. WO92/03918, WO94/02602, WO94/25585, WO96/33735, and WO96/34096).

Alternatively, lymphocytes immortalized with oncogenes may be used for monoclonal antibody production. For example, human lymphocytes infected with EB virus or such is immunized in vitro with immunogens. Next, the immunized lymphocytes are fused with human-derived myeloma cells (U266, etc) capable of unlimited division, and thus hybridomas that produce the desired human antibodies are obtained (Japanese Patent Application Kokai Publication No. (JP-A) S63-17688 (unexamined, published Japanese patent application)).

Once monoclonal antibodies can be obtained by any of the aforementioned methods, the antibodies may also be prepared using genetic engineering methods (see, for example, Borrebaeck C A K and Larrick J W, Therapeutic Monoclonal Antibodies, MacMillan Publishers, UK, 1990). For example, recombinant antibodies may be prepared by cloning DNAs that encode the desired antibodies from antibody-producing cells such as hybridomas or immunized lymphocytes that produce the antibodies, then inserting the cloned DNAs into appropriate vectors, and transfecting the vectors into suitable host cells. Such recombinant antibodies are also included in the present invention.

Examples of the monoclonal antibodies of the present invention include the following: AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, and AL-233 antibody.

In an embodiment, the antibodies of the present invention include minibodies. A minibody contains an antibody fragment lacking a portion of a whole antibody, and is not particularly limited as long as it has the ability to bind to an antigen. Examples of antibody fragments include Fab, Fab', F(ab')2, and Fv. Examples of minibodies include Fab, Fab', F(ab')2, Fv, scFv (single chain Fv), diabody, and sc(Fv)2 (single chain (Fv)2).

These minibodies can be obtained, for example, by treating an antibody with an enzyme to produce an antibody fragment. Known enzymes for producing an antibody fragment include papain, pepsin, and plasmin. Alternatively, a gene construct encoding an antibody fragment can be produced, inserted into an expression vector, and expressed in a suitable host cell (see, for example, Co, M. S. et al., J. Immunol. (1994) 152, 2968-2976, Better, M. and Horwitz, A. H. Methods in Enzymology (1989) 178, 476-496, Plueckthun, A. and Skerra, A. Methods in Enzymology (1989) 178, 476-496, Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

Herein, "antigen-binding fragments" means the abovementioned antibody fragments having antigen-binding ability, or minibodies including the antibody fragments having antigen-binding ability. Antibody fragments that bind to A beta oligomers but not to A beta monomers are also included in the present invention. Hereinafter, reference to "antibody" includes reference to the above "antigen-binding fragment".

Polyclonal antibodies of the present invention can be obtained by the following methods. To obtain the polyclonal antibodies, blood is removed from a mammal sensitized with an antigen after the mammal is immunized with an A beta oligomer (e.g., A beta tetramer) as a sensitizing antigen using a conventional method and the serum level of the desired antibody is confirmed to be increased. Serum is separated from blood by a known method. When a polyclonal antibody is used, serum containing the polyclonal antibody may be utilized. Alternatively, if necessary, a fraction containing the polyclonal antibody may be isolated from serum and then used. For example, immunoglobulin G or M can be prepared by obtaining a fraction that specifically recognizes an A beta oligomer using an affinity column coupled with an A beta oligomer, and then purifying this fraction using a Protein A or Protein G column.

The present invention provides A beta oligomers bound by the antibodies of the present invention. Preferably, the antibodies include the following: AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, and AL-233 antibody. The A beta oligomers can be used as antigens for preparing antibodies, or vaccines.

In other words, in the present invention, the A beta oligomers are antigens bound by the following antibodies: AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody.

Furthermore, the antibodies of the present invention include antibodies that bind to the antigens bound by the following antibodies: AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody.

Furthermore, the present invention provides an antibody of any one of (1) to (99) below:

(1) an antibody that comprises an H chain having CDR1, CDR2, and CDR3, which are identified in VH comprising the amino acid sequence of SEQ ID NO: 530;
(2) an antibody that comprises an L chain having CDR1, CDR2, and CDR3, which are identified in VL comprising the amino acid sequence of SEQ ID NO: 532;
(3) an antibody that comprises the H chain of (1) and the L chain of (2);
(4) an antibody that comprises an H chain having CDR1, CDR2, and CDR3, which are identified in VH comprising the amino acid sequence of SEQ ID NO: 534;
(5) an antibody that comprises an L chain having CDR1, CDR2, and CDR3, which are identified in VL comprising the amino acid sequence of SEQ ID NO: 536;
(6) an antibody that comprises the H chain of (4) and the L chain of (5);

(7) an antibody that comprises an H chain having CDR1, CDR2, and CDR3, which are identified in VH comprising the amino acid sequence of SEQ ID NO: 538;
(8) an antibody that comprises an L chain having CDR1, CDR2, and CDR3, which are identified in VL comprising the amino acid sequence of SEQ ID NO: 540;
(9) an antibody that comprises the H chain of (7) and the L chain of (8);
(10) an antibody that comprises an H chain having CDR1, CDR2, and CDR3, which are identified in VH comprising the amino acid sequence of SEQ ID NO: 542;
(11) an antibody that comprises an L chain having CDR1, CDR2, and CDR3, which are identified in VL comprising the amino acid sequence of SEQ ID NO: 544;
(12) an antibody that comprises the H chain of (10) and the L chain of (11);
(13) an antibody that comprises an H chain having CDR1, CDR2, and CDR3, which are identified in VH comprising the amino acid sequence of SEQ ID NO: 546;
(14) an antibody that comprises an L chain having CDR1, CDR2, and CDR3, which are identified in VL comprising the amino acid sequence of SEQ ID NO: 548;
(15) an antibody that comprises the H chain of (13) and the L chain of (14);
(16) an antibody that comprises an H chain having CDR1, CDR2, and CDR3, which are identified in VH comprising the amino acid sequence of SEQ ID NO: 550;
(17) an antibody that comprises an L chain having CDR1, CDR2, and CDR3, which are identified in VL comprising the amino acid sequence of SEQ ID NO: 552;
(18) an antibody that comprises the H chain of (16) and the L chain of (17);
(19) an antibody that comprises an H chain having CDR1, CDR2, and CDR3, which are identified in VH comprising the amino acid sequence of SEQ ID NO: 554;
(20) an antibody that comprises an L chain having CDR1, CDR2, and CDR3, which are identified in VL comprising the amino acid sequence of SEQ ID NO: 556;
(21) an antibody that comprises the H chain of (19) and the L chain of (20);
(22) an antibody that comprises an H chain having CDR1, CDR2, and CDR3, which are identified in VH comprising the amino acid sequence of SEQ ID NO: 558;
(23) an antibody that comprises an L chain having CDR1, CDR2, and CDR3, which are identified in VL comprising the amino acid sequence of SEQ ID NO: 560;
(24) an antibody that comprises the H chain of (22) and the L chain of (23);
(25) an antibody that comprises an H chain having CDR1, CDR2, and CDR3, which are identified in VH comprising the amino acid sequence of SEQ ID NO: 562;
(26) an antibody that comprises an L chain having CDR1, CDR2, and CDR3, which are identified in VL comprising the amino acid sequence of SEQ ID NO: 564;
(27) an antibody that comprises the H chain of (25) and the L chain of (26);
(28) an antibody that comprises an H chain having CDR1, CDR2, and CDR3, which are identified in VH comprising the amino acid sequence of SEQ ID NO: 566;
(29) an antibody that comprises an L chain having CDR1, CDR2, and CDR3, which are identified in VL comprising the amino acid sequence of SEQ ID NO: 568;
(30) an antibody that comprises the H chain of (28) and the L chain of (29);
(31) an antibody that comprises an H chain having CDR1, CDR2, and CDR3, which are identified in VH comprising the amino acid sequence of SEQ ID NO: 570;
(32) an antibody that comprises an L chain having CDR1, CDR2, and CDR3, which are identified in VL comprising the amino acid sequence of SEQ ID NO: 572;
(33) an antibody that comprises the H chain of (31) and the L chain of (32);
(34) an antibody that comprises an H chain having CDR1, CDR2, and CDR3, which are identified in VH comprising the amino acid sequence of SEQ ID NO: 574;
(35) an antibody that comprises an L chain having CDR1, CDR2, and CDR3, which are identified in VL comprising the amino acid sequence of SEQ ID NO: 576;
(36) an antibody that comprises the H chain of (34) and the L chain of (35);
(37) an antibody that comprises an H chain having CDR1, CDR2, and CDR3, which are identified in VH comprising the amino acid sequence of SEQ ID NO: 578;
(38) an antibody that comprises an L chain having CDR1, CDR2, and CDR3, which are identified in VL comprising the amino acid sequence of SEQ ID NO: 580;
(39) an antibody that comprises the H chain of (37) and the L chain of (38);
(40) an antibody that comprises an H chain having CDR1, CDR2, and CDR3, which are identified in VH comprising the amino acid sequence of SEQ ID NO: 582;
(41) an antibody that comprises an L chain having CDR1, CDR2, and CDR3, which are identified in VL comprising the amino acid sequence of SEQ ID NO: 584;
(42) an antibody that comprises the H chain of (40) and the L chain of (41);
(43) an antibody that comprises an H chain having CDR1, CDR2, and CDR3, which are identified in VH comprising the amino acid sequence of SEQ ID NO: 586;
(44) an antibody that comprises an L chain having CDR1, CDR2, and CDR3, which are identified in VL comprising the amino acid sequence of SEQ ID NO: 588;
(45) an antibody that comprises the H chain of (43) and the L chain of (44);
(46) an antibody that comprises an H chain having CDR1, CDR2, and CDR3, which are identified in VH comprising the amino acid sequence of SEQ ID NO: 590;
(47) an antibody that comprises an L chain having CDR1, CDR2, and CDR3, which are identified in VL comprising the amino acid sequence of SEQ ID NO: 592;
(48) an antibody that comprises the H chain of (46) and the L chain of (47);
(49) an antibody that comprises an H chain having CDR1, CDR2, and CDR3, which are identified in VH comprising the amino acid sequence of SEQ ID NO: 594;
(50) an antibody that comprises an L chain having CDR1, CDR2, and CDR3, which are identified in VL comprising the amino acid sequence of SEQ ID NO: 596;
(51) an antibody that comprises the H chain of (49) and the L chain of (50);
(52) an antibody that comprises an H chain having CDR1, CDR2, and CDR3, which are identified in VH comprising the amino acid sequence of SEQ ID NO: 598;
(53) an antibody that comprises an L chain having CDR1, CDR2, and CDR3, which are identified in VL comprising the amino acid sequence of SEQ ID NO: 600;
(54) an antibody that comprises the H chain of (52) and the L chain of (53);
(55) an antibody that comprises an H chain having CDR1, CDR2, and CDR3, which are identified in VH comprising the amino acid sequence of SEQ ID NO: 602;
(56) an antibody that comprises an L chain having CDR1, CDR2, and CDR3, which are identified in VL comprising the amino acid sequence of SEQ ID NO: 604;

(57) an antibody that comprises the H chain of (55) and the L chain of (56);
(58) an antibody that comprises an H chain having CDR1, CDR2, and CDR3, which are identified in VH comprising the amino acid sequence of SEQ ID NO: 606;
(59) an antibody that comprises an L chain having CDR1, CDR2, and CDR3, which are identified in VL comprising the amino acid sequence of SEQ ID NO: 608;
(60) an antibody that comprises the H chain of (58) and the L chain of (59);
(61) an antibody that comprises an H chain having CDR1, CDR2, and CDR3, which are identified in VH comprising the amino acid sequence of SEQ ID NO: 610;
(62) an antibody that comprises an L chain having CDR1, CDR2, and CDR3, which are identified in VL comprising the amino acid sequence of SEQ ID NO: 612;
(63) an antibody that comprises the H chain of (61) and the L chain of (62);
(64) an antibody that comprises an H chain having CDR1, CDR2, and CDR3, which are identified in VH comprising the amino acid sequence of SEQ ID NO: 614;
(65) an antibody that comprises an L chain having CDR1, CDR2, and CDR3, which are identified in VL comprising the amino acid sequence of SEQ ID NO: 616;
(66) an antibody that comprises the H chain of (64) and the L chain of (65);
(67) an antibody that comprises an H chain having CDR1, CDR2, and CDR3, which are identified in VH comprising the amino acid sequence of SEQ ID NO: 618;
(68) an antibody that comprises an L chain having CDR1, CDR2, and CDR3, which are identified in VL comprising the amino acid sequence of SEQ ID NO: 620;
(69) an antibody that comprises the H chain of (67) and the L chain of (68);
(70) an antibody that comprises an H chain having CDR1, CDR2, and CDR3, which are identified in VH comprising the amino acid sequence of SEQ ID NO: 622;
(71) an antibody that comprises an L chain having CDR1, CDR2, and CDR3, which are identified in VL comprising the amino acid sequence of SEQ ID NO: 624;
(72) an antibody that comprises the H chain of (70) and the L chain of (71);
(73) an antibody that comprises an H chain having CDR1, CDR2, and CDR3, which are identified in VH comprising the amino acid sequence of SEQ ID NO: 626;
(74) an antibody that comprises an L chain having CDR1, CDR2, and CDR3, which are identified in VL comprising the amino acid sequence of SEQ ID NO: 628;
(75) an antibody that comprises the H chain of (73) and the L chain of (74);
(76) an antibody that comprises an H chain having CDR1, CDR2, and CDR3, which are identified in VH comprising the amino acid sequence of SEQ ID NO: 630;
(77) an antibody that comprises an L chain having CDR1, CDR2, and CDR3, which are identified in VL comprising the amino acid sequence of SEQ ID NO: 632;
(78) an antibody that comprises the H chain of (76) and the L chain of (77);
(79) an antibody that comprises an H chain having CDR1, CDR2, and CDR3, which are identified in VH comprising the amino acid sequence of SEQ ID NO: 634;
(80) an antibody that comprises an L chain having CDR1, CDR2, and CDR3, which are identified in VL comprising the amino acid sequence of SEQ ID NO: 636;
(81) an antibody that comprises the H chain of (79) and the L chain of (80);
(82) an antibody that comprises an H chain having CDR1, CDR2, and CDR3, which are identified in VH comprising the amino acid sequence of SEQ ID NO: 638;
(83) an antibody that comprises an L chain having CDR1, CDR2, and CDR3, which are identified in VL comprising the amino acid sequence of SEQ ID NO: 640;
(84) an antibody that comprises the H chain of (82) and the L chain of (83);
(85) an antibody that comprises an H chain having CDR1, CDR2, and CDR3, which are identified in VH comprising the amino acid sequence of SEQ ID NO: 642;
(86) an antibody that comprises an L chain having CDR1, CDR2, and CDR3, which are identified in VL comprising the amino acid sequence of SEQ ID NO: 644;
(87) an antibody that comprises the H chain of (85) and the L chain of (86);
(88) an antibody that comprises an H chain having CDR1, CDR2, and CDR3, which are identified in VH comprising the amino acid sequence of SEQ ID NO: 646;
(89) an antibody that comprises an L chain having CDR1, CDR2, and CDR3, which are identified in VL comprising the amino acid sequence of SEQ ID NO: 648;
(90) an antibody that comprises the H chain of (88) and the L chain of (89);
(91) an antibody that comprises an H chain having CDR1, CDR2, and CDR3, which are identified in VH comprising the amino acid sequence of SEQ ID NO: 650;
(92) an antibody that comprises an L chain having CDR1, CDR2, and CDR3, which are identified in VL comprising the amino acid sequence of SEQ ID NO: 652;
(93) an antibody that comprises the H chain of (91) and the L chain of (92);
(94) an antibody that comprises an H chain having CDR1, CDR2, and CDR3, which are identified in VH comprising the amino acid sequence of SEQ ID NO: 654;
(95) an antibody that comprises an L chain having CDR1, CDR2, and CDR3, which are identified in VL comprising the amino acid sequence of SEQ ID NO: 656;
(96) an antibody that comprises the H chain of (94) and the L chain of (95);
(97) an antibody that comprises an H chain having CDR1, CDR2, and CDR3, which are identified in VH comprising the amino acid sequence of SEQ ID NO: 658;
(98) an antibody that comprises an L chain having CDR1, CDR2, and CDR3, which are identified in VL comprising the amino acid sequence of SEQ ID NO: 660; and
(99) an antibody that comprises the H chain of (97) and the L chain of (98);

As mentioned above, "CDR1, CDR2, and CDR3" refers to CDR determined by a method well-known in the art (e.g., see Kabat, Elvin A., Sequences of proteins of immunological interest 5th ed., National Institutes of Health, 1991; Chothia et al, J Mol Biol 196:901-917, 1987). It is a technical common knowledge in the art that the amino acid sequences of CDR1, CDR2, and CDR3 can be identified in amino acid sequences of regions including CDR1, CDR2, and CDR3, using a method well-known in the art. In the following embodiments, for each antibody, an example of the CDR amino acid sequence determined according to the definition by Kabat is shown.

In a preferred embodiment, the antibody of the present invention is any one of (1) to (200) below.

AL-201 Antibody:
(1) an antibody that comprises an H chain having the amino acid sequence of SEQ ID NO: 6 as CDR1, the amino acid sequence of SEQ ID NO: 8 as CDR2, and the amino acid sequence of SEQ ID NO: 10 as CDR3;

(2) an antibody that comprises an L chain having the amino acid sequence of SEQ ID NO: 12 as CDR1, the amino acid sequence of SEQ ID NO: 14 as CDR2, and the amino acid sequence of SEQ ID NO: 16 as CDR3;
(3) an antibody that comprises the H chain of (1) and the L chain of (2);
(4) an antibody that comprises an H chain having the amino acid sequence of SEQ ID NO: 530 as VH;
(5) an antibody that comprises an L chain having the amino acid sequence of SEQ ID NO: 532 as VL;
(6) an antibody that comprises the H chain of (4) and the L chain of (5);
   AL-202 Antibody:
(7) an antibody that comprises an H chain having the amino acid sequence of SEQ ID NO: 22 as CDR1, the amino acid sequence of SEQ ID NO: 24 as CDR2, and the amino acid sequence of SEQ ID NO: 26 as CDR3;
(8) an antibody that comprises an L chain having the amino acid sequence of SEQ ID NO: 28 as CDR1, the amino acid sequence of SEQ ID NO: 30 as CDR2, and the amino acid sequence of SEQ ID NO: 32 as CDR3;
(9) an antibody that comprises the H chain of (7) and the L chain of (8);
(10) an antibody that comprises an H chain having the amino acid sequence of SEQ ID NO: 534 as VH;
(11) an antibody that comprises an L chain having the amino acid sequence of SEQ ID NO: 536 as VL;
(12) an antibody that comprises the H chain of (10) and the L chain of (11);
AL-203 Antibody:
(13) an antibody that comprises an H chain having the amino acid sequence of SEQ ID NO: 38 as CDR1, the amino acid sequence of SEQ ID NO: 40 as CDR2, and the amino acid sequence of SEQ ID NO: 42 as CDR3;
(14) an antibody that comprises an L chain having the amino acid sequence of SEQ ID NO: 44 as CDR1, the amino acid sequence of SEQ ID NO: 46 as CDR2, and the amino acid sequence of SEQ ID NO: 48 as CDR3;
(15) an antibody that comprises the H chain of (13) and the L chain of (14);
(16) an antibody that comprises an H chain having the amino acid sequence of SEQ ID NO: 538 as VH;
(17) an antibody that comprises an L chain having the amino acid sequence of SEQ ID NO: 540 as VL;
(18) an antibody that comprises the H chain of (16) and the L chain of (17);
AL-204 Antibody:
(19) an antibody that comprises an H chain having the amino acid sequence of SEQ ID NO: 54 as CDR1, the amino acid sequence of SEQ ID NO: 56 as CDR2, and the amino acid sequence of SEQ ID NO: 58 as CDR3;
(20) an antibody that comprises an L chain having the amino acid sequence of SEQ ID NO: 60 as CDR1, the amino acid sequence of SEQ ID NO: 62 as CDR2, and the amino acid sequence of SEQ ID NO: 64 as CDR3;
(21) an antibody that comprises the H chain of (19) and the L chain of (20);
(22) an antibody that comprises an H chain having the amino acid sequence of SEQ ID NO: 542 as VH;
(23) an antibody that comprises an L chain having the amino acid sequence of SEQ ID NO: 544 as VL;
(24) an antibody that comprises the H chain of (22) and the L chain of (23);
AL-205 Antibody:
(25) an antibody that comprises an H chain having the amino acid sequence of SEQ ID NO: 70 as CDR1, the amino acid sequence of SEQ ID NO: 72 as CDR2, and the amino acid sequence of SEQ ID NO: 74 as CDR3;
(26) an antibody that comprises an L chain having the amino acid sequence of SEQ ID NO: 76 as CDR1, the amino acid sequence of SEQ ID NO: 78 as CDR2, and the amino acid sequence of SEQ H.) NO: 80 as CDR3;
(27) an antibody that comprises the H chain of (25) and the L chain of (26);
(28) an antibody that comprises an H chain having the amino acid sequence of SEQ ID NO: 546 as VH;
(29) an antibody that comprises an L chain having the amino acid sequence of SEQ ID NO: 548 as VL;
(30) an antibody that comprises the H chain of (28) and the L chain of (29);
AL-206 Antibody:
(31) an antibody that comprises an H chain having the amino acid sequence of SEQ ID NO: 86 as CDR1, the amino acid sequence of SEQ ID NO: 88 as CDR2, and the amino acid sequence of SEQ ID NO: 90 as CDR3;
(32) an antibody that comprises an L chain having the amino acid sequence of SEQ ID NO: 92 as CDR1, the amino acid sequence of SEQ ID NO: 94 as CDR2, and the amino acid sequence of SEQ ID NO: 96 as CDR3;
(33) an antibody that comprises the H chain of (31) and the L chain of (32);
(34) an antibody that comprises an H chain having the amino acid sequence of SEQ ID NO: 550 as VH;
(35) an antibody that comprises an L chain having the amino acid sequence of SEQ ID NO: 552 as VL;
(36) an antibody that comprises the H chain of (34) and the L chain of (35);
AL-207 Antibody:
(37) an antibody that comprises an H chain having the amino acid sequence of SEQ ID NO: 102 as CDR1, the amino acid sequence of SEQ ID NO: 104 as CDR2, and the amino acid sequence of SEQ ID NO: 106 as CDR3;
(38) an antibody that comprises an L chain having the amino acid sequence of SEQ ID NO: 108 as CDR1, the amino acid sequence of SEQ ID NO: 110 as CDR2, and the amino acid sequence of SEQ ID NO: 112 as CDR3;
(39) an antibody that comprises the H chain of (37) and the L chain of (38);
(40) an antibody that comprises an H chain having the amino acid sequence of SEQ ID NO: 554 as VH;
(41) an antibody that comprises an L chain having the amino acid sequence of SEQ ID NO: 556 as VL;
(42) an antibody that comprises the H chain of (40) and the L chain of (41);
AL-208 Antibody:
(43) an antibody that comprises an H chain having the amino acid sequence of SEQ ID NO: 118 as CDR1, the amino acid sequence of SEQ ID NO: 120 as CDR2, and the amino acid sequence of SEQ ID NO: 122 as CDR3;
(44) an antibody that comprises an L chain having the amino acid sequence of SEQ ID NO: 124 as CDR1, the amino acid sequence of SEQ ID NO: 126 as CDR2, and the amino acid sequence of SEQ ID NO: 128 as CDR3;
(45) an antibody that comprises the H chain of (43) and the L chain of (44);
(46) an antibody that comprises an H chain having the amino acid sequence of SEQ ID NO: 558 as VH;
(47) an antibody that comprises an L chain having the amino acid sequence of SEQ ID NO: 560 as VL;
(48) an antibody that comprises the H chain of (46) and the L chain of (47);

AL-209 Antibody:
(49) an antibody that comprises an H chain having the amino acid sequence of SEQ ID NO: 134 as CDR1, the amino acid sequence of SEQ ID NO: 136 as CDR2, and the amino acid sequence of SEQ ID NO: 138 as CDR3;
(50) an antibody that comprises an L chain having the amino acid sequence of SEQ ID NO: 140 as CDR1, the amino acid sequence of SEQ ID NO: 142 as CDR2, and the amino acid sequence of SEQ ID NO: 144 as CDR3;
(51) an antibody that comprises the H chain of (49) and the L chain of (50);
(52) an antibody that comprises an H chain having the amino acid sequence of SEQ ID NO: 562 as VH;
(53) an antibody that comprises an L chain having the amino acid sequence of SEQ ID NO: 564 as VL;
(54) an antibody that comprises the H chain of (52) and the L chain of (53);
AL-210 Antibody:
(55) an antibody that comprises an H chain having the amino acid sequence of SEQ ID NO: 150 as CDR1, the amino acid sequence of SEQ ID NO: 152 as CDR2, and the amino acid sequence of SEQ ID NO: 154 as CDR3;
(56) an antibody that comprises an L chain having the amino acid sequence of SEQ ID NO: 156 as CDR1, the amino acid sequence of SEQ ID NO: 158 as CDR2, and the amino acid sequence of SEQ ID NO: 160 as CDR3;
(57) an antibody that comprises the H chain of (55) and the L chain of (56);
(58) an antibody that comprises an H chain having the amino acid sequence of SEQ ID NO: 566 as VH;
(59) an antibody that comprises an L chain having the amino acid sequence of SEQ ID NO: 568 as VL;
(60) an antibody that comprises the H chain of (58) and the L chain of (59);
AL-211 Antibody:
(61) an antibody that comprises an H chain having the amino acid sequence of SEQ ID NO: 166 as CDR1, the amino acid sequence of SEQ ID NO: 168 as CDR2, and the amino acid sequence of SEQ ID NO: 170 as CDR3;
(62) an antibody that comprises an L chain having the amino acid sequence of SEQ ID NO: 172 as CDR1, the amino acid sequence of SEQ ID NO: 174 as CDR2, and the amino acid sequence of SEQ ID NO: 176 as CDR3;
(63) an antibody that comprises the H chain of (61) and the L chain of (62);
(64) an antibody that comprises an H chain having the amino acid sequence of SEQ ID NO: 570 as VH;
(65) an antibody that comprises an L chain having the amino acid sequence of SEQ ID NO: 572 as VL;
(66) an antibody that comprises the H chain of (64) and the L chain of (65);
AL-212 Antibody:
(67) an antibody that comprises an H chain having the amino acid sequence of SEQ ID NO: 182 as CDR1, the amino acid sequence of SEQ ID NO: 184 as CDR2, and the amino acid sequence of SEQ ID NO: 186 as CDR3;
(68) an antibody that comprises an L chain having the amino acid sequence of SEQ ID NO: 188 as CDR1, the amino acid sequence of SEQ ID NO: 190 as CDR2, and the amino acid sequence of SEQ ID NO: 192 as CDR3;
(69) an antibody that comprises the H chain of (67) and the L chain of (68);
(70) an antibody that comprises an H chain having the amino acid sequence of SEQ ID NO: 574 as VH;
(71) an antibody that comprises an L chain having the amino acid sequence of SEQ ID NO: 576 as VL;
(72) an antibody that comprises the H chain of (70) and the L chain of (71);
AL-213 Antibody:
(73) an antibody that comprises an H chain having the amino acid sequence of SEQ ID NO: 198 as CDR1, the amino acid sequence of SEQ ID NO: 200 as CDR2, and the amino acid sequence of SEQ ID NO: 202 as CDR3;
(74) an antibody that comprises an L chain having the amino acid sequence of SEQ ID NO: 204 as CDR1, the amino acid sequence of SEQ ID NO: 206 as CDR2, and the amino acid sequence of SEQ ID NO: 208 as CDR3;
(75) an antibody that comprises the H chain of (73) and the L chain of (74);
(76) an antibody that comprises an H chain having the amino acid sequence of SEQ ID NO: 578 as VH;
(77) an antibody that comprises an L chain having the amino acid sequence of SEQ ID NO: 580 as VL;
(78) an antibody that comprises the H chain of (75) and the L chain of (76);
AL-214 Antibody:
(79) an antibody that comprises an H chain having the amino acid sequence of SEQ ID NO: 214 as CDR1, the amino acid sequence of SEQ ID NO: 216 as CDR2, and the amino acid sequence of SEQ ID NO: 218 as CDR3;
(80) an antibody that comprises an L chain having the amino acid sequence of SEQ ID NO: 220 as CDR1, the amino acid sequence of SEQ ID NO: 222 as CDR2, and the amino acid sequence of SEQ ID NO: 224 as CDR3;
(81) an antibody that comprises the H chain of (79) and the L chain of (80);
(82) an antibody that comprises an H chain having the amino acid sequence of SEQ ID NO: 582 as VH;
(83) an antibody that comprises an L chain having the amino acid sequence of SEQ ID NO: 584 as VL;
(84) an antibody that comprises the H chain of (82) and the L chain of (83);
AL-215 Antibody:
(85) an antibody that comprises an H chain having the amino acid sequence of SEQ ID NO: 230 as CDR1, the amino acid sequence of SEQ ID NO: 232 as CDR2, and the amino acid sequence of SEQ ID NO: 234 as CDR3;
(86) an antibody that comprises an L chain having the amino acid sequence of SEQ ID NO: 236 as CDR1, the amino acid sequence of SEQ ID NO: 238 as CDR2, and the amino acid sequence of SEQ ID NO: 240 as CDR3;
(87) an antibody that comprises the H chain of (85) and the L chain of (86);
(88) an antibody that comprises an H chain having the amino acid sequence of SEQ ID NO: 586 as VH;
(89) an antibody that comprises an L chain having the amino acid sequence of SEQ ID NO: 588 as VL;
(90) an antibody that comprises the H chain of (88) and the L chain of (89);
AL-216 Antibody:
(91) an antibody that comprises an H chain having the amino acid sequence of SEQ ID NO: 246 as CDR1, the amino acid sequence of SEQ ID NO: 248 as CDR2, and the amino acid sequence of SEQ ID NO: 250 as CDR3;
(92) an antibody that comprises an L chain having the amino acid sequence of SEQ ID NO: 252 as CDR1, the amino acid sequence of SEQ ID NO: 254 as CDR2, and the amino acid sequence of SEQ ID NO: 256 as CDR3;
(93) an antibody that comprises the H chain of (91) and the L chain of (92);
(94) an antibody that comprises an H chain having the amino acid sequence of SEQ ID NO: 590 as VH;

(95) an antibody that comprises an L chain having the amino acid sequence of SEQ ID NO: 592 as VL;
(96) an antibody that comprises the H chain of (94) and the L chain of (95);
AL-217 Antibody:
(97) an antibody that comprises an H chain having the amino acid sequence of SEQ ID NO: 262 as CDR1, the amino acid sequence of SEQ ID NO: 264 as CDR2, and the amino acid sequence of SEQ ID NO: 266 as CDR3;
(98) an antibody that comprises an L chain having the amino acid sequence of SEQ ID NO: 268 as CDR1, the amino acid sequence of SEQ ID NO: 270 as CDR2, and the amino acid sequence of SEQ ID NO: 272 as CDR3;
(99) an antibody that comprises the H chain of (97) and the L chain of (98);
(100) an antibody that comprises an H chain having the amino acid sequence of SEQ ID NO: 594 as VH;
(101) an antibody that comprises an L chain having the amino acid sequence of SEQ ID NO: 596 as VL;
(102) an antibody that comprises the H chain of (100) and the L chain of (101);
AL-218 Antibody:
(103) an antibody that comprises an H chain having the amino acid sequence of SEQ ID NO: 278 as CDR1, the amino acid sequence of SEQ ID NO: 280 as CDR2, and the amino acid sequence of SEQ ID NO: 282 as CDR3;
(104) an antibody that comprises an L chain having the amino acid sequence of SEQ ID NO: 284 as CDR1, the amino acid sequence of SEQ ID NO: 286 as CDR2, and the amino acid sequence of SEQ ID NO: 288 as CDR3;
(105) an antibody that comprises the H chain of (103) and the L chain of (104);
(106) an antibody that comprises an H chain having the amino acid sequence of SEQ ID NO: 598 as VH;
(107) an antibody that comprises an L chain having the amino acid sequence of SEQ ID NO: 600 as VL;
(108) an antibody that comprises the H chain of (106) and the L chain of (107);
AL-219 Antibody:
(109) an antibody that comprises an H chain having the amino acid sequence of SEQ ID NO: 294 as CDR1, the amino acid sequence of SEQ ID NO: 296 as CDR2, and the amino acid sequence of SEQ ID NO: 298 as CDR3;
(110) an antibody that comprises an L chain having the amino acid sequence of SEQ ID NO: 300 as CDR1, the amino acid sequence of SEQ ID NO: 302 as CDR2, and the amino acid sequence of SEQ ID NO: 304 as CDR3;
(111) an antibody that comprises the H chain of (109) and the L chain of (110);
(112) an antibody that comprises an H chain having the amino acid sequence of SEQ ID NO: 602 as VH;
(113) an antibody that comprises an L chain having the amino acid sequence of SEQ ID NO: 604 as VL;
(114) an antibody that comprises the H chain of (112) and the L chain of (113);
AL-220 Antibody:
(115) an antibody that comprises an H chain having the amino acid sequence of SEQ ID NO: 310 as CDR1, the amino acid sequence of SEQ ID NO: 312 as CDR2, and the amino acid sequence of SEQ ID NO: 314 as CDR3;
(116) an antibody that comprises an L chain having the amino acid sequence of SEQ ID NO: 316 as CDR1, the amino acid sequence of SEQ ID NO: 318 as CDR2, and the amino acid sequence of SEQ ID NO: 320 as CDR3;
(117) an antibody that comprises the H chain of (115) and the L chain of (116);
(118) an antibody that comprises an H chain having the amino acid sequence of SEQ ID NO: 606 as VH;
(119) an antibody that comprises an L chain having the amino acid sequence of SEQ ID NO: 608 as VL;
(120) an antibody that comprises the H chain of (118) and the L chain of (119);
AL-221 Antibody:
(121) an antibody that comprises an H chain having the amino acid sequence of SEQ ID NO: 326 as CDR1, the amino acid sequence of SEQ ID NO: 328 as CDR2, and the amino acid sequence of SEQ ID NO: 330 as CDR3;
(122) an antibody that comprises an L chain having the amino acid sequence of SEQ ID NO: 332 as CDR1, the amino acid sequence of SEQ ID NO: 334 as CDR2, and the amino acid sequence of SEQ ID NO: 336 as CDR3;
(123) an antibody that comprises the H chain of (121) and the L chain of (122);
(124) an antibody that comprises an H chain having the amino acid sequence of SEQ ID NO: 610 as VH;
(125) an antibody that comprises an L chain having the amino acid sequence of SEQ ID NO: 612 as VL;
(126) an antibody that comprises the H chain of (124) and the L chain of (125);
AL-222 Antibody:
(127) an antibody that comprises an H chain having the amino acid sequence of SEQ ID NO: 342 as CDR1, the amino acid sequence of SEQ ID NO: 344 as CDR2, and the amino acid sequence of SEQ ID NO: 346 as CDR3;
(128) an antibody that comprises an L chain having the amino acid sequence of SEQ ID NO: 348 as CDR1, the amino acid sequence of SEQ ID NO: 350 as CDR2, and the amino acid sequence of SEQ ID NO: 352 as CDR3;
(129) an antibody that comprises the H chain of (127) and the L chain of (128);
(130) an antibody that comprises an H chain having the amino acid sequence of SEQ ID NO: 614 as VH;
(131) an antibody that comprises an L chain having the amino acid sequence of SEQ ID NO: 616 as VL;
(132) an antibody that comprises the H chain of (130) and the L chain of (131);
AL-223 Antibody:
(133) an antibody that comprises an H chain having the amino acid sequence of SEQ ID NO: 358 as CDR1, the amino acid sequence of SEQ ID NO: 360 as CDR2, and the amino acid sequence of SEQ ID NO: 362 as CDR3;
(134) an antibody that comprises an L chain having the amino acid sequence of SEQ ID NO: 364 as CDR1, the amino acid sequence of SEQ ID NO: 366 as CDR2, and the amino acid sequence of SEQ ID NO: 368 as CDR3;
(135) an antibody that comprises the H chain of (133) and the L chain of (134);
(136) an antibody that comprises an H chain having the amino acid sequence of SEQ ID NO: 618 as VH;
(137) an antibody that comprises an L chain having the amino acid sequence of SEQ ID NO: 620 as VL;
(138) an antibody that comprises the H chain of (136) and the L chain of (137);
AL-224 Antibody:
(139) an antibody that comprises an H chain having the amino acid sequence of SEQ ID NO: 374 as CURL the amino acid sequence of SEQ ID NO: 376 as CDR2, and the amino acid sequence of SEQ ID NO: 378 as CDR3;
(140) an antibody that comprises an L chain having the amino acid sequence of SEQ ID NO: 380 as CDR1, the amino acid sequence of SEQ ID NO: 382 as CDR2, and the amino acid sequence of SEQ ID NO: 384 as CDR3;

(141) an antibody that comprises the H chain of (139) and the L chain of (140);
(142) an antibody that comprises an H chain having the amino acid sequence of SEQ ID NO: 622 as VH;
(143) an antibody that comprises an L chain having the amino acid sequence of SEQ ID NO: 624 as VL;
(144) an antibody that comprises the H chain of (142) and the L chain of (143);
AL-225 Antibody:
(145) an antibody that comprises an H chain having the amino acid sequence of SEQ ID NO: 390 as CDR1, the amino acid sequence of SEQ ID NO: 392 as CDR2, and the amino acid sequence of SEQ ID NO: 394 as CDR3;
(146) an antibody that comprises an L chain having the amino acid sequence of SEQ ID NO: 396 as CDR1, the amino acid sequence of SEQ ID NO: 398 as CDR2, and the amino acid sequence of SEQ ID NO: 400 as CDR3;
(147) an antibody that comprises the H chain of (145) and the L chain of (146);
(148) an antibody that comprises an H chain having the amino acid sequence of SEQ ID NO: 626 as VH;
(149) an antibody that comprises an L chain having the amino acid sequence of SEQ ID NO: 628 as VL;
(150) an antibody that comprises the H chain of (148) and the L chain of (149);
AL-226 Antibody:
(151) an antibody that comprises an H chain having the amino acid sequence of SEQ ID NO: 406 as CDR1, the amino acid sequence of SEQ ID NO: 408 as CDR2, and the amino acid sequence of SEQ ID NO: 410 as CDR3;
(152) an antibody that comprises an L chain having the amino acid sequence of SEQ ID NO: 412 as CDR1, the amino acid sequence of SEQ ID NO: 414 as CDR2, and the amino acid sequence of SEQ ID NO: 416 as CDR3;
(153) an antibody that comprises the H chain of (151) and the L chain of (152);
(154) an antibody that comprises an H chain having the amino acid sequence of SEQ ID NO: 630 as VH;
(155) an antibody that comprises an L chain having the amino acid sequence of SEQ ID NO: 632 as VL;
(156) an antibody that comprises the H chain of (154) and the L chain of (155);
AL-227 Antibody:
(157) an antibody that comprises an H chain having the amino acid sequence of SEQ ID NO: 422 as CDR1, the amino acid sequence of SEQ ID NO: 424 as CDR2, and the amino acid sequence of SEQ ID NO: 426 as CDR3;
(158) an antibody that comprises an L chain having the amino acid sequence of SEQ ID NO: 428 as CDR1, the amino acid sequence of SEQ ID NO: 430 as CDR2, and the amino acid sequence of SEQ ID NO: 432 as CDR3;
(159) an antibody that comprises the H chain of (157) and the L chain of (158);
(160) an antibody that comprises an H chain having the amino acid sequence of SEQ ID NO: 634 as VH;
(161) an antibody that comprises an L chain having the amino acid sequence of SEQ ID NO: 636 as VL;
(162) an antibody that comprises the H chain of (160) and the L chain of (161);
AL-228 Antibody:
(163) an antibody that comprises an H chain having the amino acid sequence of SEQ ID NO: 438 as CDR1, the amino acid sequence of SEQ ID NO: 440 as CDR2, and the amino acid sequence of SEQ ID NO: 442 as CDR3;
(164) an antibody that comprises an L chain having the amino acid sequence of SEQ ID NO: 444 as CDR1, the amino acid sequence of SEQ ID NO: 446 as CDR2, and the amino acid sequence of SEQ ID NO: 448 as CDR3;
(165) an antibody that comprises the H chain of (163) and the L chain of (164);
(166) an antibody that comprises an H chain having the amino acid sequence of SEQ ID NO: 638 as VH;
(167) an antibody that comprises an L chain having the amino acid sequence of SEQ ID NO: 640 as VL;
(168) an antibody that comprises the H chain of (166) and the L chain of (167);
AL-229 Antibody:
(169) an antibody that comprises an H chain having the amino acid sequence of SEQ ID NO: 454 as CDR1, the amino acid sequence of SEQ ID NO: 456 as CDR2, and the amino acid sequence of SEQ ID NO: 458 as CDR3;
(170) an antibody that comprises an L chain having the amino acid sequence of SEQ ID NO: 460 as CDR1, the amino acid sequence of SEQ ID NO: 462 as CDR2, and the amino acid sequence of SEQ ID NO: 464 as CDR3;
(171) an antibody that comprises the H chain of (169) and the L chain of (170);
(172) an antibody that comprises an H chain having the amino acid sequence of SEQ ID NO: 642 as VH;
(173) an antibody that comprises an L chain having the amino acid sequence of SEQ ID NO: 644 as VL;
(174) an antibody that comprises the H chain of (172) and the L chain of (173);
AL-230 Antibody:
(175) an antibody that comprises an H chain having the amino acid sequence of SEQ ID NO: 470 as CDR1, the amino acid sequence of SEQ ID NO: 472 as CDR2, and the amino acid sequence of SEQ ID NO: 474 as CDR3;
(176) an antibody that comprises an L chain having the amino acid sequence of SEQ ID NO: 476 as CDR1, the amino acid sequence of SEQ ID NO: 478 as CDR2, and the amino acid sequence of SEQ ID NO: 480 as CDR3;
(177) an antibody that comprises the H chain of (175) and the L chain of (176);
(178) an antibody that comprises an H chain having the amino acid sequence of SEQ ID NO: 646 as VH;
(179) an antibody that comprises an L chain having the amino acid sequence of SEQ ID NO: 648 as VL;
(180) an antibody that comprises the H chain of (178) and the L chain of (179);
AL-231 Antibody:
(181) an antibody that comprises an H chain having the amino acid sequence of SEQ ID NO: 486 as CDR1, the amino acid sequence of SEQ ID NO: 488 as CDR2, and the amino acid sequence of SEQ ID NO: 490 as CDR3;
(182) an antibody that comprises an L chain having the amino acid sequence of SEQ ID NO: 492 as CDR1, the amino acid sequence of SEQ ID NO: 494 as CDR2, and the amino acid sequence of SEQ ID NO: 496 as CDR3;
(183) an antibody that comprises the H chain of (181) and the L chain of (182);
(184) an antibody that comprises an H chain having the amino acid sequence of SEQ ID NO: 650 as VH;
(185) an antibody that comprises an L chain having the amino acid sequence of SEQ ID NO: 652 as VL;
(186) an antibody that comprises the H chain of (184) and the L chain of (185);
AL-232 Antibody:
(187) an antibody that comprises an H chain having the amino acid sequence of SEQ ID NO: 502 as CDR1, the amino acid sequence of SEQ ID NO: 504 as CDR2, and the amino acid sequence of SEQ ID NO: 506 as CDR3;

(188) an antibody that comprises an L chain having the amino acid sequence of SEQ ID NO: 508 as CDR1, the amino acid sequence of SEQ ID NO: 510 as CDR2, and the amino acid sequence of SEQ ID NO: 512 as CDR3;
(189) an antibody that comprises the H chain of (187) and the L chain of (188);
(190) an antibody that comprises an H chain having the amino acid sequence of SEQ ID NO: 654 as VH;
(191) an antibody that comprises an L chain having the amino acid sequence of SEQ ID NO: 656 as VL;
(192) an antibody that comprises the H chain of (190) and the L chain of (191);
AL-233 Antibody:
(193) an antibody that comprises an H chain having the amino acid sequence of SEQ ID NO: 518 as CDR1, the amino acid sequence of SEQ ID NO: 520 as CDR2, and the amino acid sequence of SEQ ID NO: 522 as CDR3;
(194) an antibody that comprises an L chain having the amino acid sequence of SEQ ID NO: 524 as CDR1, the amino acid sequence of SEQ ID NO: 526 as CDR2, and the amino acid sequence of SEQ ID NO: 528 as CDR3;
(195) an antibody that comprises the H chain of (193) and the L chain of (194);
(196) an antibody that comprises an H chain having the amino acid sequence of SEQ ID NO: 658 as VH;
(197) an antibody that comprises an L chain having the amino acid sequence of SEQ ID NO: 660 as VL;
(198) an antibody that comprises the H chain of (196) and the L chain of (197);
(199) an antibody that comprises one or more amino acid substitutions, deletions, additions, and/or insertions in the antibody of any one of (1) to (198), which has equivalent activity to the antibody of any one of (1) to (198); and
(200) an antibody that binds to the epitope bound by the antibody of any one of (1) to (198).

AL-201 Antibody:
An example of the VH in the above-mentioned "H chain having the amino acid sequence of SEQ ID NO: 6 (sequence of the AL-201 antibody H-chain CDR1) as CDR1, the amino acid sequence of SEQ ID NO: 8 (sequence of the AL-201 antibody H-chain CDR2) as CDR2, and the amino acid sequence of SEQ ID NO: 10 (sequence of the AL-201 antibody H-chain CDR3) as CDR3" of (1) is a VH comprising the amino acid sequence of SEQ ID NO: 530 (sequence of the AL-201 antibody VH).
An example of the VL in the above-mentioned "L chain having the amino acid sequence of SEQ ID NO: 12 (sequence of the AL-201 antibody L-chain CDR1) as CDR1, the amino acid sequence of SEQ ID NO: 14 (sequence of the AL-201 antibody L-chain CDR2) as CDR2, and the amino acid sequence of SEQ ID NO: 16 (sequence of the AL-201 antibody L-chain CDR3) as CDR3" of (2) is a VL comprising the amino acid sequence of SEQ ID NO: 4, more preferably a VL comprising the amino acid sequence of SEQ ID NO: 532 (sequence of the AL-201 antibody VL).

AL-202 Antibody:
An example of the VH in the above-mentioned "H chain having the amino acid sequence of SEQ ID NO: 22 (sequence of the AL-202 antibody H-chain CDR1) as CDR1, the amino acid sequence of SEQ ID NO: 24 (sequence of the AL-202 antibody H-chain CDR2) as CDR2, and the amino acid sequence of SEQ ID NO: 26 (sequence of the AL-202 antibody H-chain CDR3) as CDR3" of (7) is a VH comprising the amino acid sequence of SEQ ID NO: 534 (sequence of the AL-202 antibody VH).
An example of the VL in the above-mentioned "L chain having the amino acid sequence of SEQ ID NO: 28 (sequence of the AL-202 antibody L-chain CDR1) as CDR1, the amino acid sequence of SEQ ID NO: 30 (sequence of the AL-202 antibody L-chain CDR2) as CDR2, and the amino acid sequence of SEQ ID NO: 32 (sequence of the AL-202 antibody L-chain CDR3) as CDR3" of (8) is a VL comprising the amino acid sequence of SEQ ID NO: 536 (sequence of the AL-202 antibody VL).

AL-203 Antibody:
An example of the VH in the above-mentioned "H chain having the amino acid sequence of SEQ ID NO: 38 (sequence of the AL-203 antibody H-chain CDR1) as CDR1, the amino acid sequence of SEQ ID NO: 40 (sequence of the AL-203 antibody H-chain CDR2) as CDR2, and the amino acid sequence of SEQ ID NO: 42 (sequence of the AL-203 antibody H-chain CDR3) as CDR3" of (13) is a VH comprising the amino acid sequence of SEQ ID NO: 538 (sequence of the AL-203 antibody VH).
An example of the VL in the above-mentioned "L chain having the amino acid sequence of SEQ ID NO: 44 (sequence of the AL-203 antibody L-chain CDR1) as CDR1, the amino acid sequence of SEQ ID NO: 46 (sequence of the AL-203 antibody L-chain CDR2) as CDR2, and the amino acid sequence of SEQ ID NO: 48 (sequence of the AL-203 antibody L-chain CDR3) as CDR3" of (14) is a VL comprising the amino acid sequence of SEQ ID NO: 36, more preferably a VL comprising the amino acid sequence of SEQ ID NO: 540 (sequence of the AL-203 antibody VL).

AL-204 Antibody:
An example of the VH in the above-mentioned "H chain having the amino acid sequence of SEQ ID NO: 54 (sequence of the AL-204 antibody H-chain CDR1) as CDR1, the amino acid sequence of SEQ ID NO: 56 (sequence of the AL-204 antibody H-chain CDR2) as CDR2, and the amino acid sequence of SEQ ID NO: 58 (sequence of the AL-204 antibody H-chain CDR3) as CDR3" of (19) is a VH comprising the amino acid sequence of SEQ ID NO: 542 (sequence of the AL-204 antibody VH).
An example of the VL in the above-mentioned "L chain having the amino acid sequence of SEQ ID NO: 60 (sequence of the AL-204 antibody L-chain CDR1) as CDR1, the amino acid sequence of SEQ ID NO: 62 (sequence of the AL-204 antibody L-chain CDR2) as CDR2, and the amino acid sequence of SEQ ID NO: 64 (sequence of the AL-204 antibody L-chain CDR3) as CDR3" of (20) is a VL comprising the amino acid sequence of SEQ ID NO: 52, more preferably a VL comprising the amino acid sequence of SEQ ID NO: 544 (sequence of the AL-204 antibody VL).

AL-205 Antibody:
An example of the VH in the above-mentioned "H chain having the amino acid sequence of SEQ ID NO: 70 (sequence of the AL-205 antibody H-chain CDR1) as CDR1, the amino acid sequence of SEQ ID NO: 72 (sequence of the AL-205 antibody H-chain CDR2) as CDR2, and the amino acid sequence of SEQ ID NO: 74 (sequence of the AL-205 antibody H-chain CDR3) as CDR3" of (25) is a VH comprising the amino acid sequence of SEQ ID NO: 66, more preferably, a VH comprising the amino acid sequence of SEQ ID NO: 546 (sequence of the AL-205 antibody VH).
An example of the VL in the above-mentioned "L chain having the amino acid sequence of SEQ ID NO: 76 (sequence of the AL-205 antibody L-chain CDR1) as CDR1, the amino acid sequence of SEQ ID NO: 78 (sequence of the AL-205 antibody L-chain CDR2) as CDR2, and the amino acid sequence of SEQ ID NO: 80 (sequence of the AL-205 antibody L-chain CDR3) as CDR3" of (26) is a VL comprising the amino acid sequence of SEQ ID NO: 548 (sequence of the AL-205 antibody VL).

AL-206 Antibody:

An example of the VH in the above-mentioned "H chain having the amino acid sequence of SEQ ID NO: 86 (sequence of the AL-206 antibody H-chain CDR1) as CDR1, the amino acid sequence of SEQ ID NO: 88 (sequence of the AL-206 antibody H-chain CDR2) as CDR2, and the amino acid sequence of SEQ ID NO: 90 (sequence of the AL-206 antibody H-chain CDR3) as CDR3" of (31) is a VH comprising the amino acid sequence of SEQ ID NO: 550 (sequence of the AL-206 antibody VH).

An example of the VL in the above-mentioned "L chain having the amino acid sequence of SEQ ID NO: 92 (sequence of the AL-206 antibody L-chain CDR1) as CDR1, the amino acid sequence of SEQ ID NO: 94 (sequence of the AL-206 antibody L-chain CDR2) as CDR2, and the amino acid sequence of SEQ ID NO: 96 (sequence of the AL-206 antibody L-chain CDR3) as CDR3" of (32) is a VL comprising the amino acid sequence of SEQ ID NO: 84, more preferably a VL comprising the amino acid sequence of SEQ ID NO: 552 (sequence of the AL-206 antibody VL).

AL-207 Antibody:

An example of the VH in the above-mentioned "H chain having the amino acid sequence of SEQ ID NO: 102 (sequence of the AL-207 antibody H-chain CDR1) as CDR1, the amino acid sequence of SEQ ID NO: 104 (sequence of the AL-207 antibody H-chain CDR2) as CDR2, and the amino acid sequence of SEQ ID NO: 106 (sequence of the AL-207 antibody H-chain CDR3) as CDR3" of (37) is a VH comprising the amino acid sequence of SEQ ID NO: 554 (sequence of the AL-207 antibody VH).

An example of the VL in the above-mentioned "L chain having the amino acid sequence of SEQ ID NO: 108 (sequence of the AL-207 antibody L-chain CDR1) as CDR1, the amino acid sequence of SEQ ID NO: 110 (sequence of the AL-207 antibody L-chain CDR2) as CDR2, and the amino acid sequence of SEQ ID NO: 112 (sequence of the AL-207 antibody L-chain CDR3) as CDR3" of (38) is a VL comprising the amino acid sequence of SEQ ID NO: 100, more preferably a VL comprising the amino acid sequence of SEQ ID NO: 556 (sequence of the AL-207 antibody VL).

AL-208 Antibody:

An example of the VH in the above-mentioned "H chain having the amino acid sequence of SEQ ID NO: 118 (sequence of the AL-208 antibody H-chain CDR1) as CDR1, the amino acid sequence of SEQ ID NO: 120 (sequence of the AL-208 antibody H-chain CDR2) as CDR2, and the amino acid sequence of SEQ ID NO: 122 (sequence of the AL-208 antibody H-chain CDR3) as CDR3" of (43) is a VH comprising the amino acid sequence of SEQ ID NO: 558 (sequence of the AL-208 antibody VH).

An example of the VL in the above-mentioned "L chain having the amino acid sequence of SEQ ID NO: 124 (sequence of the AL-208 antibody L-chain CDR1) as CDR1, the amino acid sequence of SEQ ID NO: 126 (sequence of the AL-208 antibody L-chain CDR2) as CDR2, and the amino acid sequence of SEQ ID NO: 128 (sequence of the AL-208 antibody L-chain CDR3) as CDR3" of (44) is a VL comprising the amino acid sequence of SEQ ID NO: 116, more preferably a VL comprising the amino acid sequence of SEQ ID NO: 560 (sequence of the AL-208 antibody VL).

AL-209 Antibody:

An example of the VH in the above-mentioned "H chain having the amino acid sequence of SEQ ID NO: 134 (sequence of the AL-209 antibody H-chain CDR1) as CDR1, the amino acid sequence of SEQ ID NO: 136 (sequence of the AL-209 antibody H-chain CDR2) as CDR2, and the amino acid sequence of SEQ ID NO: 138 (sequence of the AL-209 antibody H-chain CDR3) as CDR3" of (49) is a VH comprising the amino acid sequence of SEQ ID NO: 562 (sequence of the AL-209 antibody VH).

An example of the VL in the above-mentioned "L chain having the amino acid sequence of SEQ ID NO: 140 (sequence of the AL-209 antibody L-chain CDR1) as CDR1, the amino acid sequence of SEQ ID NO: 142 (sequence of the AL-209 antibody L-chain CDR2) as CDR2, and the amino acid sequence of SEQ ID NO: 144 (sequence of the AL-209 antibody L-chain CDR3) as CDR3" of (50) is a VL comprising the amino acid sequence of SEQ ID NO: 132, more preferably a VL comprising the amino acid sequence of SEQ ID NO: 564 (sequence of the AL-209 antibody VL).

AL-210 Antibody:

An example of the VH in the above-mentioned "H chain having the amino acid sequence of SEQ ID NO: 150 (sequence of the AL-210 antibody H-chain CDR1) as CDR1, the amino acid sequence of SEQ ID NO: 152 (sequence of the AL-210 antibody H-chain CDR2) as CDR2, and the amino acid sequence of SEQ ID NO: 154 (sequence of the AL-210 antibody H-chain CDR3) as CDR3" of (55) is a VH comprising the amino acid sequence of SEQ ID NO: 566 (sequence of the AL-210 antibody VH).

An example of the VL in the above-mentioned "L chain having the amino acid sequence of SEQ ID NO: 156 (sequence of the AL-210 antibody L-chain CDR1) as CDR1, the amino acid sequence of SEQ ID NO: 158 (sequence of the AL-210 antibody L-chain CDR2) as CDR2, and the amino acid sequence of SEQ ID NO: 160 (sequence of the AL-210 antibody L-chain CDR3) as CDR3" of (56) is a VL comprising the amino acid sequence of SEQ ID NO: 148, more preferably a VL comprising the amino acid sequence of SEQ ID NO: 568 (sequence of the AL-210 antibody VL).

AL-211 Antibody:

An example of the VH in the above-mentioned "H chain having the amino acid sequence of SEQ ID NO: 166 (sequence of the AL-211 antibody H-chain CDR1) as CDR1, the amino acid sequence of SEQ ID NO: 168 (sequence of the AL-211 antibody H-chain CDR2) as CDR2, and the amino acid sequence of SEQ ID NO: 170 (sequence of the AL-211 antibody H-chain CDR3) as CDR3" of (61) is a VH comprising the amino acid sequence of SEQ ID NO: 570 (sequence of the AL-211 antibody VH).

An example of the VL in the above-mentioned "L chain having the amino acid sequence of SEQ ID NO: 172 (sequence of the AL-211 antibody L-chain CDR1) as CDR1, the amino acid sequence of SEQ ID NO: 174 (sequence of the AL-211 antibody L-chain CDR2) as CDR2, and the amino acid sequence of SEQ ID NO: 176 (sequence of the AL-211 antibody L-chain CDR3) as CDR3" of (62) is a VL comprising the amino acid sequence of SEQ ID NO: 164, more preferably a VL comprising the amino acid sequence of SEQ ID NO: 572 (sequence of the AL-211 antibody VL).

AL-212 Antibody:

An example of the VH in the above-mentioned "H chain having the amino acid sequence of SEQ ID NO: 182 (sequence of the AL-212 antibody H-chain CDR1) as CDR1, the amino acid sequence of SEQ ID NO: 184 (sequence of the AL-212 antibody H-chain CDR2) as CDR2, and the amino acid sequence of SEQ ID NO: 186 (sequence of the AL-212 antibody H-chain CDR3) as CDR3" of (67) is a VH comprising the amino acid sequence of SEQ ID NO: 574 (sequence of the AL-212 antibody VH).

An example of the VL in the above-mentioned "L chain having the amino acid sequence of SEQ ID NO: 188 (sequence of the AL-212 antibody L-chain CDR1) as CDR1, the amino acid sequence of SEQ ID NO: 190 (sequence of the AL-212 antibody L-chain CDR2) as CDR2, and the amino acid sequence of SEQ ID NO: 192 (sequence of the AL-212 antibody L-chain CDR3) as CDR3" of (68) is a VL comprising the amino acid sequence of SEQ ID NO: 180, more preferably a VL comprising the amino acid sequence of SEQ ID NO: 576 (sequence of the AL-212 antibody VL).

AL-213 Antibody:
An example of the VH in the above-mentioned "H chain having the amino acid sequence of SEQ ID NO: 198 (sequence of the AL-213 antibody H-chain CDR1) as CDR1, the amino acid sequence of SEQ ID NO: 200 (sequence of the AL-213 antibody H-chain CDR2) as CDR2, and the amino acid sequence of SEQ ID NO: 202 (sequence of the AL-213 antibody H-chain CDR3) as CDR3" of (73) is a VH comprising the amino acid sequence of SEQ ID NO: 578 (sequence of the AL-213 antibody VH).

An example of the VL in the above-mentioned "L chain having the amino acid sequence of SEQ ID NO: 204 (sequence of the AL-213 antibody L-chain CDR1) as CDR1, the amino acid sequence of SEQ ID NO: 206 (sequence of the AL-213 antibody L-chain CDR2) as CDR2, and the amino acid sequence of SEQ ID NO: 208 (sequence of the AL-213 antibody L-chain CDR3) as CDR3" of (74) is a VL comprising the amino acid sequence of SEQ ID NO: 196, more preferably a VL comprising the amino acid sequence of SEQ ID NO: 580 (sequence of the AL-213 antibody VL).

AL-214 Antibody:
An example of the VH in the above-mentioned "H chain having the amino acid sequence of SEQ ID NO: 214 (sequence of the AL-214 antibody H-chain CDR1) as CDR1, the amino acid sequence of SEQ ID NO: 216 (sequence of the AL-214 antibody H-chain CDR2) as CDR2, and the amino acid sequence of SEQ ID NO: 218 (sequence of the AL-214 antibody H-chain CDR3) as CDR3" of (79) is a VH comprising the amino acid sequence of SEQ ID NO: 582 (sequence of the AL-214 antibody VH).

An example of the VL in the above-mentioned "L chain having the amino acid sequence of SEQ ID NO: 220 (sequence of the AL-214 antibody L-chain CDR1) as CDR1, the amino acid sequence of SEQ ID NO: 222 (sequence of the AL-214 antibody L-chain CDR2) as CDR2, and the amino acid sequence of SEQ ID NO: 224 (sequence of the AL-214 antibody L-chain CDR3) as CDR3" of (80) is a VL comprising the amino acid sequence of SEQ ID NO: 212, more preferably a VL comprising the amino acid sequence of SEQ ID NO: 584 (sequence of the AL-214 antibody VL).

AL-215 Antibody:
An example of the VH in the above-mentioned "H chain having the amino acid sequence of SEQ ID NO: 230 (sequence of the AL-215 antibody H-chain CDR1) as CDR1, the amino acid sequence of SEQ ID NO: 232 (sequence of the AL-215 antibody H-chain CDR2) as CDR2, and the amino acid sequence of SEQ ID NO: 234 (sequence of the AL-215 antibody H-chain CDR3) as CDR3" of (85) is a VH comprising the amino acid sequence of SEQ ID NO: 586 (sequence of the AL-215 antibody VH).

An example of the VL in the above-mentioned "L chain having the amino acid sequence of SEQ ID NO: 236 (sequence of the AL-215 antibody L-chain CDR1) as CDR1, the amino acid sequence of SEQ ID NO: 238 (sequence of the AL-215 antibody L-chain CDR2) as CDR2, and the amino acid sequence of SEQ ID NO: 240 (sequence of the AL-215 antibody L-chain CDR3) as CDR3" of (86) is a VL comprising the amino acid sequence of SEQ ID NO: 228, more preferably a VL comprising the amino acid sequence of SEQ ID NO: 588 (sequence of the AL-215 antibody VL).

AL-216 Antibody:
An example of the VH in the above-mentioned "H chain having the amino acid sequence of SEQ ID NO: 246 (sequence of the AL-216 antibody H-chain CDR1) as CDR1, the amino acid sequence of SEQ ID NO: 248 (sequence of the AL-216 antibody H-chain CDR2) as CDR2, and the amino acid sequence of SEQ ID NO: 250 (sequence of the AL-216 antibody H-chain CDR3) as CDR3" of (91) is a VH comprising the amino acid sequence of SEQ ID NO: 590 (sequence of the AL-216 antibody VH).

An example of the VL in the above-mentioned "L chain having the amino acid sequence of SEQ ID NO: 252 (sequence of the AL-216 antibody L-chain CDR1) as CDR1, the amino acid sequence of SEQ ID NO: 254 (sequence of the AL-216 antibody L-chain CDR2) as CDR2, and the amino acid sequence of SEQ ID NO: 256 (sequence of the AL-216 antibody L-chain CDR3) as CDR3" of (92) is a VL comprising the amino acid sequence of SEQ ID NO: 244, more preferably a VL comprising the amino acid sequence of SEQ ID NO: 592 (sequence of the AL-216 antibody VL).

AL-217 Antibody:
An example of the VH in the above-mentioned "H chain having the amino acid sequence of SEQ ID NO: 262 (sequence of the AL-217 antibody H-chain CDR1) as CDR1, the amino acid sequence of SEQ ID NO: 264 (sequence of the AL-217 antibody H-chain CDR2) as CDR2, and the amino acid sequence of SEQ ID NO: 266 (sequence of the AL-217 antibody H-chain CDR3) as CDR3" of (97) is a VH comprising the amino acid sequence of SEQ ID NO: 594 (sequence of the AL-217 antibody VH).

An example of the VL in the above-mentioned "L chain having the amino acid sequence of SEQ ID NO: 268 (sequence of the AL-217 antibody L-chain CDR1) as CDR1, the amino acid sequence of SEQ ID NO: 270 (sequence of the AL-217 antibody L-chain CDR2) as CDR2, and the amino acid sequence of SEQ ID NO: 272 (sequence of the AL-217 antibody L-chain CDR3) as CDR3" of (98) is a VL comprising the amino acid sequence of SEQ ID NO: 260, more preferably a VL comprising the amino acid sequence of SEQ ID NO: 596 (sequence of the AL-217 antibody VL).

AL-218 Antibody:
An example of the VH in the above-mentioned "H chain having the amino acid sequence of SEQ ID NO: 278 (sequence of the AL-218 antibody H-chain CDR1) as CDR1, the amino acid sequence of SEQ ID NO: 280 (sequence of the AL-218 antibody H-chain CDR2) as CDR2, and the amino acid sequence of SEQ ID NO: 282 (sequence of the AL-218 antibody H-chain CDR3) as CDR3" of (103) is a VH comprising the amino acid sequence of SEQ ID NO: 598 (sequence of the AL-218 antibody VH).

An example of the VL in the above-mentioned "L chain having the amino acid sequence of SEQ ID NO: 284 (sequence of the AL-218 antibody L-chain CDR1) as CDR1, the amino acid sequence of SEQ ID NO: 286 (sequence of the AL-218 antibody L-chain CDR2) as CDR2, and the amino acid sequence of SEQ ID NO: 288 (sequence of the AL-218 antibody L-chain CDR3) as CDR3" of (104) is a VL comprising the amino acid sequence of SEQ ID NO: 276, more preferably a VL comprising the amino acid sequence of SEQ ID NO: 600 (sequence of the AL-218 antibody VL).

AL-219 Antibody:
An example of the VH in the above-mentioned "H chain having the amino acid sequence of SEQ ID NO: 294 (sequence of the AL-219 antibody H-chain CDR1) as CDR1, the amino acid sequence of SEQ ID NO: 296 (sequence of the AL-219 antibody H-chain CDR2) as CDR2, and the amino acid sequence of SEQ ID NO: 298 (sequence of the AL-219 antibody H-chain CDR3) as CDR3" of (109) is a VH comprising the amino acid sequence of SEQ ID NO: 602 (sequence of the AL-219 antibody VH).

An example of the VL in the above-mentioned "L chain having the amino acid sequence of SEQ ID NO: 300 (sequence of the AL-219 antibody L-chain CDR1) as CDR1, the amino acid sequence of SEQ ID NO: 302 (sequence of the AL-219 antibody L-chain CDR2) as CDR2, and the amino acid sequence of SEQ ID NO: 304 (sequence of the AL-219 antibody L-chain CDR3) as CDR3" of (110) is a VL comprising the amino acid sequence of SEQ ID NO: 292, more preferably a VL comprising the amino acid sequence of SEQ ID NO: 604 (sequence of the AL-219 antibody VL).

AL-220 Antibody:

An example of the VH in the above-mentioned "H chain having the amino acid sequence of SEQ ID NO: 310 (sequence of the AL-220 antibody H-chain CDR1) as CDR1, the amino acid sequence of SEQ ID NO: 312 (sequence of the AL-220 antibody H-chain CDR2) as CDR2, and the amino acid sequence of SEQ ID NO: 314 (sequence of the AL-220 antibody H-chain CDR3) as CDR3" of (115) is a VH comprising the amino acid sequence of SEQ ID NO: 606 (sequence of the AL-220 antibody VH).

An example of the VL in the above-mentioned "L chain having the amino acid sequence of SEQ ID NO: 316 (sequence of the AL-220 antibody L-chain CDR1) as CDR1, the amino acid sequence of SEQ ID NO: 318 (sequence of the AL-220 antibody L-chain CDR2) as CDR2, and the amino acid sequence of SEQ ID NO: 320 (sequence of the AL-220 antibody L-chain CDR3) as CDR3" of (116) is a VL comprising the amino acid sequence of SEQ ID NO: 308, more preferably a VL comprising the amino acid sequence of SEQ ID NO: 608 (sequence of the AL-220 antibody VL).

AL-221 Antibody:

An example of the VH in the above-mentioned "H chain having the amino acid sequence of SEQ ID NO: 326 (sequence of the AL-221 antibody H-chain CDR1) as CDR1, the amino acid sequence of SEQ ID NO: 328 (sequence of the AL-221 antibody H-chain CDR2) as CDR2, and the amino acid sequence of SEQ ID NO: 330 (sequence of the AL-221 antibody H-chain CDR3) as CDR3" of (121) is a VH comprising the amino acid sequence of SEQ ID NO: 610 (sequence of the AL-221 antibody VH).

An example of the VL in the above-mentioned "L chain having the amino acid sequence of SEQ ID NO: 332 (sequence of the AL-221 antibody L-chain CDR1) as CDR1, the amino acid sequence of SEQ ID NO: 334 (sequence of the AL-221 antibody L-chain CDR2) as CDR2, and the amino acid sequence of SEQ ID NO: 336 (sequence of the AL-221 antibody L-chain CDR3) as CDR3" of (122) is a VL comprising the amino acid sequence of SEQ ID NO: 324, more preferably a VL comprising the amino acid sequence of SEQ ID NO: 612 (sequence of the AL-221 antibody VL).

AL-222 Antibody:

An example of the VH in the above-mentioned "H chain having the amino acid sequence of SEQ ID NO: 342 (sequence of the AL-222 antibody H-chain CDR1) as CDR1, the amino acid sequence of SEQ ID NO: 344 (sequence of the AL-222 antibody H-chain CDR2) as CDR2, and the amino acid sequence of SEQ ID NO: 346 (sequence of the AL-222 antibody H-chain CDR3) as CDR3" of (127) is a VH comprising the amino acid sequence of SEQ ID NO: 614 (sequence of the AL-222 antibody VH).

An example of the VL in the above-mentioned "L chain having the amino acid sequence of SEQ ID NO: 348 (sequence of the AL-222 antibody L-chain CDR1) as CDR1, the amino acid sequence of SEQ ID NO: 350 (sequence of the AL-222 antibody L-chain CDR2) as CDR2, and the amino acid sequence of SEQ ID NO: 352 (sequence of the AL-222 antibody L-chain CDR3) as CDR3" of (128) is a VL comprising the amino acid sequence of SEQ ID NO: 340, more preferably a VL comprising the amino acid sequence of SEQ ID NO: 616 (sequence of the AL-222 antibody VL).

AL-223 Antibody:

An example of the VH in the above-mentioned "H chain having the amino acid sequence of SEQ ID NO: 358 (sequence of the AL-223 antibody H-chain CDR1) as CDR1, the amino acid sequence of SEQ ID NO: 360 (sequence of the AL-223 antibody H-chain CDR2) as CDR2, and the amino acid sequence of SEQ ID NO: 362 (sequence of the AL-223 antibody H-chain CDR3) as CDR3" of (133) is a VH comprising the amino acid sequence of SEQ ID NO: 618 (sequence of the AL-223 antibody VH).

An example of the VL in the above-mentioned "L chain having the amino acid sequence of SEQ ID NO: 364 (sequence of the AL-223 antibody L-chain CDR1) as CDR1, the amino acid sequence of SEQ ID NO: 366 (sequence of the AL-223 antibody L-chain CDR2) as CDR2, and the amino acid sequence of SEQ ID NO: 368 (sequence of the AL-223 antibody L-chain CDR3) as CDR3" of (134) is a VL comprising the amino acid sequence of SEQ ID NO: 356, more preferably a VL comprising the amino acid sequence of SEQ ID NO: 620 (sequence of the AL-223 antibody VL).

AL-224 Antibody:

An example of the VH in the above-mentioned "H chain having the amino acid sequence of SEQ ID NO: 374 (sequence of the AL-224 antibody H-chain CDR1) as CDR1, the amino acid sequence of SEQ ID NO: 376 (sequence of the AL-224 antibody H-chain CDR2) as CDR2, and the amino acid sequence of SEQ ID NO: 378 (sequence of the AL-224 antibody H-chain CDR3) as CDR3" of (139) is a VH comprising the amino acid sequence of SEQ ID NO: 622 (sequence of the AL-224 antibody VH).

An example of the VL in the above-mentioned "L chain having the amino acid sequence of SEQ ID NO: 380 (sequence of the AL-224 antibody L-chain CDR1) as CDR1, the amino acid sequence of SEQ ID NO: 382 (sequence of the AL-224 antibody L-chain CDR2) as CDR2, and the amino acid sequence of SEQ ID NO: 384 (sequence of the AL-224 antibody L-chain CDR3) as CDR3" of (140) is a VL comprising the amino acid sequence of SEQ ID NO: 372, more preferably a VL comprising the amino acid sequence of SEQ ID NO: 624 (sequence of the AL-224 antibody VL).

AL-225 Antibody:

An example of the VH in the above-mentioned "H chain having the amino acid sequence of SEQ ID NO: 390 (sequence of the AL-225 antibody H-chain CDR1) as CDR1, the amino acid sequence of SEQ ID NO: 392 (sequence of the AL-225 antibody H-chain CDR2) as CDR2, and the amino acid sequence of SEQ ID NO: 394 (sequence of the AL-225 antibody H-chain CDR3) as CDR3" of (145) is a VH comprising the amino acid sequence of SEQ ID NO: 626 (sequence of the AL-225 antibody VH).

An example of the VL in the above-mentioned "L chain having the amino acid sequence of SEQ ID NO: 396 (sequence of the AL-225 antibody L-chain CDR1) as CDR1, the amino acid sequence of SEQ ID NO: 398 (sequence of the AL-225 antibody L-chain CDR2) as CDR2, and the amino acid sequence of SEQ ID NO: 400 (sequence of the AL-225 antibody L-chain CDR3) as CDR3" of (146) is a VL comprising the amino acid sequence of SEQ ID NO: 388, more preferably a VL comprising the amino acid sequence of SEQ ID NO: 628 (sequence of the AL-225 antibody VL).

AL-226 Antibody:

An example of the VH in the above-mentioned "H chain having the amino acid sequence of SEQ ID NO: 406 (sequence of the AL-226 antibody H-chain CDR1) as CDR1, the amino acid sequence of SEQ ID NO: 408 (sequence of the AL-226 antibody H-chain CDR2) as CDR2, and the amino acid sequence of SEQ ID NO: 410 (sequence of the AL-226 antibody H-chain CDR3) as CDR3" of (151) is a VH comprising the amino acid sequence of SEQ ID NO: 630 (sequence of the AL-226 antibody VH).

An example of the VL in the above-mentioned "L chain having the amino acid sequence of SEQ ID NO: 412 (sequence of the AL-226 antibody L-chain CDR1) as CDR1, the amino acid sequence of SEQ ID NO: 414 (sequence of the AL-226 antibody L-chain CDR2) as CDR2, and the amino acid sequence of SEQ ID NO: 416 (sequence of the AL-226 antibody L-chain CDR3) as CDR3" of (152) is a VL comprising the amino acid sequence of SEQ ID NO: 404, more preferably a VL comprising the amino acid sequence of SEQ ID NO: 632 (sequence of the AL-226 antibody VL).

AL-227 Antibody:

An example of the VH in the above-mentioned "H chain having the amino acid sequence of SEQ ID NO: 422 (sequence of the AL-227 antibody H-chain CDR1) as CDR1, the amino acid sequence of SEQ ID NO: 424 (sequence of the AL-227 antibody H-chain CDR2) as CDR2, and the amino acid sequence of SEQ ID NO: 426 (sequence of the AL-227 antibody H-chain CDR3) as CDR3" of (157) is a VH comprising the amino acid sequence of SEQ ID NO: 634 (sequence of the AL-227 antibody VH).

An example of the VL in the above-mentioned "L chain having the amino acid sequence of SEQ ID NO: 428 (sequence of the AL-227 antibody L-chain CDR1) as CDR1, the amino acid sequence of SEQ ID NO: 430 (sequence of the AL-227 antibody L-chain CDR2) as CDR2, and the amino acid sequence of SEQ ID NO: 432 (sequence of the AL-227 antibody L-chain CDR3) as CDR3" of (158) is a VL comprising the amino acid sequence of SEQ ID NO: 420, more preferably a VL comprising the amino acid sequence of SEQ ID NO: 636 (sequence of the AL-227 antibody VL).

AL-228 Antibody:

An example of the VH in the above-mentioned "H chain having the amino acid sequence of SEQ ID NO: 438 (sequence of the AL-228 antibody H-chain CDR1) as CDR1, the amino acid sequence of SEQ ID NO: 440 (sequence of the AL-228 antibody H-chain CDR2) as CDR2, and the amino acid sequence of SEQ ID NO: 442 (sequence of the AL-228 antibody H-chain CDR3) as CDR3" of (163) is a VH comprising the amino acid sequence of SEQ ID NO: 638 (sequence of the AL-228 antibody VH).

An example of the VL in the above-mentioned "L chain having the amino acid sequence of SEQ ID NO: 444 (sequence of the AL-228 antibody L-chain CDR1) as CDR1, the amino acid sequence of SEQ ID NO: 446 (sequence of the AL-228 antibody L-chain CDR2) as CDR2, and the amino acid sequence of SEQ ID NO: 448 (sequence of the AL-228 antibody L-chain CDR3) as CDR3" of (164) is a VL comprising the amino acid sequence of SEQ ID NO: 436, more preferably a VL comprising the amino acid sequence of SEQ ID NO: 640 (sequence of the AL-228 antibody VL).

AL-229 Antibody:

An example of the VH in the above-mentioned "H chain having the amino acid sequence of SEQ ID NO: 454 (sequence of the AL-229 antibody H-chain CDR1) as CDR1, the amino acid sequence of SEQ ID NO: 456 (sequence of the AL-229 antibody H-chain CDR2) as CDR2, and the amino acid sequence of SEQ ID NO: 458 (sequence of the AL-229 antibody H-chain CDR3) as CDR3" of (169) is a VH comprising the amino acid sequence of SEQ ID NO: 642 (sequence of the AL-229 antibody VH).

An example of the VL in the above-mentioned "L chain having the amino acid sequence of SEQ ID NO: 460 (sequence of the AL-229 antibody L-chain CDR1) as CDR1, the amino acid sequence of SEQ ID NO: 462 (sequence of the AL-229 antibody L-chain CDR2) as CDR2, and the amino acid sequence of SEQ ID NO: 464 (sequence of the AL-229 antibody L-chain CDR3) as CDR3" of (170) is a VL comprising the amino acid sequence of SEQ ID NO: 452, more preferably a VL comprising the amino acid sequence of SEQ ID NO: 644 (sequence of the AL-229 antibody VL).

AL-230 Antibody:

An example of the VH in the above-mentioned "H chain having the amino acid sequence of SEQ ID NO: 470 (sequence of the AL-230 antibody H-chain CDR1) as CDR1, the amino acid sequence of SEQ ID NO: 472 (sequence of the AL-230 antibody H-chain CDR2) as CDR2, and the amino acid sequence of SEQ ID NO: 474 (sequence of the AL-230 antibody H-chain CDR3) as CDR3" of (175) is a VH comprising the amino acid sequence of SEQ ID NO: 646 (sequence of the AL-230 antibody VH).

An example of the VL in the above-mentioned "L chain having the amino acid sequence of SEQ ID NO: 476 (sequence of the AL-230 antibody L-chain CDR1) as CDR1, the amino acid sequence of SEQ ID NO: 478 (sequence of the AL-230 antibody L-chain CDR2) as CDR2, and the amino acid sequence of SEQ ID NO: 480 (sequence of the AL-230 antibody L-chain CDR3) as CDR3" of (176) is a VL comprising the amino acid sequence of SEQ ID NO: 468, more preferably a VL comprising the amino acid sequence of SEQ ID NO: 648 (sequence of the AL-230 antibody VL).

AL-231 Antibody:

An example of the VH in the above-mentioned "H chain having the amino acid sequence of SEQ ID NO: 486 (sequence of the AL-231 antibody H-chain CDR1) as CDR1, the amino acid sequence of SEQ ID NO: 488 (sequence of the AL-231 antibody H-chain CDR2) as CDR2, and the amino acid sequence of SEQ ID NO: 490 (sequence of the AL-231 antibody H-chain CDR3) as CDR3" of (181) is a VH comprising the amino acid sequence of SEQ ID NO: 650 (sequence of the AL-231 antibody VH).

An example of the VL in the above-mentioned "L chain having the amino acid sequence of SEQ ID NO: 492 (sequence of the AL-231 antibody L-chain CDR1) as CDR1, the amino acid sequence of SEQ ID NO: 494 (sequence of the AL-231 antibody L-chain CDR2) as CDR2, and the amino acid sequence of SEQ ID NO: 496 (sequence of the AL-231 antibody L-chain CDR3) as CDR3" of (182) is a VL comprising the amino acid sequence of SEQ ID NO: 484, more preferably a VL comprising the amino acid sequence of SEQ ID NO: 652 (sequence of the AL-231 antibody VL).

AL-232 Antibody:

An example of the VH in the above-mentioned "H chain having the amino acid sequence of SEQ ID NO: 502 (sequence of the AL-232 antibody H-chain CDR1) as CDR1, the amino acid sequence of SEQ ID NO: 504 (sequence of the AL-232 antibody H-chain CDR2) as CDR2, and the amino acid sequence of SEQ ID NO: 506 (sequence of the AL-232 antibody H-chain CDR3) as CDR3" of (187) is a VH comprising the amino acid sequence of SEQ ID NO: 654 (sequence of the AL-232 antibody VH).

An example of the VL in the above-mentioned "L chain having the amino acid sequence of SEQ ID NO: 508 (sequence of the AL-232 antibody L-chain CDR1) as CDR1, the amino acid sequence of SEQ ID NO: 510 (sequence of the AL-232 antibody L-chain CDR2) as CDR2, and the amino acid sequence of SEQ ID NO: 512 (sequence of the AL-232 antibody L-chain CDR3) as CDR3" of (188) is a VL comprising the amino acid sequence of SEQ ID NO: 500, more preferably a VL comprising the amino acid sequence of SEQ ID NO: 656 (sequence of the AL-232 antibody VL).

AL-233 Antibody:

An example of the VH in the above-mentioned "H chain having the amino acid sequence of SEQ ID NO: 518 (sequence of the AL-233 antibody H-chain CDR1) as CDR1, the amino acid sequence of SEQ ID NO: 520 (sequence of the AL-233 antibody H-chain CDR2) as CDR2, and the amino acid sequence of SEQ ID NO: 524 (sequence of the AL-233 antibody H-chain CDR3) as CDR3" of (193) is a VH comprising the amino acid sequence of SEQ ID NO: 658 (sequence of the AL-233 antibody VH).

An example of the VL in the above-mentioned "L chain having the amino acid sequence of SEQ ID NO: 524 (sequence of the AL-233 antibody L-chain CDR1) as CDR1, the amino acid sequence of SEQ ID NO: 526 (sequence of the AL-233 antibody L-chain CDR2) as CDR2, and the amino acid sequence of SEQ ID NO: 528 (sequence of the AL-233 antibody L-chain CDR3) as CDR3" of (188) is a VL comprising the amino acid sequence of SEQ ID NO: 660 (sequence of the AL-233 antibody VL).

The above-mentioned H chains, L chains, VHs, and VLs can be used to prepare the antibodies of the present invention. The present invention also relates to the above-mentioned H chains, L chains, VHs, and VLs.

For the AL-201 antibody of the present invention:
the amino acid sequence and the nucleotide sequence of the H-chain variable region (VH) are shown in SEQ ID NO: 530 and SEQ ID NO: 529, respectively;
the amino acid sequence and the nucleotide sequence of the L-chain variable region (VL) are shown in SEQ ID NO: 532 and SEQ ID NO: 531, respectively;
the amino acid sequence and the nucleotide sequence of the H-chain CDR1 are shown in SEQ ID NO: 6 and SEQ ID NO: 5, respectively;
the amino acid sequence and the nucleotide sequence of the H-chain CDR2 are shown in SEQ ID NO: 8 and SEQ ID NO: 7, respectively;
the amino acid sequence and the nucleotide sequence of the H-chain CDR3 are shown in SEQ ID NO: 10 and SEQ ID NO: 9, respectively;
the amino acid sequence and the nucleotide sequence of the L-chain CDR1 are shown in SEQ ID NO: 12 and SEQ ID NO: 11, respectively;
the amino acid sequence and the nucleotide sequence of the L-chain CDR2 are shown in SEQ ID NO: 14 and SEQ ID NO: 13, respectively; and
the amino acid sequence and the nucleotide sequence of the L-chain CDR3 are shown in SEQ ID NO: 16 and SEQ ID NO: 15, respectively.

For the AL-202 antibody of the present invention:
the amino acid sequence and the nucleotide sequence of the H-chain variable region (VH) are shown in SEQ ID NO: 534 and SEQ ID NO: 533, respectively;
the amino acid sequence and the nucleotide sequence of the L-chain variable region (VL) are shown in SEQ ID NO: 536 and SEQ ID NO: 535, respectively;
the amino acid sequence and the nucleotide sequence of the H-chain CDR1 are shown in SEQ ID NO: 22 and SEQ ID NO: 21, respectively;
the amino acid sequence and the nucleotide sequence of the H-chain CDR2 are shown in SEQ ID NO: 24 and SEQ ID NO: 23, respectively;
the amino acid sequence and the nucleotide sequence of the H-chain CDR3 are shown in SEQ ID NO: 26 and SEQ ID NO: 25, respectively;
the amino acid sequence and the nucleotide sequence of the L-chain CDR1 are shown in SEQ ID NO: 28 and SEQ ID NO: 27, respectively;
the amino acid sequence and the nucleotide sequence of the L-chain CDR2 are shown in SEQ ID NO: 30 and SEQ ID NO: 29, respectively; and
the amino acid sequence and the nucleotide sequence of the L-chain CDR3 are shown in SEQ ID NO: 32 and SEQ ID NO: 31, respectively.

For the AL-203 antibody of the present invention:
the amino acid sequence and the nucleotide sequence of the H-chain variable region (VH) are shown in SEQ ID NO: 538 and SEQ ID NO: 537, respectively;
the amino acid sequence and the nucleotide sequence of the L-chain variable region (VL) are shown in SEQ ID NO: 540 and SEQ ID NO: 539, respectively;
the amino acid sequence and the nucleotide sequence of the H-chain CDR1 are shown in SEQ ID NO: 38 and SEQ ID NO: 37, respectively;
the amino acid sequence and the nucleotide sequence of the H-chain CDR2 are shown in SEQ ID NO: 40 and SEQ ID NO: 39, respectively;
the amino acid sequence and the nucleotide sequence of the H-chain CDR3 are shown in SEQ ID NO: 42 and SEQ ID NO: 41, respectively;
the amino acid sequence and the nucleotide sequence of the L-chain CDR1 are shown in SEQ ID NO: 44 and SEQ ID NO: 43, respectively;
the amino acid sequence and the nucleotide sequence of the L-chain CDR2 are shown in SEQ ID NO: 46 and SEQ ID NO: 45, respectively; and
the amino acid sequence and the nucleotide sequence of the L-chain CDR3 are shown in SEQ ID NO: 48 and SEQ ID NO: 47, respectively.

For the AL-204 antibody of the present invention:
the amino acid sequence and the nucleotide sequence of the H-chain variable region (VH) are shown in SEQ ID NO: 542 and SEQ ID NO: 541, respectively;
the amino acid sequence and the nucleotide sequence of the L-chain variable region (VL) are shown in SEQ ID NO: 544 and SEQ ID NO: 543, respectively;
the amino acid sequence and the nucleotide sequence of the H-chain CDR1 are shown in SEQ ID NO: 54 and SEQ ID NO: 53, respectively;
the amino acid sequence and the nucleotide sequence of the H-chain CDR2 are shown in SEQ ID NO: 56 and SEQ ID NO: 55, respectively;
the amino acid sequence and the nucleotide sequence of the H-chain CDR3 are shown in SEQ ID NO: 58 and SEQ ID NO: 57, respectively;
the amino acid sequence and the nucleotide sequence of the L-chain CDR1 are shown in SEQ ID NO: 60 and SEQ ID NO: 59, respectively;
the amino acid sequence and the nucleotide sequence of the L-chain CDR2 are shown in SEQ ID NO: 62 and SEQ ID NO: 61, respectively; and
the amino acid sequence and the nucleotide sequence of the L-chain CDR3 are shown in SEQ ID NO: 64 and SEQ ID NO: 63, respectively.

For the AL-205 antibody of the present invention:
the amino acid sequence and the nucleotide sequence of the H-chain variable region (VH) are shown in SEQ ID NO: 546 and SEQ ID NO: 545, respectively;

the amino acid sequence and the nucleotide sequence of the L-chain variable region (VL) are shown in SEQ ID NO: 548 and SEQ ID NO: 547, respectively;

the amino acid sequence and the nucleotide sequence of the H-chain CDR1 are shown in SEQ ID NO: 70 and SEQ ID NO: 69, respectively;

the amino acid sequence and the nucleotide sequence of the H-chain CDR2 are shown in SEQ ID NO: 72 and SEQ ID NO: 71, respectively;

the amino acid sequence and the nucleotide sequence of the H-chain CDR3 are shown in SEQ ID NO: 74 and SEQ ID NO: 73, respectively;

the amino acid sequence and the nucleotide sequence of the L-chain CDR1 are shown in SEQ ID NO: 76 and SEQ ID NO: 75, respectively;

the amino acid sequence and the nucleotide sequence of the L-chain CDR2 are shown in SEQ ID NO: 78 and SEQ ID NO: 77, respectively; and the amino acid sequence and the nucleotide sequence of the L-chain CDR3 are shown in SEQ ID NO: 80 and SEQ ID NO: 79, respectively.

For the AL-206 antibody of the present invention:
the amino acid sequence and the nucleotide sequence of the H-chain variable region (VH) are shown in SEQ ID NO: 550 and SEQ ID NO: 549, respectively;

the amino acid sequence and the nucleotide sequence of the L-chain variable region (VL) are shown in SEQ ID NO: 552 and SEQ ID NO: 551, respectively;

the amino acid sequence and the nucleotide sequence of the H-chain CDR1 are shown in SEQ ID NO: 86 and SEQ ID NO: 85, respectively;

the amino acid sequence and the nucleotide sequence of the H-chain CDR2 are shown in SEQ ID NO: 88 and SEQ ID NO: 87, respectively;

the amino acid sequence and the nucleotide sequence of the H-chain CDR3 are shown in SEQ ID NO: 90 and SEQ ID NO: 89, respectively;

the amino acid sequence and the nucleotide sequence of the L-chain CDR1 are shown in SEQ ID NO: 92 and SEQ ID NO: 91, respectively;

the amino acid sequence and the nucleotide sequence of the L-chain CDR2 are shown in SEQ ID NO: 94 and SEQ ID NO: 93, respectively; and the amino acid sequence and the nucleotide sequence of the L-chain CDR3 are shown in SEQ ID NO: 96 and SEQ ID NO: 95, respectively.

For the AL-207 antibody of the present invention:
the amino acid sequence and the nucleotide sequence of the H-chain variable region (VH) are shown in SEQ ID NO: 554 and SEQ ID NO: 553, respectively;

the amino acid sequence and the nucleotide sequence of the L-chain variable region (VL) are shown in SEQ ID NO: 556 and SEQ ID NO: 555, respectively;

the amino acid sequence and the nucleotide sequence of the H-chain CDR1 are shown in SEQ ID NO: 102 and SEQ ID NO: 101, respectively;

the amino acid sequence and the nucleotide sequence of the H-chain CDR2 are shown in SEQ ID NO: 104 and SEQ ID NO: 103, respectively;

the amino acid sequence and the nucleotide sequence of the H-chain CDR3 are shown in SEQ ID NO: 106 and SEQ ID NO: 105, respectively;

the amino acid sequence and the nucleotide sequence of the L-chain CDR1 are shown in SEQ ID NO: 108 and SEQ ID NO: 107, respectively;

the amino acid sequence and the nucleotide sequence of the L-chain CDR2 are shown in SEQ ID NO: 110 and SEQ ID NO: 109, respectively; and the amino acid sequence and the nucleotide sequence of the L-chain CDR3 are shown in SEQ ID NO: 112 and SEQ ID NO: 111, respectively.

For the AL-208 antibody of the present invention:
the amino acid sequence and the nucleotide sequence of the H-chain variable region (VH) are shown in SEQ ID NO: 558 and SEQ ID NO: 557, respectively;

the amino acid sequence and the nucleotide sequence of the L-chain variable region (VL) are shown in SEQ ID NO: 560 and SEQ ID NO: 559, respectively;

the amino acid sequence and the nucleotide sequence of the H-chain CDR1 are shown in SEQ ID NO: 118 and SEQ ID NO: 117, respectively;

the amino acid sequence and the nucleotide sequence of the H-chain CDR2 are shown in SEQ ID NO: 120 and SEQ ID NO: 119, respectively;

the amino acid sequence and the nucleotide sequence of the H-chain CDR3 are shown in SEQ ID NO: 122 and SEQ ID NO: 121, respectively;

the amino acid sequence and the nucleotide sequence of the L-chain CDR1 are shown in SEQ ID NO: 124 and SEQ ID NO: 123, respectively;

the amino acid sequence and the nucleotide sequence of the L-chain CDR2 are shown in SEQ ID NO: 126 and SEQ ID NO: 125, respectively; and the amino acid sequence and the nucleotide sequence of the L-chain CDR3 are shown in SEQ ID NO: 128 and SEQ ID NO: 127, respectively.

For the AL-209 antibody of the present invention:
the amino acid sequence and the nucleotide sequence of the H-chain variable region (VH) are shown in SEQ ID NO: 562 and SEQ ID NO: 561, respectively;

the amino acid sequence and the nucleotide sequence of the L-chain variable region (VL) are shown in SEQ ID NO: 564 and SEQ ID NO: 563, respectively;

the amino acid sequence and the nucleotide sequence of the H-chain CDR1 are shown in SEQ ID NO: 134 and SEQ ID NO: 133, respectively;

the amino acid sequence and the nucleotide sequence of the H-chain CDR2 are shown in SEQ ID NO: 136 and SEQ TD NO: 135, respectively;

the amino acid sequence and the nucleotide sequence of the H-chain CDR3 are shown in SEQ ID NO: 138 and SEQ ID NO: 137, respectively;

the amino acid sequence and the nucleotide sequence of the L-chain CDR1 are shown in SEQ ID NO: 140 and SEQ ID NO: 139, respectively;

the amino acid sequence and the nucleotide sequence of the L-chain CDR2 are shown in SEQ ID NO: 142 and SEQ ID NO: 141, respectively; and the amino acid sequence and the nucleotide sequence of the L-chain CDR3 are shown in SEQ ID NO: 144 and SEQ ID NO: 143, respectively.

For the AL-210 antibody of the present invention:
the amino acid sequence and the nucleotide sequence of the H-chain variable region (VH) are shown in SEQ ID NO: 566 and SEQ ID NO: 565, respectively;

the amino acid sequence and the nucleotide sequence of the L-chain variable region (VL) are shown in SEQ ID NO: 568 and SEQ ID NO: 567, respectively;

the amino acid sequence and the nucleotide sequence of the H-chain CDR1 are shown in SEQ ID NO: 150 and SEQ ID NO: 149, respectively;

the amino acid sequence and the nucleotide sequence of the H-chain CDR2 are shown in SEQ ID NO: 152 and SEQ ID NO: 151, respectively;

the amino acid sequence and the nucleotide sequence of the H-chain CDR3 are shown in SEQ ID NO: 154 and SEQ ID NO: 153, respectively;

the amino acid sequence and the nucleotide sequence of the L-chain CDR1 are shown in SEQ ID NO: 156 and SEQ ID NO: 155, respectively;

the amino acid sequence and the nucleotide sequence of the L-chain CDR2 are shown in SEQ ID NO: 158 and SEQ ID NO: 157, respectively; and the amino acid sequence and the nucleotide sequence of the L-chain CDR3 are shown in SEQ ID NO: 160 and SEQ ID NO: 159, respectively.

For the AL-211 antibody of the present invention:
the amino acid sequence and the nucleotide sequence of the H-chain variable region (VH) are shown in SEQ ID NO: 570 and SEQ ID NO: 569, respectively;

the amino acid sequence and the nucleotide sequence of the L-chain variable region (VL) are shown in SEQ ID NO: 572 and SEQ ID NO: 571, respectively;

the amino acid sequence and the nucleotide sequence of the H-chain CDR1 are shown in SEQ ID NO: 166 and SEQ ID NO: 165, respectively;

the amino acid sequence and the nucleotide sequence of the H-chain CDR2 are shown in SEQ ID NO: 168 and SEQ ID NO: 167, respectively;

the amino acid sequence and the nucleotide sequence of the H-chain CDR3 are shown in SEQ ID NO: 170 and SEQ ID NO: 169, respectively;

the amino acid sequence and the nucleotide sequence of the L-chain CDR1 are shown in SEQ ID NO: 172 and SEQ ID NO: 171, respectively;

the amino acid sequence and the nucleotide sequence of the L-chain CDR2 are shown in SEQ ID NO: 174 and SEQ ID NO: 173, respectively; and the amino acid sequence and the nucleotide sequence of the L-chain CDR3 are shown in SEQ ID NO: 176 and SEQ ID NO: 175, respectively.

For the AL-212 antibody of the present invention:
the amino acid sequence and the nucleotide sequence of the H-chain variable region (VH) are shown in SEQ ID NO: 574 and SEQ ID NO: 573, respectively;

the amino acid sequence and the nucleotide sequence of the L-chain variable region (VL) are shown in SEQ ID NO: 576 and SEQ ID NO: 575, respectively;

the amino acid sequence and the nucleotide sequence of the H-chain CDR1 are shown in SEQ ID NO: 182 and SEQ ID NO: 181, respectively;

the amino acid sequence and the nucleotide sequence of the H-chain CDR2 are shown in SEQ ID NO: 184 and SEQ ID NO: 183, respectively;

the amino acid sequence and the nucleotide sequence of the H-chain CDR3 are shown in SEQ ID NO: 186 and SEQ ID NO: 185, respectively;

the amino acid sequence and the nucleotide sequence of the L-chain CDR1 are shown in SEQ ID NO: 188 and SEQ ID NO: 187, respectively;

the amino acid sequence and the nucleotide sequence of the L-chain CDR2 are shown in SEQ ID NO: 190 and SEQ ID NO: 189, respectively; and the amino acid sequence and the nucleotide sequence of the L-chain CDR3 are shown in SEQ ID NO: 192 and SEQ ID NO: 191, respectively.

For the AL-213 antibody of the present invention:
the amino acid sequence and the nucleotide sequence of the H-chain variable region (VH) are shown in SEQ ID NO: 578 and SEQ ID NO: 577, respectively;

the amino acid sequence and the nucleotide sequence of the L-chain variable region (VL) are shown in SEQ ID NO: 580 and SEQ ID NO: 579, respectively;

the amino acid sequence and the nucleotide sequence of the H-chain CDR1 are shown in SEQ ID NO: 198 and SEQ ID NO: 197, respectively;

the amino acid sequence and the nucleotide sequence of the H-chain CDR2 are shown in SEQ ID NO: 200 and SEQ ID NO: 199, respectively;

the amino acid sequence and the nucleotide sequence of the H-chain CDR3 are shown in SEQ ID NO: 202 and SEQ ID NO: 201, respectively;

the amino acid sequence and the nucleotide sequence of the L-chain CDR1 are shown in SEQ ID NO: 204 and SEQ ID NO: 203, respectively;

the amino acid sequence and the nucleotide sequence of the L-chain CDR2 are shown in SEQ ID NO: 206 and SEQ ID NO: 205, respectively; and the amino acid sequence and the nucleotide sequence of the L-chain CDR3 are shown in SEQ ID NO: 208 and SEQ ID NO: 207, respectively.

For the AL-214 antibody of the present invention:
the amino acid sequence and the nucleotide sequence of the H-chain variable region (VH) are shown in SEQ ID NO: 582 and SEQ ID NO: 581, respectively;

the amino acid sequence and the nucleotide sequence of the L-chain variable region (VL) are shown in SEQ ID NO: 584 and SEQ ID NO: 583, respectively;

the amino acid sequence and the nucleotide sequence of the H-chain CDR1 are shown in SEQ ID NO: 214 and SEQ ID NO: 213, respectively;

the amino acid sequence and the nucleotide sequence of the H-chain CDR2 are shown in SEQ ID NO: 216 and SEQ ID NO: 215, respectively;

the amino acid sequence and the nucleotide sequence of the H-chain CDR3 are shown in SEQ ID NO: 218 and SEQ ID NO: 217, respectively;

the amino acid sequence and the nucleotide sequence of the L-chain CDR1 are shown in SEQ ID NO: 220 and SEQ ID NO: 219, respectively;

the amino acid sequence and the nucleotide sequence of the L-chain CDR2 are shown in SEQ ID NO: 222 and SEQ ID NO: 221, respectively; and the amino acid sequence and the nucleotide sequence of the L-chain CDR3 are shown in SEQ ID NO: 224 and SEQ ID NO: 223, respectively.

For the AL-215 antibody of the present invention:
the amino acid sequence and the nucleotide sequence of the H-chain variable region (VH) are shown in SEQ ID NO: 586 and SEQ ID NO: 585, respectively;

the amino acid sequence and the nucleotide sequence of the L-chain variable region (VL) are shown in SEQ ID NO: 588 and SEQ ID NO: 587, respectively;

the amino acid sequence and the nucleotide sequence of the H-chain CDR1 are shown in SEQ ID NO: 230 and SEQ ID NO: 229, respectively;

the amino acid sequence and the nucleotide sequence of the H-chain CDR2 are shown in SEQ ID NO: 232 and SEQ ID NO: 231, respectively;

the amino acid sequence and the nucleotide sequence of the H-chain CDR3 are shown in SEQ ID NO: 234 and SEQ ID NO: 233, respectively;

the amino acid sequence and the nucleotide sequence of the L-chain CDR1 are shown in SEQ ID NO: 236 and SEQ ID NO: 235, respectively;

the amino acid sequence and the nucleotide sequence of the L-chain CDR2 are shown in SEQ ID NO: 238 and SEQ ID NO: 237, respectively; and the amino acid sequence and the nucleotide sequence of the L-chain CDR3 are shown in SEQ ID NO: 240 and SEQ ID NO: 239, respectively.

For the AL-216 antibody of the present invention:

the amino acid sequence and the nucleotide sequence of the H-chain variable region (VH) are shown in SEQ ID NO: 590 and SEQ ID NO: 589, respectively;

the amino acid sequence and the nucleotide sequence of the L-chain variable region (VL) are shown in SEQ ID NO: 592 and SEQ ID NO: 591, respectively;

the amino acid sequence and the nucleotide sequence of the H-chain CDR1 are shown in SEQ ID NO: 246 and SEQ ID NO: 245, respectively;

the amino acid sequence and the nucleotide sequence of the H-chain CDR2 are shown in SEQ ID NO: 248 and SEQ ID NO: 247, respectively;

the amino acid sequence and the nucleotide sequence of the H-chain CDR3 are shown in SEQ ID NO: 250 and SEQ ID NO: 249, respectively;

the amino acid sequence and the nucleotide sequence of the L-chain CDR1 are shown in SEQ ID NO: 252 and SEQ ID NO: 251, respectively;

the amino acid sequence and the nucleotide sequence of the L-chain CDR2 are shown in SEQ ID NO: 254 and SEQ ID NO: 253, respectively; and the amino acid sequence and the nucleotide sequence of the L-chain CDR3 are shown in SEQ ID NO: 256 and SEQ ID NO: 255, respectively.

For the AL-217 antibody of the present invention:

the amino acid sequence and the nucleotide sequence of the H-chain variable region (VH) are shown in SEQ ID NO: 594 and SEQ ID NO: 593, respectively;

the amino acid sequence and the nucleotide sequence of the L-chain variable region (VL) are shown in SEQ ID NO: 596 and SEQ ID NO: 595, respectively;

the amino acid sequence and the nucleotide sequence of the H-chain CDR1 are shown in SEQ ID NO: 262 and SEQ ID NO: 261, respectively;

the amino acid sequence and the nucleotide sequence of the H-chain CDR2 are shown in SEQ ID NO: 264 and SEQ ID NO: 263, respectively;

the amino acid sequence and the nucleotide sequence of the H-chain CDR3 are shown in SEQ ID NO: 266 and SEQ ID NO: 265, respectively;

the amino acid sequence and the nucleotide sequence of the L-chain CDR1 are shown in SEQ ID NO: 268 and SEQ ID NO: 267, respectively;

the amino acid sequence and the nucleotide sequence of the L-chain CDR2 are shown in SEQ ID NO: 270 and SEQ ID NO: 269, respectively; and the amino acid sequence and the nucleotide sequence of the L-chain CDR3 are shown in SEQ ID NO: 272 and SEQ ID NO: 271, respectively.

For the AL-218 antibody of the present invention:

the amino acid sequence and the nucleotide sequence of the H-chain variable region (VH) are shown in SEQ ID NO: 598 and SEQ ID NO: 597, respectively;

the amino acid sequence and the nucleotide sequence of the L-chain variable region (VL) are shown in SEQ ID NO: 600 and SEQ ID NO: 599, respectively;

the amino acid sequence and the nucleotide sequence of the H-chain CDR1 are shown in SEQ ID NO: 278 and SEQ ID NO: 277, respectively;

the amino acid sequence and the nucleotide sequence of the H-chain CDR2 are shown in SEQ ID NO: 280 and SEQ ID NO: 279, respectively;

the amino acid sequence and the nucleotide sequence of the H-chain CDR3 are shown in SEQ ID NO: 282 and SEQ ID NO: 281, respectively;

the amino acid sequence and the nucleotide sequence of the L-chain CDR1 are shown in SEQ ID NO: 284 and SEQ ID NO: 283, respectively;

the amino acid sequence and the nucleotide sequence of the L-chain CDR2 are shown in SEQ ID NO: 286 and SEQ ID NO: 285, respectively; and the amino acid sequence and the nucleotide sequence of the L-chain CDR3 are shown in SEQ ID NO: 288 and SEQ ID NO: 287, respectively.

For the AL-219 antibody of the present invention:

the amino acid sequence and the nucleotide sequence of the H-chain variable region (VH) are shown in SEQ ID NO: 602 and SEQ ID NO: 601, respectively;

the amino acid sequence and the nucleotide sequence of the L-chain variable region (VL) are shown in SEQ ID NO: 604 and SEQ ID NO: 603, respectively;

the amino acid sequence and the nucleotide sequence of the H-chain CDR1 are shown in SEQ ID NO: 294 and SEQ ID NO: 293, respectively;

the amino acid sequence and the nucleotide sequence of the H-chain CDR2 are shown in SEQ ID NO: 296 and SEQ ID NO: 295, respectively;

the amino acid sequence and the nucleotide sequence of the H-chain CDR3 are shown in SEQ ID NO: 298 and SEQ ID NO: 297, respectively;

the amino acid sequence and the nucleotide sequence of the L-chain CDR1 are shown in SEQ ID NO: 300 and SEQ ID NO: 299, respectively;

the amino acid sequence and the nucleotide sequence of the L-chain CDR2 are shown in SEQ ID NO: 302 and SEQ ID NO: 301, respectively; and the amino acid sequence and the nucleotide sequence of the L-chain CDR3 are shown in SEQ ID NO: 304 and SEQ ID NO: 303, respectively.

For the AL-220 antibody of the present invention:

the amino acid sequence and the nucleotide sequence of the H-chain variable region (VH) are shown in SEQ ID NO: 606 and SEQ ID NO: 605, respectively;

the amino acid sequence and the nucleotide sequence of the L-chain variable region (VL) are shown in SEQ ID NO: 608 and SEQ ID NO: 607, respectively;

the amino acid sequence and the nucleotide sequence of the H-chain CDR1 are shown in SEQ ID NO: 310 and SEQ ID NO: 309, respectively;

the amino acid sequence and the nucleotide sequence of the H-chain CDR2 are shown in SEQ ID NO: 312 and SEQ ID NO: 311, respectively;

the amino acid sequence and the nucleotide sequence of the H-chain CDR3 are shown in SEQ ID NO: 314 and SEQ ID NO: 313, respectively;

the amino acid sequence and the nucleotide sequence of the L-chain CDR1 are shown in SEQ ID NO: 316 and SEQ ID NO: 315, respectively;

the amino acid sequence and the nucleotide sequence of the L-chain CDR2 are shown in SEQ ID NO: 318 and SEQ ID NO: 317, respectively; and the amino acid sequence and the nucleotide sequence of the L-chain CDR3 are shown in SEQ ID NO: 320 and SEQ ID NO: 319, respectively.

For the AL-221 antibody of the present invention:
the amino acid sequence and the nucleotide sequence of the H-chain variable region (VH) are shown in SEQ ID NO: 610 and SEQ ID NO: 609, respectively;
the amino acid sequence and the nucleotide sequence of the L-chain variable region (VL) are shown in SEQ ID NO: 612 and SEQ ID NO: 611, respectively;
the amino acid sequence and the nucleotide sequence of the H-chain CDR1 are shown in SEQ ID NO: 326 and SEQ ID NO: 325, respectively;
the amino acid sequence and the nucleotide sequence of the H-chain CDR2 are shown in SEQ ID NO: 328 and SEQ ID NO: 327, respectively;
the amino acid sequence and the nucleotide sequence of the H-chain CDR3 are shown in SEQ ID NO: 330 and SEQ ID NO: 329, respectively;
the amino acid sequence and the nucleotide sequence of the L-chain CDR1 are shown in SEQ ID NO: 332 and SEQ ID NO: 331, respectively;
the amino acid sequence and the nucleotide sequence of the L-chain CDR2 are shown in SEQ ID NO: 334 and SEQ ID NO: 333, respectively; and
the amino acid sequence and the nucleotide sequence of the L-chain CDR3 are shown in SEQ ID NO: 336 and SEQ ID NO: 335, respectively.

For the AL-222 antibody of the present invention:
the amino acid sequence and the nucleotide sequence of the H-chain variable region (VH) are shown in SEQ ID NO: 614 and SEQ ID NO: 613, respectively;
the amino acid sequence and the nucleotide sequence of the L-chain variable region (VL) are shown in SEQ ID NO: 616 and SEQ ID NO: 615, respectively;
the amino acid sequence and the nucleotide sequence of the H-chain CDR1 are shown in SEQ ID NO: 342 and SEQ ID NO: 341, respectively;
the amino acid sequence and the nucleotide sequence of the H-chain CDR2 are shown in SEQ ID NO: 344 and SEQ ID NO: 343, respectively;
the amino acid sequence and the nucleotide sequence of the H-chain CDR3 are shown in SEQ ID NO: 346 and SEQ ID NO: 345, respectively;
the amino acid sequence and the nucleotide sequence of the L-chain CDR1 are shown in SEQ ID NO: 348 and SEQ ID NO: 347, respectively;
the amino acid sequence and the nucleotide sequence of the L-chain CDR2 are shown in SEQ ID NO: 350 and SEQ ID NO: 349, respectively; and
the amino acid sequence and the nucleotide sequence of the L-chain CDR3 are shown in SEQ ID NO: 352 and SEQ ID NO: 351, respectively.

For the AL-223 antibody of the present invention:
the amino acid sequence and the nucleotide sequence of the H-chain variable region (VH) are shown in SEQ ID NO: 618 and SEQ ID NO: 617, respectively;
the amino acid sequence and the nucleotide sequence of the L-chain variable region (VL) are shown in SEQ ID NO: 620 and SEQ ID NO: 619, respectively;
the amino acid sequence and the nucleotide sequence of the H-chain CDR1 are shown in SEQ ID NO: 358 and SEQ ID NO: 357, respectively;
the amino acid sequence and the nucleotide sequence of the H-chain CDR2 are shown in SEQ ID NO: 360 and SEQ ID NO: 359, respectively;
the amino acid sequence and the nucleotide sequence of the H-chain CDR3 are shown in SEQ ID NO: 362 and SEQ ID NO: 361, respectively;
the amino acid sequence and the nucleotide sequence of the L-chain CDR1 are shown in SEQ ID NO: 364 and SEQ ID NO: 363, respectively;
the amino acid sequence and the nucleotide sequence of the L-chain CDR2 are shown in SEQ ID NO: 366 and SEQ ID NO: 365, respectively; and
the amino acid sequence and the nucleotide sequence of the L-chain CDR3 are shown in SEQ ID NO: 368 and SEQ ID NO: 367, respectively.

For the AL-224 antibody of the present invention:
the amino acid sequence and the nucleotide sequence of the H-chain variable region (VH) are shown in SEQ ID NO: 622 and SEQ ID NO: 621, respectively;
the amino acid sequence and the nucleotide sequence of the L-chain variable region (VL) are shown in SEQ ID NO: 624 and SEQ ID NO: 623, respectively;
the amino acid sequence and the nucleotide sequence of the H-chain CDR1 are shown in SEQ ID NO: 374 and SEQ ID NO: 373, respectively;
the amino acid sequence and the nucleotide sequence of the H-chain CDR2 are shown in SEQ ID NO: 376 and SEQ ID NO: 375, respectively;
the amino acid sequence and the nucleotide sequence of the H-chain CDR3 are shown in SEQ ID NO: 378 and SEQ ID NO: 377, respectively;
the amino acid sequence and the nucleotide sequence of the L-chain CDR1 are shown in SEQ ID NO: 380 and SEQ ID NO: 379, respectively;
the amino acid sequence and the nucleotide sequence of the L-chain CDR2 are shown in SEQ ID NO: 382 and SEQ ID NO: 381, respectively; and
the amino acid sequence and the nucleotide sequence of the L-chain CDR3 are shown in SEQ ID NO: 384 and SEQ ID NO: 383, respectively.

For the AL-225 antibody of the present invention:
the amino acid sequence and the nucleotide sequence of the H-chain variable region (VH) are shown in SEQ ID NO: 626 and SEQ ID NO: 625, respectively;
the amino acid sequence and the nucleotide sequence of the L-chain variable region (VL) are shown in SEQ ID NO: 628 and SEQ ID NO: 627, respectively;
the amino acid sequence and the nucleotide sequence of the H-chain CDR1 are shown in SEQ ID NO: 390 and SEQ ID NO: 389, respectively;
the amino acid sequence and the nucleotide sequence of the H-chain CDR2 are shown in SEQ ID NO: 392 and SEQ ID NO: 391, respectively;
the amino acid sequence and the nucleotide sequence of the H-chain CDR3 are shown in SEQ ID NO: 394 and SEQ ID NO: 393, respectively;
the amino acid sequence and the nucleotide sequence of the L-chain CDR1 are shown in SEQ ID NO: 396 and SEQ ID NO: 395, respectively;
the amino acid sequence and the nucleotide sequence of the L-chain CDR2 are shown in SEQ ID NO: 398 and SEQ ID NO: 397, respectively; and
the amino acid sequence and the nucleotide sequence of the L-chain CDR3 are shown in SEQ ID NO: 400 and SEQ ID NO: 399, respectively.

For the AL-226 antibody of the present invention:
the amino acid sequence and the nucleotide sequence of the H-chain variable region (VH) are shown in SEQ ID NO: 630 and SEQ ID NO: 629, respectively;

the amino acid sequence and the nucleotide sequence of the L-chain variable region (VL) are shown in SEQ ID NO: 632 and SEQ ID NO: 631, respectively;

the amino acid sequence and the nucleotide sequence of the H-chain CDR1 are shown in SEQ ID NO: 406 and SEQ ID NO: 405, respectively;

the amino acid sequence and the nucleotide sequence of the H-chain CDR2 are shown in SEQ ID NO: 408 and SEQ ID NO: 407, respectively;

the amino acid sequence and the nucleotide sequence of the H-chain CDR3 are shown in SEQ ID NO: 410 and SEQ ID NO: 409, respectively;

the amino acid sequence and the nucleotide sequence of the L-chain CDR1 are shown in SEQ ID NO: 412 and SEQ ID NO: 411, respectively;

the amino acid sequence and the nucleotide sequence of the L-chain CDR2 are shown in SEQ ID NO: 414 and SEQ ID NO: 413, respectively; and the amino acid sequence and the nucleotide sequence of the L-chain CDR3 are shown in SEQ ID NO: 416 and SEQ ID NO: 415, respectively.

For the AL-227 antibody of the present invention:

the amino acid sequence and the nucleotide sequence of the H-chain variable region (VH) are shown in SEQ ID NO: 634 and SEQ ID NO: 633, respectively;

the amino acid sequence and the nucleotide sequence of the L-chain variable region (VL) are shown in SEQ ID NO: 636 and SEQ ID NO: 635, respectively;

the amino acid sequence and the nucleotide sequence of the H-chain CDR1 are shown in SEQ ID NO: 422 and SEQ ID NO: 421, respectively;

the amino acid sequence and the nucleotide sequence of the H-chain CDR2 are shown in SEQ ID NO: 424 and SEQ ID NO: 423, respectively;

the amino acid sequence and the nucleotide sequence of the H-chain CDR3 are shown in SEQ ID NO: 426 and SEQ ID NO: 425, respectively;

the amino acid sequence and the nucleotide sequence of the L-chain CDR1 are shown in SEQ ID NO: 428 and SEQ ID NO: 427, respectively;

the amino acid sequence and the nucleotide sequence of the L-chain CDR2 are shown in SEQ ID NO: 430 and SEQ ID NO: 429, respectively; and the amino acid sequence and the nucleotide sequence of the L-chain CDR3 are shown in SEQ ID NO: 432 and SEQ ID NO: 431, respectively.

For the AL-228 antibody of the present invention:

the amino acid sequence and the nucleotide sequence of the H-chain variable region (VH) are shown in SEQ ID NO: 638 and SEQ ID NO: 637, respectively;

the amino acid sequence and the nucleotide sequence of the L-chain variable region (VL) are shown in SEQ ID NO: 640 and SEQ ID NO: 639, respectively;

the amino acid sequence and the nucleotide sequence of the H-chain CDR1 are shown in SEQ ID NO: 438 and SEQ ID NO: 437, respectively;

the amino acid sequence and the nucleotide sequence of the H-chain CDR2 are shown in SEQ ID NO: 440 and SEQ ID NO: 439, respectively;

the amino acid sequence and the nucleotide sequence of the H-chain CDR3 are shown in SEQ ID NO: 442 and SEQ ID NO: 441, respectively;

the amino acid sequence and the nucleotide sequence of the L-chain CDR1 are shown in SEQ ID NO: 4-44 and SEQ ID NO: 443, respectively;

the amino acid sequence and the nucleotide sequence of the L-chain CDR2 are shown in SEQ ID NO: 446 and SEQ ID NO: 445, respectively; and the amino acid sequence and the nucleotide sequence of the L-chain CDR3 are shown in SEQ ID NO: 448 and SEQ ID NO: 447, respectively.

For the AL-229 antibody of the present invention:

the amino acid sequence and the nucleotide sequence of the H-chain variable region (VH) are shown in SEQ ID NO: 642 and SEQ ID NO: 641, respectively;

the amino acid sequence and the nucleotide sequence of the L-chain variable region (VL) are shown in SEQ ID NO: 644 and SEQ ID NO: 643, respectively;

the amino acid sequence and the nucleotide sequence of the H-chain CDR1 are shown in SEQ ID NO: 454 and SEQ ID NO: 453, respectively;

the amino acid sequence and the nucleotide sequence of the H-chain CDR2 are shown in SEQ ID NO: 456 and SEQ ID NO: 455, respectively;

the amino acid sequence and the nucleotide sequence of the H-chain CDR3 are shown in SEQ ID NO: 458 and SEQ ID NO: 457, respectively;

the amino acid sequence and the nucleotide sequence of the L-chain CDR1 are shown in SEQ ID NO: 460 and SEQ ID NO: 459, respectively;

the amino acid sequence and the nucleotide sequence of the L-chain CDR2 are shown in SEQ ID NO: 462 and SEQ ID NO: 461, respectively; and the amino acid sequence and the nucleotide sequence of the L-chain CDR3 are shown in SEQ ID NO: 464 and SEQ ID NO: 463, respectively.

For the AL-230 antibody of the present invention:

the amino acid sequence and the nucleotide sequence of the H-chain variable region (VH) are shown in SEQ ID NO: 646 and SEQ ID NO: 645, respectively;

the amino acid sequence and the nucleotide sequence of the L-chain variable region (VL) are shown in SEQ ID NO: 648 and SEQ ID NO: 647, respectively;

the amino acid sequence and the nucleotide sequence of the H-chain CDR1 are shown in SEQ ID NO: 470 and SEQ ID NO: 469, respectively;

the amino acid sequence and the nucleotide sequence of the H-chain CDR2 are shown in SEQ ID NO: 472 and SEQ ID NO: 471, respectively;

the amino acid sequence and the nucleotide sequence of the H-chain CDR3 are shown in SEQ ID NO: 474 and SEQ ID NO: 473, respectively;

the amino acid sequence and the nucleotide sequence of the L-chain CDR1 are shown in SEQ ID NO: 476 and SEQ ID NO: 475, respectively;

the amino acid sequence and the nucleotide sequence of the L-chain CDR2 are shown in SEQ ID NO: 478 and SEQ ID NO: 477, respectively; and the amino acid sequence and the nucleotide sequence of the L-chain CDR3 are shown in SEQ ID NO: 480 and SEQ ID NO: 479, respectively.

For the AL-231 antibody of the present invention:

the amino acid sequence and the nucleotide sequence of the H-chain variable region (VH) are shown in SEQ ID NO: 650 and SEQ ID NO: 649, respectively;

the amino acid sequence and the nucleotide sequence of the L-chain variable region (VL) are shown in SEQ ID NO: 652 and SEQ ID NO: 651, respectively;

the amino acid sequence and the nucleotide sequence of the H-chain CDR1 are shown in SEQ ID NO: 486 and SEQ ID NO: 485, respectively;

the amino acid sequence and the nucleotide sequence of the H-chain CDR2 are shown in SEQ ID NO: 488 and SEQ ID NO: 487, respectively;

the amino acid sequence and the nucleotide sequence of the H-chain CDR3 are shown in SEQ ID NO: 490 and SEQ ID NO: 489, respectively;

the amino acid sequence and the nucleotide sequence of the L-chain CDR1 are shown in SEQ ID NO: 492 and SEQ ID NO: 491, respectively;

the amino acid sequence and the nucleotide sequence of the L-chain CDR2 are shown in SEQ ID NO: 494 and SEQ ID NO: 493, respectively; and the amino acid sequence and the nucleotide sequence of the L-chain CDR3 are shown in SEQ ID NO: 496 and SEQ ID NO: 495, respectively.

For the AL-232 antibody of the present invention:

the amino acid sequence and the nucleotide sequence of the H-chain variable region (VH) are shown in SEQ ID NO: 654 and SEQ ID NO: 653, respectively;

the amino acid sequence and the nucleotide sequence of the L-chain variable region (VL) are shown in SEQ ID NO: 656 and SEQ ID NO: 655, respectively;

the amino acid sequence and the nucleotide sequence of the H-chain CDR1 are shown in SEQ ID NO: 502 and SEQ ID NO: 501, respectively;

the amino acid sequence and the nucleotide sequence of the H-chain CDR2 are shown in SEQ ID NO: 504 and SEQ ID NO: 503, respectively;

the amino acid sequence and the nucleotide sequence of the H-chain CDR3 are shown in SEQ ID NO: 506 and SEQ ID NO: 505, respectively;

the amino acid sequence and the nucleotide sequence of the L-chain CDR1 are shown in SEQ ID NO: 508 and SEQ ID NO: 507, respectively;

the amino acid sequence and the nucleotide sequence of the L-chain CDR2 are shown in SEQ ID NO: 510 and SEQ ID NO: 509, respectively; and the amino acid sequence and the nucleotide sequence of the L-chain CDR3 are shown in SEQ ID NO: 512 and SEQ ID NO: 511, respectively.

For the AL-233 antibody of the present invention:

the amino acid sequence and the nucleotide sequence of the H-chain variable region (VH) are shown in SEQ ID NO: 658 and SEQ ID NO: 657, respectively;

the amino acid sequence and the nucleotide sequence of the L-chain variable region (VL) are shown in SEQ ID NO: 660 and SEQ ID NO: 659, respectively;

the amino acid sequence and the nucleotide sequence of the H-chain CDR1 are shown in SEQ ID NO: 518 and SEQ ID NO: 517, respectively;

the amino acid sequence and the nucleotide sequence of the H-chain CDR2 are shown in SEQ ID NO: 520 and SEQ ID NO: 519, respectively;

the amino acid sequence and the nucleotide sequence of the H-chain CDR3 are shown in SEQ ID NO: 522 and SEQ ID NO: 521, respectively;

the amino acid sequence and the nucleotide sequence of the L-chain CDR1 are shown in SEQ ID NO: 524 and SEQ ID NO: 523, respectively;

the amino acid sequence and the nucleotide sequence of the L-chain CDR2 are shown in SEQ ID NO: 526 and SEQ ID NO: 525, respectively; and the amino acid sequence and the nucleotide sequence of the L-chain CDR3 are shown in SEQ ID NO: 528 and SEQ ID NO: 527, respectively.

The above-mentioned antibodies of (1) to (200) include not only monovalent antibodies but also multivalent antibodies with two or more valencies. The multivalent antibodies of the present invention include multivalent antibodies whose antigen binding sites are all the same and multivalent antibodies whose antigen binding sites are partially or completely different.

In a preferred embodiment, the above-mentioned antibody of (199) is an antibody with no modified CDRs. For example, the "antibody that comprises one or more amino acid substitutions, deletions, additions, and/or insertions in the antibody of (1), which has equivalent activity as the antibody of (1)" of the above-mentioned antibody of (199) is preferably "an antibody that has equivalent activity as the antibody of (1), and comprises one or more amino acid substitutions, deletions, additions, and/or insertions in the antibody of (1), and comprises an H chain having the amino acid sequence of SEQ ID NO: 6 as CDR1, the amino acid sequence of SEQ ID NO: 8 as CDR2, and the amino acid sequence of SEQ ID NO: 10 as CDR3". Another preferred antibody of the above-mentioned antibody of (199) can be expressed in a similar manner.

However, the above-mentioned antibody of (199) does not exclude an antibody in which CDR(s) is/are modified. Those skilled in the art can modify a CDR amino acid sequence without losing an equivalent activity. Amino acid mutations without losing an equivalent activity can be predicted, for example, using molecular modeling techniques.

Therefore, for the above-mentioned antibody of (199), an antibody having an equivalent activity as an antibody having an H-chain CDR and/or L-chain CDR of:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody, is expressed as follows:

an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, wherein the "antibody that has equivalent activity" comprises an H chain having:

as CDR1, the amino acid sequence of SEQ ID NO: a, or an amino acid sequence with one or several amino acid substitutions, deletions, additions and/or insertions in the amino acid sequence of SEQ ID NO: a;

as CDR2, the amino acid sequence of SEQ ID NO: b, or an amino acid sequence with one or several amino acid substitutions, deletions, additions and/or insertions in the amino acid sequence of SEQ ID NO: b;

as CDR3, the amino acid sequence of SEQ ID NO: c, or an amino acid sequence with one or several amino acid substitutions, deletions, additions and/or insertions in the amino acid sequence of SEQ ID NO: c;

an antibody that has equivalent activity as an antibody comprising an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises an L chain having:

as CDR1, the amino acid sequence of SEQ ID NO: d, or an amino acid sequence with one or several amino acid substitutions, deletions, additions and/or insertions in the amino acid sequence of SEQ ID NO: d;
as CDR2, the amino acid sequence of SEQ ID NO: e, or an amino acid sequence with one or several amino acid substitutions, deletions, additions and/or insertions in the amino acid sequence of SEQ ID NO: e;
as CDR3, the amino acid sequence of SEQ ID NO: f, or an amino acid sequence with one or several amino acid substitutions, deletions, additions and/or insertions in the amino acid sequence of SEQ ID NO: f; or
an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, and an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises:
an H chain having:
as CDR1, the amino acid sequence of SEQ ID NO: a, or an amino acid sequence with one or several amino acid substitutions, deletions, additions and/or insertions in the amino acid sequence of SEQ ID NO: a;
as CDR2, the amino acid sequence of SEQ ID NO: b, or an amino acid sequence with one or several amino acid substitutions, deletions, additions and/or insertions in the amino acid sequence of SEQ ID NO: b;
as CDR3, the amino acid sequence of SEQ ID NO: c, or an amino acid sequence with one or several amino acid substitutions, deletions, additions and/or insertions in the amino acid sequence of SEQ ID NO: c
and
an L chain having:
as CDR1, the amino acid sequence of SEQ ID NO: d, or an amino acid sequence with one or several amino acid substitutions, deletions, additions and/or insertions in the amino acid sequence of SEQ ID NO: d;
as CDR2, the amino acid sequence of SEQ ID NO: e, or an amino acid sequence with one or several amino acid substitutions, deletions, additions and/or insertions in the amino acid sequence of SEQ ID NO: e;
as CDR3, the amino acid sequence of SEQ ID NO: f, or an amino acid sequence with one or several amino acid substitutions, deletions, additions and/or insertions in the amino acid sequence of SEQ ID NO: f.

The antibody of (199) for each of the above antibodies can be expressed by referring to the amino acid SEQ ID NO of H chain CDR1 for "a" above, the amino acid SEQ ID NO of H chain CDR2 for "b" above, the amino acid SEQ ID NO of H chain CDR3 for "c" above, the amino acid SEQ ID NO of L chain CDR1 for "d" above, the amino acid SEQ ID NO of L chain CDR2 for "e" above, the amino acid SEQ ID NO of L chain CDR3 for "f" above. For example, the antibody of (199) for an antibody having equivalent activity as an antibody that has the H chain CDR and/or L chain CDR of the AL-201 antibody can be expressed as follows:

an antibody that has equivalent activity as an antibody comprising an H chain having the amino acid sequence of SEQ ID NO: 6 as CDR1, the amino acid sequence of SEQ ID NO: 8 as CDR2, and the amino acid sequence of SEQ ID NO: 10 as CDR3, wherein the "antibody that has equivalent activity" comprises an H chain having:
as CDR1, the amino acid sequence of SEQ ID NO: 6, or an amino acid sequence with one or several amino acid substitutions, deletions, additions and/or insertions in the amino acid sequence of SEQ ID NO: 6;
as CDR2, the amino acid sequence of SEQ ID NO: 8, or an amino acid sequence with one or several amino acid substitutions, deletions, additions and/or insertions in the amino acid sequence of SEQ ID NO: 8;
as CDR3, the amino acid sequence of SEQ ID NO: 10, or an amino acid sequence with one or several amino acid substitutions, deletions, additions and/or insertions in the amino acid sequence of SEQ ID NO: 10;
an antibody that has equivalent activity as an antibody comprising an L chain having the amino acid sequence of SEQ ID NO: 12 as CDR1, the amino acid sequence of SEQ ID NO: 14 as CDR2, and the amino acid sequence of SEQ ID NO: 16 as CDR3, wherein the "antibody that has equivalent activity" comprises an L chain having:
as CDR1, the amino acid sequence of SEQ ID NO: 12, or an amino acid sequence with one or several amino acid substitutions, deletions, additions and/or insertions in the amino acid sequence of SEQ ID NO: 12;
as CDR2, the amino acid sequence of SEQ ID NO: 14, or an amino acid sequence with one or several amino acid substitutions, deletions, additions and/or insertions in the amino acid sequence of SEQ ID NO: 14;
as CDR3, the amino acid sequence of SEQ ID NO: 16, or an amino acid sequence with one or several amino acid substitutions, deletions, additions and/or insertions in the amino acid sequence of SEQ ID NO: 16; or
an antibody that has equivalent activity as an antibody comprising an H chain having the amino acid sequence of SEQ ID NO: 6 as CDR1, the amino acid sequence of SEQ ID NO: 8 as CDR2, and the amino acid sequence of SEQ ID NO: 10 as CDR3, and an L chain having the amino acid sequence of SEQ ID NO: 12 as CDR1, the amino acid sequence of SEQ ID NO: 14 as CDR2, and the amino acid sequence of SEQ ID NO: 16 as CDR3, wherein the "antibody that has equivalent activity" comprises:
an H chain having:
as CDR1, the amino acid sequence of SEQ ID NO: 6, or an amino acid sequence with one or several amino acid substitutions, deletions, additions and/or insertions in the amino acid sequence of SEQ ID NO: 6;
as CDR2, the amino acid sequence of SEQ ID NO: 8, or an amino acid sequence with one or several amino acid substitutions, deletions, additions and/or insertions in the amino acid sequence of SEQ ID NO: 8;
as CDR3, the amino acid sequence of SEQ ID NO: 10, or an amino acid sequence with one or several amino acid substitutions, deletions, additions and/or insertions in the amino acid sequence of SEQ ID NO: 10
and
an L chain having:
as CDR1, the amino acid sequence of SEQ ID NO: 12, or an amino acid sequence with one or several amino acid substitutions, deletions, additions and/or insertions in the amino acid sequence of SEQ ID NO: 12;
as CDR2, the amino acid sequence of SEQ ID NO: 14, or an amino acid sequence with one or several amino acid substitutions, deletions, additions and/or insertions in the amino acid sequence of SEQ ID NO: 14;
as CDR3, the amino acid sequence of SEQ ID NO: 16, or an amino acid sequence with one or several amino acid substitutions, deletions, additions and/or insertions in the amino acid sequence of SEQ ID NO: 16.

Furthermore, as mentioned above, regarding the antibodies in the embodiments mentioned below, the antibody of (199) for each of the antibodies can be expressed by referring to the amino acid SEQ ID NOs of VH, VL, CDR of:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody
for "a" to "h".

In the above antibodies in which CDRs are modified, "several" means, preferably five amino acids or less, more preferably four amino acids or less, more preferably three amino acids or less, more preferably two amino acids. The number of amino acids substituted, deleted, added, and/or inserted between two amino acid sequences can be identified by aligning the amino acid sequences using sequence analysis programs. The programs for alignment include, for example, FASTA (Lipman D J, Pearson W R (1985) Science 227 (4693):1435-1441; Pearson, W R., Lipman, D J (1988) Proc. Natl. Acad. Sci. USA 85 (8): 2444-2448), BLAST (Altschul et al (1990) J. Mol. Biol. 215:403-410; Altschul et al (1997) Nucleic Acids Res. 25: 3389-402).

It is known to those skilled in the art that, in the binding specificity or affinity of an antibody to an antigen, CDR3 plays a particularly important role. Thus, in the antibodies of (199), the CDR3 sequence is preferably conserved. Therefore, in a preferred embodiment, the antibody of (199) can be expressed as follows:

an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, wherein the "antibody that has equivalent activity" comprises an H chain having:
as CDR1, the amino acid sequence of SEQ ID NO: a, or an amino acid sequence with one or several amino acid substitutions, deletions, additions and/or insertions in the amino acid sequence of SEQ ID NO: a;
as CDR2, the amino acid sequence of SEQ ID NO: b, or an amino acid sequence with one or several amino acid substitutions, deletions, additions and/or insertions in the amino acid sequence of SEQ ID NO: b;
as CDR3, the amino acid sequence of SEQ ID NO: c;
an antibody that has equivalent activity as an antibody comprising an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises an L chain having:
as CDR1, the amino acid sequence of SEQ ID NO: d, or an amino acid sequence with one or several amino acid substitutions, deletions, additions and/or insertions in the amino acid sequence of SEQ ID NO: d;
as CDR2, the amino acid sequence of SEQ ID NO: e, or an amino acid sequence with one or several amino acid substitutions, deletions, additions and/or insertions in the amino acid sequence of SEQ ID NO: e;
as CDR3, the amino acid sequence of SEQ ID NO: f; or
an antibody that has equivalent activity as an antibody comprising an H chain having the amino acid sequence of SEQ ID NO: a as CDR1, the amino acid sequence of SEQ ID NO: b as CDR2, and the amino acid sequence of SEQ ID NO: c as CDR3, and an L chain having the amino acid sequence of SEQ ID NO: d as CDR1, the amino acid sequence of SEQ ID NO: e as CDR2, and the amino acid sequence of SEQ ID NO: f as CDR3, wherein the "antibody that has equivalent activity" comprises:
an H chain having:
as CDR1, the amino acid sequence of SEQ ID NO: a, or an amino acid sequence with one or several amino acid substitutions, deletions, additions and/or insertions in the amino acid sequence of SEQ ID NO: a;
as CDR2, the amino acid sequence of SEQ ID NO: b, or an amino acid sequence with one or several amino acid substitutions, deletions, additions and/or insertions in the amino acid sequence of SEQ ID NO: b;
as CDR3, the amino acid sequence of SEQ ID NO: c
and
an L chain having:
as CDR1, the amino acid sequence of SEQ ID NO: d, or an amino acid sequence with one or several amino acid substitutions, deletions, additions and/or insertions in the amino acid sequence of SEQ ID NO: d;
as CDR2, the amino acid sequence of SEQ ID NO: e, or an amino acid sequence with one or several amino acid substitutions, deletions, additions and/or insertions in the amino acid sequence of SEQ ID NO: e;
as CDR3, the amino acid sequence of SEQ ID NO: f.

Regarding the antibodies of (199), an antibody having equivalent activity as an antibody that has the VH and/or VL of:
AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody
can be expressed as follows:
an antibody that has equivalent activity as an antibody comprising an H chain having VH comprising the amino acid sequence of SEQ ID NO: g, wherein the "antibody that has equivalent activity" comprises an H chain having VH comprising an amino acid sequence in which one or several amino acids are substituted, deleted, added, and/or inserted in the amino acid sequence of SEQ ID NO: g;
an antibody that has equivalent activity as an antibody comprising an L chain having VL comprising the amino acid sequence of SEQ ID NO: h, wherein the "antibody that has equivalent activity" comprises an H chain having VL comprising an amino acid sequence in which one or several amino acids are substituted, deleted, added, and/or inserted in the amino acid sequence of SEQ ID NO: h;
or
an antibody that has equivalent activity as an antibody comprising an H chain having VH comprising the amino acid sequence of SEQ ID NO: g and an L chain having VL comprising the amino acid sequence of SEQ ID NO: h, wherein the "antibody that has equivalent activity" comprises
an H chain having VH comprising the amino acid sequence of SEQ ID NO: g, or an amino acid sequence in which one or several amino acids are substituted, deleted, added, and/or inserted in the amino acid sequence of SEQ ID NO: g, and
an L chain having VL comprising the amino acid sequence of SEQ ID NO: h, or an amino acid sequence in which one or several amino acids are substituted, deleted, added, and/or inserted in the amino acid sequence of SEQ ID NO: h.

The antibody of (199) for each of the above antibodies can be expressed by referring to the amino acid SEQ ID NO of VH for "g" above, and the amino acid SEQ ID NO of VL for "h" above. For example, the antibody of (199) for an antibody having equivalent activity as an antibody that has the VH and/or VL chain of the AL-201 antibody can be expressed as follows:

an antibody that has equivalent activity as an antibody comprising an H chain having VH comprising the amino acid sequence of SEQ ID NO: 530, wherein the "antibody that has equivalent activity" comprises an H chain having VH comprising an amino acid sequence in which one or several amino acids are substituted, deleted, added, and/or inserted in the amino acid sequence of SEQ ID NO: 530;

an antibody that has equivalent activity as an antibody comprising an L chain having VL comprising the amino acid sequence of SEQ ID NO: 532, wherein the "antibody that has equivalent activity" comprises an H chain having VL comprising an amino acid sequence in which one or several amino acids are substituted, deleted, added, and/or inserted in the amino acid sequence of SEQ ID NO: 532;

or an antibody that has equivalent activity as an antibody comprising an H chain having VH comprising the amino acid sequence of SEQ ID NO: 530 and an L chain having VL comprising the amino acid sequence of SEQ ID NO: 532, wherein the "antibody that has equivalent activity" comprises an H chain having VH comprising the amino acid sequence of SEQ ID NO: 530, or an amino acid sequence in which one or several amino acids are substituted, deleted, added, and/or inserted in the amino acid sequence of SEQ ID NO: 530, and an L chain having VL comprising the amino acid sequence of SEQ ID NO: 532, or an amino acid sequence in which one or several amino acids are substituted, deleted, added, and/or inserted in the amino acid sequence of SEQ ID NO: 532.

In the above antibodies in which VH and/or VL are modified, "several" means, preferably 50 amino acids or less, 30 amino acids or less, 20 amino acids or less, 15 amino acids or less, or 10 amino acids or less, more preferably nine, eight, seven, six, five, four, three, or two amino acids. As long as the equivalent activity is retained, the positions of the modified amino acids are not particularly limited; however, amino acids in FR are preferably modified.

Thus, in a preferred embodiment, among the antibodies of (199), an antibody having equivalent activity as an antibody that has the VH and/or VL of:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody can be expressed as follows:

an antibody that has equivalent activity as an antibody comprising an H chain having VH comprising the amino acid sequence of SEQ ID NO: a, wherein the "antibody that has equivalent activity" comprises an H chain having VH comprising an amino acid sequence in which one or several amino acids are substituted, deleted, added, and/or inserted in the amino acid sequence of SEQ ID NO: a, and the amino acid sequence of SEQ ID NO: b as CDR1, the amino acid sequence of SEQ ID NO: c as CDR2, and the amino acid sequence of SEQ ID NO: d as CDR3;

an antibody that has equivalent activity as an antibody comprising an L chain having VL comprising the amino acid sequence of SEQ ID NO: e, wherein the "antibody that has equivalent activity" comprises an L chain having VL comprising an amino acid sequence in which one or several amino acids are substituted, deleted, added, and/or inserted in the amino acid sequence of SEQ ID NO: e, and the amino acid sequence of SEQ ID NO: f as CDR1, the amino acid sequence of SEQ ID NO: g as CDR2, and the amino acid sequence of SEQ ID NO: h as CDR3;

or an antibody that has equivalent activity as an antibody comprising an H chain having VH comprising the amino acid sequence of SEQ ID NO: a and VL comprising the amino acid sequence of SEQ ID NO: e, wherein the "antibody that has equivalent activity" comprises:

an H chain having VH comprising the amino acid sequence of SEQ ID NO: a, or an amino acid sequence in which one or several amino acids are substituted, deleted, added, and/or inserted in the amino acid sequence of SEQ ID NO: a, and the amino acid sequence of SEQ ID NO: b as CDR1, the amino acid sequence of SEQ ID NO: c as CDR2, and the amino acid sequence of SEQ ID NO: d as CDR3, and an L chain having VL comprising the amino acid sequence of SEQ ID NO: e, or an amino acid sequence in which one or several amino acids are substituted, deleted, added, and/or inserted in the amino acid sequence of SEQ ID NO: e, and the amino acid sequence of SEQ ID NO: f as CDR1, the amino acid sequence of SEQ ID NO: g as CDR2, and the amino acid sequence of SEQ ID NO: h as CDR3.

The antibody of (199) for each of the above antibodies can be expressed by referring to the amino acid SEQ ID NO of VH for "a" above, the amino acid SEQ ID NO of H chain CDR1 for "b" above, the amino acid SEQ ID NO of H chain CDR2 for "c" above, the amino acid SEQ ID NO of H chain CDR3 for "d" above, the amino acid SEQ ID NO of VL for "e" above, the amino acid SEQ ID NO of L chain CDR1 for "f" above, the amino acid SEQ ID NO of L chain CDR2 for "g" above, the amino acid SEQ ID NO of L chain CDR3 for "h" above. For example, the antibody of (199) for an antibody having equivalent activity as an antibody that has the VH and/or VL of the AL-201 antibody can be expressed as follows:

an antibody that has equivalent activity as an antibody comprising an H chain having VH comprising the amino acid sequence of SEQ ID NO: 530, wherein the "antibody that has equivalent activity" comprises an H chain having VH comprising an amino acid sequence in which one or several amino acids are substituted, deleted, added, and or inserted in the amino acid sequence of SEQ ID NO: 530, and the amino acid sequence of SEQ ID NO: 6 as CDR1, the amino acid sequence of SEQ ID NO: 8 as CDR2, and the amino acid sequence of SEQ ID NO: 10 as CDR3;

an antibody that has equivalent activity as an antibody comprising an L chain having VL comprising the amino acid sequence of SEQ ID NO: 532, wherein the "antibody that has equivalent activity" comprises an L chain having VL comprising an amino acid sequence in which one or several amino acids are substituted, deleted, added, and or inserted in the amino acid sequence of SEQ ID NO: 532, and the amino acid sequence of SEQ ID NO: 12 as CDR1, the amino acid sequence of SEQ ID NO: 14 as CDR2, and the amino acid sequence of SEQ ID NO: 16 as CDR3;
or
an antibody that has equivalent activity as an antibody comprising an H chain having VH comprising the amino acid sequence of SEQ ID NO: 530 and VL comprising the amino acid sequence of SEQ ID NO: 532, wherein the "antibody that has equivalent activity" comprises:
an H chain having VH comprising the amino acid sequence of SEQ ID NO: 530, or an amino acid sequence in which one or several amino acids are substituted, deleted, added, and/or inserted in the amino acid sequence of SEQ ID NO: 530, and the amino acid sequence of SEQ ID NO: 6 as CDR1, the amino acid sequence of SEQ ID NO: 8 as CDR2, and the amino acid sequence of SEQ ID NO: 10 as CDR3,
and
an L chain having VL comprising the amino acid sequence of SEQ ID NO: 532, or an amino acid sequence in which one or several amino acids are substituted, deleted, added, and/or inserted in the amino acid sequence of SEQ ID NO: 532, and the amino acid sequence of SEQ ID NO: 12 as CDR1, the amino acid sequence of SEQ ID NO: 14 as CDR2, and the amino acid sequence of SEQ ID NO: 16 as CDR3.

In the modified antibodies that have the H chain CDR and/or L chain CDR, or VH and/or VL of:
AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody, the amino acid modifications are preferably conserved amino acid substitutions. Thus, in a preferred embodiment, in the antibodies described above, "conservative amino acid substitution" can be performed, instead of "substitution, deletion, addition, and/or insertion"

Methods for preparing a polypeptide having activity equivalent to that of a certain polypeptide that are well known to those skilled in the art include methods for introducing mutations into a polypeptide. For example, one skilled in the art can prepare an antibody having activity equivalent to that of an antibody of the present invention by introducing appropriate mutations into the antibody using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766) and such. Amino acid mutations may also occur naturally. The antibodies of the present invention also include an antibody that comprises an amino acid sequence with one or more amino acid mutations in the amino acid sequence of an antibody of the present invention, and which has activity equivalent to that of the antibody of the present invention.

Amino acid residues are preferably mutated into other amino acids that conserve the properties of the amino acid side chains. For example, amino acids are categorized as follows depending on the side chain properties: hydrophobic amino acids (A, I, L, M, F, P, W, Y, and V), hydrophilic amino acids (R, D, N, C, E, Q, G, H, K, S, and T), amino acids with aliphatic side chains (G, A, V, L, I, and P), amino acids with hydroxyl-containing side chains (S, T, and Y), amino acids with sulfur atom-containing side chains (C and M), amino acids with carboxylic acid- and amide-containing side chains (D, N, E, and Q), amino acids with basic side chains (R, K, and H), and amino acids with aromatic ring-containing side chains (H, F, Y, and W) (amino acids are represented by one-letter codes in parentheses). "Conservative amino acid substitution" refers to substitution of an amino acid with another amino acid with a conserved amino acid side chain characteristics. In the antibodies of (199), amino acid sequence mutations in an antibody are preferably "conservative amino acid substitutions".

A polypeptide having an amino acid sequence, in which one or more amino acid residues are modified (deleted, added, and/or substituted with other amino acids) in a certain amino acid sequence, is known to retain its original biological activity (function).

In addition to the above-mentioned modifications, the antibodies of the present invention may be conjugated to other substances as long as the activity is maintained. Examples of the substances include peptides, lipids, sugars and sugar chains, acetyl groups, and natural and synthetic polymers. These modifications may be performed to confer additional functions to the antibodies, or to stabilize the antibodies.

Antibodies in which several amino acid residues have been added to the amino acid sequence of an antibody of the present invention include fusion proteins containing the antibody. In the fusion proteins, the antibody is fused with another peptide or protein. Methods for producing a fusion protein can be carried out by ligating a polynucleotide encoding an antibody of the present invention in frame with a polynucleotide encoding another peptide or polypeptide, and inserting this into an expression vector, and expressing the fusion construct in a host. Techniques known to those skilled in the art can be used for this purpose. The peptides or polypeptides fused with an antibody of the present invention include, for example, known peptides such as FLAG (Hopp, T. P. et al., BioTechnology (1988) 6, 1204-1210), 6×His consisting of six histidine (His) residues, 10×His, Influenza hemagglutinin (HA), human c-myc fragments, VSV-GP fragments, p18HIV fragments, T7-tag, HSV-tag, E-tag, SV40T antigen fragments, lck tag, alpha-tubulin fragments, B-tag, and Protein C fragments; glutathione-S-transferase (GST); immunoglobulin constant regions; beta-galactosidase; and maltose-binding protein (MBP), etc. Commercially available polynucleotides encoding these peptides or polypeptides can be fused with polynucleotides encoding the antibodies of the present invention, and the fusion polypeptides can be produced by expressing the fusion polynucleotides thus prepared.

The antibodies of the present invention may differ in the amino acid sequence, molecular weight, presence or absence of sugar chains, structure and such, depending on the cell or host producing the antibodies or the purification method. However, as long as the obtained antibody has an activity equivalent to an antibody of the present invention, it is included in the present invention.

Herein, "equivalent activity" means that the antibody of interest has the same biological or biochemical activity as an antibody of the present invention. The "activity" of the present invention includes, for example, activity to specifically bind to A beta oligomers but not bind to A beta monomers, anti-neurotoxic activity, A beta amyloid fibril formation suppressing activity, anti-synaptic toxicity activity, anti-memory impairment activity, anti-A beta deposition activity, anti-thioflavin S-positive plaque formation activity, and anti-A beta oligomer acccumulation activity.

In a preferred embodiment, the "activity" of the present invention is activity to specifically bind to A beta oligomers but not bind to A beta monomers. As shown in the Example, the "activity to specifically bind to A beta oligomers but not bind to A beta monomer" is preferably assessed by dot blot or competitive ELISA. Specific methods of dot blot or competitive ELISA include methods described in the Examples. Furthermore, the binding activity towards A beta oligomers and monomers can be assessed by other immunodetection methods, for example, absorbance measurement, enzyme-linked immunosorbent assay (ELISA), enzyme immunoassay (EIA), radioimmunoassay (RIA), immunofluorescent method, etc. For example, in ELISA, an antibody is immobilized onto a plate, an antigen for the antibody is added to the plate, and a culture supernatant of antibody-producing cells or a purified antibody is added. Then, a secondary antibody that recognizes a primary antibody and that is tagged with an enzyme such as alkali phosphatase is added, and the plate is incubated. After washing, an enzyme substrate such as p-nitrophenyl phosphate is added to the plate, and the absorbance is measured to assess the antigen-binding ability of a sample of interest. The binding abilities for A beta oligomers and monomers are preferably measured by the same method; however, they can be measured by different methods. For example, the binding to A beta oligomers can be analysed using Biacore (GE Healthcare Sciences).

When the "activity" of the present invention is anti-neurotoxic activity, this activity can be assessed by, for example, culturing neurons with A beta in the presence or absence of an antibody, and measuring the A beta-induced cytotoxicity level inhibited by the antibody. A beta-induced cytotoxicity can be measured by, for example, live/dead two color fluorescent assay, measurement of the LDH amount derived from dead cells released into a medium. For the measurement of the LDH amount, for example, CytoTox96 (Promega) or such can be used. Specific methods for measuring anti-neurotoxic activity include the methods described in the Examples.

When the "activity" of the present invention is A beta amyloid fibril formation suppressing activity, this activity can be assessed, for example, by incubating an A beta solution with or without an antibody, and detecting the A beta amyloid fibril formation level suppressed by the antibody. The amount of A beta amyloid fibril is assessed, for example, by adding a ThT (Thioflavin T) solution to a culture, and the amount of ThT bound to amyloid fibrils with ThT fluoresence. Specific methods for measuring A beta amyloid fibril formation suppressing activity include the methods described in the Examples.

When the "activity" of the present invention is anti-synaptic toxicity activity, this activity can be assessed, for example, by detecting synaptic toxicity suppressing effect by antibody administration to mutant human APP gene-expressing mice (for example, Tg2576 mice, Taconics, USA). The assessment of synaptic toxicity can be performed by mouse memory impairment test, analysis of the number of swollen dystrophic neurites using an anti-synaptophysin antibody, immunofluorescent analysis of mouse brain sections using anti-synaptophysin or anti-drebrin antibodies. When the "activity" of the present invention is anti-memory impairment activity, this activity is assessed by memory impairment test using mutant APP gene-expressing mice. If the "activity" of the present invention is anti-A beta deposition activity, anti-thioflavin S-positive plaque formation activity, or anti-A beta oligomer accumulation activity, these activities can be assessed by antibody administration test using mutant APP gene-expressing mice.

Specific methods for measuring the anti-memory impairment activity, anti-synaptic toxicity activity, anti-A beta deposition activity, anti-thioflavin S-positive plaque formation activity, and anti-A beta oligomer accumulation activity include the following method.

Female non-transgenic (non-Tg) mice for control, and Tg2576 mice having and over-expressing the Swedish-type mutant human APP gene with dual mutations (K670N and M671L) derived from familial AD are administered with the antibody of the present invention (dosage within the range of 0.4 to 5.0 mg/kg/w) or PBS into the caudal vein. The mouse age at the initiation of administration is six months or later at which memory and learning impairments are expressed, for monitoring therapeutic effect; or four months for monitoring prophylactic effect. Antibody administration period is two months for monitoring therapeutic effect, and nine months for monitoring prophylactic effect. To measure the anti-memory impairment activity, the following three behavioral paradigms are analysed after the antibody administration period (Mouri A, FASEB J, 21: 2135-2148, 2007): (1) Y-maze test for short-term memory; (2) novel object recognition test; (3) contextual fear conditioning test. To assess the other activities, mice are sacrificed after the behavioral analysis, and the brain hemispheres are sliced into 10 to 30-micro m-thick sagittal sections using a cryotome (RM 2145; Leica, Wetzlar, Germany). To observe thioflavin S-positive plaque formation, thioflavin S staining is performed as described in Wyss-Coray et al., 2001. The formation of swollen dystrophic neurites is observed using an anti-synaptophysin antibody (Chemicon, Temecula, Calif.). For each mouse, the number of thioflavin S-positive plaques and synaptophysin-positive swollen dystrophic neurites are calculated in four or five sections from a brain hemisphere at 40-fold magnification. To observe A beta deposition, serial sections briefly pre-treated with formic acid or Protease K are stained using an A beta immunostaining kit (Sigma, St. Louis, Mo.) or anti-A beta polyclonal antibody (Biosource), and immuno-positive signals are visualized using an ABC elite kit (Vector Laboratories). Images of the cerebral cortex and hippocampus are recorded using a digital camera connected with a microscope, and analyzed using a simple PCI software (Compix Imaging System, Lake Oswego, Oreg.). The number of thioflavin S-positive plaques and synaptophysin-positive swollen dystrophic neurites was determined in a double blind manner. Synaptic degeneration is observed by immunostaining using anti-synaptophysin or anti-drebrin antibodies. To assess the anti-A beta oligomer deposition activity, brain homogenates are prepared from the other brain hemisphere of the same mouse using the method by Kawarabayashi et al., J. Neuroscience 2001), and the amount of A beta oligomers is measured by SDS-PAGE and immunoblot analysis. For detection antibodies, commercially available anti-A beta oligomer monoclonal antibodies (e.g., 6E10, Covance Immuno-Technologies, Dedham, Mass.) or polyclonal antibodies (e.g., A11, Biosource, Carmarillo, Calif.) can be used.

The term "equivalent" in "equivalent activity" means that a value obtained as a biological or biochemical activity differs within 20% between two antibodies compared. The difference of the activity value is, preferably within 15%, within 10%, within 5%, or within 2.5%. Antibodies that bind to an epitope to which an antibody of any one of (1) to (198) above binds can be obtained by methods known to those skilled in the art. For example, the antibodies can be obtained by (i) determining the epitope bound by the antibody of any one of (1) to (198) using a conventional method, and producing the antibodies using a polypeptide comprising an amino acid sequence included in the epitope as an immunogen; or (ii)

determining the epitopes of antibodies produced by a conventional method, and selecting antibodies whose epitope is the same as that of the antibody of any one of (1) to (198).

The above-mentioned antibodies of (1) to (200) also include any type of antibodies such as the above-described minibodies, antibodies with modified amino acid sequences such as humanized antibodies and chimeric antibodies, non-human animal antibodies, human antibodies, modified antibodies conjugated to other molecules (for example, polymers such as polyethylene glycol), and sugar chain-modified antibodies.

In a preferred embodiment, the antibodies of the present invention include:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, and AL-233 antibody. These antibodies can be obtained by the method described in the Examples. Alternatively, the antibodies can be prepared based on their sequence information.

In a preferred embodiment, the antibodies of the present invention include modified antibodies such as chimeric antibodies or humanized antibodies. In a more preferred embodiment, the chimeric antibodies include antibodies comprise a variable region derived from:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody;
and a constant region derived from human immunoglobulin. In a more preferred embodiment, humanized antibodies include antibodies comprise CDR derived from: AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody;
and FR derived from human immunoglobulin, and a constant region derived from human immunoglobulin.

The above chimeric antibodies can be expressed as follows:
an antibody that comprises an H chain having VH comprising the amino acid sequence of SEQ ID NO: a, and CH of a human antibody;
an antibody that comprises an L chain having VL comprising the amino acid sequence of SEQ ID NO: b, and CL of a human antibody; or
an antibody that comprises an H chain having VH comprising the amino acid sequence of SEQ ID NO: a, and CH of a human antibody, and an L chain having VL comprising the amino acid sequence of SEQ ID NO: b, and CL of a human antibody.

Preferred embodiments of chimeric antibodies from each of the above antibodies can be expressed by referring to the amino acid SEQ ID NO of VH for "a" above, and the amino acid SEQ ID NO of VL for "b" above. For example, chimeric antibodies for the AL-201 antibody can be expressed as follows:
an antibody that comprises an H chain having VH comprising the amino acid sequence of SEQ ED NO: 530, and CH of a human antibody;
an antibody that comprises an L chain having VL comprising the amino acid sequence of SEQ ID NO: 532, and CL of a human antibody; or
an antibody that comprises an H chain having VH comprising the amino acid sequence of SEQ ID NO: 530, and CH of a human antibody, and an L chain having VL comprising the amino acid sequence of SEQ ID NO: 532, and CL of a human antibody.

The above humanized antibodies can be expressed as follows:
an antibody that comprises an H chain having CDR of VH comprising the amino acid sequence of SEQ ID NO: a, FR of VH of a human antibody, and CH of a human antibody;
an antibody that comprises an L chain having CDR of VL comprising the amino acid sequence of SEQ ID NO: b, FR of VL of a human antibody, and CL of a human antibody; or
an antibody that comprises an H chain having CDR of VH comprising the amino acid sequence of SEQ ID NO: a, FR of VH of a human antibody, and CH of a human antibody, and an L chain having CDR of VL comprising the amino acid sequence of SEQ ID NO: b, FR of VL of a human antibody, and CL of a human antibody.

Preferred embodiments of humanized antibodies from each of the above antibodies can be expressed by referring to the amino acid SEQ ID NO of VH for "a" above, and the amino acid SEQ ID NO of VL for "b" above. For example, humanized antibodies for the AL-201 antibody can be expressed as follows:
an antibody that comprises an H chain having CDR of VH comprising the amino acid sequence of SEQ ID NO: 530, FR of VH of a human antibody, and CH of a human antibody;
an antibody that comprises an L chain having CDR of VL comprising the amino acid sequence of SEQ ID NO: 532, FR of VL of a human antibody, and CL of a human antibody; or
an antibody that comprises an H chain having CDR of VH comprising the amino acid sequence of SEQ ID NO: 530, FR of VH of a human antibody, and CH of a human antibody, and an L chain having CDR of VL comprising the amino acid sequence of SEQ ID NO: 532, FR of VL of a human antibody, and CL of a human antibody.

The above modified antibodies can be produced using known methods.

Since the antigenicity of a chimeric antibody or a humanized antibody in the human body is reduced, such an antibody is useful for administration to humans for therapeutic purposes or such.

Chimeric antibodies are produced by combining sequences derived from different animals. Examples of chimeric antibodies include antibodies comprising the heavy-chain and light-chain variable regions of a mouse antibody and the heavy-chain and light-chain constant regions of a human antibody. The production of chimeric antibodies can be carried out using known methods (see, for example, Jones et al., Nature 321:522-5, 1986; Riechmann et al., Nature 332:323-7, 1988; and Presta, Curr. Opin. Struct. Biol. 2:593-6, 1992). For example, first, genes encoding the variable regions or CDRs of the antibody of interest are prepared from the RNAs of antibody-producing cells by polymerase chain reaction (PCR) or such (see, for example, Larrick et al., "Methods: a Companion to Methods in Enzymology", Vol. 2: 106, 1991; Courtenay-Luck, "Genetic Manipulation of Monoclonal Antibodies" in Monoclonal Antibodies: Production, Engineering and Clinical Application; Ritter et al. (eds.), page 166, Cambridge University Press, 1995, and Ward et al., "Genetic Manipulation and Expression of Antibodies" in Monoclonal Antibodies: Principles and Applications; and Birch et al. (eds.), page 137, Wiley-Liss, Inc., 1995). To prepare chimeric antibodies from any one of the AL-201 to AL-333 antibodies, a gene encoding a variable region or CDR can be synthesized based on the sequence information of each of the antibodies disclosed herein. The prepared genes encoding the variable regions or CDRs are linked to genes encoding the constant regions (e.g., human antibody constant regions) or framework regions (e.g., human antibody framework regions). The genes encoding the constant regions or framework regions may be determined in a manner similar to that for the variable region-encoding or CDR-encoding genes, or alternatively, they can be prepared based on the sequence information of known antibodies. DNA sequences encoding chimeric products and CDR-grafted products may be synthesized completely or partially using oligonucleotide synthesis techniques. For example, the oligonucleotide synthesis described by Jones et al. (Nature 321:522-5, 1986) may be performed. Furthermore, in some cases, site-directed mutagenesis and polymerase chain reaction techniques may be appropriately used. Techniques for oligonucleotide-specific mutagenesis of known variable regions described by Verhoeyen et al. (Science 239: 1534-6, 1988) and Riechmann et al. (Nature 332: 323-7, 1988) may be used for modifying the variable region sequences, for example, to enhance the binding ability of chimeric antibodies. Furthermore, if necessary, enzymatic fill-in of gapped oligonucleotides using T4 DNA polymerase may be performed, for example, as described by Queen et al. (Proc. Natl. Acad. Sci. USA 86: 10029-33, 1989; and WO 90/07861).

For example, CDR-grafting techniques are known in the art ("Immunoglobulin genes", Academic Press (London), pp 260-74, 1989; and Michael A et al., Proc. Natl. Acad. Sci. USA 91: 969-73, 1994). Using the techniques, the CDRs of a certain antibody are replaced with the CDRs of another antibody. Through such replacement, the binding specificity of the former antibody is changed to that of the latter antibody. Among such chimeric antibodies, those in which the framework amino acids are derived from a human antibody are called "humanized antibodies (CDR-grafted antibodies)". When using antibodies to treat humans, human antibodies or humanized antibodies are preferably utilized.

Generally, chimeric antibodies comprise the variable regions of a non-human mammal-derived antibody and the constant regions derived from a human antibody. On the other hand, humanized antibodies comprise the complementarity-determining regions (CDR) of a non-human mammal-derived antibody and the framework regions and constant regions derived from a human antibody.

After producing the chimeric antibodies or humanized antibodies, amino acids in the variable regions (for example, FRs) or the constant regions may be substituted with other amino acids.

The origin of the variable regions of the chimeric antibodies or the CDRs of the humanized antibodies is not particularly limited.

Human antibody-derived C-regions are used for the C-regions of the chimeric antibodies and humanized antibodies. For example, C gamma1, C gamma2, C gamma3, C gamma4, C mu, C delta, C alpha1, C alpha2, and C epsilon can be used for the H-chain C-regions, and C kappa and C lambda can be used for the L-chain C-regions. Their sequences are known. Furthermore, the human antibody C regions can be modified to improve the stability of the antibodies or their production.

The present invention provides polynucleotides encoding the above antibodies of the present invention or antigen-binding fragments thereof.

The polynucleotides of the present invention are not particularly limited as long as they encode the antibodies of the present invention, and may be a DNA or RNA. Furthermore, they may include a non-natural base. The polynucleotides of the present invention can be used for producing the antibodies of the present invention by genetic engineering techniques.

The polynucleotides of the present invention can be obtained by isolating mRNA from antibody-producing cells that produce an antibody of the present invention, obtaining cDNA by reverse transcription reaction, and amplifying the obtained cDNA by PCR or such, as described in the Examples.

In a preferred embodiment, the polynucleotides of the present invention include a polynucleotide encoding an antibody comprising the H chain CDR and/or L chain CDR of each of the following antibodies, or antigen-binding fragments thereof:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody.

In another embodiment, the polynucleotides of the present invention include a polynucleotide encoding an antibody comprising the VH and/or VL of each of the following antibodies, or antigen-binding fragments thereof:

AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, or AL-233 antibody.

In the above embodiments, the polynucleotides can be obtained by synthesizing the polynucleotides based on the amino acid sequence information of each of the above antibodies described herein.

Furthermore, the present invention provides vectors comprising the polynucleotides of the present invention. The vectors of the present invention are preferably expression vectors for expressing an antibody of the present invention in a host cell. The vectors of the present invention may be used for producing the antibodies of the present invention.

The vectors of the present invention preferably comprise a promoter sequence that enables expression in a host cell, in addition to a polypeptide of the present invention. Furthermore, they may comprise a signal sequence for secretion of an antibody of the present invention. Furthermore, they may comprise a marker gene for selection of a host cell into which a vector of the present invention has been introduced. The components comprised in the vectors are not limited thereto, and may be a suitable component appropriately selected by those skilled in the art.

For example, expression vectors for expression in *E. coli* include vectors that have "ori" for amplification in *E. coli*, and have a promoter such as lacZ promoter (Ward et al., Nature (1989) 341, 544-546; FASEB J. (1992) 6, 2422-2427), araB promoter (Better et al., Science (1988) 240, 1041-1043), or T7 promoter, and a marker gene such as a drug-resistance gene against ampicillin, tetracycline, kanamycin, chloramphenicol, etc. The vectors include M13 vectors, pUC vectors, pBR322, pBluescript, pCR-Script, etc. Furthermore, for a signal sequence, the pelB signal sequence (Lei, S. P. et al J. Bacteriol. (1987) 169, 4379) or such can be used.

The vectors of the present invention other than *E. coli* expression vectors include, for example, mammal-derived expression vectors (e.g., pcDNA3 (Invitrogen), pEGF-BOS (Nucleic Acids. Res. 1990, 18(17), p5322), pEF, pCDM8), insect cell-derived expression vectors (e.g, Bac-to-BAC baculovirus expression system (Gibco BRL), pBacPAK8), plant-derived expression vectors (e.g., pMH1, pMH2), animal virus-derived expression vectors (e.g., pHSV, pMV, pAdexLcw), retrovirus-derived expression vectors (e.g., paPneo), yeast-derived expression vectors (e.g., *Pichia* Expression Kit (Invitrogen)), pNV11, SP-Q01), and *Bacillus*-derived expression vectors (e.g., pPL608, pKTH50).

Expression vectors for expression in animal cells such as CHO cells, COS cells, NIH3T3 cells include vectors that have a promoter such as SV40 promoter (Mulligan et al., Nature (1979) 277, 108), MMTV-LTR promoter, EF1 alpha promoter (Mizushima et al., Nucleic Acids Res. (1990) 18, 5322), CMV promoter, or such; and a marker gene such as s drug-resistance gene against neomycin, G418, etc. These vectors include, for example, pMAM, pDR2, pBK-RSV, pBK-CMV, pOPRSV, pOP13, etc. As a signal sequence, any one of those described in the Examples can be used.

Furthermore, the present invention provides host cells that produce an antibody of the present invention or antigen-binding fragment thereof. The host cells include cells that have a polynucleotide of the present invention or a vector of the present invention. The host cells of the present invention may be used to produce the antibodies or antigen-binding fragments of the present invention.

The host cells of the present invention are not limited to hybridomas that produce an antibody of the present invention, and may be prokaryotes or eukaryotes into which a vector of the present invention has been introduced. When eukaryotes are used as host cells, for example, animal cells, plant cells, or fungal cells can be used. Animal cells include mammal cells (CHO (J. Exp. Med. (1995) 108, 945), COS, 3T3, myeloma, BHK (baby hamster kidney), HeLa, Vero cells, etc.), amphibian cells (*Xenopus oocytes* (Valle, et al., Nature (1981) 291, 358-340), etc.), insect cells (Sf9, Sf21, Tn5, etc.). As plant cells, for example, cells derived from *Nicotiana tabacum* are known as a protein expression system, and they may be cultured into callus and used. Fungal cells include, for example, yeast (e.g., the genus *Saccharomyces* (*Saccharomyces cerevisiae*, *Saccharomyces pombe*, etc.), filamentous fungi (e.g., the genus *Aspergillus* (*Aspergillus niger*, etc.). Prokaryotic cells include, for example, *E. coli* and *Bacillus*. Vectors can be introduced into host cell by calcium phosphate methods, DEAE dextran methods, methods using cationic liposome DOTAP (Boehringer Manheim), electroporation methods, lipofection methods, etc.

Furthermore, the present invention provides antibodies produced from the above host cells.

Furthermore, the present invention provides compositions comprising the above-mentioned antibody of the present invention and a pharmaceutically acceptable carrier.

As described below, the present invention strongly suggests that each of the following antibodies are promising candidates for therapeutic antibodies for preventing Alzheimer-like phenotypes:
AL-201 antibody, AL-202 antibody, AL-203 antibody, AL-204 antibody, AL-205 antibody, AL-206 antibody, AL-207 antibody, AL-208 antibody, AL-209 antibody, AL-210 antibody, AL-211 antibody, AL-212 antibody, AL-213 antibody, AL-214 antibody, AL-215 antibody, AL-216 antibody, AL-217 antibody, AL-218 antibody, AL-219 antibody, AL-220 antibody, AL-221 antibody, AL-222 antibody, AL-223 antibody, AL-224 antibody, AL-225 antibody, AL-226 antibody, AL-227 antibody, AL-228 antibody, AL-229 antibody, AL-230 antibody, AL-231 antibody, AL-232 antibody, and AL-233 antibody. Memory deterioration has been shown to be related to synaptic dysfunction caused by soluble A beta oligomers (Klein W L, 2001, Trends Neurosci; and Selkoe D J, 2002, Science). Excessive accumulation and deposition of A beta oligomers may trigger the complicated downstream cascades that cause Alzheimer's disease. Thus, therapeutic intervention using a composition comprising an antibody or antigen-binding fragment of the present invention and a pharmaceutically acceptable carrier could be effective for blocking the pathologic cascades, and thus this could enable the treatment of Alzheimer's disease (WO2009/051220, WO2009/099176, U.S. Ser. No. 12/533,294, and U.S. Ser. No. 12/533,348).

The "treatment" or "prevention" of the present invention does not necessarily have complete therapeutic or preventive effects against organs or tissues exhibiting symptoms of disorders or diseases, but may have partial effects or effects of suppressing the progression of symptoms.

"Treatment of Alzheimer's disease" in the present invention means amelioration or suppression of the progression of a symptom of at least one symptom that may be caused by Alzheimer's disease, and examples include amelioration or suppression of cognitive impairment, amelioration or suppression of senile plaque formation, amelioration or suppression of synaptic dysfunction, and reduction or suppression of A beta accumulation in brain tissues, blood, or such. Herein, "cognitive impairment" includes, for example, memory impairment including long term/short term memory impairment, object recognition memory impairment, spatial memory impairment, and associative and emotional memory impairment. Herein, "prevention of Alzheimer's disease" means suppression of at least one symptom that may be caused by Alzheimer's disease, and includes suppression of development of cognitive impairment, suppression of senile plaque formation, suppression of development of synaptic dysfunction, suppression of A beta accumulation in brain tissues, blood, or such.

The present invention provides pharmaceutical compositions or pharmaceutical agents which comprise as an active ingredient the above-described composition comprising an antibody or antigen-binding fragment of the present invention and a pharmaceutically acceptable carrier. The above pharmaceutical compositions or pharmaceutical agents are expressed as "pharmaceutical compositions or pharmaceutical agents containing a pharmaceutically acceptable carrier that comprise an antibody or antigen-binding fragment of the present invention as an active ingredient".

In the present invention, the phrase "comprising as an active ingredient the above-described composition comprising an antibody or antigen-binding fragment of the present invention and a pharmaceutically acceptable carrier", and "comprising as an active ingredient the above-described an antibody or antigen-binding fragment" mean comprising the above-described composition comprising an antibody or antigen-binding fragment of the present invention and a pharmaceutically acceptable carrier, or an antibody or antigen-binding fragment of the present invention as a major ingredient or a component that shows physiological activity or pharmacological function, but does not limit its content rate.

Examples of the above-mentioned pharmaceutical compositions include agents against cognitive impairment, Alzheimer's disease therapeutic agents, agents for suppressing the progression of Alzheimer's disease, agents for suppressing senile plaque formation, agents for suppressing A beta accumulation, anti-neurotoxic agents (agents for neutralizing neurotoxicity), agents for inhibiting A beta amyloid fibril formation, and anti-synaptic toxicity agents (agents for neutralizing synaptic toxicity).

The above-mentioned pharmaceutical composition of the present invention can be expressed, for example, as "methods for suppressing Alzheimer's disease" which comprise the step of administering to a subject (individual) the above-described composition comprising an antibody or antigen-binding fragment of the present invention and a pharmaceutically acceptable carrier. Alternatively, it can be expressed, for example, as "methods for suppressing Alzheimer's disease" which comprise the step of administering to a subject a therapeutically effective amount of the above-described antibody or antigen-binding fragment of the present invention. In other embodiments, examples include methods for suppressing cognitive impairment, methods for suppressing the progression of Alzheimer's disease, methods for suppressing senile plaque formation, methods for suppressing A beta accumulation, methods for neutralizing (suppressing) neurotoxic activity, methods for inhibiting A beta amyloid fibril formation, and methods for neutralizing (suppressing) synaptic toxicity. In further embodiments, examples include methods for preventing and/or treating cognitive impairment, and methods for preventing and/or treating Alzheimer's disease.

The present invention also provides use of a composition comprising the above-described antibody or antigen-binding fragment of the present invention and a pharmaceutically acceptable carrier in the production of the above-mentioned pharmaceutical composition. The present invention further provides use of the above-described antibody or antigen-binding fragment of the present invention in the production of the above-described pharmaceutical composition.

Furthermore, the present invention relates to the following antibodies or antigen-binding fragments.

The above-described antibody or antigen-binding fragment of the present invention and a pharmaceutically acceptable carrier for use in preventing and/or treating cognitive impairment.

The above-described antibody or antigen-binding fragment of the present invention for use in preventing and/or treating Alzheimer's disease.

The above-described antibody or antigen-binding fragment of the present invention for use in suppressing the progression of Alzheimer's disease.

The above-described antibody or antigen-binding fragment of the present invention for use in suppressing senile plaque formation.

The above-described antibody or antigen-binding fragment of the present invention for use in suppressing A beta accumulation.

The above-described antibody or antigen-binding fragment of the present invention for use in neutralizing (suppressing) neurotoxic activity.

The above-described antibody or antigen-binding fragment of the present invention for use in inhibiting A beta amyloid fibril formation.

The above-described antibody or antigen-binding fragment of the present invention for use in neutralizing (suppressing) synaptic toxicity.

The present invention also relates to the following:

Use of the above-described antibody or antigen-binding fragment of the present invention for preventing and/or treating cognitive impairment.

Use of the above-described antibody or antigen-binding fragment of the present invention for preventing and/or treating Alzheimer's disease.

Use of the above-described antibody or antigen-binding fragment of the present invention for suppressing the progression of Alzheimer's disease.

Use of the above-described antibody or antigen-binding fragment of the present invention for suppressing senile plaque formation.

Use of the above-described antibody or antigen-binding fragment of the present invention for suppressing A beta accumulation.

Use of the above-described antibody or antigen-binding fragment of the present invention for neutralizing (suppressing) neurotoxicity.

Use of the above-described antibody or antigen-binding fragment of the present invention for inhibiting A beta amyloid fibril formation.

Use of the above-described antibody or antigen-binding fragment of the present invention for neutralizing (suppressing) synaptic toxicity.

The above-mentioned pharmaceutical compositions or agents of the present invention can be administered to humans or other animals. In the present invention, non-human animals to which the pharmaceutical compositions or agents are administered include mice, rats, guinea pigs, rabbits, chickens, cats, dogs, sheep, pigs, cattle, monkeys, baboons, and chimpanzees. These animals preferably exhibit at least one symptom selected from, for example, cognitive impairment, senile plaque formation, synaptic dysfunction, A beta accumulation in brain tissues or blood, etc.

Antibodies or antigen-binding fragments contained in the pharmaceutical compositions of the present invention are not particularly limited as long as they are included in the above-mentioned antibodies or antigen-binding fragments of the present invention, and examples include the antibodies or antigen-binding fragments described herein.

When using the above-mentioned antibodies or antigen-binding fragments of the present invention for pharmaceutical compositions, they may be formulated by methods known to those skilled in the art. For example, as necessary, they can be prepared in the form of injectable sterile solutions or suspensions using water or another pharmaceutically acceptable liquid, and can be administered parenterally. For example, the antibodies or antigen-binding fragments to be included in the pharmaceutical compositions can be combined with pharmaceutically acceptable carriers or media, specifically, sterile water, physiological saline, vegetable oils, emulsifiers, suspensions, surfactants, stabilizers, flavoring agents, excipients, solvents, preservatives, binders, or such, and mixed into a unit dose form required for generally accepted pharmaceutical practice. The phrase "pharmaceutically acceptable" indicates that the substance is inactive, and contains conventional substances used as diluents or vehicles for pharmaceuticals. Suitable excipients and their formulations are described, for example, in Remington's Pharmaceutical Sciences, 16th ed. (1980) Mack Publishing Co., ed. Oslo et al.

Physiological saline and other isotonic solutions containing glucose or adjuvants (for example, D-sorbitol, D-mannose, D-mannitol, and sodium chloride) can be used as aqueous solutions for injection. They can be used together with appropriate solubilizers such as alcohols, more specifically, ethanol and polyalcohols (propylene glycol, polyethylene glycol, and such), and non-ionic surfactants (Polysorbate 80™, HCO-50, and such).

Sesame oil or soybean oil can be used as an oleaginous liquid, and benzyl benzoate or benzyl alcohol can be used in combination as a solubilizer. Buffers (for example, phosphate buffer and sodium acetate buffer), soothing agents (for example, procaine hydrochloride), stabilizers (for example, benzyl alcohol and phenol), and antioxidants can be used for the formulations. Prepared injection solutions can be filled into appropriate ampules.

The administration is preferably parenteral administration, and specific examples include administration by injection, transnasal administration, transpulmonary administration, and transdermal administration. Examples of administration by injection include systemic and local administration by intravenous injection, intramuscular injection, intraperitoneal injection, subcutaneous injection, and such.

The pharmaceutical compositions contain a pharmaceutically effective amount of the active component (the above-mentioned antibody of the present invention). "Pharmaceutically effective amount (of a compound)" refers to an amount sufficient for treating and/or preventing disorders in which antigens for the above-mentioned antibodies of the present invention play an important role. For example, "a pharmaceutically acceptable amount" may be an amount required for reducing A beta accumulation, neutralizing A beta-induced toxicity, reducing A beta fibril formation, or such, thereby treating or preventing conditions caused by Alzheimer's disease, when the compound is administered to individuals (patients). The reduction or neutralization may be, for example, a reduction or neutralization of at least approximately 5%, 10%, 20%, 30%, 40%, 50%, 75%, 80%, 90%, 95%, 99%, or 100%.

Assessment for determining such a pharmaceutically effective amount of the above-mentioned antibodies or antigen-binding fragments of the present invention may be carried out using a standard clinical protocol including histopathological diagnosis.

A suitable administration method may be selected depending on the age and symptoms of the patient. The dosage of an antibody-containing pharmaceutical composition may be selected, for example, within the range of 0.0001 mg to 1000 mg per kilogram body weight for each administration. Alternatively, for example, the dosage for each patient may be selected within the range of 0.001 to 100,000 mg/body; however, the dosage is not necessarily limited to these ranges. Although the dosage and administration methods vary depending on the patient's body weight, age, symptoms, and such, one skilled in the art can appropriately select them. The dosage may be selected based on the high-dose intravenous immunoglobulin therapy (400 mg/kg) covered by health insurance for humans.

In the present invention, the pharmaceutical compositions or agents comprising an antibody or antigen-binding fragment may be included in products and kits containing materials useful for treating pathological conditions of a subject. The products may comprise any labeled container for a compound. Suitable containers include bottles, vials, and test tubes. The containers may be formed from a variety of materials such as glass and plastic. The label on the container surface should indicate that the composition is used to treat or prevent one or more conditions of the disease. The label may also indicate descriptions for administration, and such.

In addition to the above-mentioned container, a kit containing a pharmaceutical composition or agent comprising an antibody or antigen-binding fragment may optionally include a second container that stores a pharmaceutically acceptable diluent. The kit may further include other materials desirable from a commercial and user's standpoint, including other buffers, diluents, filters, needles, syringes, and package inserts with descriptions for use.

If necessary, the pharmaceutical compositions may be provided in a pack or dispenser device that may contain one or more unit dosage forms comprising an active ingredient. The pack may comprise metal or plastic foil, and, for example, it is a blister pack. The pack or dispenser device may be accompanied by instructions for administration.

In the above-mentioned pharmaceutical agents and kits, besides the antibody or antigen-binding fragment of the present invention that is an active ingredient, sterile water, physiological saline, vegetable oils, surfactants, lipids, solubilizing agents, buffers, protein stabilizers (BSA, gelatin, etc.), preservatives, blocking solutions, reaction solutions, reaction quenching solutions, reagents for treating samples, and such, may be mixed as necessary.

Furthermore, the present invention provides methods for detecting A beta oligomers (examples include A beta40 (A beta 1-40), A beta42 (A beta 1-42) oligomers, and A beta40/A beta42 oligomers) in samples (specimens). Examples of "samples" of the present invention include samples collected from subjects, cell culture supernatants, cell extracts, samples collected from subject animals, or such; however, they are not particularly limited as long as they contain A beta oligomers. Specifically, the present methods include the step of detecting A beta oligomers contained in a sample (e.g., a sample collected from a subject) using an antibody or antigen-binding fragment of the present invention. A beta oligomers in a sample can be detected by common immunological detection methods, for example, using ELISA (sandwich solid-phase enzyme immunoassay methods that use chemiluminescence (chemiluminescence ELISA), etc.), RIA, immunoprecipitation methods that use the obtained antibodies, immunoblotting, flow cytometry, mass spectrometry, and immunohistochemical analysis.

When A beta oligomers are detected in a sample collected from a subject by the above-mentioned measurement methods, the subject is a possible Alzheimer's disease patient (WO2009/051220, WO2009/099176, U.S. Ser. No. 12/533, 294, and U.S. Ser. No. 12/533,348). Thus, the present invention also provides methods of diagnosing whether a subject is a possible Alzheimer's disease patient. For example, when the amount of A beta oligomers in a sample collected from a subject is compared with that from a healthy individual, and if the amount of A beta oligomers is greater in the subject than in the healthy individual, the subject is determined to be a possible Alzheimer's disease patient. Whether or not a subject is a possible Alzheimer's disease patient is diagnosed usually by physicians (including individuals under instructions from physicians; same herein below). Data on the amount of A beta oligomers in samples collected from a subject and a healthy individual, which are obtained by the present methods of diagnosis, will be useful for diagnosis by physicians. Therefore, the present methods of diagnosis can be expressed as methods of collecting and presenting data useful for diagnosis by physicians. Furthermore, "a method of diagnosing whether or not a subject is a possible Alzheimer's disease patient" is alternatively expressed as "a method of diagnosing whether or not a subject suffers from Alzheimer's disease, or is at a risk of developing Alzheimer's disease". Specifically, the present invention provides methods for diagnosing whether or not a subject is a possible Alzheimer's disease patient, wherein the methods comprise detecting A beta oligomers in a sample collected from the subject using an antibody or antigen-binding fragment of the present invention.

More specifically, the present invention provides a method of diagnosing whether or not a subject is a possible Alzheimer's disease patient, which comprises the steps of:

(a) contacting a sample collected from a subject with the antibody or antigen-binding fragment of the present invention; and (b) measuring the amount of A beta oligomer in the sample, wherein the subject is determined to be a possible Alzheimer's disease patient, when the amount measured in step (b) is higher than that of a healthy individual. Step (b) above can be alternatively expressed as "the step of detecting an A beta oligomer in the sample via the antibody or antigen-binding fragment of the present invention that has bound to an A beta oligomer in the sample".

Furthermore, the present invention provides methods of diagnosing whether or not a subject is a possible Alzheimer's disease patient, which comprise the steps of:

(a) contacting a sample collected from a subject with an antibody or antigen-binding fragment of the present invention and an antibody or antigen-binding fragment that binds to an A beta monomer; and (b) measuring the ratio of A beta oligomer to A beta monomer in the sample, wherein the subject is determined to be a possible Alzheimer's disease patient, if the ratio measured in step (b) is higher than that of a healthy individual.

First, in the present methods, a sample collected from a subject is contacted with an antibody or antigen-binding fragment of the present invention and an antibody or antigen-binding fragment that binds to an A beta monomer. Herein, "contact" may be carried out, for example, by adding each of the above-mentioned antibodies or antigen-binding fragments to a sample collected from a subject, which is placed in a test tube. In this case, the antibody or antigen-binding fragment is added suitably in the form of a solution, a solid obtained by freeze-drying, or such. When adding the antibody as an aqueous solution, the solution may purely contain the antibody alone, or may contain, for example, surfactants, excipients, coloring agents, flavors, preservatives, stabilizers, buffers, suspending agents, tonicity agents, binding agents, disintegrants, lubricants, fluidity promoters, or corrigents. The concentration at which the antibody is added is not particularly limited. For example, as with human immunoglobulin formulations, 500-mg, 1000-mg, and 2500-mg freeze-dried formulations and such may be suitably used. "Contact" may be performed, for example, by adding a sample to a carrier on which the above antibody or antigen-binding fragment has been immobilized. Preferred examples of the carrier on which the above antibody or antigen-binding fragment is immobilized include, for example, microplates, beads (magnetic beads, Sepharose beads, etc.

Next, the ratio of A beta oligomer to A beta monomer (herein, this is also referred to as "O/M index") in the aforementioned sample is measured. To measure this ratio, the measurement can be carried out using a method of comparing the oligomer and monomer ELISA values obtained from the same sample.

Then, this ratio is compared with the ratio for a healthy individual. When the ratio is higher in the subject than in the healthy individual, the subject is determined to be a possible Alzheimer's disease patient.

The methods of diagnosis of the present invention can be performed both in vitro and in vivo, but they are preferably performed in vitro.

Preferably, the "sample collected from a subject" of the present invention is not particularly limited as long as it is a tissue derived from a subject. Examples include the brain (brain parenchyma, and such), organs, and body fluids (blood, cerebrospinal fluid, and such) of a subject. In the present invention, the sample is preferably blood (more preferably, plasma) or cerebrospinal fluid. The "sample collected from a subject" includes a sample treated with an enzyme, treated using a column, treated by centrifugation, treated by extraction, after collection.

When the sample is a brain tissue, frozen tissue samples from the brain tissue may be homogenized and subjected to ultracentrifugation or such, to separate buffer-soluble fractions and buffer-insoluble fractions and measure A beta oligomers. For example, a brain tissue is homogenized in nine volumes of Tris-buffered saline (TS) containing a protease inhibitor cocktail, and the homogenates are ultracentrifuged at 265,000×g for 20 minutes. Then, a collected supernatant as a soluble fraction of the brain tissue can be used as a sample for immunoblotting, ELISA, RIA, immunoprecipitation, etc. A buffer-insoluble fraction may be solubilzed by formic acid (e.g., 70%) extraction, and used as a sample for immunoblotting, ELISA, RIA, immunoprecipitation, etc. Formic acid extracts may be appropriately neutralized or diluted with a buffer (e.g., 1 M Tris-HCl (pH 8.0)).

When A beta oligomers present in a brain tissue are visualized and measured by immunohistochemical methods, brain tissue sections from a subject can be used as samples. To enhance the immunoreactivity, the brain tissue sections can be pre-treated with Protease K. In immunohistochemical methods, it is not essential to quantify A beta oligomers in brain tissues. For example, if A beta deposition is observed, the subject is determined to be a possible Alzheimer's disease patient.

To increase the accuracy of A beta oligomer measurements, lipoproteins may be removed from a subject-derived sample. The depletion of lipoproteins can be performed by, for example, combining ultracentrifugation, ultrafiltration, and affinity chromatography. A specific method of depleting lipoproteins from a sample is exemplified below.

The density of a sample is adjusted to 1.25 g/ml with KBr. The sample is ultracentrifuged at 100,000 rpm and 16 degrees C. for eight hours. Lipoproteins floating at a density of 1.25 g/ml and lipoprotein-depleted clarified fluid are subjected to ultrafiltration using a 3 kDa cut-off membrane (Microcon 3; Arnicon, Inc), and then frozen and stored, or stored at 4 degrees C., until use. Lipoproteins are also removed by affinity chromatography using PHML-LIPOSORB (Calbiochem, La Jolla, Calif.). A sample and PHML-LIPOSORB (Calbiochem, La Jolla, Calif.) are combined at a ratio of 1.5:1, and mixed for 60 seconds. Then, the mixture is centrifuged at 3,000 rpm for ten minutes. The resulting supernatants can be used as lipoprotein-free samples. The lipoprotein-bound samples bound to PHML-LIPOSORB are eluted using 20 mM sodium deoxycholate. The removal of specific lipoproteins can be confirmed by 1% agarose gel electrophoresis, followed by staining with FAST-RED 7B (Wako, Osaka, Japan).

Furthermore, by size fractionation of A beta oligomers in a sample using size exclusion chromatography, ultrafiltration, or such, and subsequent detection of A beta oligomers in each fraction using the antibody or antigen-binding fragment of the present invention, the amount of A beta oligomer of each size in the sample can be measured. Fractionation by size exclusion chromatography can be performed by concentrating a subject-derived sample about ten-fold using a Microcon 3 kDa molecular weight cut-off filter (Millipore Corp.), and then applying the sample to a Superose 12 size exclusion column (1 cm×30 cm; Pharmacia Biotech., Uppsala, Sweden; flow rate of 0.5 ml/min) equilibrated with a phosphate buffer. Alternatively, fractionation by ultrafiltration can be performed by sequential ultrafiltration using Microcon 3 kDa, 10 kDa, 30 kDa, and 100 kDa cut-off membranes. The amount of A beta oligomer contained in each fraction can be measured by ELISA, RIA, immunoblotting, immunoprecipitation, etc.

The methods of measuring an A beta oligomer of the present invention are not particularly limited as long as they comprise the step of detecting an A beta oligomer in a sample using the antibodies or antigen-binding fragments of the present invention. Preferable methods include sandwich ELISA. When sandwich ELISA is performed, an antibody or antigen-binding fragment of the present invention may be immobilized or labeled. Alternatively, an antibody or antigen-binding fragment of the present invention may be used as a primary antibody, and a labeled secondary antibody can be bound to it. The other antibody used in sandwich ELISA may be an antibody or antigen-binding fragment of the present invention, or may be a commercially available anti-A beta antibody. A specific method of detecting A beta oligomers in a sample by sandwich ELISA is exemplified below.

Microplates are coated with an antibody or antigen-binding fragment of the present invention, and 100 micro 1 of a sample is added and incubated continuously for 24 hours at 4 degrees C. Then, horseradish peroxidase-conjugated BA27 Fab' fragment (anti-A beta1-40 specific to A beta40; Wako pure chemical, Osaka, Japan) or horseradish peroxidase-conjugated BCO5 Fab' fragment (anti-A beta35-43 specific to A beta42; Wako pure chemical, Osaka, Japan) is added and incubated at 4 degrees C. for 24 hours. The chemiluminescence generated using SuperSignal ELISA Pico Chemiluminescent Substrate (Pierce, Rockford, Ill., USA) is quantified by a Veritas Microplate Luminometer (Promega).

Furthermore, if a sample is immunoprecipitated using an antibody of the present invention, and then immunoblotting analysis is performed, the size of A beta oligomer contained in a sample can be identified without carrying out size fractionation by size exclusion chromatography, ultrafiltration, or such. A specific method is exemplified below.

Immunoprecipitation is conducted by incubating a sample with an antibody of the present invention and Protein G-Sepharose. The immunoprecipitated A beta oligomers are separated using an NuPAGE 4-12% Bis-Tris-Glycine gel, and transferred onto a nitrocellulose membrane or Immobilon P (Millipore) using 10 mM 3-cyclohexylamino-1-propane sulfonic acid (pH 11) containing 10% methanol at 400 mA for one hour. Non-specific binding sites on the membrane were blocked with a phosphate buffer containing 5% low-fat milk, 1% BSA, and 0.05% Tween-20 at room temperature for three hours. The A beta oligomers are detected by reaction with an antibody of the present invention, or a commercially available anti-A beta antibody such as 4G8 or 6E10 (Covance Immuno-Technologies, Dedham, Mass.).

Furthermore, to quantify the amount of A beta oligomer in a sample, a calibration curve may be prepared using standard samples containing a known concentration of A beta oligomer. A beta oligomers used for preparation of standard samples can be prepared by diluting a synthetic A beta (HCl form) dissolved in an HCl solution with PBS or such to a suitable concentration (e.g., 0.1 mg/ml), and incubating at 37 degrees C. for an hour. The incubation temperature and time for synthetic A beta can be suitably selected. In the methods of the present invention, to obtain the ratio of A beta oligomer to A beta monomer, a calibration curve may be also prepared for A beta monomers. A beta monomers used for preparation of standard A beta monomer samples can be prepared by diluting a synthetic A beta (TFA form) dissolved in TFA (trifluoroacetic acid) with PBS or such to a suitable concentration (e.g., 0.1 mg/ml). For synthetic A beta, A beta1-40, A beta1-42, or such can be used.

Furthermore, the present invention provides pharmaceutical agents (reagents) or kits for use in the above-mentioned methods of measuring A beta oligomers in a sample, or methods of diagnosing whether or not a subject is a possible Alzheimer's disease patient.

The pharmaceutical agents for use in the above-mentioned methods of measuring A beta oligomers, or methods of diagnosing whether or not a subject is a possible Alzheimer's disease patient include pharmaceutical agents comprising an antibody or antigen-binding fragment of the present invention. In a preferred embodiment, the pharmaceutical agents include antibody solutions and immobilized antibodies; however, they are not limited thereto. When the pharmaceutical agents are in a form of antibody solution, an antibody or antigen-binding fragment of the present invention is being dissolved in a suitable solvent. Those skilled in the art can select suitable solvents for dissolving the antibody or antigen-binding fragment of the present invention such as water, physiological saline, phosphate buffer, Tris buffer, etc. The above antibody solution of the present invention may comprise, in addition to an antibody of the present invention, a buffer, protein stabilizing agent, preservative agent, blocking agent, surfactant, solubilizing agent, or such, as necessary.

When the pharmaceutical agent of the present invention is an immobilized antibody, the antibody or antigen-binding fragment of the present invention is being carried by a suitable carrier. Examples of the carrier include microplates, beads (magnetic beads, Sepharose beads, etc.), nitrocellulose membranes, and such; however, they are not limited thereto. Those skilled in the art can select suitable carriers for immobilizing the antibodies of the present invention. Antibodies or antigen-binding fragments of the present invention can be bound to carriers using known methods.

Antibodies or antigen-binding fragments of the present invention comprised in the pharmaceutical agents may be suitably labeled with an enzyme label, radioactive label, fluorescent label, dye label, chemical luminescence label, etc.

The kits for use in the above-mentioned methods of measuring A beta oligomers, or methods of diagnosing whether or not a subject is a possible Alzheimer's disease patient include kits comprising pharmaceutical agents comprising an antibody or antigen-binding fragment of the present invention. Preferable examples of pharmaceutical agents comprising an antibody or antigen-binding fragment of the present invention are as mentioned above. The kits may comprise an antibody or antigen-binding fragment of the present invention in a form of lymphilized powder. In this case, kit users dissolve the lymphilized powder of antibody or antigen-binding fragment with a suitable solvent. The kits may comprise such a solvent for dissolving the antibody or antigen-binding fragment. The kits further comprise a dilution solution for diluting the above-mentioned antibody solutions.

The kits may comprise, in addition to a pharmaceutical agent comprising an antibody or antigen-binding fragment of the present invention, a reagent such as blocking agent, chromogenic reagent, chromogenic substrate, reaction termination solution, washing solution, buffer, primary antibody, secondary antibody, or such, as necessary. Those skilled in the art can select a suitable reagent depending on the A beta oligomer measurement method. For example, a sandwich ELISA kit comprising a microplate on which the antibody is immobilized may further comprise a labeled anti-A beta antibody, chromogenic substrate, reaction termination solution, washing solution, plate seal, etc. Furthermore, in a sandwich ELISA kit comprising an antibody solution of the present invention may further comprise a microplate on which an anti-A beta antibody is immobilized, chromogenic substrate, reaction termination solution, washing solution, plate seal, labeled secondary antibody (if the antibody of the present invention is not labeled), etc.

The kits may further comprise a standard sample for preparing a calibration curve of A beta oligomer. The standard sample may be a solution containing a known concentration of A beta oligomer. The kits may comprise a diluting solution for stepwise dilution of the standard solution. Alternatively, lymphilized powder of A beta oligomers may be included, and a solvent for dissolving the lymphilized powder may be comprised. Furthermore, the kits may comprise a solution or lymphilized powder of an A beta monomer, and kit uses may prepare an A beta oligomer standard solution by incubating the A beta monomer solution to polymerize A beta monomers.

When the kits are for use in methods of diagnosing whether or not a subject is a possible Alzheimer's disease patient, they may comprise a sample (a brain tissue, cerebrospinal fluid, blood, plasma, etc.) collected from a healthy individual as a negative control, and a sample collected from a AD brain patient as a positive control.

The kit may further include other materials desirable from a commercial and user's standpoint, including buffers, diluents, filters, needles, syringes, and attached documents including descriptions for use (instructions, CD-ROM, etc.). The pharmaceutical agents comprise a kit may be included in a container with a label. Such a container includes a bottle, vial, test tube, microtube, etc.

All prior art references cited herein are incorporated by reference into this description.

EXAMPLES

Hereinbelow, the present invention is specifically described with reference to the Examples, but it is not to be construed as being limited thereto.

Methods:
Preparation of Antigens
Synthetic A beta1-42 (Peptide Institute, Inc., Osaka) was dissolved in distilled deionized water or 10 mM phosphate buffer, and incubated at 37 degrees C. for 18 hours. Then, the peptides were separated using a NuPAGE 4-12% Tris-Glycine Gel SDS-PAGE, and after visualization by CBB staining, just the A beta1-42 tetramer was excised without contamination of the A beta1-42 monomer. Antigen was prepared by finely crushing the gel containing the tetramer or extracting the tetramer from the gel.

Preparation of Antibody-Producing Hybridomas
BALB/c mice were immunized by injecting the antigen prepared by the method described above into their foot pads or abdominal cavities. Then, booster immunization was carried out six times. Hybridomas were prepared from inguinal lymph node cells or spleen cells by fusion with Sp2/O—Ag14 cells using Polyethylene Glycol 1500.

ELISA Screening (Primary Screening)
Hybridoma culture supernatants were added to ELISA plates immobilized with A beta oligomers and reacted. Color development was carried out using TMB solution after reacting with HRP-conjugated anti-mouse IgG antibody. A beta oligomers used in this method is A beta1-40 (HCl form) after one hour incubation or above-described extracted antigens of A beta1-42 tetramer.

Dot Blot Analysis (Secondary Screening)
Dot blot analysis was carried out for hybridomas that gave positive result for primary screening. In this analysis, 0.1 micro g/dot of three types of A beta; synthesized A beta 1-40 (TFA form) as A beta monomer, synthesized A beta1-40 (HCl form) after 1 hour incubation as A beta oligomer, and synthesized A beta1-42, were immobilized onto nitrocellulose membrane and used. The membrane was blocked with Tris Buffer containing 5% low-fat milk and 0.05% Tween-20, and reacted with hybridoma culture supernatants and detected with chemiluminescence kit (ECL) after reacting with HRP-conjugated anti-mouse IgG antibody.

Antibody Isotyping
Isotyping of purified immunoglobulins were carried out using a Serotec (Oxford, UK) Mouse Monoclonal Antibody Isotyping Test Kit.

Identification of Antibody Sequences
RNAs were purified from hybridomas (1×10$^6$ cells) produced by the method described above using FastPure RNA Kit (TaKaRa, Japan). Using the RNAs as templates, cDNAs were synthesized using 5' RACE System (Invitrogen, USA) and primers specific to H chains or L chains of antibodies that are produced from each hybridomas. 3' side primer sequences that were used for cDNA syntheses are shown below.

```
H chain (G1) mIGC1Rv:
                                    (SEQ ID NO: 707)
AAGGCTTACAACCACAATCCCT H chain (G2a) mIGC2aRv:
                                    (SEQ ID NO: 708)
TGCTGGGCATTTGCATGGA H chain (G2b) mIGC2bRv:
                                    (SEQ ID NO: 709)
TGGGCATTTGTGACACTCC H chain (G3) mIGC3Rv:
                                    (SEQ ID NO: 710)
ACTGGGCTTGGGTATTCTAGG L chain (kappa) mIKCNRv1:
                                    (SEQ ID NO: 711)
GTCCAACTGTTCAGGACGCCATTTTGTCGTT L chain (lambda) mILCNRv1:
                                    (SEQ ID NO: 712)
TCCACAGTGTGACCTTCATGAGTGACC
```

Furthermore, using the cDNAs, VH and VL resions were amplified by PCR method. 3' side primer sequences specific to H chains or L chains used for PCR are shown below.

```
H chain mIGCNRv:
                                      (SEQ ID NO: 713)
ACAGGGATCCAGAGTTCCA L chain (kappa) mIKCNRv2:
                                      (SEQ ID NO: 714)
TAACTGCTCACTGGATGG L chain (lambda) mILCNRv2:
                                      (SEQ ID NO: 715)
AGTGTGGCCTTGTTAGTCTCGAGC
``` cDNA syntheses and PCR were carried out according to the manual attached to the product, and primers attached to the product (AAP: GGCCACGCGTCGACTAG-TACGGGGGGGGGG (SEQ ID NO: 716), AUAP: GGC-CACGCGTCGACTAGTAC (SEQ ID NO: 717)) were used as 5' side primers. Moreover, Taq DNA polymerase High Fidelity (Invitrogen, USA) was used for PCR.

VH and VL region fragments amplified by PCR was ligated with linear vector (pGEM™-T Easy Vector (Promega, USA)) for one hour and transformed into *E. coli* DH5 alpha strain. Formed colonies were cultured overnight in a liquid selection medium and plasmids were purified using High Purity Plasmid Miniprep System (MARIGEN BIOSCIENCES, USA). Antibody sequences were determined by gene sequence analysis using BigDye Terminator V3.1 Cycle Sequence Kit (Applied Biosystems) and 3730×1 DNA Analyzer (Applied Biosystems). Two primers described below were used for sequence analysis.

```
SP6:
                                      (SEQ ID NO: 718)
CGCCAGGGTTTTCCCAGTCACGAC

M13Rv:
                                      (SEQ ID NO: 719)
TCACACAGGAAACAGCTATGAC
```

Control Antibodies

Anti-A beta antibody 6E10 was used as a control antibody to compare to the antibodies of the present invention. Anti-A beta antibody 6E10 (Covance Immuno-Technologies, Dedham, Mass.) is a mouse monoclonal antibody that recognizes a sequence in A beta1-16 as an epitope, and has no selectivity against A beta oligomer (binds to A beta monomer).

Competitive ELISA

A beta oligomer antigens were prepared by diluting synthetic A beta1-40 (HCl form) at 0.1 mg/ml with PBS and incubating at 37 degrees C. for one hour. A beta monomer was prepared by diluting synthetic A beta1-40 (TFA form) at 0.1 mg/ml with PBS. First, 400 ng/well of A beta oligomer was immobilized onto 96-well immunopate and the plate was blocked with BSA. Next, antibodies of the present invention or a control anti-A beta antibody (6E10) were each mixed with serially-diluted A beta monomer or A beta oligomer at a range of 100 pg/ml to 100 micro g/ml and incubated for two hours, then each mixture was added to 96-well immunoplate and incubated at room temperature for ten minutes. Binding abilities of each antibodies to immobilized A beta oligomer were detected by reacting with HRP-conjugated anti-mouse IgG antibody and visualized by measuring absorbance at 450 nm using TMB solution. In the present method, two types of A beta1-40 (A beta1-40 monomer and A beta1-40 oligomer), which have the same sequence but have different structure and polymerization characters due to their structure, was compared as competitive substance. Accordingly, the method can compare the binding difference of the antibodies only derived from the existence of A beta1-40 polymerization, and thus can obtain extremely reliable results.

Analysis of Affinity to A Beta Oligomer

The analysis was carried out by Surface Plasmon Resonance (SPR) using Biacore 3000 (GE Healthcare Sciences). A beta oligomer was immobilized onto a sensor chip (CM5) as a ligand and antibodies of the present invention and control 6E10 antibody were used as analyte, kinetics analysis was carried out. Analysis was conducted at analyte antibodies at the following five concentrations: 1.25, 2.50, 5.00, 10.00, and 20.00 micro g/ml, and association rate constant (ka), dissociaton rate constant (kd), and dissociation constant (KD) was calculated using BiaEvaluation software. A beta oligomer used in the analysis was prepared by diluting synthetic A beta1-40 (HCl form) at 0.1 mg/ml with PBS and incubating at 37 degrees C. for one hour.

A Beta-Induced Neurotoxicity Assay

Human neuroblastoma cell (SH-SY5Y cell) was plated into 24-well plates at a density of 150,000 cells/well, and cultured for 24 hours in DMEM containing 10% FBS. Then, the medium was replaced a serum-free medium containing 12.5 micro M A beta1-42 in the presence or absence of antibodies and cells were cultured for another 24 hours. To determine the cytotoxicity induced by A beta1-42, LDH contents released into the medium from dead cells was determined using CytoTox96 Kit (manufactured by Promega).

Activity of Suppressing A Beta Amyloid Fibril Formation

A beta1-42 solution diluted to 12.5 micro M with cell culture medium was incubated in the presence or absence of antibodies of the present invention at 37 degrees C. for 24 hours. Then, the solutions were mixed with Thioflavin T (ThT) solution (5 micro M ThT, 50 mM Glycine-NaOH, pH8.5), ThT fluorescence intensity, which is correlated with A beta amyloid fibril contents, were determined using fluorescence spectrophotometer (RF-5300PC; Shimadzu Co., Kyoto, Japan). Excitation and emission wavelengths were set at 446 nm and 490 nm, respectively. Fluorescence intensity was measured immediately after the mixture was prepared.

Immunoblotting

Brain homogenates of Tg2576 or wild type mice were used for APP binding assay. The homogenates were electrophoresed in NuPAGE Tris-Glycine 4-12% gel and transferred to a PVDF membrane. The membrane was reacted to each antibody after blocking by PVDF blocking reagent (TOYOBO). The binding ability was detected by an HRP-conjugated anti-mouse IgG antibody and chemiluminescent reagent (Immobilon western, Millipore).

Result:

Selection of Anti-A Beta Oligomer Antibodies 67 mice were immunized with A beta tetramer antigen and inguinal lympho node or spleen were isolated from each mice. Cells derived from each organs were fused with myeloma (Sp2/O—Ag14) and dispensed into seven plates of 96-well plate per mice and cultured. Hybridomas producing the antibodies of interest were selected by adding culture supernatant from the 96-well plate onto ELISA plates immobilized with A beta oligomer, and reacting them to analyze. As a result, 45 positive cells were selected from 45,024 wells ((67 mice)×(7 plates)×(96 wells)).

The above-described ELISA screening also select antibodies that do not specifically bind to A beta oligomer (antibodies that bind to ELISA plate other than A beta oligomer). By performing dot blot analysis, these non-specific antibodies can be excluded. Accordingly, dot blot analysis using ELISA-positive cells were carried out. For dot blot analysis, two types of oligomers and A beta monomer were spotted and excluded non-specific antibodies (antibodies that do not bind to the spotted A beta oligomer were excluded), as well as specificity against A beta oligomer (absence of binding to A beta monomer) was confirmed. As a result, 33 positive antibodies among 45 ELISA-positive cells were selected (FIG. 1).

Identification of Antibody Sequences

The variable region sequences were analyzed by the above-mentioned method, for 33 antibodies (i.e., AL-201 to AL-233) selected by the above dot blot analysis. As a result, the following nucleotide sequences of regions comprising VH CDR1, CDR2, and were obtained:

SEQ ID NO: 1(AL-201), SEQ ID NO: 17(AL-202), SEQ ID NO: 33(AL-203), SEQ ID NO: 49(AL-204), SEQ ID NO: 65(AL-205), SEQ ID NO: 81(AL-206), SEQ ID NO: 97(AL-207), SEQ ID NO: 113(AL-208), SEQ ID NO: 129(AL-209), SEQ ID NO: 145(AL-210), SEQ ID NO: 161(AL-211), SEQ ID NO: 177(AL-212), SEQ ID NO: 193(AL-213), SEQ ID NO: 209(AL-214), SEQ ID NO: 225(AL-215), SEQ ID NO: 241(AL-216), SEQ ID NO: 257(AL-217), SEQ ID NO: 273 (AL-218), SEQ ID NO: 289(AL-219), SEQ ID NO: 305(AL-220), SEQ ID NO: 321(AL-221), SEQ ID NO: 337(AL-222), SEQ ID NO: 353(AL-223), SEQ ID NO: 369(AL-224), SEQ ID NO: 385(AL-225), SEQ ID NO: 401(AL-226), SEQ ID NO: 417(AL-227), SEQ ID NO: 433(AL-228), SEQ ID NO: 449(AL-229), SEQ ID NO: 465(AL-230), SEQ ID NO: 481 (AL-231), SEQ ID NO: 497(AL-232), and SEQ ID NO: 513(AL-233). From the above nucleotide sequence, the following amino acid sequences were obtained:

SEQ ID NO: 2(AL-201), SEQ ID NO: 18(AL-202), SEQ ID NO: 34(AL-203), SEQ ID NO: 50(AL-204), SEQ ID NO: 66(AL-205), SEQ ID NO: 82(AL-206), SEQ ID NO: 98(AL-207), SEQ ID NO: 114(AL-208), SEQ ID NO: 130(AL-209), SEQ ID NO: 146(AL-210), SEQ ID NO: 162(AL-211), SEQ ID NO: 178(AL-212), SEQ ID NO: 194(AL-213), SEQ ID NO: 210(AL-214), SEQ ID NO: 226(AL-215), SEQ ID NO: 242(AL-216), SEQ ID NO: 258(AL-217), SEQ ID NO: 274 (AL-218), SEQ ID NO: 290(AL-219), SEQ ID NO: 306(AL-220), SEQ ID NO: 322(AL-221), SEQ ID NO: 338(AL-222), SEQ ID NO: 354(AL-223), SEQ ID NO: 370(AL-224), SEQ ID NO: 386(AL-225), SEQ ID NO: 402(AL-226), SEQ ID NO: 418(AL-227), SEQ ID NO: 434(AL-228), SEQ ID NO: 450(AL-229), SEQ ID NO: 466(AL-230), SEQ ID NO: 482 (AL-231), SEQ ID NO: 498(AL-232), and SEQ ID NO: 514(AL-233).

Furthermore, the following nucleotide sequences of regions comprising VL CDR1, CDR2, and were obtained:

SEQ ID NO: 3(AL-201), SEQ ID NO: 19(AL-202), SEQ ID NO: 35(AL-203), SEQ ID NO: 51(AL-204), SEQ ID NO: 67(AL-205), SEQ ID NO: 83(AL-206), SEQ ID NO: 99(AL-207), SEQ ID NO: 115(AL-208), SEQ ID NO: 131(AL-209), SEQ ID NO: 147(AL-210), SEQ ID NO: 163(AL-211), SEQ ID NO: 179(AL-212), SEQ ID NO: 195(AL-213), SEQ ID NO: 211(AL-214), SEQ ID NO: 227(AL-215), SEQ ID NO: 243(AL-216), SEQ ID NO: 259(AL-217), SEQ ID NO: 275 (AL-218), SEQ ID NO: 291(AL-219), SEQ ID NO: 307(AL-220), SEQ ID NO: 323(AL-221), SEQ ID NO: 339(AL-222), SEQ ID NO: 355(AL-223), SEQ ID NO: 371(AL-224), SEQ ID NO: 387(AL-225), SEQ ID NO: 403(AL-226), SEQ ID NO: 419(AL-227), SEQ ID NO: 435(AL-228), SEQ ID NO: 451(AL-229), SEQ ID NO: 467(AL-230), SEQ ID NO: 483 (AL-231), SEQ ID NO: 499(AL-232), and SEQ ID NO: 515(AL-233). From the above nucleotide sequence, the following amino acid sequences were obtained:

SEQ ID NO: 4(AL-201), SEQ ID NO: 20(AL-202), SEQ ID NO: 36(AL-203), SEQ ID NO: 52(AL-204), SEQ ID NO: 68(AL-205), SEQ ID NO: 84(AL-206), SEQ ID NO: 100 (AL-207), SEQ ID NO: 116(AL-208), SEQ ID NO: 132(AL-209), SEQ ID NO: 148(AL-210), SEQ ID NO: 164(AL-211), SEQ ID NO: 180(AL-212), SEQ ID NO: 196(AL-213), SEQ ID NO: 212(AL-214), SEQ ID NO: 228(AL-215), SEQ ID NO: 244(AL-216), SEQ ID NO: 260(AL-217), SEQ ID NO: 276(AL-218), SEQ ID NO: 292(AL-219), SEQ ID NO: 308 (AL-220), SEQ ID NO: 324(AL-221), SEQ ID NO: 340(AL-222), SEQ ID NO: 356(AL-223), SEQ ID NO: 372(AL-224), SEQ ID NO: 388(AL-225), SEQ ID NO: 404(AL-226), SEQ ID NO: 420(AL-227), SEQ ID NO: 436(AL-228), SEQ ID NO: 452(AL-229), SEQ ID NO: 468(AL-230), SEQ ID NO: 484(AL-231), SEQ ID NO: 500(AL-232), and SEQ ID NO: 516(AL-233).

CDR sequences were determined from the amino acid sequences, based on the definition by Kabat (Kabat, Elvin A., Sequences of proteins of immunological interest 5th ed., National Institutes of Health, 1991). The CDR sequences of the antibodies are shown in Table 1. In Table 1, "Name" shows the name of each antibody, "class" shows the IgG subclass of each antibody, "chain" shows whether the chain is an H or L chain, and "(na)" means "nucleic acid". The L chain of AL-233 was a lambda chain, while that of the other antibodies was kappa chain.

TABLE 1

| Name | class | chain | CDR1 | SEQ ID NO | SEQ ID NO (na) | CDR2 | SEQ ID NO | SEQ ID NO (na) | CDR3 | SEQ ID NO | SEQ ID NO (na) |
|---|---|---|---|---|---|---|---|---|---|---|---|
| AL-201 | 2b | H | SYWMH | 6 | 5 | EINPSNGRTNYNEKFKS | 8 | 7 | QGYRHGYFAY | 10 | 9 |
|  |  | L | KASQSVSNDVA | 12 | 11 | YASNRYT | 14 | 13 | QQDYSSPT | 16 | 15 |
| AL-202 | 2a | H | SYGMS | 22 | 21 | TISSGGSYTYYPDSVKG | 24 | 23 | PLYYRHGVFAY | 26 | 25 |
|  |  | L | RASKSISKYLA | 28 | 27 | SGSTLQS | 30 | 29 | QQHNEYPWT | 32 | 31 |
| AL-203 | 1 | H | DYYMY | 38 | 37 | TISDGGSYTYYPDSVKG | 40 | 39 | AKYYRYDGGGAYAMDY | 42 | 41 |
|  |  | L | KSSQSVLYSSNQKNYLA | 44 | 43 | RASTRES | 46 | 45 | HQYSSYT | 48 | 47 |
| AL-204 | 1 | H | DYYMY | 54 | 53 | TISDGGSYTYYPDSVKG | 56 | 55 | AKYYRYDGGGAYAMDY | 58 | 57 |
|  |  | L | KSSQSVLYSSNQKNYLA | 60 | 59 | WASTRES | 62 | 61 | HQYLSSYT | 64 | 63 |
| AL-205 | 2a | H | NYWMN | 70 | 69 | EIRLKSNNATNYAESVKG | 72 | 71 | GTRVMLRREAWFAY | 74 | 73 |
|  |  | L | RASESVDNYGISFMN | 76 | 75 | AASNQGS | 78 | 77 | QQSKEVPWT | 80 | 79 |
| AL-206 | 2b | H | SDYAWN | 86 | 85 | YISYSGTTRYNPSLKS | 88 | 87 | YGSSYYWYFDV | 90 | 89 |
|  |  | L | TASSSVSSSYLH | 92 | 91 | STSNLAS | 94 | 93 | HQYHRSPPT | 96 | 95 |

TABLE 1-continued

| Name | class | chain | CDR1 | SEQ ID NO | SEQ ID NO (na) | CDR2 | SEQ ID NO | SEQ ID NO (na) | CDR3 | SEQ ID NO | SEQ ID NO (na) |
|---|---|---|---|---|---|---|---|---|---|---|---|
| AL-207 | 2b | H | TSGMGVG | 102 | 101 | HIWNDDDEYYNPSLKS | 104 | 103 | RAIHYYGYDAMDY | 106 | 105 |
|  |  | L | TASSSVSSSYLH | 108 | 107 | STSNLAS | 110 | 109 | HQYHRSPPT | 112 | 111 |
| AL-208 | 2b | H | SYWMH | 118 | 117 | EINPSNGRTNYNEKFKS | 120 | 119 | QGYRHGVFAY | 122 | 121 |
|  |  | L | TASSSVSSSYLH | 124 | 123 | STSNLAS | 126 | 125 | HQYHRSPPT | 128 | 127 |
| AL-209 | 2a | H | TSGMGVS | 134 | 133 | HLYWDDDKRYNPSLKS | 136 | 135 | YAKGFAY | 138 | 137 |
|  |  | L | KASQDINKYIA | 140 | 139 | YTSTLQP | 142 | 141 | LQYDNLYT | 144 | 143 |
| AL-210 | 2a | H | TSGMGVS | 150 | 149 | HIYHDDDKRYNPSLKS | 152 | 151 | RGDFDY | 154 | 153 |
|  |  | L | RSSQSLVHSNGNTYLH | 156 | 155 | KVSNRFS | 158 | 157 | SQSTHVPPT | 160 | 159 |
| AL-211 | 2b | H | TSGMGVG | 166 | 165 | HIWNDDDKYYNPSLKS | 168 | 167 | RSLSRDYFDY | 170 | 169 |
|  |  | L | RSSQSLVHSNGNTYLH | 172 | 171 | KVSNRFS | 174 | 173 | SQSTHVPLT | 176 | 175 |
| AL-212 | 2b | H | TSGMGVG | 182 | 181 | HIWNDDDKYYNPSLKS | 184 | 183 | STNITTFAY | 186 | 185 |
|  |  | L | RSSQSLVHSNGNTYLH | 188 | 187 | KVSNRFS | 190 | 189 | SQSTHVPLY | 192 | 191 |
| AL-213 | 2b | H | SYGVH | 198 | 197 | VIWRGGSTDYNAAFMS | 200 | 199 | NRYERGGYYAMDY | 202 | 201 |
|  |  | L | RSSQSIVHSNGNTYLE | 204 | 203 | KVSNRFS | 206 | 205 | FQGSHVPLT | 208 | 207 |
| AL-214 | 2b | H | SYGVH | 214 | 213 | VIWRGGSTDYNAAFMS | 216 | 215 | NRYERGGYYAMDY | 218 | 217 |
|  |  | L | RSSQSIVHSNGNTYLE | 220 | 219 | KVSNRFS | 222 | 221 | FQGSHVPLT | 224 | 223 |
| AL-215 | 2a | H | TSGMGVS | 230 | 229 | HIYWDDDKRYNPSLKS | 232 | 231 | YGNSFAY | 234 | 233 |
|  |  | L | RSSQSIVHSNGNTYLE | 236 | 235 | KVSNRFS | 238 | 237 | FQGSHYPLT | 240 | 239 |
| AL-216 | 2b | H | SYWMH | 246 | 245 | EINPSNGRTNYNEKFKS | 248 | 247 | EHYYGYAY | 250 | 249 |
|  |  | L | RSSQSIVHSNGNTYLE | 252 | 251 | KVSNRFS | 254 | 253 | FQGSHVPLT | 256 | 255 |
| AL-217 | 1 | H | TSGMGVS | 262 | 261 | HIYMDDDKRYNPSLKS | 264 | 263 | RGPSYYRYRDYFDY | 266 | 265 |
|  |  | L | RSSQSIVHSNGNTYLE | 268 | 267 | KVSNRFS | 270 | 269 | FQGSHVPLT | 272 | 271 |
| AL-218 | 2b | H | TSGMGVG | 278 | 277 | HIWMDDDKYYNPSLKS | 280 | 279 | RALYGYDAMDY | 282 | 281 |
|  |  | L | RSSQSIVHSNGNTYLE | 284 | 283 | KVSNRFS | 286 | 285 | FQGSHVPLT | 288 | 287 |
| AL-219 | 2b | H | TSGMGVS | 294 | 293 | HIYWDDDKRYNPSLKS | 296 | 295 | YRSGFAY | 298 | 297 |
|  |  | L | RSSQSIVHSNGNTYLE | 300 | 299 | KVSNRFS | 302 | 301 | FQGSHVPLT | 304 | 303 |
| AL-220 | 2b | H | SYWMH | 310 | 309 | EINPSNGRTNYNEKFKS | 312 | 311 | EHYYGYAY | 314 | 313 |
|  |  | L | RSSQSIVHSNGNTYLE | 316 | 315 | KVSNRFS | 318 | 317 | FQGSHYPYT | 320 | 319 |
| AL-221 | 2b | H | TSGMGVG | 326 | 325 | HIWNDDDKYYNPSLKS | 328 | 327 | RSLSRDYFDY | 330 | 329 |
|  |  | L | RSSQSIVHSNGNTYLE | 332 | 331 | KVSNRFS | 334 | 333 | FQGSHVPLT | 336 | 335 |
| AL-222 | 2b | H | TAGMGVG | 342 | 341 | HIWNDDDKYYNPSLKS | 344 | 343 | RGLYYGNYDAMDY | 346 | 345 |
|  |  | L | RSSQSIVHSNGNTYLE | 248 | 347 | KVSTRFS | 350 | 349 | FQGSRVPLT | 352 | 351 |
| AL-223 | 2a | H | TSGMGVG | 358 | 357 | HIWNDDDKYYNPSLKS | 360 | 359 | RALITTRDYFDY | 362 | 361 |
|  |  | L | RSSQSIVHSNGNTYLE | 364 | 363 | KVSNRFS | 366 | 365 | FQGSHYPLT | 368 | 367 |
| AL-224 | 2a | H | SFGMH | 374 | 373 | YISSGSTIYYADTVKG | 376 | 375 | YGNYAMDY | 378 | 377 |
|  |  | L | RSSQSIVHSNGNTYLE | 380 | 379 | KVSNRFS | 382 | 381 | FQGSHVPPY | 384 | 383 |
| AL-225 | 2a | H | TSGMGVG | 390 | 389 | HIWNDDDKYYNPSLKS | 392 | 391 | RGLIRQDYFDY | 394 | 393 |
|  |  | L | RSSQSIVHSNGNTYLE | 396 | 395 | KVSNRFS | 398 | 397 | FQGSHVPLT | 400 | 399 |
| AL-226 | 2b | H | TSGMGVS | 406 | 405 | HIYNDDDKRYNPSLKS | 408 | 407 | GDYRYDGAY | 410 | 409 |
|  |  | L | RSSQSLVHSNGNTYLH | 412 | 411 | KVSNRFS | 414 | 413 | SQSTHVPLT | 416 | 415 |
| AL-227 | 2a | H | TSGMGVS | 422 | 421 | HIYWDDDKRYNPSLKS | 424 | 423 | CYGNYGAMDY | 426 | 425 |
|  |  | L | RSSQSLVHSNGNTYLH | 428 | 427 | KVSNRFS | 430 | 429 | SQSTHVPLT | 432 | 431 |
| AL-428 | 2a | H | TSGMGVG | 438 | 437 | HIWNDDDKYYNPSLKS | 440 | 439 | RALLRLQGDYFDY | 442 | 441 |
|  |  | L | RSSQSIVHSNGNTYLE | 444 | 443 | KVSNRFS | 446 | 445 | FQGSHVPLT | 448 | 447 |
| AL-229 | 2b | H | TSGMGVS | 454 | 453 | HIYWDDDKRYNPSLKS | 456 | 455 | RGDFDY | 458 | 457 |
|  |  | L | RSSQSLVHSNGNTYLH | 460 | 459 | KVSNRFS | 462 | 461 | SQSTHVPPT | 464 | 463 |
| AL-230 | 2b | H | TSGMGVS | 470 | 469 | HIYWDDDKRYNPSLKS | 472 | 471 | YYYGLY | 474 | 473 |
|  |  | L | RSSQSIVHSNGNTYLE | 476 | 475 | KVSNRFS | 4.8 | 477 | FQGSHVPLT | 480 | 479 |
| AL-231 | 2a | H | TSGMGVG | 486 | 485 | HIWNDDDKYYNPSLKS | 488 | 487 | RALNWDVFDY | 490 | 489 |
|  |  | L | RSSQSIVHSNGNTYLE | 492 | 491 | KVSNRFS | 494 | 493 | FQGSHVPLT | 496 | 495 |

TABLE 1-continued

| Name | class | chain | CDR1 | SEQ ID NO | SEQ ID NO (na) | CDR2 | SEQ ID NO | SEQ ID NO (na) | CDR3 | SEQ ID NO | SEQ ID NO (na) |
|---|---|---|---|---|---|---|---|---|---|---|---|
| AL-232 | 3 | H | TSGMGVG | 502 | 501 | HIWNDDDKYYNPSLKS | 504 | 503 | RALYDYDAMDY | 506 | 505 |
|  |  | L | RSSQSIVHSNGNTYLE | 508 | 507 | KVSNRFS | 510 | 509 | RQGSHVPLT | 512 | 511 |
| AL-233 | 2b λ | H | SGYSWH | 518 | 517 | YIHYSGSTNYNPSLKS | 520 | 519 | RGYDGYYSWFAY | 522 | 521 |
|  |  | L | RSSTGAVTTSNYAN | 524 | 523 | GTNNRAP | 526 | 525 | ALWYSNHWV | 528 | 527 |

Some of the obtained VH and VL sequences contained signal peptides or lacked N-terminal or C-terminal sequences. If sequences are lacked, they are supplemented. Thus, the VH and VL sequences without signal sequences were determined based on the homology with previously-reported antibody sequences.

The VH amino acid sequences, excluding signal peptides, of each antibody are shown in the following sequence ID numbers:

SEQ ID NO: 530(AL-201), SEQ ID NO: 534(AL-202), SEQ ID NO: 538(AL-203), SEQ ID NO: 542(AL-204), SEQ ID NO: 546(AL-205), SEQ ID NO: 550(AL-206), SEQ ID NO: 554(AL-207), SEQ ID NO: 558(AL-208), SEQ ID NO: 562(AL-209), SEQ ID NO: 566(AL-210), SEQ ID NO: 570 (AL-211), SEQ ID NO: 574(AL-212), SEQ ID NO: 578(AL-213), SEQ ID NO: 582(AL-214), SEQ ID NO: 586(AL-215), SEQ ID NO: 590(AL-216), SEQ ID NO: 594(AL-217), SEQ ID NO: 598(AL-218), SEQ ID NO: 602(AL-219), SEQ ID NO: 606(AL-220), SEQ ID NO: 610(AL-221), SEQ ID NO: 614(AL-222), SEQ ID NO: 618(AL-223), SEQ ID NO: 622 (AL-224), SEQ ID NO: 626(AL-225), SEQ ID NO: 630(AL-226), SEQ ID NO: 634(AL-227), SEQ ID NO: 638(AL-228), SEQ ID NO: 642(AL-229), SEQ ID NO: 646(AL-230), SEQ ID NO: 650(AL-231), SEQ ID NO: 654(AL-232), and SEQ ID NO: 658(AL-233). The nucleotide sequences corresponding to the above amino acid sequences are shown in the following sequence ID numbers:

SEQ ID NO: 529(AL-201), SEQ ID NO: 533(AL-202), SEQ ID NO: 537(AL-203), SEQ ID NO: 541(AL-204), SEQ ID NO: 545(AL-205), SEQ ID NO: 549(AL-206), SEQ ID NO: 553(AL-207), SEQ ID NO: 557(AL-208), SEQ ID NO: 561(AL-209), SEQ ID NO: 565(AL-210), SEQ ID NO: 569 (AL-211), SEQ ID NO: 573(AL-212), SEQ ID NO: 577(AL-213), SEQ ID NO: 581(AL-214), SEQ ID NO: 585(AL-215), SEQ ID NO: 589(AL-216), SEQ ID NO: 593(AL-217), SEQ ID NO: 597(AL-218), SEQ ID NO: 601(AL-219), SEQ ID NO: 605(AL-220), SEQ ID NO: 609(AL-221), SEQ ID NO: 613(AL-222), SEQ ID NO: 617(AL-223), SEQ ID NO: 621 (AL-224), SEQ ID NO: 625(AL-225), SEQ ID NO: 629(AL-226), SEQ ID NO: 633(AL-227), SEQ ID NO: 637(AL-228), SEQ ID NO: 641(AL-229), SEQ ID NO: 645(AL-230), SEQ ID NO: 649(AL-231), SEQ ID NO: 653(AL-232), and SEQ ID NO: 657(AL-233).

The VL amino acid sequences, excluding signal peptides, of each antibody are shown in the following sequence ID numbers:

SEQ ID NO: 532(AL-201), SEQ ID NO: 536(AL-202), SEQ ID NO: 540(AL-203), SEQ ID NO: 544(AL-204), SEQ ID NO: 548(AL-205), SEQ ID NO: 552(AL-206), SEQ ID NO: 556(AL-207), SEQ ID NO: 560(AL-208), SEQ ID NO: 564(AL-209), SEQ ID NO: 568(AL-210), SEQ ID NO: 572 (AL-211), SEQ ID NO: 576(AL-212), SEQ ID NO: 580(AL-213), SEQ ID NO: 584(AL-214), SEQ ID NO: 588(AL-215), SEQ ID NO: 592(AL-216), SEQ ID NO: 596(AL-217), SEQ ID NO: 600(AL-218), SEQ ID NO: 604(AL-219), SEQ NO: 608(AL-220), SEQ ID NO: 612(AL-221), SEQ ID NO: 616 (AL-222), SEQ ID NO: 620(AL-223), SEQ ID NO: 624(AL-224), SEQ ID NO: 628(AL-225), SEQ ID NO: 632(AL-226), SEQ ID NO: 636(AL-227), SEQ ID NO: 640(AL-228), SEQ ID NO: 644(AL-229), SEQ ID NO: 648(AL-230), SEQ ID NO: 652(AL-231), SEQ ID NO: 656(AL-232), and SEQ ID NO: 660(AL-233). The nucleotide sequences corresponding to the above amino acid sequences are shown in the following sequence ID numbers:

SEQ ID NO: 531(AL-201), SEQ ID NO: 535(AL-202), SEQ ID NO: 539(AL-203), SEQ ID NO: 543(AL-204), SEQ ID NO: 547(AL-205), SEQ ID NO: 551(AL-206), SEQ ID NO: 555(AL-207), SEQ ID NO: 559(AL-208), SEQ ID NO: 563 (AL-209), SEQ ID NO: 567(AL-210), SEQ ID NO: 571(AL-211), SEQ ID NO: 575(AL-212), SEQ ID NO: 579(AL-213), SEQ ID NO: 583(AL-214), SEQ ID NO: 587(AL-215), SEQ ID NO: 591(AL-216), SEQ ID NO: 595(AL-217), SEQ ID NO: 599(AL-218), SEQ ID NO: 603(AL-219), SEQ ID NO: 607(AL-220), SEQ ID NO: 611(AL-221), SEQ ID NO: 615 (AL-222), SEQ ID NO: 619(AL-223), SEQ ID NO: 623(AL-224), SEQ ID NO: 627(AL-225), SEQ ID NO: 631(AL-226), SEQ ID NO: 635(AL-227), SEQ ID NO: 639(AL-228), SEQ ID NO: 643(AL-229), SEQ ID NO: 647(AL-230), SEQ ID NO: 651(AL-231), SEQ ID NO: 655(AL-232), and SEQ ID NO: 659(AL-233).

The amino acid sequences of H-chain signal peptides of each antibody are shown in the following sequence ID numbers:

SEQ ID NO: 662(AL-213, AL-214), SEQ ID NO: 664(AL-207), SEQ ID NO: 667(AL-211, AL-212, AL-215, AL-218, AL-221, AL-222, AL-223, AL-225, AL-227, AL-228, AL-229, AL-231, AL-232), SEQ ID NO: 669(AL-209), SEQ ID NO: 671(AL-224), SEQ ID NO: 673(AL-201, AL-208, AL-216, AL-220), SEQ ID NO: 675(AL-202), SEQ ID NO: 677(AL-203, AL-204), SEQ ID NO: 679(AL-210, AL-217, AL-219, AL-226, AL-230), SEQ ID NO: 681(AL-233), SEQ ID NO: 683(AL-206), and SEQ ID NO: 685(AL-205). The nucleotide sequences encoding H-chain signal peptides of each antibody are shown in the following sequence ID numbers:

SEQ ID NO: 661(AL-213, AL-214), SEQ ID NO: 663(AL-207), SEQ ID NO: 665(AL-215, AL-227, AL-229), SEQ ID NO: 666(AL-211, AL-212, AL-218, AL-221, AL-222, AL-223, AL-225, AL-228, AL-231, AL-232), SEQ ID NO: 668(AL-209), SEQ ID NO: 670(AL-224), SEQ ID NO: 672 (AL-201, AL-208, AL-216, AL-220), SEQ ID NO: 674(AL-202), SEQ ID NO: 676(AL-203, AL-204), SEQ ID NO: 678 (AL-210, AL-217, AL-219, AL-226, AL-230), SEQ ID NO: 680(AL-233), SEQ ID NO: 682(AL-206), and SEQ ID NO: 684(AL-205).

The amino acid sequences of L-chain signal peptides of each antibody are shown in the following sequence ID numbers:

SEQ ID NO: 687(AL-233), SEQ ID NO: 689(AL-206, AL-207, AL-208), SEQ ID NO: 691(AL-205), SEQ ID NO: 694(AL-203, AL-204), SEQ ID NO: 696(AL-228), SEQ ID NO: 698(AL-222), SEQ ID NO: 700(AL-210, AL-211, AL-212, AL-213, AL-214, AL-215, AL-216, AL-217, AL-218, AL-220, AL-221, AL-223, AL-224, AL-225, AL-226, AL-227, AL-229, AL-230, AL-231, AL-232), SEQ ID NO: 702(AL-201), SEQ ID NO: 704(AL-202), and SEQ ID NO: 706(AL-209). The nucleotide sequences encoding L-chain signal peptides of each antibody are shown in the following sequence ID numbers:
SEQ ID NO: 686(AL-233), SEQ ID NO: 688(AL-206, AL-207, AL-208), SEQ ID NO: 690(AL-205), SEQ ID NO: 692(AL-204), SEQ ID NO: 693(AL-203), SEQ ID NO: 695(AL-228), SEQ ID NO: 697(AL-222), SEQ ID NO: 699(AL-210, AL-211, AL-212, AL-213, AL-214, AL-215, AL-216, AL-217, AL-218, AL-220, AL-221, AL-223, AL-224, AL-225, AL-226, AL-227, AL-229, AL-230, AL-231, AL-232), SEQ ID NO: 701(AL-201), SEQ ID NO: 703(AL-202), and SEQ ID NO: 705(AL-209). The L-chain signal peptide sequence of AL-291 was not determined. An N-terminal portion of the L-chain signal peptide sequence of AL-228 was not determined.

Competitive ELISA Analysis

Dot blot analysis is a method for analyzing a reactivity against A beta monomer or oligomer immobilized onto nitrocellulose membrane. However, A betas are solubilized into fluids such as interstitial fluid, cerebral fluid, or blood. Then, the present analysis was carried out for investigating specific binding to A beta oligomers in solutions and difference of selectivity to A beta monomer. Competitive ELISA is a method for determining oligomer specificity by preliminarily reacting with antibodies to be measured and serially-diluted A beta monomer or oligomer in solutions, and carrying out ELISA by adding the solutions to a plate immobilized with A beta oligomer. When an antibody is an A beta oligomer-specific antibody, ELISA reaction decreases in an A beta oligomer concentration-dependent manner in a solution reacted with A beta oligomer, but does not decrease in a solution reacted with A beta monomer or decreases when A beta concentration becomes higher than the oligomer concentration. 19 antibodies were analyzed and the result shown in FIG. 2 was obtained. Eight antibodies (AL-213, 217, 220, 224, 225, 226, 229, and 233) showed high binding specificity even in the solution. Meanwhile, antibody that react with both A beta monomer and oligomer (6E10) used as a control showed equivalent ELISA reactivity against monomer and oligomer. $IC_{50}$ and A beta oligomer selectivity over A beta monomer (A beta monomer $IC_{50}$/A beta oligomer $IC_{50}$) calculated by the competitive ELISA are shown in Table 2.

TABLE 2

| Antibody Name | $IC_{50}$ (nmol/L) | | Selectivity (vs monomer) |
|---|---|---|---|
| | monomer | oligomer | |
| AL-209 | 532 | 87 | 6.1 |
| AL-210 | 1680 | 361 | 4.7 |
| AL-213 | 2200 | 74 | 29.7 |
| AL-215 | 1644 | 575 | 2.9 |
| AL-217 | >2200 | 4.48 | >491 |
| AL-218 | 1794 | 202 | 8.9 |
| AL-219 | 999 | 199 | 5.0 |
| AL-220 | >2200 | 1958 | >1.1 |
| AL-221 | 49 | 56 | 0.9 |
| AL-222 | 16 | 26 | 0.6 |
| AL-223 | 269 | 74 | 3.6 |
| AL-224 | >2200 | 3.8 | >579 |

TABLE 2-continued

| Antibody Name | $IC_{50}$ (nmol/L) | | Selectivity (vs monomer) |
|---|---|---|---|
| | monomer | oligomer | |
| AL-225 | >2200 | 10.3 | >214 |
| AL-226 | >2200 | 24.5 | >90 |
| AL-228 | 1073 | 56.5 | 19.0 |
| AL-229 | >2200 | 9.2 | >239 |
| AL-231 | 1652 | 561 | 2.9 |
| AL-232 | 1524 | 248 | 6.1 |
| AL-233 | >2200 | 31 | >71 |
| Control (6E10) | 6.84 | 7.58 | 0.9 |

Analysis of Affinity for A Beta Oligomer

To investigate the binding ability of the antibodies of the present invention to A beta oligomer, affinity was analyzed (see Methods). From eight antibodies that exhibit high specificity by the competitive ELISA, three antibodies were analyzed and results shown in FIG. 3 was obtained. Calculated association rate constant (ka), dissociation rate constant (kd), and dissociation constant (KD) was shown in Table 3.

TABLE 3

| Antibody Name | Kinetics assay (five dose) | | |
|---|---|---|---|
| | ka ($M^{-1}s^{-1}$) | kd ($s^{-1}$) | KD = kd/ka (M) |
| AL-217 | 1.91E+05 | 1.23E−03 | 6.44E−09 |
| AL-224 | 2.85E+05 | 0.155 | 5.44E−07 |
| AL-225 | 1.52E+05 | 0.0192 | 1.26E−07 |
| 6E10 | 5.78E+04 | 1.68E−04 | 2.91E−09 |

Assay of Neutralization Ability of Anti-A Beta Oligomer Antibodies Against A Beta-Induced Cytotoxicity A beta oligomers cause cytotoxicity to neuronal cells. To assess whether the present anti-A beta oligomer antibodies neutralize A beta-induced cytotoxicity, in vitro assay using human neuroblastoma cells (SH-SY5Y cells) was performed. Three kinds of anti-A beta oligomer antibodies (AL-217, AL-224 and AL-225) were examined. They neutralized the A beta-induced cytotoxicity (FIG. 4). By contrast, non-A beta IgG which was used as a negative control antibody did not neutralize the cytotoxicity. In the graphs, the value of Y axis indicates the relative rate to the cytotoxicity of A beta only (no antibody).

Assay of Inhibition Ability of Anti-A Beta Oligomer Antibodies Against A Beta-Fibril Formation A beta monomers form fibrils as a result of multimerization when they are incubated in neutral pH buffer. To assess whether the present antibodies inhibit the fibril formation, an antibody and A beta were mixed and incubated for 24 hours and the mixture were measured by fluorescence of ThioflavinT which reflects the amount of fibrils. Three kinds of anti-A beta oligomer antibodies (AL-217, AL-224 and AL-225) were examined. They inhibited formation of A beta fibrils compared to non-A beta IgG which was used as a negative control antibody (FIG. 5). In the graph, the values of Y axis indicates the relative rate to the fibril formation of A beta only (no antibody).

Immunoblotting to Confirm that Anti-A Beta Oligomer Antibodies do not Bind to APP (Amyloid Precursor Protein)

It is important for escape of side effect that anti-A beta antibodies do not bind APP which is a physiological protein expressed in a healthy body. Anti-A beta oligomer antibodies are expected not to bind to APP because they recognize a conformational domain of A beta oligomer that does not present in APP. Therefore, the present inventor performed immunoblotting to assess whether the present anti-A beta oligomer antibodies do not bind to APP. Three antibodies (AL-217, AL-224 and AL-225) were examined, and the results showed that they do not bind to APP (FIG. 6).

INDUSTRIAL APPLICABILITY

The antibodies provided by the present invention are expected to contribute to the establishment of preventive/therapeutic methods selective to molecules responsible for evoking pathological conditions of Alzheimer's disease, and the establishment of early diagnostic markers for Alzheimer's disease.

The invention claimed is:

1. An antibody that recognizes an isolated A beta (Aβ) tetramer as an antigen, wherein the antibody does not bind to an Aβ monomer, and wherein the antibody comprises a heavy chain having CDR1, CDR2, and CDR3, which are identified in heavy chain variable region comprising the amino acid sequence of SEQ ID NO: 594, and a light chain having CDR1, CDR2, and CDR3, which are identified in light chain variable region comprising the amino acid sequence of SEQ ID NO: 596.

2. The antibody of claim 1, which comprises:
(1) a heavy chain having the amino acid sequence of SEQ ID NO: 262 as CDR1, the amino acid sequence of SEQ ID NO: 264 as CDR2, and the amino acid sequence of SEQ ID NO: 266 as CDR3; or
(2) a light chain having the amino acid sequence of SEQ ID NO: 268 as CDR1, the amino acid sequence of SEQ ID NO: 270 as CDR2, and the amino acid sequence of SEQ ID NO: 272 as CDR3.

3. The antibody of claim 1, wherein the antibody is a chimeric antibody or a humanized antibody.

4. An antigen-binding fragment of the antibody of claim 1.

5. A pharmaceutical composition comprising the antibody of claim 1, and a pharmaceutically acceptable carrier.

6. The composition of claim 5, which is formulated for administration as an agent against cognitive impairment, a therapeutic agent for Alzheimer's disease, an agent for suppressing the progression of Alzheimer's disease, an agent for suppressing senile plaque formation, an agent for suppressing Aβ accumulation, an anti-neurotoxic agent, an agent for inhibiting Aβ amyloid fibril formation, or an agent against synaptic toxicity.

7. A method for detecting an Aβ oligomer, which comprises:
(a) contacting a sample collected from a subject with the antibody of claim 1; and
(b) immunologically detecting the presence of an Aβ oligomer in the sample.

8. A method of diagnosing whether or not a subject is a possible Alzheimer's disease patient, which comprises:
(a) contacting a sample collected from the subject with the antibody of claim 1; and
(b) measuring the amount of Aβ oligomer in the sample, wherein the subject is determined to be a possible Alzheimer's disease patient, when the amount measured in (b) is higher than that of a healthy individual.

9. A method of diagnosing whether or not a subject is a possible Alzheimer's disease patient, which comprises:
(a) contacting a sample collected from the subject with the antibody of claim 1, and an antibody that binds to an Aβ monomer; and (b) measuring the ratio of Aβ oligomer to Aβ monomer in the sample, wherein the subject is determined to be a possible Alzheimer's disease patient, when the ratio measured in (b) is higher than that of a healthy individual.

10. The method of claim 7, wherein the sample is blood or cerebrospinal fluid.

11. A kit for detecting an Aβ oligomer contained in a sample or for diagnosing whether or not a subject is a possible Alzheimer's disease patient, the kit comprising the antibody of claim 1.

12. The method of claim 8, wherein the sample is blood or cerebrospinal fluid.

13. The method of claim 9, wherein the sample is blood or cerebrospinal fluid.

* * * * *

SEQUENCE LISTING

```
<160> NUMBER OF SEQ ID NOS: 719

<210> SEQ ID NO 1
<211> LENGTH: 414
<212> TYPE: DNA
<213> ORGANISM: Mus musculus

<400> SEQUENCE: 1
atgggatgga gctatatcat cctcttttg gtagcaacag ctacagatgt ccactcccag      60
gtccaactgc agcagcctgg ggctgaactg gtgaagcctg gggcttcagt gaagctgtcc     120
tgcaaggctt ctggctacac cttcaccagc tactggatgc actgggtgaa gcagaggcct    180
ggacaaggcc ttgagtggat tggagagatt aatcctagca acgtcgtac taactacaat    240 gagaagttca gagcaaggc cacactgact gtagacaaat cctccagcac agcctacatg   300
caactcagca gcctgacatc tgaggactct gcggtctatt actgtgcaag acaagggtat   360
aggcacgggg ttttgctta ctggggccaa gggactctgg tcactgtctc tgca             414

<210> SEQ ID NO 2
<211> LENGTH: 138
<212> TYPE: PRT
<213> ORGANISM: Mus musculus

<400> SEQUENCE: 2

Met Gly Trp Ser Tyr Ile Ile Leu Phe Leu Val Ala Thr Ala Thr Asp
1               5                   10                  15

Val His Ser Gln Val Gln Leu Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asn Pro Ser Asn Gly Arg Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gln Gly Tyr Arg His Gly Val Phe Ala Tyr Trp
        115                 120                 125

Gly Gln Gly Thr Leu Val Thr Val Ser Ala
    130                 135

<210> SEQ ID NO 3
<211> LENGTH: 309
<212> TYPE: DNA
<213> ORGANISM: Mus musculus

<400> SEQUENCE: 3
atgacccaga ctcccaaatt cctgcttgta tcagcaggag acagggttac cataacctgc      60
```

```
aaggccagtc agagtgtgag taatgatgta gcttggtacc aacagaagcc agggcagtct      120
cctaaactgc tgatatacta tgcatccaat cgctacactg gagtccctga tcgcttcact      180
ggcagtggat atgggacgga tttcactttc accatcagca ctgtgcaggc tgaagacctg      240
gcagtttatt tctgtcagca ggattatagc tctcccacgt tcggtgctgg gaccaagctg      300
gagctgaaa                                                              309
```

<210> SEQ ID NO 4
<211> LENGTH: 103
<212> TYPE: PRT
<213> ORGANISM: Mus musculus

<400> SEQUENCE: 4

```
Met Thr Gln Thr Pro Lys Phe Leu Leu Val Ser Ala Gly Asp Arg Val
1               5                   10                  15

Thr Ile Thr Cys Lys Ala Ser Gln Ser Val Ser Asn Asp Val Ala Trp
            20                  25                  30

Tyr Gln Gln Lys Pro Gly Gln Ser Pro Lys Leu Leu Ile Tyr Tyr Ala
        35                  40                  45

Ser Asn Arg Tyr Thr Gly Val Pro Asp Arg Phe Thr Gly Ser Gly Tyr
    50                  55                  60

Gly Thr Asp Phe Thr Phe Thr Ile Ser Thr Val Gln Ala Glu Asp Leu
65                  70                  75                  80

Ala Val Tyr Phe Cys Gln Gln Asp Tyr Ser Ser Pro Thr Phe Gly Ala
                85                  90                  95

Gly Thr Lys Leu Glu Leu Lys
            100
```

<210> SEQ ID NO 5
<211> LENGTH: 15
<212> TYPE: DNA
<213> ORGANISM: Mus musculus

<400> SEQUENCE: 5

```
agctactgga tgcac                                                        15
```

<210> SEQ ID NO 6
<211> LENGTH: 5
<212> TYPE: PRT
<213> ORGANISM: Mus musculus

<400> SEQUENCE: 6

```
Ser Tyr Trp Met His
1               5
```

<210> SEQ ID NO 7
<211> LENGTH: 51
<212> TYPE: DNA
<213> ORGANISM: Mus musculus

<400> SEQUENCE: 7

```
gagattaatc ctagcaacgg tcgtactaac tacaatgaga agttcaagag c               51
```

<210> SEQ ID NO 8
<211> LENGTH: 17
<212> TYPE: PRT
<213> ORGANISM: Mus musculus

<400> SEQUENCE: 8

```
Glu Ile Asn Pro Ser Asn Gly Arg Thr Asn Tyr Asn Glu Lys Phe Lys
1               5                   10                  15

Ser

<210> SEQ ID NO 9
<211> LENGTH: 30
<212> TYPE: DNA
<213> ORGANISM: Mus musculus

<400> SEQUENCE: 9
caagggtata ggcacggggt ttttgcttac                                    30

<210> SEQ ID NO 10
<211> LENGTH: 10
<212> TYPE: PRT
<213> ORGANISM: Mus musculus

<400> SEQUENCE: 10

Gln Gly Tyr Arg His Gly Val Phe Ala Tyr
1               5                   10

<210> SEQ ID NO 11
<211> LENGTH: 33
<212> TYPE: DNA
<213> ORGANISM: Mus musculus

<400> SEQUENCE: 11
aaggccagtc agagtgtgag taatgatgta gct                                33

<210> SEQ ID NO 12
<211> LENGTH: 11
<212> TYPE: PRT
<213> ORGANISM: Mus musculus

<400> SEQUENCE: 12

Lys Ala Ser Gln Ser Val Ser Asn Asp Val Ala
1               5                   10

<210> SEQ ID NO 13
<211> LENGTH: 21
<212> TYPE: DNA
<213> ORGANISM: Mus musculus

<400> SEQUENCE: 13
tatgcatcca atcgctacac t                                             21

<210> SEQ ID NO 14
<211> LENGTH: 7
<212> TYPE: PRT
<213> ORGANISM: Mus musculus

<400> SEQUENCE: 14

Tyr Ala Ser Asn Arg Tyr Thr
1               5

<210> SEQ ID NO 15
<211> LENGTH: 24
<212> TYPE: DNA
<213> ORGANISM: Mus musculus

<400> SEQUENCE: 15
cagcaggatt atagctctcc cacg                                          24
```

<210> SEQ ID NO 16
<211> LENGTH: 8
<212> TYPE: PRT
<213> ORGANISM: Mus musculus

<400> SEQUENCE: 16

Gln Gln Asp Tyr Ser Ser Pro Thr
1               5

<210> SEQ ID NO 17
<211> LENGTH: 417
<212> TYPE: DNA
<213> ORGANISM: Mus musculus

<400> SEQUENCE: 17

```
atgaacttcg gactcagctt gattttcctt gccctcattt taaaaggtgt ccagtgtgag      60
gtgcagctgg tggagtctgg gggagactta gtgaagcctg agggtccct gaaactctcc     120
tgtgcagcct ctggattcac tttcagtagc tatggcatgt cttgggttcg ccagactcca    180
gacaagaggc tggagtgggt cgcaaccatt agtagtggtg gtagttacac ctactatcca    240
gacagtgtga aggggcgatt caccatctcc agagacaatg ccaagaacac cctgtacctg    300
caaatgagca gtctgaagtc tgaggacaca gccatgtatt actgtgcaag accctctac    360
tataggcacg gggttttgc ttactggggc aagggactc tggtcactgt ctctgca        417
```

<210> SEQ ID NO 18
<211> LENGTH: 139
<212> TYPE: PRT
<213> ORGANISM: Mus musculus

<400> SEQUENCE: 18

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Pro Leu Tyr Tyr Arg His Gly Val Phe Ala Tyr
        115                 120                 125

Trp Gly Gln Gly Thr Leu Val Thr Val Ser Ala
    130                 135

<210> SEQ ID NO 19
<211> LENGTH: 381
<212> TYPE: DNA
<213> ORGANISM: Mus musculus

<400> SEQUENCE: 19

```
atgaggttcc aggttcaggt tctgggactc cttctgctct ggatatcagg tgcccagtgt      60
gatgtccaga taacccagtc tccatcttat cttgctgcat ctcctggaga aaccattact     120
```

```
attaattgca gggcaagtaa gagcattagc aaatatttag cctggtatca agagaaacct      180
gggaaaacta ataagcttct tatctactct ggatccactt tgcaatctgg aattccatca      240
aggttcagtg gcagtggatc tggtacagat ttcactctca ccatcagtag cctggagcct      300
gaagattttg caatgtatta ctgtcaacag cataatgaat acccgtggac gttcggtgga      360
ggcaccaagc tggaaatcaa a                                                381
```

<210> SEQ ID NO 20
<211> LENGTH: 127
<212> TYPE: PRT
<213> ORGANISM: Mus musculus

<400> SEQUENCE: 20

```
Met Arg Phe Gln Val Gln Val Leu Gly Leu Leu Leu Leu Trp Ile Ser
1               5                   10                  15

Gly Ala Gln Cys Asp Val Gln Ile Thr Gln Ser Pro Ser Tyr Leu Ala
            20                  25                  30

Ala Ser Pro Gly Glu Thr Ile Thr Ile Asn Cys Arg Ala Ser Lys Ser
        35                  40                  45

Ile Ser Lys Tyr Leu Ala Trp Tyr Gln Glu Lys Pro Gly Lys Thr Asn
50                  55                  60

Lys Leu Leu Ile Tyr Ser Gly Ser Thr Leu Gln Ser Gly Ile Pro Ser
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Met Tyr Tyr Cys Gln Gln His Asn
            100                 105                 110

Glu Tyr Pro Trp Thr Phe Gly Gly Gly Thr Lys Leu Glu Ile Lys
        115                 120                 125
```

<210> SEQ ID NO 21
<211> LENGTH: 15
<212> TYPE: DNA
<213> ORGANISM: Mus musculus

<400> SEQUENCE: 21

```
agctatggca tgtct                                                       15
```

<210> SEQ ID NO 22
<211> LENGTH: 5
<212> TYPE: PRT
<213> ORGANISM: Mus musculus

<400> SEQUENCE: 22

```
Ser Tyr Gly Met Ser
1               5
```

<210> SEQ ID NO 23
<211> LENGTH: 51
<212> TYPE: DNA
<213> ORGANISM: Mus musculus

<400> SEQUENCE: 23

```
accattagta gtggtggtag ttacacctac tatccagaca gtgtgaaggg g              51
```

<210> SEQ ID NO 24
<211> LENGTH: 17
<212> TYPE: PRT
<213> ORGANISM: Mus musculus

```
<400> SEQUENCE: 24

Thr Ile Ser Ser Gly Gly Ser Tyr Thr Tyr Tyr Pro Asp Ser Val Lys
1               5                   10                  15

Gly

<210> SEQ ID NO 25
<211> LENGTH: 33
<212> TYPE: DNA
<213> ORGANISM: Mus musculus

<400> SEQUENCE: 25
cccctctact ataggcacgg ggtttttgct tac                              33

<210> SEQ ID NO 26
<211> LENGTH: 11
<212> TYPE: PRT
<213> ORGANISM: Mus musculus

<400> SEQUENCE: 26

Pro Leu Tyr Tyr Arg His Gly Val Phe Ala Tyr
1               5                   10

<210> SEQ ID NO 27
<211> LENGTH: 33
<212> TYPE: DNA
<213> ORGANISM: Mus musculus

<400> SEQUENCE: 27
agggcaagta agagcattag caaatattta gcc                              33

<210> SEQ ID NO 28
<211> LENGTH: 11
<212> TYPE: PRT
<213> ORGANISM: Mus musculus

<400> SEQUENCE: 28

Arg Ala Ser Lys Ser Ile Ser Lys Tyr Leu Ala
1               5                   10

<210> SEQ ID NO 29
<211> LENGTH: 21
<212> TYPE: DNA
<213> ORGANISM: Mus musculus

<400> SEQUENCE: 29
tctggatcca ctttgcaatc t                                           21

<210> SEQ ID NO 30
<211> LENGTH: 7
<212> TYPE: PRT
<213> ORGANISM: Mus musculus

<400> SEQUENCE: 30

Ser Gly Ser Thr Leu Gln Ser
1               5

<210> SEQ ID NO 31
<211> LENGTH: 27
<212> TYPE: DNA
<213> ORGANISM: Mus musculus

<400> SEQUENCE: 31
caacagcata atgaataccc gtggacg                                     27
```

<210> SEQ ID NO 32
<211> LENGTH: 9
<212> TYPE: PRT
<213> ORGANISM: Mus musculus

<400> SEQUENCE: 32

Gln Gln His Asn Glu Tyr Pro Trp Thr
1               5

<210> SEQ ID NO 33
<211> LENGTH: 432
<212> TYPE: DNA
<213> ORGANISM: Mus musculus

<400> SEQUENCE: 33

```
atgaacttcg ggctcagctt gattttcctt gtccttgttt taaaaggtgt ccagtgtgaa      60
gtgcagctgg tggagtctgg gggaggctta gtgaagcctg agggtccct gaaactctcc      120 tgtgcagcct ctggattcac tttcagtgac tattacatgt attgggttcg ccagactccg     180
gaaaagaggc tggagtgggt cgcaaccatt agtgatggtg gtagttacac ctactatcca     240
gacagtgtga agggccgatt caccatctcc agagacaatg ccaagaacaa cctgtacctg     300
caaatgagca gtctgaagtc tgaggacaca gccatgtatt actgtgcaag agccaaatac     360
tataggtacg acgaggggg ggcctatgct atggactact ggggtcaagg aacctcagtc      420
accgtctcct ca                                                         432
```

<210> SEQ ID NO 34
<211> LENGTH: 144
<212> TYPE: PRT
<213> ORGANISM: Mus musculus

<400> SEQUENCE: 34

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
                20                  25                  30

Pro Gly Gly Ser Leu Lys Leu Ser Cys Ala Ala Ser Gly Phe Thr Phe
            35                  40                  45

Ser Asp Tyr Tyr Met Tyr Trp Val Arg Gln Thr Pro Glu Lys Arg Leu
        50                  55                  60

Glu Trp Val Ala Thr Ile Ser Asp Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Lys Ser Glu Asp Thr Ala Met
            100                 105                 110

Tyr Tyr Cys Ala Arg Ala Lys Tyr Tyr Arg Tyr Asp Gly Gly Ala
        115                 120                 125

Tyr Ala Met Asp Tyr Trp Gly Gln Gly Thr Ser Val Thr Val Ser Ser
    130                 135                 140

<210> SEQ ID NO 35
<211> LENGTH: 276
<212> TYPE: DNA
<213> ORGANISM: Mus musculus

<400> SEQUENCE: 35

```
atgagctgta agtccagtca aagtgtttta tacagttcaa atcagaagaa ctacttggcc    60
tggtaccagc agaaaccagg gcagtctcct aaactgctga tctactgggc atccactagg   120
gaatctggtg tccctgatcg cttcacaggc agtggatctg ggacagattt tactcttacc   180
atcagcagtg tacaagctga agacctggca gtttattact gtcatcaata cctctcctcg   240
tacacgttcg gagggggggac caagctggaa ataaaa                            276
```

<210> SEQ ID NO 36
<211> LENGTH: 92
<212> TYPE: PRT
<213> ORGANISM: Mus musculus

<400> SEQUENCE: 36

```
Met Ser Cys Lys Ser Ser Gln Ser Val Leu Tyr Ser Ser Asn Gln Lys
1               5                   10                  15

Asn Tyr Leu Ala Trp Tyr Gln Gln Lys Pro Gly Gln Ser Pro Lys Leu
            20                  25                  30

Leu Ile Tyr Trp Ala Ser Thr Arg Glu Ser Gly Val Pro Asp Arg Phe
        35                  40                  45

Thr Gly Ser Gly Ser Gly Thr Asp Phe Thr Leu Thr Ile Ser Ser Val
    50                  55                  60

Gln Ala Glu Asp Leu Ala Val Tyr Tyr Cys His Gln Tyr Leu Ser Ser
65                  70                  75                  80

Tyr Thr Phe Gly Gly Gly Thr Lys Leu Glu Ile Lys
                85                  90
```

<210> SEQ ID NO 37
<211> LENGTH: 15
<212> TYPE: DNA
<213> ORGANISM: Mus musculus

<400> SEQUENCE: 37

```
gactattaca tgtat                                                    15
```

<210> SEQ ID NO 38
<211> LENGTH: 5
<212> TYPE: PRT
<213> ORGANISM: Mus musculus

<400> SEQUENCE: 38

```
Asp Tyr Tyr Met Tyr
1               5
```

<210> SEQ ID NO 39
<211> LENGTH: 51
<212> TYPE: DNA
<213> ORGANISM: Mus musculus

<400> SEQUENCE: 39

```
accattagtg atggtggtag ttacacctac tatccagaca gtgtgaaggg g            51
```

<210> SEQ ID NO 40
<211> LENGTH: 17
<212> TYPE: PRT
<213> ORGANISM: Mus musculus

<400> SEQUENCE: 40

```
Thr Ile Ser Asp Gly Gly Ser Tyr Thr Tyr Tyr Pro Asp Ser Val Lys
1               5                   10                  15

Gly
```

<210> SEQ ID NO 41
<211> LENGTH: 48
<212> TYPE: DNA
<213> ORGANISM: Mus musculus

<400> SEQUENCE: 41
gccaaatact ataggtacga cggaggggg gcctatgcta tggactac                48

<210> SEQ ID NO 42
<211> LENGTH: 16
<212> TYPE: PRT
<213> ORGANISM: Mus musculus

<400> SEQUENCE: 42

Ala Lys Tyr Tyr Arg Tyr Asp Gly Gly Gly Ala Tyr Ala Met Asp Tyr
1               5                   10                  15

<210> SEQ ID NO 43
<211> LENGTH: 51
<212> TYPE: DNA
<213> ORGANISM: Mus musculus

<400> SEQUENCE: 43
aagtccagtc aaagtgtttt atacagttca atcagaaga actacttggc c            51

<210> SEQ ID NO 44
<211> LENGTH: 17
<212> TYPE: PRT
<213> ORGANISM: Mus musculus

<400> SEQUENCE: 44

Lys Ser Ser Gln Ser Val Leu Tyr Ser Ser Asn Gln Lys Asn Tyr Leu
1               5                   10                  15

Ala

<210> SEQ ID NO 45
<211> LENGTH: 21
<212> TYPE: DNA
<213> ORGANISM: Mus musculus

<400> SEQUENCE: 45
tgggcatcca ctagggaatc t                                            21

<210> SEQ ID NO 46
<211> LENGTH: 7
<212> TYPE: PRT
<213> ORGANISM: Mus musculus

<400> SEQUENCE: 46

Trp Ala Ser Thr Arg Glu Ser
1               5

<210> SEQ ID NO 47
<211> LENGTH: 24
<212> TYPE: DNA
<213> ORGANISM: Mus musculus

<400> SEQUENCE: 47
catcaatacc tctcctcgta cacg                                         24

<210> SEQ ID NO 48
<211> LENGTH: 8

```
<212> TYPE: PRT
<213> ORGANISM: Mus musculus

<400> SEQUENCE: 48

His Gln Tyr Leu Ser Ser Tyr Thr
1               5

<210> SEQ ID NO 49
<211> LENGTH: 432
<212> TYPE: DNA
<213> ORGANISM: Mus musculus

<400> SEQUENCE: 49
atgaacttcg ggctcagctt gattttcctt gtccttgttt taaaaggtgt ccagtgtgaa      60
gtgcaactgg tggagtctgg gggaggctta gtgaagcctg agggtccct gaaactctcc     120 tgtgcagcct ctggattcac tttcagtgac tattacatgt attgggttcg ccagactccg     180
gaaaagaggc tggagtgggt cgcaaccatt agtgatggtg gtagttacac ctactatcca     240
gacagtgtga aggggcgatt caccatctcc agagacaatg ccaagaacaa cctgtacctg     300
caaatgagca gtctgaagtc tgaggacaca gccatgtatt actgtgcaag agccaaatac     360
tataggtacg acgaggggg ggcctatgct atggactact ggggtcaagg aacctcagtc     420
accgtctcct ca                                                          432

<210> SEQ ID NO 50
<211> LENGTH: 144
<212> TYPE: PRT
<213> ORGANISM: Mus musculus

<400> SEQUENCE: 50

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Asp Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Lys Ser Glu Asp Thr Ala Met
            100                 105                 110

Tyr Tyr Cys Ala Arg Ala Lys Tyr Tyr Arg Tyr Asp Gly Gly Ala
        115                 120                 125

Tyr Ala Met Asp Tyr Trp Gly Gln Gly Thr Ser Val Thr Val Ser Ser
    130                 135                 140

<210> SEQ ID NO 51
<211> LENGTH: 276
<212> TYPE: DNA
<213> ORGANISM: Mus musculus

<400> SEQUENCE: 51
atgagctgta agtccagtca aagtgtttta tacagttcaa atcagaagaa ctacttggcc      60
tggtaccagc agaaaccagg gcagtctcct aaactgctga tctactgggc atccactagg     120
```

```
gaatctggtg tccctgatcg cttcacaggc agtggatctg ggacagattt tactcttacc    180
atcagcagtg tacaagctga agacctggca gtttattact gtcatcaata cctctcctcg    240
tacacgttcg gagggggggac caagctggaa ataaaa                              276
```

<210> SEQ ID NO 52
<211> LENGTH: 92
<212> TYPE: PRT
<213> ORGANISM: Mus musculus

<400> SEQUENCE: 52

```
Met Ser Cys Lys Ser Ser Gln Ser Val Leu Tyr Ser Ser Asn Gln Lys
1               5                   10                  15

Asn Tyr Leu Ala Trp Tyr Gln Gln Lys Pro Gly Gln Ser Pro Lys Leu
            20                  25                  30

Leu Ile Tyr Trp Ala Ser Thr Arg Glu Ser Gly Val Pro Asp Arg Phe
        35                  40                  45

Thr Gly Ser Gly Ser Gly Thr Asp Phe Thr Leu Thr Ile Ser Ser Val
    50                  55                  60

Gln Ala Glu Asp Leu Ala Val Tyr Tyr Cys His Gln Tyr Leu Ser Ser
65                  70                  75                  80

Tyr Thr Phe Gly Gly Gly Thr Lys Leu Glu Ile Lys
                85                  90
```

<210> SEQ ID NO 53
<211> LENGTH: 15
<212> TYPE: DNA
<213> ORGANISM: Mus musculus

<400> SEQUENCE: 53

```
gactattaca tgtat                                                      15
```

<210> SEQ ID NO 54
<211> LENGTH: 5
<212> TYPE: PRT
<213> ORGANISM: Mus musculus

<400> SEQUENCE: 54

```
Asp Tyr Tyr Met Tyr
1               5
```

<210> SEQ ID NO 55
<211> LENGTH: 51
<212> TYPE: DNA
<213> ORGANISM: Mus musculus

<400> SEQUENCE: 55

```
accattagtg atggtggtag ttacacctac tatccagaca gtgtgaaggg g              51
```

<210> SEQ ID NO 56
<211> LENGTH: 17
<212> TYPE: PRT
<213> ORGANISM: Mus musculus

<400> SEQUENCE: 56

```
Thr Ile Ser Asp Gly Gly Ser Tyr Thr Tyr Tyr Pro Asp Ser Val Lys
1               5                   10                  15

Gly
```

<210> SEQ ID NO 57
<211> LENGTH: 48

```
<212> TYPE: DNA
<213> ORGANISM: Mus musculus

<400> SEQUENCE: 57
gccaaatact ataggtacga cggaggggg gcctatgcta tggactac          48

<210> SEQ ID NO 58
<211> LENGTH: 16
<212> TYPE: PRT
<213> ORGANISM: Mus musculus

<400> SEQUENCE: 58

Ala Lys Tyr Tyr Arg Tyr Asp Gly Gly Gly Ala Tyr Ala Met Asp Tyr
1               5                   10                  15

<210> SEQ ID NO 59
<211> LENGTH: 51
<212> TYPE: DNA
<213> ORGANISM: Mus musculus

<400> SEQUENCE: 59
aagtccagtc aaagtgtttt atacagttca atcagaaga actacttggc c          51

<210> SEQ ID NO 60
<211> LENGTH: 17
<212> TYPE: PRT
<213> ORGANISM: Mus musculus

<400> SEQUENCE: 60

Lys Ser Ser Gln Ser Val Leu Tyr Ser Ser Asn Gln Lys Asn Tyr Leu
1               5                   10                  15

Ala

<210> SEQ ID NO 61
<211> LENGTH: 21
<212> TYPE: DNA
<213> ORGANISM: Mus musculus

<400> SEQUENCE: 61
tgggcatcca ctagggaatc t          21

<210> SEQ ID NO 62
<211> LENGTH: 7
<212> TYPE: PRT
<213> ORGANISM: Mus musculus

<400> SEQUENCE: 62

Trp Ala Ser Thr Arg Glu Ser
1               5

<210> SEQ ID NO 63
<211> LENGTH: 24
<212> TYPE: DNA
<213> ORGANISM: Mus musculus

<400> SEQUENCE: 63
catcaatacc tctcctcgta cacg          24

<210> SEQ ID NO 64
<211> LENGTH: 8
<212> TYPE: PRT
<213> ORGANISM: Mus musculus

<400> SEQUENCE: 64
```

His Gln Tyr Leu Ser Ser Tyr Thr
1               5

<210> SEQ ID NO 65
<211> LENGTH: 321
<212> TYPE: DNA
<213> ORGANISM: Mus musculus

<400> SEQUENCE: 65
atgaaactct cctgtgttgc ctctggattc actttcagta actactggat gaactgggtc    60
cgccagtctc cagagaaggg gcttgagtgg gttgctgaaa ttagattgaa atctaataat   120
tatgcaacac attatgcgga gtctgtgaaa gggaggttca ccatctcaag agatgattcc   180
aaaagtagtg tctacctgca aatgaacaac ttaagagctg aagacactgg catttattac   240
tgtaccaggg ggaccagggt atggttacga cgtgaggctt ggtttgctta ctggggccaa   300
gggactctgg tcactgtctc t                                              321

<210> SEQ ID NO 66
<211> LENGTH: 107
<212> TYPE: PRT
<213> ORGANISM: Mus musculus

<400> SEQUENCE: 66

Met Lys Leu Ser Cys Val Ala Ser Gly Phe Thr Phe Ser Asn Tyr Trp
1               5                   10                  15

Met Asn Trp Val Arg Gln Ser Pro Glu Lys Gly Leu Glu Trp Val Ala
            20                  25                  30

Glu Ile Arg Leu Lys Ser Asn Asn Tyr Ala Thr His Tyr Ala Glu Ser
        35                  40                  45

Val Lys Gly Arg Phe Thr Ile Ser Arg Asp Asp Ser Lys Ser Ser Val
    50                  55                  60

Tyr Leu Gln Met Asn Asn Leu Arg Ala Glu Asp Thr Gly Ile Tyr Tyr
65                  70                  75                  80

Cys Thr Arg Gly Thr Arg Val Trp Leu Arg Arg Glu Ala Trp Phe Ala
                85                  90                  95

Tyr Trp Gly Gln Gly Thr Leu Val Thr Val Ser
            100                 105

<210> SEQ ID NO 67
<211> LENGTH: 393
<212> TYPE: DNA
<213> ORGANISM: Mus musculus

<400> SEQUENCE: 67
atggagaaag acacactcct gctatgggtc ctgcttctct gggttccagg ttccacaggt    60
gacattgtgc tgacccaatc tccagcttct ttggctgtgt ctctagggca gagggccacc   120
atctcctgca gagccagcga aagtgttgat aattatggca ttagttttat gaactggttc   180
caacagaaac caggacagcc acccaaactc ctcatctatg ctgcatccaa ccaaggatcc   240
ggggtccctg ccaggtttgg tggcagtggg tctgggacag acttcagcct caacatccat   300
cctatggagg aagatgatac tgcaatgtat ttctgtcagc aaagtaagga ggttccgtgg   360
acgttcggtg gaggcaccaa gctggaaatc aaa                                393

<210> SEQ ID NO 68
<211> LENGTH: 131
<212> TYPE: PRT

<210> ORGANISM: Mus musculus

<400> SEQUENCE: 68

Met Glu Lys Asp Thr Leu Leu Leu Trp Val Leu Leu Leu Trp Val Pro
1               5                   10                  15
Gly Ser Thr Gly Asp Ile Val Leu Thr Gln Ser Pro Ala Ser Leu Ala
            20                  25                  30
Val Ser Leu Gly Gln Arg Ala Thr Ile Ser Cys Arg Ala Ser Glu Ser
        35                  40                  45
Val Asp Asn Tyr Gly Ile Ser Phe Met Asn Trp Phe Gln Gln Lys Pro
    50                  55                  60
Gly Gln Pro Pro Lys Leu Leu Ile Tyr Ala Ala Ser Asn Gln Gly Ser
65                  70                  75                  80
Gly Val Pro Ala Arg Phe Gly Gly Ser Gly Ser Gly Thr Asp Phe Ser
                85                  90                  95
Leu Asn Ile His Pro Met Glu Glu Asp Asp Thr Ala Met Tyr Phe Cys
            100                 105                 110
Gln Gln Ser Lys Glu Val Pro Trp Thr Phe Gly Gly Gly Thr Lys Leu
        115                 120                 125
Glu Ile Lys
    130

<210> SEQ ID NO 69
<211> LENGTH: 15
<212> TYPE: DNA
<213> ORGANISM: Mus musculus

<400> SEQUENCE: 69
aactactgga tgaac                                                          15

<210> SEQ ID NO 70
<211> LENGTH: 5
<212> TYPE: PRT
<213> ORGANISM: Mus musculus

<400> SEQUENCE: 70

Asn Tyr Trp Met Asn
1               5

<210> SEQ ID NO 71
<211> LENGTH: 57
<212> TYPE: DNA
<213> ORGANISM: Mus musculus

<400> SEQUENCE: 71
gaaattagat tgaaatctaa taattatgca acacattatg cggagtctgt gaaaggg           57

<210> SEQ ID NO 72
<211> LENGTH: 19
<212> TYPE: PRT
<213> ORGANISM: Mus musculus

<400> SEQUENCE: 72

Glu Ile Arg Leu Lys Ser Asn Asn Tyr Ala Thr His Tyr Ala Glu Ser
1               5                   10                  15
Val Lys Gly

<210> SEQ ID NO 73
<211> LENGTH: 42
<212> TYPE: DNA

-continued

<213> ORGANISM: Mus musculus

<400> SEQUENCE: 73
gggaccaggg tatggttacg acgtgaggct tggtttgctt ac                42

<210> SEQ ID NO 74
<211> LENGTH: 14
<212> TYPE: PRT
<213> ORGANISM: Mus musculus

<400> SEQUENCE: 74

Gly Thr Arg Val Trp Leu Arg Arg Glu Ala Trp Phe Ala Tyr
1               5                   10

<210> SEQ ID NO 75
<211> LENGTH: 45
<212> TYPE: DNA
<213> ORGANISM: Mus musculus

<400> SEQUENCE: 75
agagccagcg aaagtgttga taattatggc attagtttta tgaac            45

<210> SEQ ID NO 76
<211> LENGTH: 15
<212> TYPE: PRT
<213> ORGANISM: Mus musculus

<400> SEQUENCE: 76

Arg Ala Ser Glu Ser Val Asp Asn Tyr Gly Ile Ser Phe Met Asn
1               5                   10                  15

<210> SEQ ID NO 77
<211> LENGTH: 21
<212> TYPE: DNA
<213> ORGANISM: Mus musculus

<400> SEQUENCE: 77
gctgcatcca accaaggatc c                                      21

<210> SEQ ID NO 78
<211> LENGTH: 7
<212> TYPE: PRT
<213> ORGANISM: Mus musculus

<400> SEQUENCE: 78

Ala Ala Ser Asn Gln Gly Ser
1               5

<210> SEQ ID NO 79
<211> LENGTH: 27
<212> TYPE: DNA
<213> ORGANISM: Mus musculus

<400> SEQUENCE: 79
cagcaaagta aggaggttcc gtggacg                                27

<210> SEQ ID NO 80
<211> LENGTH: 9
<212> TYPE: PRT
<213> ORGANISM: Mus musculus

<400> SEQUENCE: 80

Gln Gln Ser Lys Glu Val Pro Trp Thr
1               5

<210> SEQ ID NO 81
<211> LENGTH: 414
<212> TYPE: DNA
<213> ORGANISM: Mus musculus

<400> SEQUENCE: 81

```
atgagagtgc tgattctttt gtggctgttc acagcctttc ctggtatcct gtccgatgtg      60
cagcttcagg agtcgggacc tggcctggtg aaaccttctc agtctctgtc cctcgcctgc     120
actgtcactg gctactcaat caccagtgat tatgcctgga ctggatccg gcagtttcca     180
ggaaacaaac tggagtggct gggctacata agctacagtg gtaccactag gtacaaccca     240
tctctcaaaa gtcgaatctc tatcactcga gacacatcca agaaccagtt cttcctgcag     300
ttgaattctg tgactactga ggacacagcc acatattact gtgcaatata cggtagtagc     360
tactactggt acttcgatgt ctggggcgca gggaccacgg tcaccgtctc ctca           414
```

<210> SEQ ID NO 82
<211> LENGTH: 138
<212> TYPE: PRT
<213> ORGANISM: Mus musculus

<400> SEQUENCE: 82

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Ala Cys Thr Val Thr Gly Tyr Ser Ile Thr
            35                  40                  45

Ser Asp Tyr Ala Trp Asn Trp Ile Arg Gln Phe Pro Gly Asn Lys Leu
        50                  55                  60

Glu Trp Leu Gly Tyr Ile Ser Tyr Ser Gly Thr Thr Arg Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Ile Tyr Gly Ser Ser Tyr Tyr Trp Tyr Phe Asp Val Trp
        115                 120                 125

Gly Ala Gly Thr Thr Val Thr Val Ser Ser
    130                 135

<210> SEQ ID NO 83
<211> LENGTH: 264
<212> TYPE: DNA
<213> ORGANISM: Mus musculus

<400> SEQUENCE: 83

```
atgacctgca ctgccagctc aagtgtaagt tccagttact gcactggta ccagcagaag       60
ccaggatcct cccccaaact ctggatttat agcacatcca acctggcttc tggagtccca     120
gctcgcttca gtggcagtgg gtctgggacc tcttactctc tcacaatcag cagcatggag     180
gctgaagatg ctgccactta ttactgccac cagtatcatc gttccccacc cacgttcggt     240
gctgggacca agctggagct gaaa                                             264
```

<210> SEQ ID NO 84
<211> LENGTH: 88

<212> TYPE: PRT
<213> ORGANISM: Mus musculus

<400> SEQUENCE: 84

Met Thr Cys Thr Ala Ser Ser Val Ser Ser Tyr Leu His Trp
1               5                   10                  15

Tyr Gln Gln Lys Pro Gly Ser Ser Pro Lys Leu Trp Ile Tyr Ser Thr
                20                  25                  30

Ser Asn Leu Ala Ser Gly Val Pro Ala Arg Phe Ser Gly Ser Gly Ser
            35                  40                  45

Gly Thr Ser Tyr Ser Leu Thr Ile Ser Ser Met Glu Ala Glu Asp Ala
        50                  55                  60

Ala Thr Tyr Tyr Cys His Gln Tyr His Arg Ser Pro Pro Thr Phe Gly
65                  70                  75                  80

Ala Gly Thr Lys Leu Glu Leu Lys
                85

<210> SEQ ID NO 85
<211> LENGTH: 18
<212> TYPE: DNA
<213> ORGANISM: Mus musculus

<400> SEQUENCE: 85
agtgattatg cctggaac                                                    18

<210> SEQ ID NO 86
<211> LENGTH: 6
<212> TYPE: PRT
<213> ORGANISM: Mus musculus

<400> SEQUENCE: 86

Ser Asp Tyr Ala Trp Asn
1               5

<210> SEQ ID NO 87
<211> LENGTH: 48
<212> TYPE: DNA
<213> ORGANISM: Mus musculus

<400> SEQUENCE: 87
tacataagct acagtggtac cactaggtac aacccatctc tcaaaagt                   48

<210> SEQ ID NO 88
<211> LENGTH: 16
<212> TYPE: PRT
<213> ORGANISM: Mus musculus

<400> SEQUENCE: 88

Tyr Ile Ser Tyr Ser Gly Thr Thr Arg Tyr Asn Pro Ser Leu Lys Ser
1               5                   10                  15

<210> SEQ ID NO 89
<211> LENGTH: 33
<212> TYPE: DNA
<213> ORGANISM: Mus musculus

<400> SEQUENCE: 89
tacggtagta gctactactg gtacttcgat gtc                                   33

<210> SEQ ID NO 90
<211> LENGTH: 11
<212> TYPE: PRT

<213> ORGANISM: Mus musculus

<400> SEQUENCE: 90

Tyr Gly Ser Ser Tyr Tyr Trp Tyr Phe Asp Val
1               5                   10

<210> SEQ ID NO 91
<211> LENGTH: 36
<212> TYPE: DNA
<213> ORGANISM: Mus musculus

<400> SEQUENCE: 91
actgccagct caagtgtaag ttccagttac ttgcac                          36

<210> SEQ ID NO 92
<211> LENGTH: 12
<212> TYPE: PRT
<213> ORGANISM: Mus musculus

<400> SEQUENCE: 92

Thr Ala Ser Ser Ser Val Ser Ser Ser Tyr Leu His
1               5                   10

<210> SEQ ID NO 93
<211> LENGTH: 21
<212> TYPE: DNA
<213> ORGANISM: Mus musculus

<400> SEQUENCE: 93
agcacatcca acctggcttc t                                          21

<210> SEQ ID NO 94
<211> LENGTH: 7
<212> TYPE: PRT
<213> ORGANISM: Mus musculus

<400> SEQUENCE: 94

Ser Thr Ser Asn Leu Ala Ser
1               5

<210> SEQ ID NO 95
<211> LENGTH: 27
<212> TYPE: DNA
<213> ORGANISM: Mus musculus

<400> SEQUENCE: 95
caccagtatc atcgttcccc acccacg                                    27

<210> SEQ ID NO 96
<211> LENGTH: 9
<212> TYPE: PRT
<213> ORGANISM: Mus musculus

<400> SEQUENCE: 96

His Gln Tyr His Arg Ser Pro Pro Thr
1               5

<210> SEQ ID NO 97
<211> LENGTH: 426
<212> TYPE: DNA
<213> ORGANISM: Mus musculus

<400> SEQUENCE: 97
atggacaggc ttacttcttc attcctgctg ctgattgtcc ctgcatatgt cttgccccaa    60

```
gttactctaa aagagtctgg ccctgggata ttgaagccct cacagaccct cagtctgact    120
tgttctttct ctgggttttc actgagcact tctggtatgg gtgtaggctg gattcgtcag    180
ccttcaggga agggtctgga gtggctggca cacatttggt gggatgatga cgagtactat    240
aacccatccc tgaagagcca gctcacaatc tccaaggata ccaccagaaa ccaggtattc    300
ctcaagatca ccagtgtgga cactgcagat actgccactt actactgtgc tcgaagagca    360
attcattact acggctacga tgctatggac tactggggtc aaggaacctc agtcaccgtc    420
tcctca                                                               426
```

<210> SEQ ID NO 98
<211> LENGTH: 142
<212> TYPE: PRT
<213> ORGANISM: Mus musculus

<400> SEQUENCE: 98

```
Met Asp Arg Leu Thr Ser Ser Phe Leu Leu Ile Val Pro Ala Tyr
1               5                   10                  15

Val Leu Pro Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Glu Tyr Tyr
65                  70                  75                  80

Asn Pro Ser Leu Lys Ser Gln Leu Thr Ile Ser Lys Asp Thr Thr Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Ala Ile His Tyr Tyr Gly Tyr Asp Ala
        115                 120                 125

Met Asp Tyr Trp Gly Gln Gly Thr Ser Val Thr Val Ser Ser
    130                 135                 140
```

<210> SEQ ID NO 99
<211> LENGTH: 264
<212> TYPE: DNA
<213> ORGANISM: Mus musculus

<400> SEQUENCE: 99

```
atgacctgca ctgccagctc aagtgtaagt tccagttact tgcactggta ccagcagaag    60
ccaggatcct cccccaaact ctggatttat agcacatcca acctggcttc tggagtccca    120
gctcgcttca gtggcagtgg gtctgggacc tcttactctc tcacaatcag cagcatggag    180
gctgaagatg ctgccactta ttactgccac cagtatcatc gttccccacc cacgttcggt    240
gctgggacca gctggagct gaaa                                            264
```

<210> SEQ ID NO 100
<211> LENGTH: 88
<212> TYPE: PRT
<213> ORGANISM: Mus musculus

<400> SEQUENCE: 100

```
Met Thr Cys Thr Ala Ser Ser Ser Val Ser Ser Ser Tyr Leu His Trp
1               5                   10                  15
```

```
Tyr Gln Gln Lys Pro Gly Ser Ser Pro Lys Leu Trp Ile Tyr Ser Thr
                20                  25                  30

Ser Asn Leu Ala Ser Gly Val Pro Ala Arg Phe Ser Gly Ser Gly Ser
            35                  40                  45

Gly Thr Ser Tyr Ser Leu Thr Ile Ser Ser Met Glu Ala Glu Asp Ala
        50                  55                  60

Ala Thr Tyr Tyr Cys His Gln Tyr His Arg Ser Pro Pro Thr Phe Gly
65                  70                  75                  80

Ala Gly Thr Lys Leu Glu Leu Lys
                85

<210> SEQ ID NO 101
<211> LENGTH: 21
<212> TYPE: DNA
<213> ORGANISM: Mus musculus

<400> SEQUENCE: 101
acttctggta tgggtgtagg c                                          21

<210> SEQ ID NO 102
<211> LENGTH: 7
<212> TYPE: PRT
<213> ORGANISM: Mus musculus

<400> SEQUENCE: 102

Thr Ser Gly Met Gly Val Gly
1               5

<210> SEQ ID NO 103
<211> LENGTH: 48
<212> TYPE: DNA
<213> ORGANISM: Mus musculus

<400> SEQUENCE: 103
cacatttggt gggatgatga cgagtactat aacccatccc tgaagagc              48

<210> SEQ ID NO 104
<211> LENGTH: 16
<212> TYPE: PRT
<213> ORGANISM: Mus musculus

<400> SEQUENCE: 104

His Ile Trp Trp Asp Asp Asp Glu Tyr Tyr Asn Pro Ser Leu Lys Ser
1               5                   10                  15

<210> SEQ ID NO 105
<211> LENGTH: 39
<212> TYPE: DNA
<213> ORGANISM: Mus musculus

<400> SEQUENCE: 105
agagcaattc attactacgg ctacgatgct atggactac                        39

<210> SEQ ID NO 106
<211> LENGTH: 13
<212> TYPE: PRT
<213> ORGANISM: Mus musculus

<400> SEQUENCE: 106

Arg Ala Ile His Tyr Tyr Gly Tyr Asp Ala Met Asp Tyr
1               5                   10
```

```
<210> SEQ ID NO 107
<211> LENGTH: 36
<212> TYPE: DNA
<213> ORGANISM: Mus musculus

<400> SEQUENCE: 107
actgccagct caagtgtaag ttccagttac ttgcac                         36

<210> SEQ ID NO 108
<211> LENGTH: 12
<212> TYPE: PRT
<213> ORGANISM: Mus musculus

<400> SEQUENCE: 108

Thr Ala Ser Ser Ser Val Ser Ser Ser Tyr Leu His
1               5                   10

<210> SEQ ID NO 109
<211> LENGTH: 21
<212> TYPE: DNA
<213> ORGANISM: Mus musculus

<400> SEQUENCE: 109
agcacatcca acctggcttc t                                         21

<210> SEQ ID NO 110
<211> LENGTH: 7
<212> TYPE: PRT
<213> ORGANISM: Mus musculus

<400> SEQUENCE: 110

Ser Thr Ser Asn Leu Ala Ser
1               5

<210> SEQ ID NO 111
<211> LENGTH: 27
<212> TYPE: DNA
<213> ORGANISM: Mus musculus

<400> SEQUENCE: 111
caccagtatc atcgttcccc acccacg                                   27

<210> SEQ ID NO 112
<211> LENGTH: 9
<212> TYPE: PRT
<213> ORGANISM: Mus musculus

<400> SEQUENCE: 112

His Gln Tyr His Arg Ser Pro Pro Thr
1               5

<210> SEQ ID NO 113
<211> LENGTH: 417
<212> TYPE: DNA
<213> ORGANISM: Mus musculus

<400> SEQUENCE: 113
atgggatgga gctatatcat cctcttttg gtagcaacag ctacagatgt ccactcccag    60
gtccaactgc agcagcctgg ggctgaactg gtgaagcctg ggcttcagt gaagctgtcc    120 tgcaaggctt ctggctacac cttcaccagc tactggatgc actgggtgaa gcagaggcct    180
ggacaaggcc ttgagtggat tggagagatt aatcctagca acggtcgtac taactacaat    240
gagaagttca agagcaaggc cacactgact gtagacaaat cctccagcac agcctacatg    300
```

```
caactcagca gcctgacatc tgaggactct gcggtctatt actgtgcaag acaagggtat    360
aggcacgggg ttttgctta ctggggccaa gggactctgg tcactgtctc tgcagcc       417
```

<210> SEQ ID NO 114
<211> LENGTH: 139
<212> TYPE: PRT
<213> ORGANISM: Mus musculus

<400> SEQUENCE: 114

```
Met Gly Trp Ser Tyr Ile Ile Leu Phe Leu Val Ala Thr Ala Thr Asp
1               5                   10                  15
Val His Ser Gln Val Gln Leu Gln Gln Pro Gly Ala Glu Leu Val Lys
            20                  25                  30
Pro Gly Ala Ser Val Lys Leu Ser Cys Lys Ala Ser Gly Tyr Thr Phe
        35                  40                  45
Thr Ser Tyr Trp Met His Trp Val Lys Gln Arg Pro Gly Gln Gly Leu
    50                  55                  60
Glu Trp Ile Gly Glu Ile Asn Pro Ser Asn Gly Arg Thr Asn Tyr Asn
65                  70                  75                  80
Glu Lys Phe Lys Ser Lys Ala Thr Leu Thr Val Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Gln Gly Tyr Arg His Gly Val Phe Ala Tyr Trp
        115                 120                 125
Gly Gln Gly Thr Leu Val Thr Val Ser Ala Ala
    130                 135
```

<210> SEQ ID NO 115
<211> LENGTH: 264
<212> TYPE: DNA
<213> ORGANISM: Mus musculus

<400> SEQUENCE: 115

```
atgacctgca ctgccagctc aagtgtaagt tccagttact tgcactggta ccagcagaag    60
ccaggatcct cccccaaact ctggatttat agcacatcca acctggcttc tggagtccca   120
gctcgcttca gtggcagtgg gtctgggacc tcttactctc tcacaatcag cagcatggag   180
gctgaagatg ctgccactta ttactgccac cagtatcatc gttccccacc cacgttcggt   240
gctgggacca agctggagct gaaa                                           264
```

<210> SEQ ID NO 116
<211> LENGTH: 88
<212> TYPE: PRT
<213> ORGANISM: Mus musculus

<400> SEQUENCE: 116

```
Met Thr Cys Thr Ala Ser Ser Ser Val Ser Ser Ser Tyr Leu His Trp
1               5                   10                  15
Tyr Gln Gln Lys Pro Gly Ser Ser Pro Lys Leu Trp Ile Tyr Ser Thr
            20                  25                  30
Ser Asn Leu Ala Ser Gly Val Pro Ala Arg Phe Ser Gly Ser Gly Ser
        35                  40                  45
Gly Thr Ser Tyr Ser Leu Thr Ile Ser Ser Met Glu Ala Glu Asp Ala
    50                  55                  60
Ala Thr Tyr Tyr Cys His Gln Tyr His Arg Ser Pro Pro Thr Phe Gly
```

```
65                  70                  75                  80
Ala Gly Thr Lys Leu Glu Leu Lys
                85
```

<210> SEQ ID NO 117
<211> LENGTH: 15
<212> TYPE: DNA
<213> ORGANISM: Mus musculus

<400> SEQUENCE: 117
agctactgga tgcac                                                     15

<210> SEQ ID NO 118
<211> LENGTH: 5
<212> TYPE: PRT
<213> ORGANISM: Mus musculus

<400> SEQUENCE: 118

```
Ser Tyr Trp Met His
1               5
```

<210> SEQ ID NO 119
<211> LENGTH: 51
<212> TYPE: DNA
<213> ORGANISM: Mus musculus

<400> SEQUENCE: 119
gagattaatc ctagcaacgg tcgtactaac tacaatgaga agttcaagag c              51

<210> SEQ ID NO 120
<211> LENGTH: 17
<212> TYPE: PRT
<213> ORGANISM: Mus musculus

<400> SEQUENCE: 120

```
Glu Ile Asn Pro Ser Asn Gly Arg Thr Asn Tyr Asn Glu Lys Phe Lys
1               5                   10                  15
Ser
```

<210> SEQ ID NO 121
<211> LENGTH: 30
<212> TYPE: DNA
<213> ORGANISM: Mus musculus

<400> SEQUENCE: 121
caagggtata ggcacggggt ttttgcttac                                     30

<210> SEQ ID NO 122
<211> LENGTH: 10
<212> TYPE: PRT
<213> ORGANISM: Mus musculus

<400> SEQUENCE: 122

```
Gln Gly Tyr Arg His Gly Val Phe Ala Tyr
1               5                   10
```

<210> SEQ ID NO 123
<211> LENGTH: 36
<212> TYPE: DNA
<213> ORGANISM: Mus musculus

<400> SEQUENCE: 123
actgccagct caagtgtaag ttccagttac ttgcac                              36

<210> SEQ ID NO 124
<211> LENGTH: 12
<212> TYPE: PRT
<213> ORGANISM: Mus musculus

<400> SEQUENCE: 124

Thr Ala Ser Ser Val Ser Ser Ser Tyr Leu His
1               5                   10

<210> SEQ ID NO 125
<211> LENGTH: 21
<212> TYPE: DNA
<213> ORGANISM: Mus musculus

<400> SEQUENCE: 125
agcacatcca acctggcttc t                                         21

<210> SEQ ID NO 126
<211> LENGTH: 7
<212> TYPE: PRT
<213> ORGANISM: Mus musculus

<400> SEQUENCE: 126

Ser Thr Ser Asn Leu Ala Ser
1               5

<210> SEQ ID NO 127
<211> LENGTH: 27
<212> TYPE: DNA
<213> ORGANISM: Mus musculus

<400> SEQUENCE: 127
caccagtatc atcgttcccc acccacg                                   27

<210> SEQ ID NO 128
<211> LENGTH: 9
<212> TYPE: PRT
<213> ORGANISM: Mus musculus

<400> SEQUENCE: 128

His Gln Tyr His Arg Ser Pro Pro Thr
1               5

<210> SEQ ID NO 129
<211> LENGTH: 408
<212> TYPE: DNA
<213> ORGANISM: Mus musculus

<400> SEQUENCE: 129
atggacaggc ttacttcctc attgctgctg ctgattgtct ctgcatatgt cctgtcccag    60
gttactctga aagagtctgg ccctgggata ttgcagccct cccagaccct cagtctgact   120
tgttctttct ctgggttttc actgagcact tctggtatgg gtgtgagctg gattcgtcag   180
ccttcaggaa agggtctgga gtggctggca cacatttact gggatgatga caagcgctat   240
aacccatccc tgaagagccg gctcacaatc tccaaggata cctccagcaa ccaggtattc   300
ctcaagatca ccagtgtgga cactgcagat actgccacat actactgtgc tctctatgcc   360
aaagggtttg cttactgggg ccaagggact ctggtcactg tctctgca              408

<210> SEQ ID NO 130
<211> LENGTH: 136

```
<212> TYPE: PRT
<213> ORGANISM: Mus musculus

<400> SEQUENCE: 130

Met Asp Arg Leu Thr Ser Ser Leu Leu Leu Ile Val Ser Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Ala Leu Tyr Ala Lys Gly Phe Ala Tyr Trp Gly Gln
        115                 120                 125

Gly Thr Leu Val Thr Val Ser Ala
    130                 135

<210> SEQ ID NO 131
<211> LENGTH: 309
<212> TYPE: DNA
<213> ORGANISM: Mus musculus

<400> SEQUENCE: 131
atgacacagt ctccatcctc actgtctgca tctctgggag gcaaagtcac catcacttgc      60
aaggcaagcc aagacattaa caagtatata gcttggtacc aacacaagcc tggaaaaggt     120
cctaggctgc tcatacatta cacatctaca ttacagccag gcatcccatc aaggttcagt     180
ggaagtgggt ctgggagaga ttattccttc agcatcagca acctggagcc tgaagatatt     240
gcaacttatt attgtctaca gtatgataat ctgtacacgt tcggaggggg gaccaagctg     300
gaaataaaa                                                             309

<210> SEQ ID NO 132
<211> LENGTH: 103
<212> TYPE: PRT
<213> ORGANISM: Mus musculus

<400> SEQUENCE: 132

Met Thr Gln Ser Pro Ser Ser Leu Ser Ala Ser Leu Gly Gly Lys Val
1               5                   10                  15

Thr Ile Thr Cys Lys Ala Ser Gln Asp Ile Asn Lys Tyr Ile Ala Trp
            20                  25                  30

Tyr Gln His Lys Pro Gly Lys Gly Pro Arg Leu Leu Ile His Tyr Thr
            35                  40                  45

Ser Thr Leu Gln Pro Gly Ile Pro Ser Arg Phe Ser Gly Ser Gly Ser
    50                  55                  60

Gly Arg Asp Tyr Ser Phe Ser Ile Ser Asn Leu Glu Pro Glu Asp Ile
65                  70                  75                  80

Ala Thr Tyr Tyr Cys Leu Gln Tyr Asp Asn Leu Tyr Thr Phe Gly Gly
                85                  90                  95

Gly Thr Lys Leu Glu Ile Lys
```

<210> SEQ ID NO 133
<211> LENGTH: 21
<212> TYPE: DNA
<213> ORGANISM: Mus musculus

<400> SEQUENCE: 133
acttctggta tgggtgtgag c                                              21

<210> SEQ ID NO 134
<211> LENGTH: 7
<212> TYPE: PRT
<213> ORGANISM: Mus musculus

<400> SEQUENCE: 134

Thr Ser Gly Met Gly Val Ser
1               5

<210> SEQ ID NO 135
<211> LENGTH: 48
<212> TYPE: DNA
<213> ORGANISM: Mus musculus

<400> SEQUENCE: 135
cacatttact gggatgatga caagcgctat aacccatccc tgaagagc                 48

<210> SEQ ID NO 136
<211> LENGTH: 16
<212> TYPE: PRT
<213> ORGANISM: Mus musculus

<400> SEQUENCE: 136

His Ile Tyr Trp Asp Asp Asp Lys Arg Tyr Asn Pro Ser Leu Lys Ser
1               5                   10                  15

<210> SEQ ID NO 137
<211> LENGTH: 21
<212> TYPE: DNA
<213> ORGANISM: Mus musculus

<400> SEQUENCE: 137
tatgccaaag ggtttgctta c                                              21

<210> SEQ ID NO 138
<211> LENGTH: 7
<212> TYPE: PRT
<213> ORGANISM: Mus musculus

<400> SEQUENCE: 138

Tyr Ala Lys Gly Phe Ala Tyr
1               5

<210> SEQ ID NO 139
<211> LENGTH: 33
<212> TYPE: DNA
<213> ORGANISM: Mus musculus

<400> SEQUENCE: 139
aaggcaagcc aagacattaa caagtatata gct                                 33

<210> SEQ ID NO 140
<211> LENGTH: 11
<212> TYPE: PRT

<210> SEQ ID NO 140
<211> LENGTH: 11
<212> TYPE: PRT
<213> ORGANISM: Mus musculus

<400> SEQUENCE: 140

Lys Ala Ser Gln Asp Ile Asn Lys Tyr Ile Ala
1               5                   10

<210> SEQ ID NO 141
<211> LENGTH: 21
<212> TYPE: DNA
<213> ORGANISM: Mus musculus

<400> SEQUENCE: 141
tacacatcta cattacagcc a                                        21

<210> SEQ ID NO 142
<211> LENGTH: 7
<212> TYPE: PRT
<213> ORGANISM: Mus musculus

<400> SEQUENCE: 142

Tyr Thr Ser Thr Leu Gln Pro
1               5

<210> SEQ ID NO 143
<211> LENGTH: 24
<212> TYPE: DNA
<213> ORGANISM: Mus musculus

<400> SEQUENCE: 143
ctacagtatg ataatctgta cacg                                     24

<210> SEQ ID NO 144
<211> LENGTH: 8
<212> TYPE: PRT
<213> ORGANISM: Mus musculus

<400> SEQUENCE: 144

Leu Gln Tyr Asp Asn Leu Tyr Thr
1               5

<210> SEQ ID NO 145
<211> LENGTH: 405
<212> TYPE: DNA
<213> ORGANISM: Mus musculus

<400> SEQUENCE: 145
atgaacaggc ttacttcctc attgctgctg ctgattgtcc ctgcatatgt cctgtcccag    60
gttactctga aagagtctgg ccctgggata ttgcagccct cccagaccct cagtctgact   120
tgttctttct ctgggttttc actgagcact tctggtatgg gtgtgagctg gattcgtcag   180
ccttcaggaa agggtctgga gtggctggca cacatttact gggatgatga caagcgctat   240
aacccatccc tgaagagccg gctcacaatc tccaaggata cctccagcaa ccaggtattc   300
ctcaagatca ccagtgtgga cactgcagat actgccacat actactgtgc tcgaagaggg   360
gactttgact actggggcca aggcaccact ctcacagtct cctca                  405

<210> SEQ ID NO 146
<211> LENGTH: 135
<212> TYPE: PRT
<213> ORGANISM: Mus musculus

<400> SEQUENCE: 146

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Gly Asp Phe Asp Tyr Trp Gly Gln Gly
            115                 120                 125

Thr Thr Leu Thr Val Ser Ser
    130                 135

<210> SEQ ID NO 147
<211> LENGTH: 327
<212> TYPE: DNA
<213> ORGANISM: Mus musculus

<400> SEQUENCE: 147
atgacccaaa ctccactctc cctgcctgtc agtcttggag atcaagcctc catctcttgc      60
agatctagtc agagccttgt acacagtaat ggaaacacct atttacattg gtacctgcag     120
aagccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttatttctgc tctcaaagta cacatgttcc tcccacgttc     300
ggtgctggga ccaagctgga gctgaaa                                          327

<210> SEQ ID NO 148
<211> LENGTH: 109
<212> TYPE: PRT
<213> ORGANISM: Mus musculus

<400> SEQUENCE: 148

Met Thr Gln Thr Pro Leu Ser Leu Pro Val Ser Leu Gly Asp Gln Ala
1               5                   10                  15

Ser Ile Ser Cys Arg Ser Ser Gln Ser Leu Val His Ser Asn Gly Asn
            20                  25                  30

Thr Tyr Leu His Trp Tyr Leu Gln Lys Pro Gly Gln Ser Pro Lys Leu
            35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Phe Cys Ser Gln Ser Thr His Val
                85                  90                  95

Pro Pro Thr Phe Gly Ala Gly Thr Lys Leu Glu Leu Lys
            100                 105

<210> SEQ ID NO 149
<211> LENGTH: 21

```
<212> TYPE: DNA
<213> ORGANISM: Mus musculus

<400> SEQUENCE: 149
acttctggta tgggtgtgag c                                             21

<210> SEQ ID NO 150
<211> LENGTH: 7
<212> TYPE: PRT
<213> ORGANISM: Mus musculus

<400> SEQUENCE: 150

Thr Ser Gly Met Gly Val Ser
1               5

<210> SEQ ID NO 151
<211> LENGTH: 48
<212> TYPE: DNA
<213> ORGANISM: Mus musculus

<400> SEQUENCE: 151
cacatttact gggatgatga caagcgctat aacccatccc tgaagagc                48

<210> SEQ ID NO 152
<211> LENGTH: 16
<212> TYPE: PRT
<213> ORGANISM: Mus musculus

<400> SEQUENCE: 152

His Ile Tyr Trp Asp Asp Asp Lys Arg Tyr Asn Pro Ser Leu Lys Ser
1               5                   10                  15

<210> SEQ ID NO 153
<211> LENGTH: 18
<212> TYPE: DNA
<213> ORGANISM: Mus musculus

<400> SEQUENCE: 153 agagggact ttgactac                                                  18

<210> SEQ ID NO 154
<211> LENGTH: 6
<212> TYPE: PRT
<213> ORGANISM: Mus musculus

<400> SEQUENCE: 154

Arg Gly Asp Phe Asp Tyr
1               5

<210> SEQ ID NO 155
<211> LENGTH: 48
<212> TYPE: DNA
<213> ORGANISM: Mus musculus

<400> SEQUENCE: 155
agatctagtc agagccttgt acacagtaat ggaaacacct atttacat                48

<210> SEQ ID NO 156
<211> LENGTH: 16
<212> TYPE: PRT
<213> ORGANISM: Mus musculus

<400> SEQUENCE: 156

Arg Ser Ser Gln Ser Leu Val His Ser Asn Gly Asn Thr Tyr Leu His
```

<210> SEQ ID NO 157
<211> LENGTH: 21
<212> TYPE: DNA
<213> ORGANISM: Mus musculus

<400> SEQUENCE: 157
aaagtttcca accgattttc t                                        21

<210> SEQ ID NO 158
<211> LENGTH: 7
<212> TYPE: PRT
<213> ORGANISM: Mus musculus

<400> SEQUENCE: 158

Lys Val Ser Asn Arg Phe Ser
1               5

<210> SEQ ID NO 159
<211> LENGTH: 27
<212> TYPE: DNA
<213> ORGANISM: Mus musculus

<400> SEQUENCE: 159
tctcaaagta cacatgttcc tcccacg                                  27

<210> SEQ ID NO 160
<211> LENGTH: 9
<212> TYPE: PRT
<213> ORGANISM: Mus musculus

<400> SEQUENCE: 160

Ser Gln Ser Thr His Val Pro Pro Thr
1               5

<210> SEQ ID NO 161
<211> LENGTH: 417
<212> TYPE: DNA
<213> ORGANISM: Mus musculus

<400> SEQUENCE: 161
atggacaggc ttacttcttc attcctgctg ctgattgtcc ctgcatatgt cttgtcccaa    60
gttactctaa aagagtctgg ccctgggata ttgaagccct cacagaccct cagtctgact   120
tgttctttct ctgggttttc actgagcact tctggtatgg gtgtaggctg gattcgtcag   180
ccttcaggga agggtctgga gtggctggca cacatttggt gggatgatga taagtactat   240
aacccatccc tgaagagcca gctcacaatc tccaaggata cctccagaaa ccaggtattc   300
ctcaagatca ccagtgtgga cactgcagat actgccactt actactgtgc tcgaagatca   360
ctatccaggg actactttga ctactggggc caaggcacca ctctcacagt ctcctca      417

<210> SEQ ID NO 162
<211> LENGTH: 139
<212> TYPE: PRT
<213> ORGANISM: Mus musculus

<400> SEQUENCE: 162

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
            20                  25                  30

```
Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
 50                  55                  60

Gly Leu Glu Trp Leu Ala His Ile Trp Trp Asp Asp Lys Tyr Tyr
 65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
                100                 105                 110

Thr Tyr Tyr Cys Ala Arg Arg Ser Leu Ser Arg Asp Tyr Phe Asp Tyr
                115                 120                 125

Trp Gly Gln Gly Thr Thr Leu Thr Val Ser Ser
                130                 135
```

<210> SEQ ID NO 163
<211> LENGTH: 327
<212> TYPE: DNA
<213> ORGANISM: Mus musculus

<400> SEQUENCE: 163

```
atgacccaaa ctccactctc cctgcctgtc agtcttggag atcaagcctc catctcttgc      60
agatctagtc agagccttgt acacagtaat ggaaacacct atttacattg gtacctgcag     120
aagccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttatttctgc tctcaaagta cacatgttcc tctcacgttc     300
ggtgctggga ccaagctgga gctgaaa                                         327
```

<210> SEQ ID NO 164
<211> LENGTH: 109
<212> TYPE: PRT
<213> ORGANISM: Mus musculus

<400> SEQUENCE: 164

```
Met Thr Gln Thr Pro Leu Ser Leu Pro Val Ser Leu Gly Asp Gln Ala
 1               5                  10                  15

Ser Ile Ser Cys Arg Ser Ser Gln Ser Leu Val His Ser Asn Gly Asn
                20                  25                  30

Thr Tyr Leu His Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
 50                  55                  60

Ser Gly Ser Gly Ser Gly Thr Asp Phe Thr Leu Lys Ile Ser Arg Val
 65                  70                  75                  80

Glu Ala Glu Asp Leu Gly Val Tyr Phe Cys Ser Gln Ser Thr His Val
                85                  90                  95

Pro Leu Thr Phe Gly Ala Gly Thr Lys Leu Glu Leu Lys
                100                 105
```

<210> SEQ ID NO 165
<211> LENGTH: 21
<212> TYPE: DNA
<213> ORGANISM: Mus musculus

<400> SEQUENCE: 165
acttctggta tgggtgtagg c     21

<210> SEQ ID NO 166
<211> LENGTH: 7
<212> TYPE: PRT
<213> ORGANISM: Mus musculus

<400> SEQUENCE: 166

Thr Ser Gly Met Gly Val Gly
1               5

<210> SEQ ID NO 167
<211> LENGTH: 48
<212> TYPE: DNA
<213> ORGANISM: Mus musculus

<400> SEQUENCE: 167
cacatttggt gggatgatga taagtactat aacccatccc tgaagagc     48

<210> SEQ ID NO 168
<211> LENGTH: 16
<212> TYPE: PRT
<213> ORGANISM: Mus musculus

<400> SEQUENCE: 168

His Ile Trp Trp Asp Asp Asp Lys Tyr Tyr Asn Pro Ser Leu Lys Ser
1               5                   10                  15

<210> SEQ ID NO 169
<211> LENGTH: 30
<212> TYPE: DNA
<213> ORGANISM: Mus musculus

<400> SEQUENCE: 169
agatcactat ccagggacta ctttgactac     30

<210> SEQ ID NO 170
<211> LENGTH: 10
<212> TYPE: PRT
<213> ORGANISM: Mus musculus

<400> SEQUENCE: 170

Arg Ser Leu Ser Arg Asp Tyr Phe Asp Tyr
1               5                   10

<210> SEQ ID NO 171
<211> LENGTH: 48
<212> TYPE: DNA
<213> ORGANISM: Mus musculus

<400> SEQUENCE: 171
agatctagtc agagccttgt acacagtaat ggaaacacct atttacat     48

<210> SEQ ID NO 172
<211> LENGTH: 16
<212> TYPE: PRT
<213> ORGANISM: Mus musculus

<400> SEQUENCE: 172

Arg Ser Ser Gln Ser Leu Val His Ser Asn Gly Asn Thr Tyr Leu His
1               5                   10                  15

<210> SEQ ID NO 173
<211> LENGTH: 21

```
<212> TYPE: DNA
<213> ORGANISM: Mus musculus

<400> SEQUENCE: 173
aaagtttcca accgattttc t                                              21

<210> SEQ ID NO 174
<211> LENGTH: 7
<212> TYPE: PRT
<213> ORGANISM: Mus musculus

<400> SEQUENCE: 174

Lys Val Ser Asn Arg Phe Ser
1               5

<210> SEQ ID NO 175
<211> LENGTH: 27
<212> TYPE: DNA
<213> ORGANISM: Mus musculus

<400> SEQUENCE: 175
tctcaaagta cacatgttcc tctcacg                                        27

<210> SEQ ID NO 176
<211> LENGTH: 9
<212> TYPE: PRT
<213> ORGANISM: Mus musculus

<400> SEQUENCE: 176

Ser Gln Ser Thr His Val Pro Leu Thr
1               5

<210> SEQ ID NO 177
<211> LENGTH: 414
<212> TYPE: DNA
<213> ORGANISM: Mus musculus

<400> SEQUENCE: 177
atggacaggc ttacttcttc attcctgctg ctgattgtcc ctgcatatgt cttgtcccaa     60
gttactctaa aagagtctgg ccctgggata ttgaagccct cacagaccct cagtctgact    120
tgttctttct ctgggttttc actgagcact tctggtatgg gtgtaggctg gattcgtcag    180
ccttcaggga agggtctgga gtggctggca cacatttggt gggatgatga taagtactat    240
aacccatccc tgaagagcca gctcacaatc tccaaggata cctccagaaa ccaggtattc    300
ctcaagatca ccagtgtgga cactgcagat actgccactt actactgtgc tccatctact    360
atgattacaa cctttgctta ctggggccaa gggactctgg tcactgtctc tgca          414

<210> SEQ ID NO 178
<211> LENGTH: 138
<212> TYPE: PRT
<213> ORGANISM: Mus musculus

<400> SEQUENCE: 178

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
                20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
```

```
            50                  55                  60
Gly Leu Glu Trp Leu Ala His Ile Trp Trp Asp Asp Lys Tyr Tyr
 65                  70                  75                  80

Asn Pro Ser Leu Lys Ser Gln Leu Thr Ile Ser Lys Asp Thr Ser Arg
                 85                  90                  95

Asn Gln Val Phe Leu Lys Ile Thr Ser Val Asp Thr Ala Asp Thr Ala
            100                 105                 110

Thr Tyr Tyr Cys Ala Pro Ser Thr Met Ile Thr Phe Ala Tyr Trp
        115                 120                 125

Gly Gln Gly Thr Leu Val Thr Val Ser Ala
    130                 135
```

<210> SEQ ID NO 179
<211> LENGTH: 327
<212> TYPE: DNA
<213> ORGANISM: Mus musculus

<400> SEQUENCE: 179

```
atgacccaaa ctccactctc cctgcctgtc agtcttggag atcaagcctc catctcttgc    60
agatctagtc agagccttgt acacagtaat ggaaacacct atttacattg gtacctgcag   120
aagccaggcc agtctccaaa gctcctgatc tacaaagttt ccaaccgatt ttctggggtc   180
ccagacaggt tcagtggcag tggatcaggg acagatttca cactcaagat cagcagagtg   240
gaggctgagg atctgggagt ttatttctgc tctcaaagta cacatgttcc ctcacgttc    300
ggtgctggga ccaagctgga gctgaaa                                       327
```

<210> SEQ ID NO 180
<211> LENGTH: 109
<212> TYPE: PRT
<213> ORGANISM: Mus musculus

<400> SEQUENCE: 180

```
Met Thr Gln Thr Pro Leu Ser Leu Pro Val Ser Leu Gly Asp Gln Ala
  1               5                  10                  15

Ser Ile Ser Cys Arg Ser Ser Gln Ser Leu Val His Ser Asn Gly Asn
             20                  25                  30

Thr Tyr Leu His Trp Tyr Leu Gln Lys Pro Gly Gln Ser Pro Lys Leu
         35                  40                  45

Leu Ile Tyr Lys Val Ser Asn Arg Phe Ser Gly Val Pro Asp Arg Phe
     50                  55                  60

Ser Gly Ser Gly Ser Gly Thr Asp Phe Thr Leu Lys Ile Ser Arg Val
 65                  70                  75                  80

Glu Ala Glu Asp Leu Gly Val Tyr Phe Cys Ser Gln Ser Thr His Val
                 85                  90                  95

Pro Leu Thr Phe Gly Ala Gly Thr Lys Leu Glu Leu Lys
            100                 105
```

<210> SEQ ID NO 181
<211> LENGTH: 21
<212> TYPE: DNA
<213> ORGANISM: Mus musculus

<400> SEQUENCE: 181

```
acttctggta tgggtgtagg c                                              21
```

<210> SEQ ID NO 182
<211> LENGTH: 7

```
<212> TYPE: PRT
<213> ORGANISM: Mus musculus

<400> SEQUENCE: 182

Thr Ser Gly Met Gly Val Gly
1               5

<210> SEQ ID NO 183
<211> LENGTH: 48
<212> TYPE: DNA
<213> ORGANISM: Mus musculus

<400> SEQUENCE: 183
cacatttggt gggatgatga taagtactat aacccatccc tgaagagc             48

<210> SEQ ID NO 184
<211> LENGTH: 16
<212> TYPE: PRT
<213> ORGANISM: Mus musculus

<400> SEQUENCE: 184

His Ile Trp Trp Asp Asp Asp Lys Tyr Tyr Asn Pro Ser Leu Lys Ser
1               5                   10                  15

<210> SEQ ID NO 185
<211> LENGTH: 27
<212> TYPE: DNA
<213> ORGANISM: Mus musculus

<400> SEQUENCE: 185
tctactatga ttacaacctt tgcttac                                    27

<210> SEQ ID NO 186
<211> LENGTH: 9
<212> TYPE: PRT
<213> ORGANISM: Mus musculus

<400> SEQUENCE: 186

Ser Thr Met Ile Thr Thr Phe Ala Tyr
1               5

<210> SEQ ID NO 187
<211> LENGTH: 48
<212> TYPE: DNA
<213> ORGANISM: Mus musculus

<400> SEQUENCE: 187
agatctagtc agagccttgt acacagtaat ggaaacacct atttacat             48

<210> SEQ ID NO 188
<211> LENGTH: 16
<212> TYPE: PRT
<213> ORGANISM: Mus musculus

<400> SEQUENCE: 188

Arg Ser Ser Gln Ser Leu Val His Ser Asn Gly Asn Thr Tyr Leu His
1               5                   10                  15

<210> SEQ ID NO 189
<211> LENGTH: 21
<212> TYPE: DNA
<213> ORGANISM: Mus musculus

<400> SEQUENCE: 189
```

```
aaagtttcca accgattttc t                                              21
```

<210> SEQ ID NO 190
<211> LENGTH: 7
<212> TYPE: PRT
<213> ORGANISM: Mus musculus

<400> SEQUENCE: 190

```
Lys Val Ser Asn Arg Phe Ser
1               5
```

<210> SEQ ID NO 191
<211> LENGTH: 27
<212> TYPE: DNA
<213> ORGANISM: Mus musculus

<400> SEQUENCE: 191

```
tctcaaagta cacatgttcc tctcacg                                        27
```

<210> SEQ ID NO 192
<211> LENGTH: 9
<212> TYPE: PRT
<213> ORGANISM: Mus musculus

<400> SEQUENCE: 192

```
Ser Gln Ser Thr His Val Pro Leu Thr
1               5
```

<210> SEQ ID NO 193
<211> LENGTH: 420
<212> TYPE: DNA
<213> ORGANISM: Mus musculus

<400> SEQUENCE: 193

```
atggctgtcc tggtgctgct cctctgcctg gtgacattcc caagctgtgt cctgtcccag    60
gtgcagctga agcagtcagg acctggccta gtgcagccct cacagagcct gtccataacc   120
tgcacagtct ctggtttctc attaactagc tatggtgtac actgggttcg ccagtctcca   180
ggaaagggtc tggagtggct gggagtgata tggagaggtg gaagcacaga ctacaatgca   240
gctttcatgt ccagactgag catcaccaag acaactcca agagccaagt tttctttaaa   300
atgaacagtc tgcaagctga tgacactgcc atatactact gtgccaacaa taggtacgag   360 agaggggtt actatgctat ggactactgg ggtcaaggaa cctcagtcac cgtctcctca   420
```

<210> SEQ ID NO 194
<211> LENGTH: 140
<212> TYPE: PRT
<213> ORGANISM: Mus musculus

<400> SEQUENCE: 194

```
Met Ala Val Leu Val Leu Leu Leu Cys Leu Val Thr Phe Pro Ser Cys
1               5                   10                  15

Val Leu Ser Gln Val Gln Leu Lys Gln Ser Gly Pro Gly Leu Val Gln
                20                  25                  30

Pro Ser Gln Ser Leu Ser Ile Thr Cys Thr Val Ser Gly Phe Ser Leu
            35                  40                  45

Thr Ser Tyr Gly Val His Trp Val Arg Gln Ser Pro Gly Lys Gly Leu
        50                  55                  60

Glu Trp Leu Gly Val Ile Trp Arg Gly Gly Ser Thr Asp Tyr Asn Ala
65                  70                  75                  80
```

```
Ala Phe Met Ser Arg Leu Ser Ile Thr Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Asn Asn Arg Tyr Glu Arg Gly Gly Tyr Tyr Ala Met Asp
        115                 120                 125

Tyr Trp Gly Gln Gly Thr Ser Val Thr Val Ser Ser
130                 135                 140

<210> SEQ ID NO 195
<211> LENGTH: 327
<212> TYPE: DNA
<213> ORGANISM: Mus musculus

<400> SEQUENCE: 195
atgacccaaa ctccactctc cctgcctgtc agtcttggag atcaagcctc catctcttgc      60
agatctagtc agagcattgt acatagtaat ggaaacacct atttagaatg gtacctgcat     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                          327

<210> SEQ ID NO 196
<211> LENGTH: 109
<212> TYPE: PRT
<213> ORGANISM: Mus musculus

<400> SEQUENCE: 196

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu His Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

<210> SEQ ID NO 197
<211> LENGTH: 15
<212> TYPE: DNA
<213> ORGANISM: Mus musculus

<400> SEQUENCE: 197
agctatggtg tacac                                                       15

<210> SEQ ID NO 198
<211> LENGTH: 5
<212> TYPE: PRT
<213> ORGANISM: Mus musculus

<400> SEQUENCE: 198
```

Ser Tyr Gly Val His
1               5

<210> SEQ ID NO 199
<211> LENGTH: 48
<212> TYPE: DNA
<213> ORGANISM: Mus musculus

<400> SEQUENCE: 199
gtgatatgga gaggtggaag cacagactac aatgcagctt tcatgtcc                48

<210> SEQ ID NO 200
<211> LENGTH: 16
<212> TYPE: PRT
<213> ORGANISM: Mus musculus

<400> SEQUENCE: 200

Val Ile Trp Arg Gly Gly Ser Thr Asp Tyr Asn Ala Ala Phe Met Ser
1               5                   10                  15

<210> SEQ ID NO 201
<211> LENGTH: 39
<212> TYPE: DNA
<213> ORGANISM: Mus musculus

<400> SEQUENCE: 201
aataggtacg agagagggggg ttactatgct atggactac                         39

<210> SEQ ID NO 202
<211> LENGTH: 13
<212> TYPE: PRT
<213> ORGANISM: Mus musculus

<400> SEQUENCE: 202

Asn Arg Tyr Glu Arg Gly Gly Tyr Tyr Ala Met Asp Tyr
1               5                   10

<210> SEQ ID NO 203
<211> LENGTH: 48
<212> TYPE: DNA
<213> ORGANISM: Mus musculus

<400> SEQUENCE: 203
agatctagtc agagcattgt acatagtaat ggaaacacct atttagaa                48

<210> SEQ ID NO 204
<211> LENGTH: 16
<212> TYPE: PRT
<213> ORGANISM: Mus musculus

<400> SEQUENCE: 204

Arg Ser Ser Gln Ser Ile Val His Ser Asn Gly Asn Thr Tyr Leu Glu
1               5                   10                  15

<210> SEQ ID NO 205
<211> LENGTH: 21
<212> TYPE: DNA
<213> ORGANISM: Mus musculus

<400> SEQUENCE: 205
aaagtttcca accgattttc t                                             21

<210> SEQ ID NO 206
<211> LENGTH: 7

```
<212> TYPE: PRT
<213> ORGANISM: Mus musculus

<400> SEQUENCE: 206

Lys Val Ser Asn Arg Phe Ser
1               5

<210> SEQ ID NO 207
<211> LENGTH: 27
<212> TYPE: DNA
<213> ORGANISM: Mus musculus

<400> SEQUENCE: 207
tttcaaggtt cacatgttcc gctcacg                                         27

<210> SEQ ID NO 208
<211> LENGTH: 9
<212> TYPE: PRT
<213> ORGANISM: Mus musculus

<400> SEQUENCE: 208

Phe Gln Gly Ser His Val Pro Leu Thr
1               5

<210> SEQ ID NO 209
<211> LENGTH: 420
<212> TYPE: DNA
<213> ORGANISM: Mus musculus

<400> SEQUENCE: 209
atggctgtcc tggtgctgct cctctgcctg gtgacattcc caagctgtgt cctgtcccag     60
gtgcagctga agcagtcagg acctggccta gtgcagccct cacagagcct gtccataacc    120
tgcacagtct ctggtttctc attaactagc tatggtgtac actgggttcg ccagtctcca    180
ggaaagggtc tggagtggct gggagtgata tggagaggtg aagcacaga ctacaatgca     240 gctttcatgt ccagactgag catcaccaag acaactcca agagccaagt tttctttaaa     300
atgaacagtc tgcaagctga tgacactgcc atatactact gtgccaacaa taggtacgag    360 agaggggggtt actatgctat ggactactgg ggtcaaggaa cctcagtcac cgtctcctca    420

<210> SEQ ID NO 210
<211> LENGTH: 140
<212> TYPE: PRT
<213> ORGANISM: Mus musculus

<400> SEQUENCE: 210

Met Ala Val Leu Val Leu Leu Cys Leu Val Thr Phe Pro Ser Cys
1               5                   10                  15

Val Leu Ser Gln Val Gln Leu Lys Gln Ser Gly Pro Gly Leu Val Gln
                20                  25                  30

Pro Ser Gln Ser Leu Ser Ile Thr Cys Thr Val Ser Gly Phe Ser Leu
            35                  40                  45

Thr Ser Tyr Gly Val His Trp Val Arg Gln Ser Pro Gly Lys Gly Leu
        50                  55                  60

Glu Trp Leu Gly Val Ile Trp Arg Gly Gly Ser Thr Asp Tyr Asn Ala
65                  70                  75                  80

Ala Phe Met Ser Arg Leu Ser Ile Thr Lys Asp Asn Ser Lys Ser Gln
                85                  90                  95

Val Phe Phe Lys Met Asn Ser Leu Gln Ala Asp Asp Thr Ala Ile Tyr
                100                 105                 110
```

Tyr Cys Ala Asn Asn Arg Tyr Glu Arg Gly Gly Tyr Tyr Ala Met Asp
            115                 120                 125

Tyr Trp Gly Gln Gly Thr Ser Val Thr Val Ser Ser
    130                 135                 140

<210> SEQ ID NO 211
<211> LENGTH: 327
<212> TYPE: DNA
<213> ORGANISM: Mus musculus

<400> SEQUENCE: 211
atgacccaaa ctccactctc cctgcctgtc agtcttggag atcaagcctc catctcttgc     60
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgagg atctgggagt ttattactgc tttcaaggtt cacatgttcc gctcacgttc    300
ggtgctggga ccaagctgga gctgaaa                                        327

<210> SEQ ID NO 212
<211> LENGTH: 109
<212> TYPE: PRT
<213> ORGANISM: Mus musculus

<400> SEQUENCE: 212

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

<210> SEQ ID NO 213
<211> LENGTH: 15
<212> TYPE: DNA
<213> ORGANISM: Mus musculus

<400> SEQUENCE: 213
agctatggtg tacac                                                      15

<210> SEQ ID NO 214
<211> LENGTH: 5
<212> TYPE: PRT
<213> ORGANISM: Mus musculus

<400> SEQUENCE: 214

Ser Tyr Gly Val His
1               5

<210> SEQ ID NO 215

```
<211> LENGTH: 48
<212> TYPE: DNA
<213> ORGANISM: Mus musculus

<400> SEQUENCE: 215
gtgatatgga gaggtggaag cacagactac aatgcagctt tcatgtcc                48

<210> SEQ ID NO 216
<211> LENGTH: 16
<212> TYPE: PRT
<213> ORGANISM: Mus musculus

<400> SEQUENCE: 216

Val Ile Trp Arg Gly Gly Ser Thr Asp Tyr Asn Ala Ala Phe Met Ser
1               5                   10                  15

<210> SEQ ID NO 217
<211> LENGTH: 39
<212> TYPE: DNA
<213> ORGANISM: Mus musculus

<400> SEQUENCE: 217
aataggtacg agagaggggg ttactatgct atggactac                          39

<210> SEQ ID NO 218
<211> LENGTH: 13
<212> TYPE: PRT
<213> ORGANISM: Mus musculus

<400> SEQUENCE: 218

Asn Arg Tyr Glu Arg Gly Gly Tyr Tyr Ala Met Asp Tyr
1               5                   10

<210> SEQ ID NO 219
<211> LENGTH: 48
<212> TYPE: DNA
<213> ORGANISM: Mus musculus

<400> SEQUENCE: 219
agatctagtc agagcattgt acatagtaat ggaaacacct atttagaa                48

<210> SEQ ID NO 220
<211> LENGTH: 16
<212> TYPE: PRT
<213> ORGANISM: Mus musculus

<400> SEQUENCE: 220

Arg Ser Ser Gln Ser Ile Val His Ser Asn Gly Asn Thr Tyr Leu Glu
1               5                   10                  15

<210> SEQ ID NO 221
<211> LENGTH: 21
<212> TYPE: DNA
<213> ORGANISM: Mus musculus

<400> SEQUENCE: 221
aaagtttcca accgattttc t                                             21

<210> SEQ ID NO 222
<211> LENGTH: 7
<212> TYPE: PRT
<213> ORGANISM: Mus musculus

<400> SEQUENCE: 222
```

Lys Val Ser Asn Arg Phe Ser
1               5

<210> SEQ ID NO 223
<211> LENGTH: 27
<212> TYPE: DNA
<213> ORGANISM: Mus musculus

<400> SEQUENCE: 223
tttcaaggtt cacatgttcc gctcacg                                      27

<210> SEQ ID NO 224
<211> LENGTH: 9
<212> TYPE: PRT
<213> ORGANISM: Mus musculus

<400> SEQUENCE: 224

Phe Gln Gly Ser His Val Pro Leu Thr
1               5

<210> SEQ ID NO 225
<211> LENGTH: 408
<212> TYPE: DNA
<213> ORGANISM: Mus musculus

<400> SEQUENCE: 225
atggacaggc ttacttcctc attcctgctg ctgattgtcc ctgcatatgt cctttcccag    60
gttactctga aagagtctgg ccctgggata ttgcagccct cccagaccct cagtctgact   120
tgttctttct ctgggttttc actgagcact tctggtatgg gtgtgagctg gattcgtcag   180
ccttcaggaa agggtctgga gtggctggca cacatttact gggatgatga caagcgctat   240
aacccatccc tgaagagccg gctcacaatc tccaaggata cctccagaaa ccaggtattc   300
ctcaagatca ccagtgtgga cactgcagat actgccacat actactgtgc tcggtatggt   360
aactcctttg cttactgggg ccaagggact ctggtcactg tctctgca              408

<210> SEQ ID NO 226
<211> LENGTH: 136
<212> TYPE: PRT
<213> ORGANISM: Mus musculus

<400> SEQUENCE: 226

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Asp Lys Arg Tyr
65                  70                  75                  80

Asn Pro Ser Leu Lys Ser Arg Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Tyr Gly Asn Ser Phe Ala Tyr Trp Gly Gln
        115                 120                 125

Gly Thr Leu Val Thr Val Ser Ala
    130                 135

<210> SEQ ID NO 227
<211> LENGTH: 327
<212> TYPE: DNA
<213> ORGANISM: Mus musculus

<400> SEQUENCE: 227

```
atgacccaaa ctccactctc cctgcctgtc agtcttggag atcaagcctc catctcttgc    60
agatctagtc agagcattgt acatagtaat ggaaacacct atttagaatg gtacctgcag   120
aaaccaggcc agtctccaaa gctcctgatc tacaaagttt ccaaccgatt ttctggggtc   180
ccagacaggt tcagtggcag tggatcaggg acagattttca cactcaagat cagcagagtg   240
gaggctgagg atctgggagt ttattactgc tttcaaggtt cacatgttcc gctcacgttc   300
ggtgctggga ccaagctgga gctgaaa                                       327
```

<210> SEQ ID NO 228
<211> LENGTH: 109
<212> TYPE: PRT
<213> ORGANISM: Mus musculus

<400> SEQUENCE: 228

```
Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105
```

<210> SEQ ID NO 229
<211> LENGTH: 21
<212> TYPE: DNA
<213> ORGANISM: Mus musculus

<400> SEQUENCE: 229

```
acttctggta tgggtgtgag c                                              21
```

<210> SEQ ID NO 230
<211> LENGTH: 7
<212> TYPE: PRT
<213> ORGANISM: Mus musculus

<400> SEQUENCE: 230

```
Thr Ser Gly Met Gly Val Ser
1               5
```

<210> SEQ ID NO 231
<211> LENGTH: 48
<212> TYPE: DNA
<213> ORGANISM: Mus musculus

<400> SEQUENCE: 231

```
cacatttact gggatgatga caagcgctat aacccatccc tgaagagc                48
```

<210> SEQ ID NO 232
<211> LENGTH: 16
<212> TYPE: PRT
<213> ORGANISM: Mus musculus

<400> SEQUENCE: 232

```
His Ile Tyr Trp Asp Asp Asp Lys Arg Tyr Asn Pro Ser Leu Lys Ser
1               5                   10                  15
```

<210> SEQ ID NO 233
<211> LENGTH: 21
<212> TYPE: DNA
<213> ORGANISM: Mus musculus

<400> SEQUENCE: 233

```
tatggtaact cctttgctta c                                             21
```

<210> SEQ ID NO 234
<211> LENGTH: 7
<212> TYPE: PRT
<213> ORGANISM: Mus musculus

<400> SEQUENCE: 234

```
Tyr Gly Asn Ser Phe Ala Tyr
1               5
```

<210> SEQ ID NO 235
<211> LENGTH: 48
<212> TYPE: DNA
<213> ORGANISM: Mus musculus

<400> SEQUENCE: 235

```
agatctagtc agagcattgt acatagtaat ggaaacacct atttagaa                48
```

<210> SEQ ID NO 236
<211> LENGTH: 16
<212> TYPE: PRT
<213> ORGANISM: Mus musculus

<400> SEQUENCE: 236

```
Arg Ser Ser Gln Ser Ile Val His Ser Asn Gly Asn Thr Tyr Leu Glu
1               5                   10                  15
```

<210> SEQ ID NO 237
<211> LENGTH: 21
<212> TYPE: DNA
<213> ORGANISM: Mus musculus

<400> SEQUENCE: 237

```
aaagtttcca accgattttc t                                             21
```

<210> SEQ ID NO 238
<211> LENGTH: 7
<212> TYPE: PRT
<213> ORGANISM: Mus musculus

<400> SEQUENCE: 238

```
Lys Val Ser Asn Arg Phe Ser
1               5
```

<210> SEQ ID NO 239

```
<211> LENGTH: 27
<212> TYPE: DNA
<213> ORGANISM: Mus musculus

<400> SEQUENCE: 239
tttcaaggtt cacatgttcc gctcacg                                              27

<210> SEQ ID NO 240
<211> LENGTH: 9
<212> TYPE: PRT
<213> ORGANISM: Mus musculus

<400> SEQUENCE: 240

Phe Gln Gly Ser His Val Pro Leu Thr
1               5

<210> SEQ ID NO 241
<211> LENGTH: 411
<212> TYPE: DNA
<213> ORGANISM: Mus musculus

<400> SEQUENCE: 241
atgggatgga gctatatcat cctctttttg gtagcaacag ctacagatgt ccactcccag          60
gtccaactgc agcagcctgg ggctgaactg gtgaagcctg ggcttcagt gaagctgtcc          120 tgcaaggctt ctggctacac cttcaccagc tactggatgc actgggtgaa gcagaggcct         180
ggacaaggcc ttgagtggat tggagagatt aatcctagca acggtcgtac taactacaat        240
gagaagttca gagcaaggc cacactgact gtagacaaat cctccagcac agcctacatg          300
caactcagca gcctgacatc tgaggactct gcggtctatt actgtgcaag agagcattac         360
tacggctacg gtgcttactg gggccaaggg actctggtca ctgtctctgc a                  411

<210> SEQ ID NO 242
<211> LENGTH: 137
<212> TYPE: PRT
<213> ORGANISM: Mus musculus

<400> SEQUENCE: 242

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Gln Gly Leu
        50                  55                  60

Glu Trp Ile Gly Glu Ile Asn Pro Ser Asn Gly Arg Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Glu His Tyr Tyr Gly Tyr Gly Ala Tyr Trp Gly
        115                 120                 125

Gln Gly Thr Leu Val Thr Val Ser Ala
    130                 135

<210> SEQ ID NO 243
<211> LENGTH: 327
```

<212> TYPE: DNA
<213> ORGANISM: Mus musculus

<400> SEQUENCE: 243

```
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                          327
```

<210> SEQ ID NO 244
<211> LENGTH: 109
<212> TYPE: PRT
<213> ORGANISM: Mus musculus

<400> SEQUENCE: 244

```
Met Thr Gln Thr Pro Leu Ser Leu Pro Val Ser Leu Gly Asp Gln Ala
1               5                   10                  15
Ser Ile Ser Cys Arg Ser Ser Gln Ser Ile Val His Ser Asn Gly Asn
            20                  25                  30
Thr Tyr Leu Glu Trp Tyr Leu Gln Lys Pro Gly Gln Ser Pro Lys Leu
        35                  40                  45
Leu Ile Tyr Lys Val Ser Asn Arg Phe Ser Gly Val Pro Asp Arg Phe
    50                  55                  60
Ser Gly Ser Gly Ser Gly Thr Asp Phe Thr Leu Lys Ile Ser Arg Val
65                  70                  75                  80
Glu Ala Glu Asp Leu Gly Val Tyr Tyr Cys Phe Gln Gly Ser His Val
                85                  90                  95
Pro Leu Thr Phe Gly Ala Gly Thr Lys Leu Glu Leu Lys
            100                 105
```

<210> SEQ ID NO 245
<211> LENGTH: 15
<212> TYPE: DNA
<213> ORGANISM: Mus musculus

<400> SEQUENCE: 245

```
agctactgga tgcac                                                       15
```

<210> SEQ ID NO 246
<211> LENGTH: 5
<212> TYPE: PRT
<213> ORGANISM: Mus musculus

<400> SEQUENCE: 246

```
Ser Tyr Trp Met His
1               5
```

<210> SEQ ID NO 247
<211> LENGTH: 51
<212> TYPE: DNA
<213> ORGANISM: Mus musculus

<400> SEQUENCE: 247

```
gagattaatc ctagcaacgg tcgtactaac tacaatgaga agttcaagag c               51
```

<210> SEQ ID NO 248

```
<211> LENGTH: 17
<212> TYPE: PRT
<213> ORGANISM: Mus musculus

<400> SEQUENCE: 248

Glu Ile Asn Pro Ser Asn Gly Arg Thr Asn Tyr Asn Glu Lys Phe Lys
1               5                   10                  15

Ser

<210> SEQ ID NO 249
<211> LENGTH: 27
<212> TYPE: DNA
<213> ORGANISM: Mus musculus

<400> SEQUENCE: 249
gagcattact acggctacgg tgcttac                                         27

<210> SEQ ID NO 250
<211> LENGTH: 9
<212> TYPE: PRT
<213> ORGANISM: Mus musculus

<400> SEQUENCE: 250

Glu His Tyr Tyr Gly Tyr Gly Ala Tyr
1               5

<210> SEQ ID NO 251
<211> LENGTH: 48
<212> TYPE: DNA
<213> ORGANISM: Mus musculus

<400> SEQUENCE: 251
agatctagtc agagcattgt acatagtaat ggaaacacct atttagaa                  48

<210> SEQ ID NO 252
<211> LENGTH: 16
<212> TYPE: PRT
<213> ORGANISM: Mus musculus

<400> SEQUENCE: 252

Arg Ser Ser Gln Ser Ile Val His Ser Asn Gly Asn Thr Tyr Leu Glu
1               5                   10                  15

<210> SEQ ID NO 253
<211> LENGTH: 21
<212> TYPE: DNA
<213> ORGANISM: Mus musculus

<400> SEQUENCE: 253
aaagtttcca accgattttc t                                               21

<210> SEQ ID NO 254
<211> LENGTH: 7
<212> TYPE: PRT
<213> ORGANISM: Mus musculus

<400> SEQUENCE: 254

Lys Val Ser Asn Arg Phe Ser
1               5

<210> SEQ ID NO 255
<211> LENGTH: 27
<212> TYPE: DNA
<213> ORGANISM: Mus musculus
```

<400> SEQUENCE: 255
tttcaaggtt cacatgttcc gctcacg               27

<210> SEQ ID NO 256
<211> LENGTH: 9
<212> TYPE: PRT
<213> ORGANISM: Mus musculus

<400> SEQUENCE: 256

Phe Gln Gly Ser His Val Pro Leu Thr
1               5

<210> SEQ ID NO 257
<211> LENGTH: 429
<212> TYPE: DNA
<213> ORGANISM: Mus musculus

<400> SEQUENCE: 257
atgaacaggc ttacttcctc attgctgctg ctgattgtcc ctgcatatgt cctgtcccag      60
gttactctga aagagtctgg ccctgggata ttgcagccct cccagaccct cagtctgact     120
tgttctttct ctgggttttc actgagcact tctggtatgg gtgtgagctg gattcgtcag     180
ccttcaggaa agggtctgga gtggctggca cacatttact gggatgatga caagcgctat     240
aacccatccc tgaagagccg gctcacaatc tccaaggata cctccagcaa ccaggtattc     300
ctcaagatca ccagtgtgga cactgcagat actgccacat actactgtgc tcgaaggggc     360
ccctcctact ataggtacag ggactacttt gactactggg gccaaggcac cactctcaca     420
gtctcctca                                                             429

<210> SEQ ID NO 258
<211> LENGTH: 143
<212> TYPE: PRT
<213> ORGANISM: Mus musculus

<400> SEQUENCE: 258

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Asp Lys Arg Tyr
65                  70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Gly Pro Ser Tyr Tyr Arg Tyr Arg Asp
        115                 120                 125

Tyr Phe Asp Tyr Trp Gly Gln Gly Thr Thr Leu Thr Val Ser Ser
    130                 135                 140

<210> SEQ ID NO 259
<211> LENGTH: 327
<212> TYPE: DNA

<213> ORGANISM: Mus musculus

<400> SEQUENCE: 259

| | |
|---|---|
| atgacccaaa ctccactctc cctgcctgtc agtcttggag atcaagcctc catctcttgc | 60 |
| agatctagtc agagcattgt acatagtaat ggaaacacct atttagaatg gtacctgcag | 120 |
| aaaccaggcc agtctccaaa gctcctgatc tacaaagttt ccaaccgatt ttctggggtc | 180 |
| ccagacaggt tcagtggcag tggatcaggg acagatttca cactcaagat cagcagagtg | 240 |
| gaggctgagg atctgggagt ttattactgc tttcaaggtt cacatgttcc gctcacgttc | 300 |
| ggtgctggga ccaagctgga gctgaaa | 327 |

<210> SEQ ID NO 260
<211> LENGTH: 109
<212> TYPE: PRT
<213> ORGANISM: Mus musculus

<400> SEQUENCE: 260

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

<210> SEQ ID NO 261
<211> LENGTH: 21
<212> TYPE: DNA
<213> ORGANISM: Mus musculus

<400> SEQUENCE: 261

| | |
|---|---|
| acttctggta tgggtgtgag c | 21 |

<210> SEQ ID NO 262
<211> LENGTH: 7
<212> TYPE: PRT
<213> ORGANISM: Mus musculus

<400> SEQUENCE: 262

Thr Ser Gly Met Gly Val Ser
1               5

<210> SEQ ID NO 263
<211> LENGTH: 48
<212> TYPE: DNA
<213> ORGANISM: Mus musculus

<400> SEQUENCE: 263

| | |
|---|---|
| cacatttact gggatgatga caagcgctat aacccatccc tgaagagc | 48 |

<210> SEQ ID NO 264
<211> LENGTH: 16

```
<212> TYPE: PRT
<213> ORGANISM: Mus musculus

<400> SEQUENCE: 264

His Ile Tyr Trp Asp Asp Asp Lys Arg Tyr Asn Pro Ser Leu Lys Ser
1               5                   10                  15

<210> SEQ ID NO 265
<211> LENGTH: 42
<212> TYPE: DNA
<213> ORGANISM: Mus musculus

<400> SEQUENCE: 265
aggggcccct cctactatag gtacagggac tactttgact ac                              42

<210> SEQ ID NO 266
<211> LENGTH: 14
<212> TYPE: PRT
<213> ORGANISM: Mus musculus

<400> SEQUENCE: 266

Arg Gly Pro Ser Tyr Tyr Arg Tyr Arg Asp Tyr Phe Asp Tyr
1               5                   10

<210> SEQ ID NO 267
<211> LENGTH: 48
<212> TYPE: DNA
<213> ORGANISM: Mus musculus

<400> SEQUENCE: 267
agatctagtc agagcattgt acatagtaat ggaaacacct atttagaa                        48

<210> SEQ ID NO 268
<211> LENGTH: 16
<212> TYPE: PRT
<213> ORGANISM: Mus musculus

<400> SEQUENCE: 268

Arg Ser Ser Gln Ser Ile Val His Ser Asn Gly Asn Thr Tyr Leu Glu
1               5                   10                  15

<210> SEQ ID NO 269
<211> LENGTH: 21
<212> TYPE: DNA
<213> ORGANISM: Mus musculus

<400> SEQUENCE: 269
aaagtttcca accgattttc t                                                     21

<210> SEQ ID NO 270
<211> LENGTH: 7
<212> TYPE: PRT
<213> ORGANISM: Mus musculus

<400> SEQUENCE: 270

Lys Val Ser Asn Arg Phe Ser
1               5

<210> SEQ ID NO 271
<211> LENGTH: 27
<212> TYPE: DNA
<213> ORGANISM: Mus musculus

<400> SEQUENCE: 271
```

-continued tttcaaggtt cacatgttcc gctcacg    27

<210> SEQ ID NO 272
<211> LENGTH: 9
<212> TYPE: PRT
<213> ORGANISM: Mus musculus

<400> SEQUENCE: 272

Phe Gln Gly Ser His Val Pro Leu Thr
1               5

<210> SEQ ID NO 273
<211> LENGTH: 420
<212> TYPE: DNA
<213> ORGANISM: Mus musculus

<400> SEQUENCE: 273
atggacaggc ttacttcttc attcctgctg ctgattgtcc ctgcatatgt cttgtcccaa    60
gttactctaa aagagtctgg ccctgggata ttgaagccct cacagaccct cagtctgact   120
tgttctttct ctgggttttc actgagcact tctggtatgg gtgtaggctg gattcgtcag   180
ccttcaggga agggtctgga gtggctggca cacatttggt gggatgatga aagtactat   240 aacccatccc tgaagagcca gctcacaatc tccaaggata cctccagaaa ccaggtattc   300
ctcaagatca ccagtgtgga cactgcagat actgccactt actactgtgc tcgaagagcc   360
ctctatggtt acgacgctat ggactactgg ggtcaaggaa cctcagtcac cgtctcctca   420

<210> SEQ ID NO 274
<211> LENGTH: 140
<212> TYPE: PRT
<213> ORGANISM: Mus musculus

<400> SEQUENCE: 274

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
                20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
        50                  55                  60

Gly Leu Glu Trp Leu Ala His Ile Trp Trp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Ala Leu Tyr Gly Tyr Asp Ala Met Asp
        115                 120                 125

Tyr Trp Gly Gln Gly Thr Ser Val Thr Val Ser Ser
    130                 135                 140

<210> SEQ ID NO 275
<211> LENGTH: 327
<212> TYPE: DNA
<213> ORGANISM: Mus musculus

<400> SEQUENCE: 275
atgacccaaa ctccactctc cctgcctgtc agtcttggag atcaagcctc catctcttgc    60

```
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgagg atctgggagt ttattactgc tttcaaggtt cacatgttcc tctcacgttc    300
ggtgctggga ccaagctgga gctgaaa                                        327
```

<210> SEQ ID NO 276
<211> LENGTH: 109
<212> TYPE: PRT
<213> ORGANISM: Mus musculus

<400> SEQUENCE: 276

```
Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105
```

<210> SEQ ID NO 277
<211> LENGTH: 21
<212> TYPE: DNA
<213> ORGANISM: Mus musculus

<400> SEQUENCE: 277

```
acttctggta tgggtgtagg c                                              21
```

<210> SEQ ID NO 278
<211> LENGTH: 7
<212> TYPE: PRT
<213> ORGANISM: Mus musculus

<400> SEQUENCE: 278

```
Thr Ser Gly Met Gly Val Gly
1               5
```

<210> SEQ ID NO 279
<211> LENGTH: 48
<212> TYPE: DNA
<213> ORGANISM: Mus musculus

<400> SEQUENCE: 279

```
cacatttggt gggatgatga taagtactat aacccatccc tgaagagc                 48
```

<210> SEQ ID NO 280
<211> LENGTH: 16
<212> TYPE: PRT
<213> ORGANISM: Mus musculus

<400> SEQUENCE: 280

```
His Ile Trp Trp Asp Asp Asp Lys Tyr Tyr Asn Pro Ser Leu Lys Ser
1               5                   10                  15
```

<210> SEQ ID NO 281
<211> LENGTH: 33
<212> TYPE: DNA
<213> ORGANISM: Mus musculus

<400> SEQUENCE: 281
agagccctct atggttacga cgctatggac tac                    33

<210> SEQ ID NO 282
<211> LENGTH: 11
<212> TYPE: PRT
<213> ORGANISM: Mus musculus

<400> SEQUENCE: 282

```
Arg Ala Leu Tyr Gly Tyr Asp Ala Met Asp Tyr
1               5                   10
```

<210> SEQ ID NO 283
<211> LENGTH: 48
<212> TYPE: DNA
<213> ORGANISM: Mus musculus

<400> SEQUENCE: 283
agatctagtc agagcattgt acatagtaat ggaaacacct atttagaa    48

<210> SEQ ID NO 284
<211> LENGTH: 16
<212> TYPE: PRT
<213> ORGANISM: Mus musculus

<400> SEQUENCE: 284

```
Arg Ser Ser Gln Ser Ile Val His Ser Asn Gly Asn Thr Tyr Leu Glu
1               5                   10                  15
```

<210> SEQ ID NO 285
<211> LENGTH: 21
<212> TYPE: DNA
<213> ORGANISM: Mus musculus

<400> SEQUENCE: 285
aaagtttcca accgattttc t                                 21

<210> SEQ ID NO 286
<211> LENGTH: 7
<212> TYPE: PRT
<213> ORGANISM: Mus musculus

<400> SEQUENCE: 286

```
Lys Val Ser Asn Arg Phe Ser
1               5
```

<210> SEQ ID NO 287
<211> LENGTH: 27
<212> TYPE: DNA
<213> ORGANISM: Mus musculus

<400> SEQUENCE: 287
tttcaaggtt cacatgttcc tctcacg                           27

<210> SEQ ID NO 288
<211> LENGTH: 9

```
<212> TYPE: PRT
<213> ORGANISM: Mus musculus

<400> SEQUENCE: 288

Phe Gln Gly Ser His Val Pro Leu Thr
1               5

<210> SEQ ID NO 289
<211> LENGTH: 408
<212> TYPE: DNA
<213> ORGANISM: Mus musculus

<400> SEQUENCE: 289
atgaacaggc ttacttcctc attgctgctg ctgattgtcc ctgcatatgt cctgtcccag      60
gttactctga aagagtctgg ccctgggata ttgcagccct cccagaccct cagtctgact     120
tgttctttct ctgggttttc actgagcact tctggtatgg gtgtgagctg gattcgtcag     180
ccttcaggaa agggtctgga gtggctggca cacatttact gggatgatga caagcgctat     240
aacccatccc tgaagagccg gctcacaatc tccaaggata cctccagcaa ccaggtattc     300
ctcaagatca ccagtgtgga cactgcagat actgccacat actactgtgc ctactatagg     360
tccggttttg cttactgggg ccaagggact ctggtcactg tctctgca                  408

<210> SEQ ID NO 290
<211> LENGTH: 136
<212> TYPE: PRT
<213> ORGANISM: Mus musculus

<400> SEQUENCE: 290

Met Asn Arg Leu Thr Ser Ser Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Ala Tyr Tyr Arg Ser Gly Phe Ala Tyr Trp Gly Gln
        115                 120                 125

Gly Thr Leu Val Thr Val Ser Ala
    130                 135

<210> SEQ ID NO 291
<211> LENGTH: 327
<212> TYPE: DNA
<213> ORGANISM: Mus musculus

<400> SEQUENCE: 291
atgacccaaa ctccactctc cctgcctgtc agtcttggag atcaagcctc catctcttgc      60
agatctagtc agagcattgt acatagtaat ggcaacacct atttagaatg gtacctgcag     120
aaaccaggcc agtctccaaa gctcctgatc tacaaagttt ccaaccgatt ttctggggtc     180
```

```
ccagacaggt tcagtggcag tggatcaggg acagatttca cactcaagat cagcagagtg    240
gaggctgagg atctgggagt ttattactgc tttcaaggtt cacatgttcc gctcacgttc    300
ggtgctggga ccaagctgga gctgaaa                                       327
```

```
<210> SEQ ID NO 292
<211> LENGTH: 109
<212> TYPE: PRT
<213> ORGANISM: Mus musculus

<400> SEQUENCE: 292
```

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

```
<210> SEQ ID NO 293
<211> LENGTH: 21
<212> TYPE: DNA
<213> ORGANISM: Mus musculus

<400> SEQUENCE: 293
acttctggta tgggtgtgag c                                              21

<210> SEQ ID NO 294
<211> LENGTH: 7
<212> TYPE: PRT
<213> ORGANISM: Mus musculus

<400> SEQUENCE: 294
```

Thr Ser Gly Met Gly Val Ser
1               5

```
<210> SEQ ID NO 295
<211> LENGTH: 48
<212> TYPE: DNA
<213> ORGANISM: Mus musculus

<400> SEQUENCE: 295
cacatttact gggatgatga caagcgctat aacccatccc tgaagagc                  48

<210> SEQ ID NO 296
<211> LENGTH: 16
<212> TYPE: PRT
<213> ORGANISM: Mus musculus

<400> SEQUENCE: 296
```

His Ile Tyr Trp Asp Asp Asp Lys Arg Tyr Asn Pro Ser Leu Lys Ser
1               5                   10                  15

```
<210> SEQ ID NO 297
```

<210> SEQ ID NO 297
<211> LENGTH: 21
<212> TYPE: DNA
<213> ORGANISM: Mus musculus

<400> SEQUENCE: 297
tataggtccg gttttgctta c                                             21

<210> SEQ ID NO 298
<211> LENGTH: 7
<212> TYPE: PRT
<213> ORGANISM: Mus musculus

<400> SEQUENCE: 298

Tyr Arg Ser Gly Phe Ala Tyr
1               5

<210> SEQ ID NO 299
<211> LENGTH: 48
<212> TYPE: DNA
<213> ORGANISM: Mus musculus

<400> SEQUENCE: 299
agatctagtc agagcattgt acatagtaat ggcaacacct atttagaa                 48

<210> SEQ ID NO 300
<211> LENGTH: 16
<212> TYPE: PRT
<213> ORGANISM: Mus musculus

<400> SEQUENCE: 300

Arg Ser Ser Gln Ser Ile Val His Ser Asn Gly Asn Thr Tyr Leu Glu
1               5                   10                  15

<210> SEQ ID NO 301
<211> LENGTH: 21
<212> TYPE: DNA
<213> ORGANISM: Mus musculus

<400> SEQUENCE: 301
aaagtttcca accgattttc t                                             21

<210> SEQ ID NO 302
<211> LENGTH: 7
<212> TYPE: PRT
<213> ORGANISM: Mus musculus

<400> SEQUENCE: 302

Lys Val Ser Asn Arg Phe Ser
1               5

<210> SEQ ID NO 303
<211> LENGTH: 27
<212> TYPE: DNA
<213> ORGANISM: Mus musculus

<400> SEQUENCE: 303
tttcaaggtt cacatgttcc gctcacg                                       27

<210> SEQ ID NO 304
<211> LENGTH: 9
<212> TYPE: PRT
<213> ORGANISM: Mus musculus

<400> SEQUENCE: 304

Phe Gln Gly Ser His Val Pro Leu Thr
1               5

<210> SEQ ID NO 305
<211> LENGTH: 411
<212> TYPE: DNA
<213> ORGANISM: Mus musculus

<400> SEQUENCE: 305
atgggatgga gctatatcat cctcttttg gtagcaacag ctacagatgt ccactcccag     60
gtccaactgc agcagcctgg ggctgaactg gtgaagcctg gggcttcagt gaagctgtcc    120
tgcaaggctt ctggctacac cttcaccagc tactggatgc actgggtgaa gcagaggcct    180
ggacaaggcc ttgagtggat tggagagatt aatcctagca acggtcgtac taactacaat    240
gagaagttca agagcaaggc cacactgact gtagacaaat cctccagcac agcctacatg    300
caactcagca gcctgacatc tgaggactct gcggtctatt actgtgcaag agagcattac    360
tacggctacg gtgcttactg gggccaaggg actctggtca ctgtctctgc a             411

<210> SEQ ID NO 306
<211> LENGTH: 137
<212> TYPE: PRT
<213> ORGANISM: Mus musculus

<400> SEQUENCE: 306

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Glu Ile Asn Pro Ser Asn Gly Arg Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Glu His Tyr Tyr Gly Tyr Gly Ala Tyr Trp Gly
        115                 120                 125

Gln Gly Thr Leu Val Thr Val Ser Ala
    130                 135

<210> SEQ ID NO 307
<211> LENGTH: 327
<212> TYPE: DNA
<213> ORGANISM: Mus musculus

<400> SEQUENCE: 307
atgacccaaa ctccactctc cctgcctgtc agtcttggag atcaagcctc catctcttgc     60
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgaga tctgggagt ttattactgc tttcaaggtt cacatgttcc gtacacgttc    300
ggagggggga ccaagctgga aataaaa                                          327

<210> SEQ ID NO 308
<211> LENGTH: 109
<212> TYPE: PRT
<213> ORGANISM: Mus musculus

<400> SEQUENCE: 308

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Tyr Thr Phe Gly Gly Gly Thr Lys Leu Glu Ile Lys
            100                 105

<210> SEQ ID NO 309
<211> LENGTH: 15
<212> TYPE: DNA
<213> ORGANISM: Mus musculus

<400> SEQUENCE: 309
agctactgga tgcac                                                        15

<210> SEQ ID NO 310
<211> LENGTH: 5
<212> TYPE: PRT
<213> ORGANISM: Mus musculus

<400> SEQUENCE: 310

Ser Tyr Trp Met His
1               5

<210> SEQ ID NO 311
<211> LENGTH: 51
<212> TYPE: DNA
<213> ORGANISM: Mus musculus

<400> SEQUENCE: 311
gagattaatc ctagcaacgg tcgtactaac tacaatgaga gttcaagag c                  51

<210> SEQ ID NO 312
<211> LENGTH: 17
<212> TYPE: PRT
<213> ORGANISM: Mus musculus

<400> SEQUENCE: 312

Glu Ile Asn Pro Ser Asn Gly Arg Thr Asn Tyr Asn Glu Lys Phe Lys
1               5                   10                  15

Ser

<210> SEQ ID NO 313
<211> LENGTH: 27
<212> TYPE: DNA
<213> ORGANISM: Mus musculus

<400> SEQUENCE: 313
gagcattact acggctacgg tgcttac       27

<210> SEQ ID NO 314
<211> LENGTH: 9
<212> TYPE: PRT
<213> ORGANISM: Mus musculus

<400> SEQUENCE: 314

Glu His Tyr Tyr Gly Tyr Gly Ala Tyr
1               5

<210> SEQ ID NO 315
<211> LENGTH: 48
<212> TYPE: DNA
<213> ORGANISM: Mus musculus

<400> SEQUENCE: 315
agatctagtc agagcattgt acatagtaat ggaaacacct atttagaa       48

<210> SEQ ID NO 316
<211> LENGTH: 16
<212> TYPE: PRT
<213> ORGANISM: Mus musculus

<400> SEQUENCE: 316

Arg Ser Ser Gln Ser Ile Val His Ser Asn Gly Asn Thr Tyr Leu Glu
1               5                   10                  15

<210> SEQ ID NO 317
<211> LENGTH: 21
<212> TYPE: DNA
<213> ORGANISM: Mus musculus

<400> SEQUENCE: 317
aaagtttcca accgattttc t       21

<210> SEQ ID NO 318
<211> LENGTH: 7
<212> TYPE: PRT
<213> ORGANISM: Mus musculus

<400> SEQUENCE: 318

Lys Val Ser Asn Arg Phe Ser
1               5

<210> SEQ ID NO 319
<211> LENGTH: 27
<212> TYPE: DNA
<213> ORGANISM: Mus musculus

<400> SEQUENCE: 319
tttcaaggtt cacatgttcc gtacacg       27

<210> SEQ ID NO 320
<211> LENGTH: 9
<212> TYPE: PRT
<213> ORGANISM: Mus musculus

<400> SEQUENCE: 320

Phe Gln Gly Ser His Val Pro Tyr Thr
1               5

<210> SEQ ID NO 321
<211> LENGTH: 417
<212> TYPE: DNA
<213> ORGANISM: Mus musculus

<400> SEQUENCE: 321

| | | |
|---|---|---|
| atggacaggc ttacttcttc attcctgctg ctgattgtcc ctgcatatgt cttgtcccaa | 60 |
| gttactctaa aagagtctgg ccctgggata ttgaagccct cacagaccct cagtctgact | 120 |
| tgttctttct ctgggttttc actgagcact tctggtatgg gtgtaggctg gattcgtcag | 180 |
| ccttcaggga agggtctgga gtggctggca cacatttggt gggatgatga taagtactat | 240 |
| aacccatccc tgaagagcca gctcacaatc tccaaggata cctccagaaa ccaggtattc | 300 |
| ctcaagatca ccagtgtgga cactgcagat actgccactt actactgtgc tcgaagatca | 360 |
| ctatccaggg actactttga ctactggggc caaggcacca ctctcacagt ctcctca | 417 |

<210> SEQ ID NO 322
<211> LENGTH: 139
<212> TYPE: PRT
<213> ORGANISM: Mus musculus

<400> SEQUENCE: 322

Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Ser Leu Ser Arg Asp Tyr Phe Asp Tyr
        115                 120                 125

Trp Gly Gln Gly Thr Thr Leu Thr Val Ser Ser
    130                 135

<210> SEQ ID NO 323
<211> LENGTH: 327
<212> TYPE: DNA
<213> ORGANISM: Mus musculus

<400> SEQUENCE: 323

| | | |
|---|---|---|
| atgacccaaa ctccactctc cctgcctgtc agtcttggag atcaagcctc catctcttgc | 60 |
| agatctagtc agagcattgt acatagtaat ggaaacacct atttagaatg gtacctgcag | 120 |
| aaaccaggcc agtctccaaa gctcctgatc tacaaagttt ccaaccgatt ttctggggtc | 180 |
| ccagacaggt tcagtggcag tggatcaggg acagatttca cactcaagat cagcagagtg | 240 |
| gaggctgagg atctgggagt ttattactgc tttcaaggtt cacatgttcc gctcacgttc | 300 |
| ggtgctggga ccaagctgga gctgaaa | 327 |

<210> SEQ ID NO 324

```
<211> LENGTH: 109
<212> TYPE: PRT
<213> ORGANISM: Mus musculus

<400> SEQUENCE: 324

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

<210> SEQ ID NO 325
<211> LENGTH: 21
<212> TYPE: DNA
<213> ORGANISM: Mus musculus

<400> SEQUENCE: 325
acttctggta tgggtgtagg c                                             21

<210> SEQ ID NO 326
<211> LENGTH: 7
<212> TYPE: PRT
<213> ORGANISM: Mus musculus

<400> SEQUENCE: 326

Thr Ser Gly Met Gly Val Gly
1               5

<210> SEQ ID NO 327
<211> LENGTH: 48
<212> TYPE: DNA
<213> ORGANISM: Mus musculus

<400> SEQUENCE: 327
cacatttggt gggatgatga taagtactat aacccatccc tgaagagc                48

<210> SEQ ID NO 328
<211> LENGTH: 16
<212> TYPE: PRT
<213> ORGANISM: Mus musculus

<400> SEQUENCE: 328

His Ile Trp Trp Asp Asp Asp Lys Tyr Tyr Asn Pro Ser Leu Lys Ser
1               5                   10                  15

<210> SEQ ID NO 329
<211> LENGTH: 30
<212> TYPE: DNA
<213> ORGANISM: Mus musculus

<400> SEQUENCE: 329
agatcactat ccagggacta ctttgactac                                    30
```

<210> SEQ ID NO 330
<211> LENGTH: 10
<212> TYPE: PRT
<213> ORGANISM: Mus musculus

<400> SEQUENCE: 330

Arg Ser Leu Ser Arg Asp Tyr Phe Asp Tyr
1               5                   10

<210> SEQ ID NO 331
<211> LENGTH: 48
<212> TYPE: DNA
<213> ORGANISM: Mus musculus

<400> SEQUENCE: 331
agatctagtc agagcattgt acatagtaat ggaaacacct atttagaa          48

<210> SEQ ID NO 332
<211> LENGTH: 16
<212> TYPE: PRT
<213> ORGANISM: Mus musculus

<400> SEQUENCE: 332

Arg Ser Ser Gln Ser Ile Val His Ser Asn Gly Asn Thr Tyr Leu Glu
1               5                   10                  15

<210> SEQ ID NO 333
<211> LENGTH: 21
<212> TYPE: DNA
<213> ORGANISM: Mus musculus

<400> SEQUENCE: 333
aaagtttcca accgattttc t                                       21

<210> SEQ ID NO 334
<211> LENGTH: 7
<212> TYPE: PRT
<213> ORGANISM: Mus musculus

<400> SEQUENCE: 334

Lys Val Ser Asn Arg Phe Ser
1               5

<210> SEQ ID NO 335
<211> LENGTH: 27
<212> TYPE: DNA
<213> ORGANISM: Mus musculus

<400> SEQUENCE: 335
tttcaaggtt cacatgttcc gctcacg                                 27

<210> SEQ ID NO 336
<211> LENGTH: 9
<212> TYPE: PRT
<213> ORGANISM: Mus musculus

<400> SEQUENCE: 336

Phe Gln Gly Ser His Val Pro Leu Thr
1               5

<210> SEQ ID NO 337
<211> LENGTH: 426
<212> TYPE: DNA
<213> ORGANISM: Mus musculus

<400> SEQUENCE: 337

```
atggacaggc ttacttcttc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact gctggtatgg gtgtaggctg gattcgtcag     180
ccttcaggga agggtctgga gtggctggca cacatttggt gggatgatga taagtactat     240
aatccatccc tgaagagcca gctcacaatc tccaaggata cctccagaaa ccaggtattc     300
ctcaagatca ccagtgtgga cactgcagat actgccactt actactgtgc tcgaagaggt     360
ctctactatg gtaactacga tgctatggac tactggggtc aaggaacctc agtcaccgtc     420
tcctca                                                                426
```

<210> SEQ ID NO 338
<211> LENGTH: 142
<212> TYPE: PRT
<213> ORGANISM: Mus musculus

<400> SEQUENCE: 338

```
Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ala Gly Met Gly Val Gly Trp Ile Arg Gln Pro Ser Gly Lys
    50                  55                  60

Gly Leu Glu Trp Leu Ala His Ile Trp Trp Asp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Gly Leu Tyr Tyr Gly Asn Tyr Asp Ala
        115                 120                 125

Met Asp Tyr Trp Gly Gln Gly Thr Ser Val Thr Val Ser Ser
    130                 135                 140
```

<210> SEQ ID NO 339
<211> LENGTH: 327
<212> TYPE: DNA
<213> ORGANISM: Mus musculus

<400> SEQUENCE: 339

```
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccacccgatt ttctggggtc     180
ccagacaggt tcagtggcag tggatcaggg acagatttca cactcaagat cagcagagtg     240
gaggctgagg atctgggagt ttattactgc tttcaaggtt cacgtgttcc gctcacgttc     300
ggtgctggga ccaagctgga gctgaaa                                         327
```

<210> SEQ ID NO 340
<211> LENGTH: 109
<212> TYPE: PRT
<213> ORGANISM: Mus musculus

<400> SEQUENCE: 340

Met Thr Gln Thr Pro Leu Ser Leu Pro Val Ser Leu Gly Asp Gln Ala
1               5                   10                  15
Ser Ile Ser Cys Arg Ser Ser Gln Ser Ile Val His Ser Asn Gly Asn
            20                  25                  30
Thr Tyr Leu Glu Trp Tyr Leu Gln Lys Pro Gly Gln Ser Pro Lys Leu
        35                  40                  45
Leu Ile Tyr Lys Val Ser Thr Arg Phe Ser Gly Val Pro Asp Arg Phe
    50                  55                  60
Ser Gly Ser Gly Ser Gly Thr Asp Phe Thr Leu Lys Ile Ser Arg Val
65                  70                  75                  80
Glu Ala Glu Asp Leu Gly Val Tyr Tyr Cys Phe Gln Gly Ser Arg Val
                85                  90                  95
Pro Leu Thr Phe Gly Ala Gly Thr Lys Leu Glu Leu Lys
            100                 105

<210> SEQ ID NO 341
<211> LENGTH: 21
<212> TYPE: DNA
<213> ORGANISM: Mus musculus

<400> SEQUENCE: 341
actgctggta tgggtgtagg c                                      21

<210> SEQ ID NO 342
<211> LENGTH: 7
<212> TYPE: PRT
<213> ORGANISM: Mus musculus

<400> SEQUENCE: 342

Thr Ala Gly Met Gly Val Gly
1               5

<210> SEQ ID NO 343
<211> LENGTH: 48
<212> TYPE: DNA
<213> ORGANISM: Mus musculus

<400> SEQUENCE: 343
cacatttggt gggatgatga taagtactat aatccatccc tgaagagc         48

<210> SEQ ID NO 344
<211> LENGTH: 16
<212> TYPE: PRT
<213> ORGANISM: Mus musculus

<400> SEQUENCE: 344

His Ile Trp Trp Asp Asp Asp Lys Tyr Tyr Asn Pro Ser Leu Lys Ser
1               5                   10                  15

<210> SEQ ID NO 345
<211> LENGTH: 39
<212> TYPE: DNA
<213> ORGANISM: Mus musculus

<400> SEQUENCE: 345
agaggtctct actatggtaa ctacgatgct atggactac                   39

<210> SEQ ID NO 346
<211> LENGTH: 13

```
<212> TYPE: PRT
<213> ORGANISM: Mus musculus

<400> SEQUENCE: 346

Arg Gly Leu Tyr Tyr Gly Asn Tyr Asp Ala Met Asp Tyr
1               5                   10

<210> SEQ ID NO 347
<211> LENGTH: 48
<212> TYPE: DNA
<213> ORGANISM: Mus musculus

<400> SEQUENCE: 347
agatctagtc agagcattgt acatagtaat ggaaacacct atttagaa            48

<210> SEQ ID NO 348
<211> LENGTH: 16
<212> TYPE: PRT
<213> ORGANISM: Mus musculus

<400> SEQUENCE: 348

Arg Ser Ser Gln Ser Ile Val His Ser Asn Gly Asn Thr Tyr Leu Glu
1               5                   10                  15

<210> SEQ ID NO 349
<211> LENGTH: 21
<212> TYPE: DNA
<213> ORGANISM: Mus musculus

<400> SEQUENCE: 349
aaagtttcca cccgattttc t                                         21

<210> SEQ ID NO 350
<211> LENGTH: 7
<212> TYPE: PRT
<213> ORGANISM: Mus musculus

<400> SEQUENCE: 350

Lys Val Ser Thr Arg Phe Ser
1               5

<210> SEQ ID NO 351
<211> LENGTH: 27
<212> TYPE: DNA
<213> ORGANISM: Mus musculus

<400> SEQUENCE: 351
tttcaaggtt cacgtgttcc gctcacg                                   27

<210> SEQ ID NO 352
<211> LENGTH: 9
<212> TYPE: PRT
<213> ORGANISM: Mus musculus

<400> SEQUENCE: 352

Phe Gln Gly Ser Arg Val Pro Leu Thr
1               5

<210> SEQ ID NO 353
<211> LENGTH: 423
<212> TYPE: DNA
<213> ORGANISM: Mus musculus

<400> SEQUENCE: 353
```

```
atggacaggc ttacttcttc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact tctggtatgg gtgtaggctg gattcgtcag     180
ccttcaggga agggtctgga gtggctggca cacatttggt gggatgatga taagtactat     240
aacccatccc tgaagagcca gctcacaatc tccaaggata cctccagaaa ccaggtattc     300
ctcaagatca ccagtgtgga cactgcagat actgccactt actactgtgc tcgaagagct     360
ttgattacga cgagagacta ctttgactac tggggccaag gcaccactct cacagtctcc     420
tca                                                                   423
```

<210> SEQ ID NO 354
<211> LENGTH: 141
<212> TYPE: PRT
<213> ORGANISM: Mus musculus

<400> SEQUENCE: 354

```
Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Ala Leu Ile Thr Thr Arg Asp Tyr Phe
        115                 120                 125

Asp Tyr Trp Gly Gln Gly Thr Thr Leu Thr Val Ser Ser
    130                 135                 140
```

<210> SEQ ID NO 355
<211> LENGTH: 327
<212> TYPE: DNA
<213> ORGANISM: Mus musculus

<400> SEQUENCE: 355

```
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                         327
```

<210> SEQ ID NO 356
<211> LENGTH: 109
<212> TYPE: PRT
<213> ORGANISM: Mus musculus

<400> SEQUENCE: 356

```
Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105
```

<210> SEQ ID NO 357
<211> LENGTH: 21
<212> TYPE: DNA
<213> ORGANISM: Mus musculus

<400> SEQUENCE: 357
acttctggta tgggtgtagg c                                              21

<210> SEQ ID NO 358
<211> LENGTH: 7
<212> TYPE: PRT
<213> ORGANISM: Mus musculus

<400> SEQUENCE: 358

```
Thr Ser Gly Met Gly Val Gly
1               5
```

<210> SEQ ID NO 359
<211> LENGTH: 48
<212> TYPE: DNA
<213> ORGANISM: Mus musculus

<400> SEQUENCE: 359
cacatttggt gggatgatga taagtactat aacccatccc tgaagagc                 48

<210> SEQ ID NO 360
<211> LENGTH: 16
<212> TYPE: PRT
<213> ORGANISM: Mus musculus

<400> SEQUENCE: 360

```
His Ile Trp Trp Asp Asp Asp Lys Tyr Tyr Asn Pro Ser Leu Lys Ser
1               5                   10                  15
```

<210> SEQ ID NO 361
<211> LENGTH: 36
<212> TYPE: DNA
<213> ORGANISM: Mus musculus

<400> SEQUENCE: 361
agagctttga ttacgacgag agactacttt gactac                              36

<210> SEQ ID NO 362
<211> LENGTH: 12
<212> TYPE: PRT
<213> ORGANISM: Mus musculus

<400> SEQUENCE: 362

Arg Ala Leu Ile Thr Thr Arg Asp Tyr Phe Asp Tyr
1               5                   10

<210> SEQ ID NO 363
<211> LENGTH: 48
<212> TYPE: DNA
<213> ORGANISM: Mus musculus

<400> SEQUENCE: 363
agatctagtc agagcattgt acatagtaat ggaaacacct atttagaa         48

<210> SEQ ID NO 364
<211> LENGTH: 16
<212> TYPE: PRT
<213> ORGANISM: Mus musculus

<400> SEQUENCE: 364

Arg Ser Ser Gln Ser Ile Val His Ser Asn Gly Asn Thr Tyr Leu Glu
1               5                   10                  15

<210> SEQ ID NO 365
<211> LENGTH: 21
<212> TYPE: DNA
<213> ORGANISM: Mus musculus

<400> SEQUENCE: 365
aaagtttcca accgattttc t                                      21

<210> SEQ ID NO 366
<211> LENGTH: 7
<212> TYPE: PRT
<213> ORGANISM: Mus musculus

<400> SEQUENCE: 366

Lys Val Ser Asn Arg Phe Ser
1               5

<210> SEQ ID NO 367
<211> LENGTH: 27
<212> TYPE: DNA
<213> ORGANISM: Mus musculus

<400> SEQUENCE: 367
tttcaaggtt cacatgttcc gctcacg                                27

<210> SEQ ID NO 368
<211> LENGTH: 9
<212> TYPE: PRT
<213> ORGANISM: Mus musculus

<400> SEQUENCE: 368

Phe Gln Gly Ser His Val Pro Leu Thr
1               5

<210> SEQ ID NO 369
<211> LENGTH: 402
<212> TYPE: DNA
<213> ORGANISM: Mus musculus

<400> SEQUENCE: 369
atggactcca ggctcaattt agttttcctt attttaaaag gtgtccagtg tgatgtgcag    60
ctggtggagt ctgggggagg cttagtgcag cctggagggt cccggaaact ctcctgtgca   120

```
gcctctggat tcactttcag tagctttgga atgcactggg ttcgtcaggc tccagagaag    180
gggctggagt gggtcgcata cattagtagt ggcagtagta ccatctacta tgcagacaca    240
gtgaagggcc gattcaccat ctccagagac aatcccaaga acaccctgtt cctgcaaatg    300
accagtctaa ggtctgagga cacggccatg tattactgtg caagatatgg taactacgct    360
atggactact ggggtcaagg aacctcagtc accgtctcct ca                       402
```

```
<210> SEQ ID NO 370
<211> LENGTH: 134
<212> TYPE: PRT
<213> ORGANISM: Mus musculus

<400> SEQUENCE: 370
```

Met Asp Ser Arg Leu Asn Leu Val Phe Leu Ile Leu Lys Gly Val Gln
1               5                   10                  15

Cys Asp Val Gln Leu Val Glu Ser Gly Gly Gly Leu Val Gln Pro Gly
            20                  25                  30

Gly Ser Arg Lys Leu Ser Cys Ala Ala Ser Gly Phe Thr Phe Ser Ser
        35                  40                  45

Phe Gly Met His Trp Val Arg Gln Ala Pro Glu Lys Gly Leu Glu Trp
    50                  55                  60

Val Ala Tyr Ile Ser Ser Gly Ser Ser Thr Ile Tyr Tyr Ala Asp Thr
65                  70                  75                  80

Val Lys Gly Arg Phe Thr Ile Ser Arg Asp Asn Pro Lys Asn Thr Leu
                85                  90                  95

Phe Leu Gln Met Thr Ser Leu Arg Ser Glu Asp Thr Ala Met Tyr Tyr
            100                 105                 110

Cys Ala Arg Tyr Gly Asn Tyr Ala Met Asp Tyr Trp Gly Gln Gly Thr
        115                 120                 125

Ser Val Thr Val Ser Ser
    130

```
<210> SEQ ID NO 371
<211> LENGTH: 327
<212> TYPE: DNA
<213> ORGANISM: Mus musculus

<400> SEQUENCE: 371
```

```
atgacccaaa ctccactctc cctgcctgtc agtcttggag atcaagcctc catctcttgc    60
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cggcagagtg    240
gaggctgagg atctgggagt ttattactgc tttcaaggtt cacatgttcc tcgacgttc    300 ggtggaggca ccgagctgga aatcaaa                                        327
```

```
<210> SEQ ID NO 372
<211> LENGTH: 109
<212> TYPE: PRT
<213> ORGANISM: Mus musculus

<400> SEQUENCE: 372
```

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

```
Thr Tyr Leu Glu Trp Tyr Leu Gln Lys Pro Gly Gln Ser Pro Lys Leu
         35                  40                  45
Leu Ile Tyr Lys Val Ser Asn Arg Phe Ser Gly Val Pro Asp Arg Phe
     50                  55                  60
Ser Gly Ser Gly Ser Gly Thr Asp Phe Thr Leu Lys Ile Gly Arg Val
65                  70                  75                  80
Glu Ala Glu Asp Leu Gly Val Tyr Tyr Cys Phe Gln Gly Ser His Val
                 85                  90                  95
Pro Pro Thr Phe Gly Gly Gly Thr Glu Leu Glu Ile Lys
            100                 105
```

<210> SEQ ID NO 373
<211> LENGTH: 15
<212> TYPE: DNA
<213> ORGANISM: Mus musculus

<400> SEQUENCE: 373
agctttggaa tgcac                                             15

<210> SEQ ID NO 374
<211> LENGTH: 5
<212> TYPE: PRT
<213> ORGANISM: Mus musculus

<400> SEQUENCE: 374

```
Ser Phe Gly Met His
1               5
```

<210> SEQ ID NO 375
<211> LENGTH: 51
<212> TYPE: DNA
<213> ORGANISM: Mus musculus

<400> SEQUENCE: 375
tacattagta gtggcagtag taccatctac tatgcagaca cagtgaaggg c      51

<210> SEQ ID NO 376
<211> LENGTH: 17
<212> TYPE: PRT
<213> ORGANISM: Mus musculus

<400> SEQUENCE: 376

```
Tyr Ile Ser Ser Gly Ser Ser Thr Ile Tyr Tyr Ala Asp Thr Val Lys
1               5                   10                  15
Gly
```

<210> SEQ ID NO 377
<211> LENGTH: 24
<212> TYPE: DNA
<213> ORGANISM: Mus musculus

<400> SEQUENCE: 377
tatggtaact acgctatgga ctac                                   24

<210> SEQ ID NO 378
<211> LENGTH: 8
<212> TYPE: PRT
<213> ORGANISM: Mus musculus

<400> SEQUENCE: 378

```
Tyr Gly Asn Tyr Ala Met Asp Tyr
1               5
```

<210> SEQ ID NO 379
<211> LENGTH: 48
<212> TYPE: DNA
<213> ORGANISM: Mus musculus

<400> SEQUENCE: 379
agatctagtc agagcattgt acatagtaat ggaaacacct atttagaa            48

<210> SEQ ID NO 380
<211> LENGTH: 16
<212> TYPE: PRT
<213> ORGANISM: Mus musculus

<400> SEQUENCE: 380

Arg Ser Ser Gln Ser Ile Val His Ser Asn Gly Asn Thr Tyr Leu Glu
1               5                   10                  15

<210> SEQ ID NO 381
<211> LENGTH: 21
<212> TYPE: DNA
<213> ORGANISM: Mus musculus

<400> SEQUENCE: 381
aaagtttcca accgattttc t                                         21

<210> SEQ ID NO 382
<211> LENGTH: 7
<212> TYPE: PRT
<213> ORGANISM: Mus musculus

<400> SEQUENCE: 382

Lys Val Ser Asn Arg Phe Ser
1               5

<210> SEQ ID NO 383
<211> LENGTH: 27
<212> TYPE: DNA
<213> ORGANISM: Mus musculus

<400> SEQUENCE: 383
tttcaaggtt cacatgttcc tccgacg                                   27

<210> SEQ ID NO 384
<211> LENGTH: 9
<212> TYPE: PRT
<213> ORGANISM: Mus musculus

<400> SEQUENCE: 384

Phe Gln Gly Ser His Val Pro Pro Thr
1               5

<210> SEQ ID NO 385
<211> LENGTH: 420
<212> TYPE: DNA
<213> ORGANISM: Mus musculus

<400> SEQUENCE: 385
atggacaggc ttacttcttc attcctgctg ctgattgtcc ctgcatatgt cttgtcccaa    60
gttactctaa aagagtctgg ccctgggata ttgaagccct cacagaccct cagtctgact   120
tgttctttct ctgggttttc actgagcact tctggtatgg gtgtaggctg gattcgtcag   180

```
ccttcaggga agggtctgga gtggctggca cacatttggt gggatgatga taagtactat    240
aacccatccc tgaagagcca gctcacaatc tccaaggata cctccagaaa ccaggtattc    300
ctcaagatca ccagtgtgga cactgcagat actgccactt actactgtgc tcgaaggga     360 ttgatacggc aagactactt tgactactgg ggccaaggca ccactctcac agtctcctca    420
```

```
<210> SEQ ID NO 386
<211> LENGTH: 140
<212> TYPE: PRT
<213> ORGANISM: Mus musculus

<400> SEQUENCE: 386

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
                20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
        50                  55                  60

Gly Leu Glu Trp Leu Ala His Ile Trp Trp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Gly Leu Ile Arg Gln Asp Tyr Phe Asp
        115                 120                 125

Tyr Trp Gly Gln Gly Thr Thr Leu Thr Val Ser Ser
    130                 135                 140
```

```
<210> SEQ ID NO 387
<211> LENGTH: 327
<212> TYPE: DNA
<213> ORGANISM: Mus musculus

<400> SEQUENCE: 387
atgacccaaa ctccactctc cctgcctgtc agtcttggag atcaagcctc catctcttgc    60
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgagg atctgggagt ttattactgc tttcaaggtt cacatgttcc tctcacgttc    300
ggtgctggga ccaagctgga gctgaaa                                        327
```

```
<210> SEQ ID NO 388
<211> LENGTH: 109
<212> TYPE: PRT
<213> ORGANISM: Mus musculus

<400> SEQUENCE: 388

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
                20                  25                  30

Thr Tyr Leu Glu Trp Tyr Leu Gln Lys Pro Gly Gln Ser Pro Lys Leu
            35                  40                  45
```

Leu Ile Tyr Lys Val Ser Asn Arg Phe Ser Gly Val Pro Asp Arg Phe
            50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

<210> SEQ ID NO 389
<211> LENGTH: 21
<212> TYPE: DNA
<213> ORGANISM: Mus musculus

<400> SEQUENCE: 389
acttctggta tgggtgtagg c                                             21

<210> SEQ ID NO 390
<211> LENGTH: 7
<212> TYPE: PRT
<213> ORGANISM: Mus musculus

<400> SEQUENCE: 390

Thr Ser Gly Met Gly Val Gly
1               5

<210> SEQ ID NO 391
<211> LENGTH: 48
<212> TYPE: DNA
<213> ORGANISM: Mus musculus

<400> SEQUENCE: 391
cacatttggt gggatgatga taagtactat aacccatccc tgaagagc                48

<210> SEQ ID NO 392
<211> LENGTH: 16
<212> TYPE: PRT
<213> ORGANISM: Mus musculus

<400> SEQUENCE: 392

His Ile Trp Trp Asp Asp Asp Lys Tyr Tyr Asn Pro Ser Leu Lys Ser
1               5                   10                  15

<210> SEQ ID NO 393
<211> LENGTH: 33
<212> TYPE: DNA
<213> ORGANISM: Mus musculus

<400> SEQUENCE: 393
aggggattga tacggcaaga ctactttgac tac                                33

<210> SEQ ID NO 394
<211> LENGTH: 11
<212> TYPE: PRT
<213> ORGANISM: Mus musculus

<400> SEQUENCE: 394

Arg Gly Leu Ile Arg Gln Asp Tyr Phe Asp Tyr
1               5                   10

<210> SEQ ID NO 395
<211> LENGTH: 48

```
<212> TYPE: DNA
<213> ORGANISM: Mus musculus

<400> SEQUENCE: 395
agatctagtc agagcattgt acatagtaat ggaaacacct atttagaa            48

<210> SEQ ID NO 396
<211> LENGTH: 16
<212> TYPE: PRT
<213> ORGANISM: Mus musculus

<400> SEQUENCE: 396

Arg Ser Ser Gln Ser Ile Val His Ser Asn Gly Asn Thr Tyr Leu Glu
1               5                   10                  15

<210> SEQ ID NO 397
<211> LENGTH: 21
<212> TYPE: DNA
<213> ORGANISM: Mus musculus

<400> SEQUENCE: 397
aaagtttcca accgattttc t                                          21

<210> SEQ ID NO 398
<211> LENGTH: 7
<212> TYPE: PRT
<213> ORGANISM: Mus musculus

<400> SEQUENCE: 398

Lys Val Ser Asn Arg Phe Ser
1               5

<210> SEQ ID NO 399
<211> LENGTH: 27
<212> TYPE: DNA
<213> ORGANISM: Mus musculus

<400> SEQUENCE: 399
tttcaaggtt cacatgttcc tctcacg                                    27

<210> SEQ ID NO 400
<211> LENGTH: 9
<212> TYPE: PRT
<213> ORGANISM: Mus musculus

<400> SEQUENCE: 400

Phe Gln Gly Ser His Val Pro Leu Thr
1               5

<210> SEQ ID NO 401
<211> LENGTH: 414
<212> TYPE: DNA
<213> ORGANISM: Mus musculus

<400> SEQUENCE: 401
atgaacaggc ttacttcctc attgctgctg ctgattgtcc ctgcatatgt cctgtcccag    60
gttactctga aagagtctgg ccctgggata ttgcagccct cccagaccct cagtctgact   120
tgttctttct ctgggttttc actgagcact tctggtatgg gtgtgagctg gattcgtcag   180
ccttcaggaa agggtctgga gtggctggca cacattttact gggatgatga caagcgctat   240
aacccatccc tgaagagccg gctcacaatc tccaaggata cctccagcaa ccaggtattc   300
ctcaagatca ccagtgtgga cactgcagat actgccacat actactgtgc tcgaggggac   360
```

```
taTaggtacg acggggctta ctggggccaa gggactctgg tcactgtctc tgca            414
```

<210> SEQ ID NO 402
<211> LENGTH: 138
<212> TYPE: PRT
<213> ORGANISM: Mus musculus

<400> SEQUENCE: 402

```
Met Asn Arg Leu Thr Ser Ser Leu Leu Leu Ile Val Pro Ala Tyr
1               5                  10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Thr Ile Ser Lys Asp Thr Ser Ser
                85                  90                  95

Asn Gln Val Phe Leu Lys Ile Thr Ser Val Asp Thr Ala Asp Thr Ala
            100                 105                 110

Thr Tyr Tyr Cys Ala Arg Gly Asp Tyr Arg Tyr Asp Gly Ala Tyr Trp
        115                 120                 125

Gly Gln Gly Thr Leu Val Thr Val Ser Ala
    130                 135
```

<210> SEQ ID NO 403
<211> LENGTH: 327
<212> TYPE: DNA
<213> ORGANISM: Mus musculus

<400> SEQUENCE: 403

```
atgacccaaa ctccactctc cctgcctgtc agtcttggag atcaagcctc catctcttgc      60
agatctagtc agagccttgt acacagtaat ggaaacacct atttacattg gtacctgcag     120
aagccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttatttctgc tctcaaagta cacatgttcc gctcacgttc     300
ggtgctggga ccaagctgga gctgaaa                                          327
```

<210> SEQ ID NO 404
<211> LENGTH: 109
<212> TYPE: PRT
<213> ORGANISM: Mus musculus

<400> SEQUENCE: 404

```
Met Thr Gln Thr Pro Leu Ser Leu Pro Val Ser Leu Gly Asp Gln Ala
1               5                  10                  15

Ser Ile Ser Cys Arg Ser Ser Gln Ser Leu Val His Ser Asn Gly Asn
            20                  25                  30

Thr Tyr Leu His Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
```

```
                65                  70                  75                  80
Glu Ala Glu Asp Leu Gly Val Tyr Phe Cys Ser Gln Ser Thr His Val
                    85                  90                  95
Pro Leu Thr Phe Gly Ala Gly Thr Lys Leu Glu Leu Lys
                100                 105
```

<210> SEQ ID NO 405
<211> LENGTH: 21
<212> TYPE: DNA
<213> ORGANISM: Mus musculus

<400> SEQUENCE: 405
acttctggta tgggtgtgag c                                              21

<210> SEQ ID NO 406
<211> LENGTH: 7
<212> TYPE: PRT
<213> ORGANISM: Mus musculus

<400> SEQUENCE: 406

```
Thr Ser Gly Met Gly Val Ser
1               5
```

<210> SEQ ID NO 407
<211> LENGTH: 48
<212> TYPE: DNA
<213> ORGANISM: Mus musculus

<400> SEQUENCE: 407
cacatttact gggatgatga caagcgctat aacccatccc tgaagagc                 48

<210> SEQ ID NO 408
<211> LENGTH: 16
<212> TYPE: PRT
<213> ORGANISM: Mus musculus

<400> SEQUENCE: 408

```
His Ile Tyr Trp Asp Asp Asp Lys Arg Tyr Asn Pro Ser Leu Lys Ser
1               5                   10                  15
```

<210> SEQ ID NO 409
<211> LENGTH: 27
<212> TYPE: DNA
<213> ORGANISM: Mus musculus

<400> SEQUENCE: 409
ggggactata ggtacgacgg ggcttac                                        27

<210> SEQ ID NO 410
<211> LENGTH: 9
<212> TYPE: PRT
<213> ORGANISM: Mus musculus

<400> SEQUENCE: 410

```
Gly Asp Tyr Arg Tyr Asp Gly Ala Tyr
1               5
```

<210> SEQ ID NO 411
<211> LENGTH: 48
<212> TYPE: DNA
<213> ORGANISM: Mus musculus

<400> SEQUENCE: 411

```
agatctagtc agagccttgt acacagtaat ggaaacacct atttacat        48
```

<210> SEQ ID NO 412
<211> LENGTH: 16
<212> TYPE: PRT
<213> ORGANISM: Mus musculus

<400> SEQUENCE: 412

```
Arg Ser Ser Gln Ser Leu Val His Ser Asn Gly Asn Thr Tyr Leu His
1               5                   10                  15
```

<210> SEQ ID NO 413
<211> LENGTH: 21
<212> TYPE: DNA
<213> ORGANISM: Mus musculus

<400> SEQUENCE: 413

```
aaagtttcca accgattttc t        21
```

<210> SEQ ID NO 414
<211> LENGTH: 7
<212> TYPE: PRT
<213> ORGANISM: Mus musculus

<400> SEQUENCE: 414

```
Lys Val Ser Asn Arg Phe Ser
1               5
```

<210> SEQ ID NO 415
<211> LENGTH: 27
<212> TYPE: DNA
<213> ORGANISM: Mus musculus

<400> SEQUENCE: 415

```
tctcaaagta cacatgttcc gctcacg        27
```

<210> SEQ ID NO 416
<211> LENGTH: 9
<212> TYPE: PRT
<213> ORGANISM: Mus musculus

<400> SEQUENCE: 416

```
Ser Gln Ser Thr His Val Pro Leu Thr
1               5
```

<210> SEQ ID NO 417
<211> LENGTH: 417
<212> TYPE: DNA
<213> ORGANISM: Mus musculus

<400> SEQUENCE: 417

```
atggacaggc ttacttcctc attcctgctg ctgattgtcc ctgcatatgt cctttcccag        60
gttactctga aagagtctgg ccctgggata ttgcagccct cccagaccct cagtctgact       120
tgttctttct ctgggttttc actgagcact tctggtatgg gtgtgagctg gattcgtcag       180
ccttcaggaa agggtctgga gtggctggca cacatttact gggatgatga caagcgctat       240
aacccatccc tgaagagccg gctcacaatc tccaaggata cctccagaaa ccaggtattc       300
ctcaagatca ccagtgtgga cactgcagat actgccacat actactgtgc tcgatgctat       360
ggtaactacg gagctatgga ctactggggt caaggaacct cagtcaccgt ctcctca        417
```

<210> SEQ ID NO 418

<211> LENGTH: 139
<212> TYPE: PRT
<213> ORGANISM: Mus musculus

<400> SEQUENCE: 418

```
Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Ser Trp Ile Arg Gln Pro Ser Gly Lys
50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Cys Tyr Gly Asn Tyr Gly Ala Met Asp Tyr
        115                 120                 125

Trp Gly Gln Gly Thr Ser Val Thr Val Ser Ser
130                 135
```

<210> SEQ ID NO 419
<211> LENGTH: 327
<212> TYPE: DNA
<213> ORGANISM: Mus musculus

<400> SEQUENCE: 419

```
atgacccaaa ctccactctc cctgcctgtc agtcttggag atcaagcctc catctcttgc    60
agatctagtc agagccttgt acacagtaat ggaaacacct atttacattg gtacctgcag   120
aagccaggcc agtctccaaa gctcctgatc tacaaagttt ccaaccgatt ttctggggtc   180
ccagacaggt tcagtggcag tggatcaggg acagatttca cactcaagat cagcagagtg   240
gaggctgagg atctgggagt ttatttctgc tctcaaagta cacatgttcc gctcacgttc   300
ggtgctggga ccaagctgga gctgaaa                                       327
```

<210> SEQ ID NO 420
<211> LENGTH: 109
<212> TYPE: PRT
<213> ORGANISM: Mus musculus

<400> SEQUENCE: 420

```
Met Thr Gln Thr Pro Leu Ser Leu Pro Val Ser Leu Gly Asp Gln Ala
1               5                   10                  15

Ser Ile Ser Cys Arg Ser Ser Gln Ser Leu Val His Ser Asn Gly Asn
            20                  25                  30

Thr Tyr Leu His Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Phe Cys Ser Gln Ser Thr His Val
                85                  90                  95
```

Pro Leu Thr Phe Gly Ala Gly Thr Lys Leu Glu Leu Lys
            100                 105

<210> SEQ ID NO 421
<211> LENGTH: 21
<212> TYPE: DNA
<213> ORGANISM: Mus musculus

<400> SEQUENCE: 421
acttctggta tgggtgtgag c                                              21

<210> SEQ ID NO 422
<211> LENGTH: 7
<212> TYPE: PRT
<213> ORGANISM: Mus musculus

<400> SEQUENCE: 422

Thr Ser Gly Met Gly Val Ser
1               5

<210> SEQ ID NO 423
<211> LENGTH: 48
<212> TYPE: DNA
<213> ORGANISM: Mus musculus

<400> SEQUENCE: 423
cacatttact gggatgatga caagcgctat aacccatccc tgaagagc                 48

<210> SEQ ID NO 424
<211> LENGTH: 16
<212> TYPE: PRT
<213> ORGANISM: Mus musculus

<400> SEQUENCE: 424

His Ile Tyr Trp Asp Asp Asp Lys Arg Tyr Asn Pro Ser Leu Lys Ser
1               5                   10                  15

<210> SEQ ID NO 425
<211> LENGTH: 30
<212> TYPE: DNA
<213> ORGANISM: Mus musculus

<400> SEQUENCE: 425
tgctatggta actacggagc tatggactac                                     30

<210> SEQ ID NO 426
<211> LENGTH: 10
<212> TYPE: PRT
<213> ORGANISM: Mus musculus

<400> SEQUENCE: 426

Cys Tyr Gly Asn Tyr Gly Ala Met Asp Tyr
1               5                   10

<210> SEQ ID NO 427
<211> LENGTH: 48
<212> TYPE: DNA
<213> ORGANISM: Mus musculus

<400> SEQUENCE: 427
agatctagtc agagccttgt acacagtaat ggaaacacct atttacat                 48

<210> SEQ ID NO 428
<211> LENGTH: 16

-continued

<212> TYPE: PRT
<213> ORGANISM: Mus musculus

<400> SEQUENCE: 428

Arg Ser Ser Gln Ser Leu Val His Ser Asn Gly Asn Thr Tyr Leu His
1               5                   10                  15

<210> SEQ ID NO 429
<211> LENGTH: 21
<212> TYPE: DNA
<213> ORGANISM: Mus musculus

<400> SEQUENCE: 429
aaagtttcca accgattttc t                                           21

<210> SEQ ID NO 430
<211> LENGTH: 7
<212> TYPE: PRT
<213> ORGANISM: Mus musculus

<400> SEQUENCE: 430

Lys Val Ser Asn Arg Phe Ser
1               5

<210> SEQ ID NO 431
<211> LENGTH: 27
<212> TYPE: DNA
<213> ORGANISM: Mus musculus

<400> SEQUENCE: 431
tctcaaagta cacatgttcc gctcacg                                     27

<210> SEQ ID NO 432
<211> LENGTH: 9
<212> TYPE: PRT
<213> ORGANISM: Mus musculus

<400> SEQUENCE: 432

Ser Gln Ser Thr His Val Pro Leu Thr
1               5

<210> SEQ ID NO 433
<211> LENGTH: 426
<212> TYPE: DNA
<213> ORGANISM: Mus musculus

<400> SEQUENCE: 433
atggacaggc ttacttcttc attcctgctg ctgattgtcc ctgcatatgt cttgtcccaa    60
gttactctaa aagagtctgg ccctgggata ttgaagccct cacagaccct cagtctgact   120
tgttctttct ctgggttttc actgagcact tctggtatgg gtgtaggctg gattcgtcag   180
ccttcaggga agggtctgga gtggctggca cacatttggt gggatgatga taagtactat   240
aacccatccc tgaagagccg gctcactatc tccaaggata cctccagaaa ccaggtattc   300
ctcaagatca ccagtgtgga cactgcagat actgccactt actactgtac tcgaagagct   360
ttactacggc tacaagggga ctactttgac tactggggcc aaggcaccac tctcacagtc   420
tcctca                                                             426

<210> SEQ ID NO 434
<211> LENGTH: 142
<212> TYPE: PRT
<213> ORGANISM: Mus musculus

<400> SEQUENCE: 434

Met Asp Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
50                      55                  60

Gly Leu Glu Trp Leu Ala His Ile Trp Trp Asp Asp Lys Tyr Tyr
65                  70                  75                  80

Asn Pro Ser Leu Lys Ser Arg Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Thr Arg Arg Ala Leu Leu Arg Leu Gly Asp Tyr
        115                 120                 125

Phe Asp Tyr Trp Gly Gln Gly Thr Thr Leu Thr Val Ser Ser
130                 135                 140

<210> SEQ ID NO 435
<211> LENGTH: 327
<212> TYPE: DNA
<213> ORGANISM: Mus musculus

<400> SEQUENCE: 435
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                         327

<210> SEQ ID NO 436
<211> LENGTH: 109
<212> TYPE: PRT
<213> ORGANISM: Mus musculus

<400> SEQUENCE: 436

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Ala Gly Thr Lys Leu Glu Leu Lys
            100                 105

```
<210> SEQ ID NO 437
<211> LENGTH: 21
<212> TYPE: DNA
<213> ORGANISM: Mus musculus

<400> SEQUENCE: 437
acttctggta tgggtgtagg c                                                    21

<210> SEQ ID NO 438
<211> LENGTH: 7
<212> TYPE: PRT
<213> ORGANISM: Mus musculus

<400> SEQUENCE: 438

Thr Ser Gly Met Gly Val Gly
1               5

<210> SEQ ID NO 439
<211> LENGTH: 48
<212> TYPE: DNA
<213> ORGANISM: Mus musculus

<400> SEQUENCE: 439
cacatttggt gggatgatga taagtactat aacccatccc tgaagagc                       48

<210> SEQ ID NO 440
<211> LENGTH: 16
<212> TYPE: PRT
<213> ORGANISM: Mus musculus

<400> SEQUENCE: 440

His Ile Trp Trp Asp Asp Asp Lys Tyr Tyr Asn Pro Ser Leu Lys Ser
1               5                   10                  15

<210> SEQ ID NO 441
<211> LENGTH: 39
<212> TYPE: DNA
<213> ORGANISM: Mus musculus

<400> SEQUENCE: 441
agagctttac tacggctaca agggactac tttgactac                                  39

<210> SEQ ID NO 442
<211> LENGTH: 13
<212> TYPE: PRT
<213> ORGANISM: Mus musculus

<400> SEQUENCE: 442

Arg Ala Leu Leu Arg Leu Gln Gly Asp Tyr Phe Asp Tyr
1               5                   10

<210> SEQ ID NO 443
<211> LENGTH: 48
<212> TYPE: DNA
<213> ORGANISM: Mus musculus

<400> SEQUENCE: 443
agatctagtc agagcattgt acatagtaat ggaaacacct atttagaa                       48

<210> SEQ ID NO 444
<211> LENGTH: 16
<212> TYPE: PRT
<213> ORGANISM: Mus musculus
```

```
<400> SEQUENCE: 444

Arg Ser Ser Gln Ser Ile Val His Ser Asn Gly Asn Thr Tyr Leu Glu
1               5                   10                  15

<210> SEQ ID NO 445
<211> LENGTH: 21
<212> TYPE: DNA
<213> ORGANISM: Mus musculus

<400> SEQUENCE: 445
aaagtttcca accgattttc t                                             21

<210> SEQ ID NO 446
<211> LENGTH: 7
<212> TYPE: PRT
<213> ORGANISM: Mus musculus

<400> SEQUENCE: 446

Lys Val Ser Asn Arg Phe Ser
1               5

<210> SEQ ID NO 447
<211> LENGTH: 27
<212> TYPE: DNA
<213> ORGANISM: Mus musculus

<400> SEQUENCE: 447
tttcaaggtt cacatgttcc gctcacg                                       27

<210> SEQ ID NO 448
<211> LENGTH: 9
<212> TYPE: PRT
<213> ORGANISM: Mus musculus

<400> SEQUENCE: 448

Phe Gln Gly Ser His Val Pro Leu Thr
1               5

<210> SEQ ID NO 449
<211> LENGTH: 405
<212> TYPE: DNA
<213> ORGANISM: Mus musculus

<400> SEQUENCE: 449
atggacaggc ttacttcctc attcctgctg ctgattgtcc ctgcatatgt cctttcccag    60
gttactctga aagagtctgg ccctgggata ttgcagccct cccagaccct cagtctgact   120
tgttctttct ctgggttttc actgagcact tctggtatgg gtgtgagctg gattcgtcag   180
ccttcaggaa agggtctgga gtggctggca cacatttact gggatgatga caagcgctat   240
aacccatccc tgaagagccg gctcacaatc tccaaggata cctccagaaa ccaggtattc   300
ctcaagatca ccagtgtgga cactgcagat actgccacat actactgtgc tcgaagggggg   360 gactttgact actggggcca aggcaccact ctcacagtct cctca                   405

<210> SEQ ID NO 450
<211> LENGTH: 135
<212> TYPE: PRT
<213> ORGANISM: Mus musculus

<400> SEQUENCE: 450

Met Asp Arg Leu Thr Ser Ser Phe Leu Leu Leu Ile Val Pro Ala Tyr
1               5                   10                  15
```

```
Val Leu Ser Gln Val Thr Leu Lys Glu Ser Gly Pro Gly Ile Leu Gln
         20                  25                  30

Pro Ser Gln Thr Leu Ser Leu Thr Cys Ser Phe Ser Gly Phe Ser Leu
             35                  40                  45

Ser Thr Ser Gly Met Gly Val Ser Trp Ile Arg Gln Pro Ser Gly Lys
     50                  55                  60

Gly Leu Glu Trp Leu Ala His Ile Tyr Trp Asp Asp Lys Arg Tyr
 65                  70                  75                  80

Asn Pro Ser Leu Lys Ser Arg Leu Thr Ile Ser Lys Asp Thr Ser Arg
                 85                  90                  95

Asn Gln Val Phe Leu Lys Ile Thr Ser Val Asp Thr Ala Asp Thr Ala
                100                 105                 110

Thr Tyr Tyr Cys Ala Arg Arg Gly Asp Phe Asp Tyr Trp Gly Gln Gly
            115                 120                 125

Thr Thr Leu Thr Val Ser Ser
        130                 135
```

<210> SEQ ID NO 451
<211> LENGTH: 327
<212> TYPE: DNA
<213> ORGANISM: Mus musculus

<400> SEQUENCE: 451

```
atgacccaaa ctccactctc cctgcctgtc agtcttggag atcaagcctc catctcttgc    60
agatctagtc agagccttgt acacagtaat ggaaacacct atttacattg gtacctgcag   120
aagccaggcc agtctccaaa gctcctgatc tacaaagttt ccaaccgatt ttctggggtc   180
ccagacaggt tcagtggcag tggatcaggg acagatttca cactcaagat cagcagagtg   240
gaggctgagg atctgggagt ttatttctgc tctcaaagta cacatgttcc tccgacgttc   300
ggtggaggca ccaagctgga aatcaaa                                        327
```

<210> SEQ ID NO 452
<211> LENGTH: 109
<212> TYPE: PRT
<213> ORGANISM: Mus musculus

<400> SEQUENCE: 452

```
Met Thr Gln Thr Pro Leu Ser Leu Pro Val Ser Leu Gly Asp Gln Ala
 1               5                  10                  15

Ser Ile Ser Cys Arg Ser Ser Gln Ser Leu Val His Ser Asn Gly Asn
             20                  25                  30

Thr Tyr Leu His Trp Tyr Leu Gln Lys Pro Gly Gln Ser Pro Lys Leu
         35                  40                  45

Leu Ile Tyr Lys Val Ser Asn Arg Phe Ser Gly Val Pro Asp Arg Phe
     50                  55                  60

Ser Gly Ser Gly Ser Gly Thr Asp Phe Thr Leu Lys Ile Ser Arg Val
 65                  70                  75                  80

Glu Ala Glu Asp Leu Gly Val Tyr Phe Cys Ser Gln Ser Thr His Val
                 85                  90                  95

Pro Pro Thr Phe Gly Gly Gly Thr Lys Leu Glu Ile Lys
                100                 105
```

<210> SEQ ID NO 453
<211> LENGTH: 21
<212> TYPE: DNA
<213> ORGANISM: Mus musculus

<400> SEQUENCE: 453
acttctggta tgggtgtgag c						21

<210> SEQ ID NO 454
<211> LENGTH: 7
<212> TYPE: PRT
<213> ORGANISM: Mus musculus

<400> SEQUENCE: 454

Thr Ser Gly Met Gly Val Ser
1               5

<210> SEQ ID NO 455
<211> LENGTH: 48
<212> TYPE: DNA
<213> ORGANISM: Mus musculus

<400> SEQUENCE: 455
cacatttact gggatgatga caagcgctat aacccatccc tgaagagc						48

<210> SEQ ID NO 456
<211> LENGTH: 16
<212> TYPE: PRT
<213> ORGANISM: Mus musculus

<400> SEQUENCE: 456

His Ile Tyr Trp Asp Asp Asp Lys Arg Tyr Asn Pro Ser Leu Lys Ser
1               5                   10                  15

<210> SEQ ID NO 457
<211> LENGTH: 18
<212> TYPE: DNA
<213> ORGANISM: Mus musculus

<400> SEQUENCE: 457 agggggggact ttgactac						18

<210> SEQ ID NO 458
<211> LENGTH: 6
<212> TYPE: PRT
<213> ORGANISM: Mus musculus

<400> SEQUENCE: 458

Arg Gly Asp Phe Asp Tyr
1               5

<210> SEQ ID NO 459
<211> LENGTH: 48
<212> TYPE: DNA
<213> ORGANISM: Mus musculus

<400> SEQUENCE: 459
agatctagtc agagccttgt acacagtaat ggaaacacct atttacat						48

<210> SEQ ID NO 460
<211> LENGTH: 16
<212> TYPE: PRT
<213> ORGANISM: Mus musculus

<400> SEQUENCE: 460

Arg Ser Ser Gln Ser Leu Val His Ser Asn Gly Asn Thr Tyr Leu His
1               5                   10                  15

<210> SEQ ID NO 461
<211> LENGTH: 21
<212> TYPE: DNA
<213> ORGANISM: Mus musculus

<400> SEQUENCE: 461
aaagtttcca accgattttc t                                          21

<210> SEQ ID NO 462
<211> LENGTH: 7
<212> TYPE: PRT
<213> ORGANISM: Mus musculus

<400> SEQUENCE: 462

Lys Val Ser Asn Arg Phe Ser
1               5

<210> SEQ ID NO 463
<211> LENGTH: 27
<212> TYPE: DNA
<213> ORGANISM: Mus musculus

<400> SEQUENCE: 463
tctcaaagta cacatgttcc tccgacg                                    27

<210> SEQ ID NO 464
<211> LENGTH: 9
<212> TYPE: PRT
<213> ORGANISM: Mus musculus

<400> SEQUENCE: 464

Ser Gln Ser Thr His Val Pro Pro Thr
1               5

<210> SEQ ID NO 465
<211> LENGTH: 405
<212> TYPE: DNA
<213> ORGANISM: Mus musculus

<400> SEQUENCE: 465
atgaacaggc ttacttcctc attgctgctg ctgattgtcc ctgcatatgt cctgtcccag     60
gttactctga aagagtctgg ccctgggata ttgcagccct cccagaccct cagtctgact    120
tgttctttct ctgggttttc actgagcact tctggtatgg gtgtgagctg gattcgtcag    180
ccttcaggaa agggtctgga gtggctggca cacatttact gggatgatga caagcgctat    240
aacccatccc tgaagagccg gctcacaatc tccaaggata cctccagcaa ccaggtattc    300
ctcaagatca ccagtgtgga cactgcagat actgccacat actactgtgc tctttattac    360
tacggtctct actggggcca aggactctg gtcactgtct ctgca                     405

<210> SEQ ID NO 466
<211> LENGTH: 135
<212> TYPE: PRT
<213> ORGANISM: Mus musculus

<400> SEQUENCE: 466

Met Asn Arg Leu Thr Ser Ser Leu Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu

```
                35                  40                  45
Ser Thr Ser Gly Met Gly Val Ser Trp Ile Arg Gln Pro Ser Gly Lys
 50                  55                  60

Gly Leu Glu Trp Leu Ala His Ile Tyr Trp Asp Asp Lys Arg Tyr
 65                  70                  75                  80

Asn Pro Ser Leu Lys Ser Arg Leu Thr Ile Ser Lys Asp Thr Ser Ser
                 85                  90                  95

Asn Gln Val Phe Leu Lys Ile Thr Ser Val Asp Thr Ala Asp Thr Ala
                100                 105                 110

Thr Tyr Tyr Cys Ala Leu Tyr Tyr Gly Leu Tyr Trp Gly Gln Gly
                115                 120                 125

Thr Leu Val Thr Val Ser Ala
                130                 135
```

```
<210> SEQ ID NO 467
<211> LENGTH: 327
<212> TYPE: DNA
<213> ORGANISM: Mus musculus

<400> SEQUENCE: 467
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                         327
```

```
<210> SEQ ID NO 468
<211> LENGTH: 109
<212> TYPE: PRT
<213> ORGANISM: Mus musculus

<400> SEQUENCE: 468

Met Thr Gln Thr Pro Leu Ser Leu Pro Val Ser Leu Gly Asp Gln Ala
  1               5                  10                  15

Ser Ile Ser Cys Arg Ser Ser Gln Ser Ile Val His Ser Asn Gly Asn
                 20                  25                  30

Thr Tyr Leu Glu Trp Tyr Leu Gln Lys Pro Gly Gln Ser Pro Lys Leu
             35                  40                  45

Leu Ile Tyr Lys Val Ser Asn Arg Phe Ser Gly Val Pro Asp Arg Phe
 50                  55                  60

Ser Gly Ser Gly Ser Gly Thr Asp Phe Thr Leu Lys Ile Ser Arg Val
 65                  70                  75                  80

Glu Ala Glu Asp Leu Gly Val Tyr Tyr Cys Phe Gln Gly Ser His Val
                 85                  90                  95

Pro Leu Thr Phe Gly Ala Gly Thr Lys Leu Glu Leu Lys
                100                 105
```

```
<210> SEQ ID NO 469
<211> LENGTH: 21
<212> TYPE: DNA
<213> ORGANISM: Mus musculus

<400> SEQUENCE: 469
acttctggta tgggtgtgag c                                                21
```

<210> SEQ ID NO 470
<211> LENGTH: 7
<212> TYPE: PRT
<213> ORGANISM: Mus musculus

<400> SEQUENCE: 470

Thr Ser Gly Met Gly Val Ser
1               5

<210> SEQ ID NO 471
<211> LENGTH: 48
<212> TYPE: DNA
<213> ORGANISM: Mus musculus

<400> SEQUENCE: 471
cacatttact gggatgatga caagcgctat aacccatccc tgaagagc            48

<210> SEQ ID NO 472
<211> LENGTH: 16
<212> TYPE: PRT
<213> ORGANISM: Mus musculus

<400> SEQUENCE: 472

His Ile Tyr Trp Asp Asp Asp Lys Arg Tyr Asn Pro Ser Leu Lys Ser
1               5                   10                  15

<210> SEQ ID NO 473
<211> LENGTH: 18
<212> TYPE: DNA
<213> ORGANISM: Mus musculus

<400> SEQUENCE: 473
tattactacg gtctctac                                              18

<210> SEQ ID NO 474
<211> LENGTH: 6
<212> TYPE: PRT
<213> ORGANISM: Mus musculus

<400> SEQUENCE: 474

Tyr Tyr Tyr Gly Leu Tyr
1               5

<210> SEQ ID NO 475
<211> LENGTH: 48
<212> TYPE: DNA
<213> ORGANISM: Mus musculus

<400> SEQUENCE: 475
agatctagtc agagcattgt acatagtaat ggaaacacct atttagaa             48

<210> SEQ ID NO 476
<211> LENGTH: 16
<212> TYPE: PRT
<213> ORGANISM: Mus musculus

<400> SEQUENCE: 476

Arg Ser Ser Gln Ser Ile Val His Ser Asn Gly Asn Thr Tyr Leu Glu
1               5                   10                  15

<210> SEQ ID NO 477
<211> LENGTH: 21
<212> TYPE: DNA
<213> ORGANISM: Mus musculus

<400> SEQUENCE: 477
aaagtttcca accgattttc t    21

<210> SEQ ID NO 478
<211> LENGTH: 7
<212> TYPE: PRT
<213> ORGANISM: Mus musculus

<400> SEQUENCE: 478

Lys Val Ser Asn Arg Phe Ser
1               5

<210> SEQ ID NO 479
<211> LENGTH: 27
<212> TYPE: DNA
<213> ORGANISM: Mus musculus

<400> SEQUENCE: 479
tttcaaggtt cacatgttcc gctcacg    27

<210> SEQ ID NO 480
<211> LENGTH: 9
<212> TYPE: PRT
<213> ORGANISM: Mus musculus

<400> SEQUENCE: 480

Phe Gln Gly Ser His Val Pro Leu Thr
1               5

<210> SEQ ID NO 481
<211> LENGTH: 417
<212> TYPE: DNA
<213> ORGANISM: Mus musculus

<400> SEQUENCE: 481
atggacaggc ttacttcttc attcctgctg ctgattgtcc ctgcatatgt cttgtcccaa    60
gttactctaa aagagtctgg ccctgggata ttgaagccct cacagaccct cagtctgact    120
tgttctttct ctgggttttc actgagcact tctggtatgg gtgtaggctg gattcgtcag    180
ccttcaggga agggtctgga gtggctggca cacatttggt gggatgatga taagtactat    240
aacccatccc tgaagagcca gctcacaatc tccaaggata cctccagaaa ccaggtattc    300
ctcaagatca ccagtgtgga cactgcagat actgccactt actactgtgc tcgaagagcc    360
ctcaactggg acgtatttga ctactggggc caaggcacca ctctcacagt ctcctca    417

<210> SEQ ID NO 482
<211> LENGTH: 139
<212> TYPE: PRT
<213> ORGANISM: Mus musculus

<400> SEQUENCE: 482

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
        35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Lys Tyr Tyr
65                  70                  75                  80

Asn Pro Ser Leu Lys Ser Gln Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Arg Ala Leu Asn Trp Asp Val Phe Asp Tyr
        115                 120                 125

Trp Gly Gln Gly Thr Thr Leu Thr Val Ser Ser
    130                 135

<210> SEQ ID NO 483
<211> LENGTH: 327
<212> TYPE: DNA
<213> ORGANISM: Mus musculus

<400> SEQUENCE: 483
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccaaccgatt tctggggtc     180 ccagacaggt tcagtggcag tggatcaggg acagatttca cactcaagat cagcagagtg     240
gaggctgagg atctgggagt ttattactgc tttcaaggtt cacatgttcc gctcacgttc     300
ggtgctggga ccaagctgga gctgaaa                                          327

<210> SEQ ID NO 484
<211> LENGTH: 109
<212> TYPE: PRT
<213> ORGANISM: Mus musculus

<400> SEQUENCE: 484

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
            85                  90                  95

Pro Leu Thr Phe Gly Ala Gly Thr Lys Leu Glu Leu Lys
        100                 105

<210> SEQ ID NO 485
<211> LENGTH: 21
<212> TYPE: DNA
<213> ORGANISM: Mus musculus

<400> SEQUENCE: 485
acttctggta tgggtgtagg c                                                 21

<210> SEQ ID NO 486
<211> LENGTH: 7
<212> TYPE: PRT
<213> ORGANISM: Mus musculus

```
<400> SEQUENCE: 486

Thr Ser Gly Met Gly Val Gly
1               5

<210> SEQ ID NO 487
<211> LENGTH: 48
<212> TYPE: DNA
<213> ORGANISM: Mus musculus

<400> SEQUENCE: 487
cacatttggt gggatgatga taagtactat aacccatccc tgaagagc          48

<210> SEQ ID NO 488
<211> LENGTH: 16
<212> TYPE: PRT
<213> ORGANISM: Mus musculus

<400> SEQUENCE: 488

His Ile Trp Trp Asp Asp Asp Lys Tyr Tyr Asn Pro Ser Leu Lys Ser
1               5                   10                  15

<210> SEQ ID NO 489
<211> LENGTH: 30
<212> TYPE: DNA
<213> ORGANISM: Mus musculus

<400> SEQUENCE: 489
agagccctca actgggacgt atttgactac                              30

<210> SEQ ID NO 490
<211> LENGTH: 10
<212> TYPE: PRT
<213> ORGANISM: Mus musculus

<400> SEQUENCE: 490

Arg Ala Leu Asn Trp Asp Val Phe Asp Tyr
1               5                   10

<210> SEQ ID NO 491
<211> LENGTH: 48
<212> TYPE: DNA
<213> ORGANISM: Mus musculus

<400> SEQUENCE: 491
agatctagtc agagcattgt acatagtaat ggaaacacct atttagaa          48

<210> SEQ ID NO 492
<211> LENGTH: 16
<212> TYPE: PRT
<213> ORGANISM: Mus musculus

<400> SEQUENCE: 492

Arg Ser Ser Gln Ser Ile Val His Ser Asn Gly Asn Thr Tyr Leu Glu
1               5                   10                  15

<210> SEQ ID NO 493
<211> LENGTH: 21
<212> TYPE: DNA
<213> ORGANISM: Mus musculus

<400> SEQUENCE: 493
aaagtttcca accgattttc t                                       21
```

<210> SEQ ID NO 494
<211> LENGTH: 7
<212> TYPE: PRT
<213> ORGANISM: Mus musculus

<400> SEQUENCE: 494

Lys Val Ser Asn Arg Phe Ser
1               5

<210> SEQ ID NO 495
<211> LENGTH: 27
<212> TYPE: DNA
<213> ORGANISM: Mus musculus

<400> SEQUENCE: 495
tttcaaggtt cacatgttcc gctcacg                                          27

<210> SEQ ID NO 496
<211> LENGTH: 9
<212> TYPE: PRT
<213> ORGANISM: Mus musculus

<400> SEQUENCE: 496

Phe Gln Gly Ser His Val Pro Leu Thr
1               5

<210> SEQ ID NO 497
<211> LENGTH: 420
<212> TYPE: DNA
<213> ORGANISM: Mus musculus

<400> SEQUENCE: 497
atggacaggc ttacttcttc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact tctggtatgg gtgtaggctg gattcgtcag     180
ccttcaggga agggtctgga gtggctggca cacatttggt gggatgatga taagtactat     240
aacccatccc tgaagagcca gctcacaatc tccaaggata cctccagaaa ccaggtattc     300
ctcaagatca ccagtgtgga cactgcagat actgccactt actactgtac tcgaagagcc     360
ctctatgatt acgacgctat ggactactgg ggtcaaggaa cctcagtcac cgtctcctca     420

<210> SEQ ID NO 498
<211> LENGTH: 140
<212> TYPE: PRT
<213> ORGANISM: Mus musculus

<400> SEQUENCE: 498

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Lys
                20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
        50                  55                  60

Gly Leu Glu Trp Leu Ala His Ile Trp Trp Asp Asp Lys Tyr Tyr
65                  70                  75                  80

Asn Pro Ser Leu Lys Ser Gln Leu Thr Ile Ser Lys Asp Thr Ser Arg
                85                  90                  95

```
Asn Gln Val Phe Leu Lys Ile Thr Ser Val Asp Thr Ala Asp Thr Ala
                100                 105                 110

Thr Tyr Tyr Cys Thr Arg Arg Ala Leu Tyr Asp Tyr Asp Ala Met Asp
            115                 120                 125

Tyr Trp Gly Gln Gly Thr Ser Val Thr Val Ser Ser
    130                 135                 140
```

```
<210> SEQ ID NO 499
<211> LENGTH: 327
<212> TYPE: DNA
<213> ORGANISM: Mus musculus

<400> SEQUENCE: 499
atgacccaaa ctccactctc cctgcctgtc agtcttggag atcaagcctc catctcttgc      60
agatctagtc agagcattgt acatagtaat ggaaacacct atttagaatg gtacctgcag     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gaggctgagg atctgggagt ttattactgc tttcaaggtt cacatgttcc gctcacgttc     300
ggtcctggga ccaagctgga gctgaaa                                         327
```

```
<210> SEQ ID NO 500
<211> LENGTH: 109
<212> TYPE: PRT
<213> ORGANISM: Mus musculus

<400> SEQUENCE: 500

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val His Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Pro Leu Thr Phe Gly Pro Gly Thr Lys Leu Glu Leu Lys
            100                 105
```

```
<210> SEQ ID NO 501
<211> LENGTH: 21
<212> TYPE: DNA
<213> ORGANISM: Mus musculus

<400> SEQUENCE: 501
acttctggta tgggtgtagg c                                               21
```

```
<210> SEQ ID NO 502
<211> LENGTH: 7
<212> TYPE: PRT
<213> ORGANISM: Mus musculus

<400> SEQUENCE: 502

Thr Ser Gly Met Gly Val Gly
1               5
```

<210> SEQ ID NO 503
<211> LENGTH: 48
<212> TYPE: DNA
<213> ORGANISM: Mus musculus

<400> SEQUENCE: 503
cacatttggt gggatgatga taagtactat aacccatccc tgaagagc        48

<210> SEQ ID NO 504
<211> LENGTH: 16
<212> TYPE: PRT
<213> ORGANISM: Mus musculus

<400> SEQUENCE: 504

His Ile Trp Trp Asp Asp Asp Lys Tyr Tyr Asn Pro Ser Leu Lys Ser
1               5                   10                  15

<210> SEQ ID NO 505
<211> LENGTH: 33
<212> TYPE: DNA
<213> ORGANISM: Mus musculus

<400> SEQUENCE: 505
agagccctct atgattacga cgctatggac tac        33

<210> SEQ ID NO 506
<211> LENGTH: 11
<212> TYPE: PRT
<213> ORGANISM: Mus musculus

<400> SEQUENCE: 506

Arg Ala Leu Tyr Asp Tyr Asp Ala Met Asp Tyr
1               5                   10

<210> SEQ ID NO 507
<211> LENGTH: 48
<212> TYPE: DNA
<213> ORGANISM: Mus musculus

<400> SEQUENCE: 507
agatctagtc agagcattgt acatagtaat ggaaacacct atttagaa        48

<210> SEQ ID NO 508
<211> LENGTH: 16
<212> TYPE: PRT
<213> ORGANISM: Mus musculus

<400> SEQUENCE: 508

Arg Ser Ser Gln Ser Ile Val His Ser Asn Gly Asn Thr Tyr Leu Glu
1               5                   10                  15

<210> SEQ ID NO 509
<211> LENGTH: 21
<212> TYPE: DNA
<213> ORGANISM: Mus musculus

<400> SEQUENCE: 509
aaagtttcca accgattttc t        21

<210> SEQ ID NO 510
<211> LENGTH: 7
<212> TYPE: PRT
<213> ORGANISM: Mus musculus

<400> SEQUENCE: 510

Lys Val Ser Asn Arg Phe Ser
1               5

<210> SEQ ID NO 511
<211> LENGTH: 27
<212> TYPE: DNA
<213> ORGANISM: Mus musculus

<400> SEQUENCE: 511
tttcaaggtt cacatgttcc gctcacg                                        27

<210> SEQ ID NO 512
<211> LENGTH: 9
<212> TYPE: PRT
<213> ORGANISM: Mus musculus

<400> SEQUENCE: 512

Phe Gln Gly Ser His Val Pro Leu Thr
1               5

<210> SEQ ID NO 513
<211> LENGTH: 417
<212> TYPE: DNA
<213> ORGANISM: Mus musculus

<400> SEQUENCE: 513
atgagagtgc tgattctttt gtgcctgttc acagcctttc ctggtatcct gtctgatgtg    60
cagcttcagg agtcaggacc tgacctggtg aaaccttctc agtcactttc actcacctgc   120
actgtcactg gctactccat caccagtggt tatagctggc actggatccg gcagtttcca   180
ggaaacaaac tggaatggat gggctacata cactacagtg gtagcactaa ctacaaccca   240
tctctcaaaa gtcgaatctc tatcactcga gacacatcca agaaccagtt cttcctgcag   300
ttgaattctg tgactactga ggacacagcc acatattact gtgcaagaag gggctatgat   360
ggttactact cctggtttgc ttactggggc caagggactc tggtcactgt ctctgca      417

<210> SEQ ID NO 514
<211> LENGTH: 139
<212> TYPE: PRT
<213> ORGANISM: Mus musculus

<400> SEQUENCE: 514

Met Arg Val Leu Ile Leu Leu Cys Leu Phe Thr Ala Phe Pro Gly Ile
1               5                   10                  15

Leu Ser Asp Val Gln Leu Gln Glu Ser Gly Pro Asp Leu Val Lys Pro
            20                  25                  30

Ser Gln Ser Leu Ser Leu Thr Cys Thr Val Thr Gly Tyr Ser Ile Thr
        35                  40                  45

Ser Gly Tyr Ser Trp His Trp Ile Arg Gln Phe Pro Gly Asn Lys Leu
    50                  55                  60

Glu Trp Met Gly Tyr Ile His Tyr Ser Gly Ser Thr Asn Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Arg Gly Tyr Asp Gly Tyr Tyr Ser Trp Phe Ala Tyr 115                 120                 125
Trp Gly Gln Gly Thr Leu Val Thr Val Ser Ala
    130                 135

<210> SEQ ID NO 515
<211> LENGTH: 369
<212> TYPE: DNA
<213> ORGANISM: Mus musculus

<400> SEQUENCE: 515
atggcctgga tttcacttat actctctctc ctggctctca gctcaggggc catttcccag    60
gctgttgtga ctcaggaatc tgcactcacc acatcacctg gtgaaacagt cacactcact   120
tgtcgctcaa gtactgggc tgttacaact agtaactatg ccaactgggt ccaagaaaaa    180
ccagatcatt tattcactgg tctaataggt ggtaccaaca accgagctcc aggtgttcct   240
gccagattct caggctccct gattggagac aaggctgccc tcaccatcac aggggcacag   300
actgaggatg aggcaatata tttctgtgct ctatggtaca gcaaccattg ggtgttcggt   360
ggagggacc                                                           369

<210> SEQ ID NO 516
<211> LENGTH: 123
<212> TYPE: PRT
<213> ORGANISM: Mus musculus

<400> SEQUENCE: 516

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Thr
        115                 120

<210> SEQ ID NO 517
<211> LENGTH: 18
<212> TYPE: DNA
<213> ORGANISM: Mus musculus

<400> SEQUENCE: 517
agtggttata gctggcac                                                 18

<210> SEQ ID NO 518
<211> LENGTH: 6
<212> TYPE: PRT
<213> ORGANISM: Mus musculus

<400> SEQUENCE: 518

Ser Gly Tyr Ser Trp His
1               5

<210> SEQ ID NO 519
<211> LENGTH: 48
<212> TYPE: DNA
<213> ORGANISM: Mus musculus

<400> SEQUENCE: 519
tacatacact acagtggtag cactaactac aacccatctc tcaaaagt            48

<210> SEQ ID NO 520
<211> LENGTH: 16
<212> TYPE: PRT
<213> ORGANISM: Mus musculus

<400> SEQUENCE: 520

Tyr Ile His Tyr Ser Gly Ser Thr Asn Tyr Asn Pro Ser Leu Lys Ser
1               5                   10                  15

<210> SEQ ID NO 521
<211> LENGTH: 36
<212> TYPE: DNA
<213> ORGANISM: Mus musculus

<400> SEQUENCE: 521
aggggctatg atggttacta ctcctggttt gcttac                         36

<210> SEQ ID NO 522
<211> LENGTH: 12
<212> TYPE: PRT
<213> ORGANISM: Mus musculus

<400> SEQUENCE: 522

Arg Gly Tyr Asp Gly Tyr Tyr Ser Trp Phe Ala Tyr
1               5                   10

<210> SEQ ID NO 523
<211> LENGTH: 42
<212> TYPE: DNA
<213> ORGANISM: Mus musculus

<400> SEQUENCE: 523
cgctcaagta ctggggctgt tacaactagt aactatgcca ac                  42

<210> SEQ ID NO 524
<211> LENGTH: 14
<212> TYPE: PRT
<213> ORGANISM: Mus musculus

<400> SEQUENCE: 524

Arg Ser Ser Thr Gly Ala Val Thr Thr Ser Asn Tyr Ala Asn
1               5                   10

<210> SEQ ID NO 525
<211> LENGTH: 21
<212> TYPE: DNA
<213> ORGANISM: Mus musculus

<400> SEQUENCE: 525
ggtaccaaca accgagctcc a                                         21

<210> SEQ ID NO 526
<211> LENGTH: 7
<212> TYPE: PRT
<213> ORGANISM: Mus musculus

<400> SEQUENCE: 526

Gly Thr Asn Asn Arg Ala Pro
1               5

<210> SEQ ID NO 527
<211> LENGTH: 27
<212> TYPE: DNA
<213> ORGANISM: Mus musculus

<400> SEQUENCE: 527
gctctatggt acagcaacca ttgggtg                                       27

<210> SEQ ID NO 528
<211> LENGTH: 9
<212> TYPE: PRT
<213> ORGANISM: Mus musculus

<400> SEQUENCE: 528

Ala Leu Trp Tyr Ser Asn His Trp Val
1               5

<210> SEQ ID NO 529
<211> LENGTH: 357
<212> TYPE: DNA
<213> ORGANISM: Mus musculus

<400> SEQUENCE: 529
caggtccaac tgcagcagcc tggggctgaa ctggtgaagc ctggggcttc agtgaagctg    60
tcctgcaagg cttctggcta caccttcacc agctactgga tgcactgggt gaagcagagg   120
cctggacaag ccttgagtg gattggagag attaatccta gcaacggtcg tactaactac   180
aatgagaagt tcaagagcaa ggccacactg actgtagaca atcctccag cacagcctac   240 atgcaactca gcagcctgac atctgaggac tctgcggtct attactgtgc aagacaaggg   300
tataggcacg ggttttttgc ttactggggc caagggactc tggtcactgt ctctgca      357

<210> SEQ ID NO 530
<211> LENGTH: 119
<212> TYPE: PRT
<213> ORGANISM: Mus musculus

<400> SEQUENCE: 530

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gln Gly Tyr Arg His Gly Val Phe Ala Tyr Trp Gly Gln Gly
                100                 105                 110

Thr Leu Val Thr Val Ser Ala
            115

<210> SEQ ID NO 531
<211> LENGTH: 318
<212> TYPE: DNA
<213> ORGANISM: Mus musculus

<400> SEQUENCE: 531

```
agtattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gatatactat gcatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctcccacgtt cggtgctggg     300
accaagctgg agctgaaa                                                   318
```

<210> SEQ ID NO 532
<211> LENGTH: 106
<212> TYPE: PRT
<213> ORGANISM: Mus musculus

<400> SEQUENCE: 532

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Thr
                85                  90                  95

Phe Gly Ala Gly Thr Lys Leu Glu Leu Lys
            100                 105
```

<210> SEQ ID NO 533
<211> LENGTH: 360
<212> TYPE: DNA
<213> ORGANISM: Mus musculus

<400> SEQUENCE: 533

```
gaggtgcagc tggtggagtc tgggggagac ttagtgaagc ctggagggtc cctgaaactc      60
tcctgtgcag cctctggatt cactttcagt agctatggca tgtcttgggt tcgccagact     120
ccagacaaga ggctggagtg ggtcgcaacc attagtagtg gtggtagtta cacctactat     180
ccagacagtg tgaaggggcg attcaccatc tccagagaca atgccaagaa caccctgtac     240
ctgcaaatga gcagtctgaa gtctgaggac acagccatgt attactgtgc aagacccctc     300
tactataggc acggggtttt tgcttactgg ggccaaggga ctctggtcac tgtctctgca     360
```

<210> SEQ ID NO 534
<211> LENGTH: 120
<212> TYPE: PRT
<213> ORGANISM: Mus musculus

<400> SEQUENCE: 534

```
Glu Val Gln Leu Val Glu Ser Gly Gly Asp Leu Val Lys Pro Gly Gly
1               5                   10                  15
```

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Pro Leu Tyr Tyr Arg His Gly Val Phe Ala Tyr Trp Gly Gln
                100                 105                 110

Gly Thr Leu Val Thr Val Ser Ala
            115                 120

<210> SEQ ID NO 535
<211> LENGTH: 321
<212> TYPE: DNA
<213> ORGANISM: Mus musculus

<400> SEQUENCE: 535
gatgtccaga taacccagtc tccatcttat cttgctgcat ctcctggaga aaccattact      60
attaattgca gggcaagtaa gagcattagc aaatatttag cctggtatca agagaaacct    120
gggaaaacta ataagcttct tatctactct ggatccactt tgcaatctgg aattccatca    180
aggttcagtg gcagtggatc tggtacagat ttcactctca ccatcagtag cctggagcct    240
gaagattttg caatgtatta ctgtcaacag cataatgaat acccgtggac gttcggtgga    300
ggcaccaagc tggaaatcaa a                                              321

<210> SEQ ID NO 536
<211> LENGTH: 107
<212> TYPE: PRT
<213> ORGANISM: Mus musculus

<400> SEQUENCE: 536

Asp Val Gln Ile Thr Gln Ser Pro Ser Tyr Leu Ala Ala Ser Pro Gly
 1               5                  10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Trp
                 85                  90                  95

Thr Phe Gly Gly Gly Thr Lys Leu Glu Ile Lys
            100                 105

<210> SEQ ID NO 537
<211> LENGTH: 375
<212> TYPE: DNA
<213> ORGANISM: Mus musculus

<400> SEQUENCE: 537

```
gaagtgcagc tggtggagtc tgggggaggc ttagtgaagc ctggagggtc cctgaaactc      60
tcctgtgcag cctctggatt cactttcagt gactattaca tgtattgggt tcgccagact     120
ccggaaaaga ggctggagtg ggtcgcaacc attagtgatg gtggtagtta cacctactat     180
ccagacagtg tgaaggggcg attcaccatc tccagagaca tgccaagaa caacctgtac      240 ctgcaaatga gcagtctgaa gtctgaggac acagccatgt attactgtgc aagagccaaa     300
tactataggt acgacggagg gggggcctat gctatggact actggggtca aggaaccctca    360 gtcaccgtct cctca                                                       375
```

<210> SEQ ID NO 538
<211> LENGTH: 125
<212> TYPE: PRT
<213> ORGANISM: Mus musculus

<400> SEQUENCE: 538

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Ala Lys Tyr Tyr Arg Tyr Asp Gly Gly Gly Ala Tyr Ala Met
            100                 105                 110

Asp Tyr Trp Gly Gln Gly Thr Ser Val Thr Val Ser Ser
        115                 120                 125
```

<210> SEQ ID NO 539
<211> LENGTH: 336
<212> TYPE: DNA
<213> ORGANISM: Mus musculus

<400> SEQUENCE: 539

```
aacattatga tgacacagtc gccatcatct ctggctgtgt ctgcaggaga aaaggtcact      60
atgagctgta gtccagtca aagtgtttta tacagttcaa atcagaagaa ctacttggcc     120
tggtaccagc agaaaccagg gcagtctcct aaactgctga tctactgggc atccactagg    180
gaatctggtg tccctgatcg cttcacaggc agtggatctg ggacagattt tactcttacc    240
atcagcagtg tacaagctga agacctggca gtttattact gtcatcaata cctctcctcg    300
tacacgttcg gagggggac caagctggaa ataaaa                                336
```

<210> SEQ ID NO 540
<211> LENGTH: 112
<212> TYPE: PRT
<213> ORGANISM: Mus musculus

<400> SEQUENCE: 540

```
Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Val Leu Tyr Ser
            20                  25                  30
```

```
Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
                100                 105                 110

<210> SEQ ID NO 541
<211> LENGTH: 375
<212> TYPE: DNA
<213> ORGANISM: Mus musculus

<400> SEQUENCE: 541
gaagtgcaac tggtggagtc tgggggaggc ttagtgaagc ctggagggtc cctgaaactc      60
tcctgtgcag cctctggatt cactttcagt gactattaca tgtattgggt tcgccagact     120
ccggaaaaga ggctggagtg ggtcgcaacc attagtgatg gtggtagtta cacctactat     180
ccagacagtg tgaaggggcg attcaccatc tccagagaca atgccaagaa caacctgtac     240
ctgcaaatga gcagtctgaa gtctgaggac acagccatgt attactgtgc aagagccaaa     300
tactataggt acgacggagg ggggcctat gctatggact actggggtca aggaacctca     360
gtcaccgtct cctca                                                     375

<210> SEQ ID NO 542
<211> LENGTH: 125
<212> TYPE: PRT
<213> ORGANISM: Mus musculus

<400> SEQUENCE: 542

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Thr Ile Ser Asp Gly Gly Ser Tyr Thr Tyr Tyr Pro Asp Ser Val
 50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Ala Lys Tyr Tyr Arg Tyr Asp Gly Gly Gly Ala Tyr Ala Met
                100                 105                 110

Asp Tyr Trp Gly Gln Gly Thr Ser Val Thr Val Ser Ser
            115                 120                 125

<210> SEQ ID NO 543
<211> LENGTH: 336
<212> TYPE: DNA
<213> ORGANISM: Mus musculus

<400> SEQUENCE: 543
aacattatga tgacacagtc gccatcatct ctggctgtgt ctgcaggaga aaaggtcact      60
```

```
atgagctgta agtccagtca aagtgtttta tacagttcaa atcagaagaa ctacttggcc    120
tggtaccagc agaaaccagg gcagtctcct aaactgctga tctactgggc atccactagg    180
gaatctggtg tccctgatcg cttcacaggc agtggatctg ggacagattt tactcttacc    240
atcagcagtg tacaagctga agacctggca gtttattact gtcatcaata cctctcctcg    300
tacacgttcg gagggggac caagctggaa ataaaa                               336
```

<210> SEQ ID NO 544
<211> LENGTH: 112
<212> TYPE: PRT
<213> ORGANISM: Mus musculus

<400> SEQUENCE: 544

```
Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
                100                 105                 110
```

<210> SEQ ID NO 545
<211> LENGTH: 375
<212> TYPE: DNA
<213> ORGANISM: Mus musculus

<400> SEQUENCE: 545

```
gaagtgaagc ttgaggagtc tggaggaggc ttggtgcaac ctggaggatc catgaaactc    60
tcctgtgttg cctctggatt cactttcagt aactactgga tgaactgggt ccgccagtct    120
ccagagaagg ggcttgagtg ggttgctgaa attagattga aatctaataa ttatgcaaca    180
cattatgcgg agtctgtgaa agggaggttc accatctcaa gagatgattc aaaaagtagt    240
gtctacctgc aaatgaacaa cttaagagct gaagacactg gcatttatta ctgtaccagg    300
gggaccaggg tatggttacg acgtgaggct tggtttgctt actggggcca agggactctg    360
gtcactgtct ctgca                                                     375
```

<210> SEQ ID NO 546
<211> LENGTH: 125
<212> TYPE: PRT
<213> ORGANISM: Mus musculus

<400> SEQUENCE: 546

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45
```

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Gly Thr Arg Val Trp Leu Arg Arg Glu Ala Trp Phe
            100                 105                 110

Ala Tyr Trp Gly Gln Gly Thr Leu Val Thr Val Ser Ala
            115                 120                 125

<210> SEQ ID NO 547
<211> LENGTH: 333
<212> TYPE: DNA
<213> ORGANISM: Mus musculus

<400> SEQUENCE: 547
gacattgtgc tgacccaatc tccagcttct ttggctgtgt ctctagggca gagggccacc     60
atctcctgca gagccagcga agtgttgat aattatggca ttagttttat gaactggttc    120
caacagaaac caggacagcc acccaaactc ctcatctatg ctgcatccaa ccaaggatcc    180
ggggtccctg ccaggtttgg tggcagtggg tctgggacag acttcagcct caacatccat    240
cctatggagg aagatgatac tgcaatgtat ttctgtcagc aaagtaagga ggttccgtgg    300
acgttcggtg gaggcaccaa gctggaaatc aaa                                 333

<210> SEQ ID NO 548
<211> LENGTH: 111
<212> TYPE: PRT
<213> ORGANISM: Mus musculus

<400> SEQUENCE: 548

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
 50                  55                  60

Arg Phe Gly Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Trp Thr Phe Gly Gly Gly Thr Lys Leu Glu Ile Lys
            100                 105                 110

<210> SEQ ID NO 549
<211> LENGTH: 360
<212> TYPE: DNA
<213> ORGANISM: Mus musculus

<400> SEQUENCE: 549
gatgtgcagc ttcaggagtc gggacctggc ctggtgaaac cttctcagtc tctgtccctc     60
gcctgcactg tcactggcta ctcaatcacc agtgattatg cctggaactg gatccggcag    120
tttccaggaa acaaactgga gtggctgggc tacataagct acagtggtac cactaggtac    180
aacccatctc tcaaaagtcg aatctctatc actcgagaca catccaagaa ccagttcttc    240
ctgcagttga attctgtgac tactgaggac acagccacat attactgtgc aatatacggt    300
agtagctact actggtactt cgatgtctgg ggcgcaggga ccacggtcac cgtctcctca    360

<210> SEQ ID NO 550
<211> LENGTH: 120
<212> TYPE: PRT
<213> ORGANISM: Mus musculus

<400> SEQUENCE: 550

Asp Val Gln Leu Gln Glu Ser Gly Pro Gly Leu Val Lys Pro Ser Gln
1               5                   10                  15

Ser Leu Ser Leu Ala Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Leu Gly Tyr Ile Ser Tyr Ser Gly Thr Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ile Tyr Gly Ser Ser Tyr Tyr Trp Tyr Phe Asp Val Trp Gly Ala
            100                 105                 110

Gly Thr Thr Val Thr Val Ser Ser
        115                 120

<210> SEQ ID NO 551
<211> LENGTH: 324
<212> TYPE: DNA
<213> ORGANISM: Mus musculus

<400> SEQUENCE: 551
caaattgttc tcacccagtc tccagcaatc atgtctgcat ctctagggga acgggtcacc     60
atgacctgca ctgccagctc aagtgtaagt tccagttact tgcactggta ccagcagaag    120
ccaggatcct cccccaaact ctggatttat agcacatcca acctggcttc tggagtccca    180
gctcgcttca gtggcagtgg gtctgggacc tcttactctc tcacaatcag cagcatggag    240
gctgaagatg ctgccactta ttactgccac cagtatcatc gttccccacc cacgttcggt    300
gctgggacca agctggagct gaaa                                           324

<210> SEQ ID NO 552
<211> LENGTH: 108
<212> TYPE: PRT
<213> ORGANISM: Mus musculus

<400> SEQUENCE: 552

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ala Gly Thr Lys Leu Glu Leu Lys
            100                 105

<210> SEQ ID NO 553
<211> LENGTH: 369
<212> TYPE: DNA
<213> ORGANISM: Mus musculus

<400> SEQUENCE: 553
caagttactc taaaagagtc tggccctggg atattgaagc cctcacagac cctcagtctg      60
acttgttctt tctctgggtt ttcactgagc acttctggta tgggtgtagg ctggattcgt     120
cagccttcag ggaagggtct ggagtggctg gcacacattt ggtgggatga tgacgagtac     180
tataacccat ccctgaagag ccagctcaca atctccaagg ataccaccag aaaccaggta     240
ttcctcaaga tcaccagtgt ggacactgca gatactgcca cttactactg tgctcgaaga     300
gcaattcatt actacggcta cgatgctatg gactactggg gtcaaggaac ctcagtcacc     360
gtctcctca                                                              369

<210> SEQ ID NO 554
<211> LENGTH: 123
<212> TYPE: PRT
<213> ORGANISM: Mus musculus

<400> SEQUENCE: 554

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Glu Tyr Tyr Asn Pro Ser
    50                  55                  60

Leu Lys Ser Gln Leu Thr Ile Ser Lys Asp Thr Thr Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Ile His Tyr Tyr Gly Tyr Asp Ala Met Asp Tyr
            100                 105                 110

Trp Gly Gln Gly Thr Ser Val Thr Val Ser Ser
        115                 120

<210> SEQ ID NO 555
<211> LENGTH: 324
<212> TYPE: DNA
<213> ORGANISM: Mus musculus

<400> SEQUENCE: 555
caaattgttc tcacccagtc tccagcaatc atgtctgcat ctctagggga acgggtcacc      60
atgacctgca ctgccagctc aagtgtaagt tccagttact tgcactggta ccagcagaag     120
ccaggatcct cccccaaact ctggatttat agcacatcca acctggcttc tggagtccca     180
gctcgcttca gtggcagtgg gtctgggacc tcttactctc tcacaatcag cagcatggag     240
gctgaagatg ctgccactta ttactgccac cagtatcatc gttccccacc cacgttcggt     300
gctgggacca agctggagct gaaa                                              324

<210> SEQ ID NO 556
<211> LENGTH: 108
<212> TYPE: PRT
<213> ORGANISM: Mus musculus

<400> SEQUENCE: 556

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ala Gly Thr Lys Leu Glu Leu Lys
            100                 105

<210> SEQ ID NO 557
<211> LENGTH: 357
<212> TYPE: DNA
<213> ORGANISM: Mus musculus

<400> SEQUENCE: 557
caggtccaac tgcagcagcc tggggctgaa ctggtgaagc ctggggcttc agtgaagctg     60
tcctgcaagg cttctggcta caccttcacc agctactgga tgcactgggt gaagcagagg    120
cctggacaag gccttgagtg gattggagag attaatccta gcaacggtcg tactaactac    180
aatgagaagt tcaagagcaa ggccacactg actgtagaca atcctccag cacagcctac     240 atgcaactca gcagcctgac atctgaggac tctgcggtct attactgtgc aagacaaggg    300
tataggcacg gggtttttgc ttactggggc caagggactc tggtcactgt ctctgca       357

<210> SEQ ID NO 558
<211> LENGTH: 119
<212> TYPE: PRT
<213> ORGANISM: Mus musculus

<400> SEQUENCE: 558

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gln Gly Tyr Arg His Gly Val Phe Ala Tyr Trp Gly Gln Gly
            100                 105                 110

<210> SEQ ID NO 559
<211> LENGTH: 324
<212> TYPE: DNA
<213> ORGANISM: Mus musculus

<400> SEQUENCE: 559

```
caaattgttc tcacccagtc tccagcaatc atgtctgcat ctctagggga acgggtcacc      60
atgacctgca ctgccagctc aagtgtaagt tccagttact tgcactggta ccagcagaag     120
ccaggatcct cccccaaact ctggatttat agcacatcca acctggcttc tggagtccca     180
gctcgcttca gtggcagtgg gtctgggacc tcttactctc tcacaatcag cagcatggag     240
gctgaagatg ctgccactta ttactgccac cagtatcatc gttccccacc cacgttcggt     300
gctgggacca agctggagct gaaa                                            324
```

<210> SEQ ID NO 560
<211> LENGTH: 108
<212> TYPE: PRT
<213> ORGANISM: Mus musculus

<400> SEQUENCE: 560

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ala Gly Thr Lys Leu Glu Leu Lys
            100                 105

<210> SEQ ID NO 561
<211> LENGTH: 351
<212> TYPE: DNA
<213> ORGANISM: Mus musculus

<400> SEQUENCE: 561

```
caggttactc tgaaagagtc tggccctggg atattgcagc cctcccagac cctcagtctg      60
acttgttctt tctctgggtt ttcactgagc acttctggta tgggtgtgag ctggattcgt     120
cagccttcag gaaagggtct ggagtggctg gcacacattt actggatgat gacaagcgc      180
tataacccat ccctgaagag ccggctcaca atctccaagg atacctccag caaccaggta     240
ttcctcaaga tcaccagtgt ggacactgca gatactgcca catactactg tgctctctat     300
gccaaagggt tgcttactg gggccaaggg actctggtca ctgtctctgc a              351
```

<210> SEQ ID NO 562
<211> LENGTH: 117
<212> TYPE: PRT
<213> ORGANISM: Mus musculus

<400> SEQUENCE: 562

Gln Val Thr Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Ser Thr Ser
            20                  25                  30
Gly Met Gly Val Ser Trp Ile Arg Gln Pro Ser Gly Lys Gly Leu Glu
        35                  40                  45
Trp Leu Ala His Ile Tyr Trp Asp Asp Asp Lys Arg Tyr Asn Pro Ser
    50                  55                  60
Leu Lys Ser Arg Leu Thr Ile Ser Lys Asp Thr Ser Ser Asn Gln Val
65                  70                  75                  80
Phe Leu Lys Ile Thr Ser Val Asp Thr Ala Asp Thr Ala Thr Tyr Tyr
                85                  90                  95
Cys Ala Leu Tyr Ala Lys Gly Phe Ala Tyr Trp Gly Gln Gly Thr Leu
            100                 105                 110
Val Thr Val Ser Ala
        115

<210> SEQ ID NO 563
<211> LENGTH: 318
<212> TYPE: DNA
<213> ORGANISM: Mus musculus

<400> SEQUENCE: 563
gacatccaga tgacacagtc tccatcctca ctgtctgcat ctctgggagg caaagtcacc    60
atcacttgca aggcaagcca agacattaac aagtatatag cttggtacca acacaagcct   120
ggaaaaggtc ctaggctgct catacattac acatctacat tacagccagg catcccatca   180
aggttcagtg gaagtgggtc tgggagagat tattccttca gcatcagcaa cctggagcct   240
gaagatattg caacttatta ttgtctacag tatgataatc tgtacacgtt cggaggggggg   300
accaagctgg aaataaaa                                                  318

<210> SEQ ID NO 564
<211> LENGTH: 106
<212> TYPE: PRT
<213> ORGANISM: Mus musculus

<400> SEQUENCE: 564

Asp Ile Gln Met Thr Gln Ser Pro Ser Ser Leu Ser Ala Ser Leu Gly
1               5                   10                  15
Gly Lys Val Thr Ile Thr Cys Lys Ala Ser Gln Asp Ile Asn Lys Tyr
            20                  25                  30
Ile Ala Trp Tyr Gln His Lys Pro Gly Lys Gly Pro Arg Leu Leu Ile
        35                  40                  45
His Tyr Thr Ser Thr Leu Gln Pro Gly Ile Pro Ser Arg Phe Ser Gly
    50                  55                  60
Ser Gly Ser Gly Arg Asp Tyr Ser Phe Ser Ile Ser Asn Leu Glu Pro
65                  70                  75                  80
Glu Asp Ile Ala Thr Tyr Tyr Cys Leu Gln Tyr Asp Asn Leu Tyr Thr
                85                  90                  95
Phe Gly Gly Gly Thr Lys Leu Glu Ile Lys
            100                 105

<210> SEQ ID NO 565
<211> LENGTH: 348
<212> TYPE: DNA

<213> ORGANISM: Mus musculus

<400> SEQUENCE: 565

```
caggttactc tgaaagagtc tggccctggg atattgcagc cctcccagac cctcagtctg     60
acttgttctt tctctgggtt ttcactgagc acttctggta tgggtgtgag ctggattcgt    120
cagccttcag gaaagggtct ggagtggctg gcacacattt actgggatga tgacaagcgc    180
tataacccat ccctgaagag ccggctcaca atctccaagg atacctccag caaccaggta    240
ttcctcaaga tcaccagtgt ggacactgca gatactgcca catactactg tgctcgaaga    300
ggggactttg actactgggg ccaaggcacc actctcacag tctcctca                 348
```

<210> SEQ ID NO 566
<211> LENGTH: 116
<212> TYPE: PRT
<213> ORGANISM: Mus musculus

<400> SEQUENCE: 566

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Asp Phe Asp Tyr Trp Gly Gln Gly Thr Thr Leu
            100                 105                 110

Thr Val Ser Ser
        115

<210> SEQ ID NO 567
<211> LENGTH: 336
<212> TYPE: DNA
<213> ORGANISM: Mus musculus

<400> SEQUENCE: 567

```
gatgttgtga tgacccaaac tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
cccacgttcg gtgctgggac caagctggag ctgaaa                              336
```

<210> SEQ ID NO 568
<211> LENGTH: 112
<212> TYPE: PRT
<213> ORGANISM: Mus musculus

<400> SEQUENCE: 568

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ala Gly Thr Lys Leu Glu Leu Lys
            100                 105                 110

<210> SEQ ID NO 569
<211> LENGTH: 360
<212> TYPE: DNA
<213> ORGANISM: Mus musculus

<400> SEQUENCE: 569
caagttactc taaaagagtc tggccctggg atattgaagc cctcacagac cctcagtctg     60
acttgttctt tctctgggtt ttcactgagc acttctggta tgggtgtagg ctggattcgt    120
cagccttcag ggaagggtct ggagtggctg gcacacattt ggtgggatga tgataagtac    180
tataacccat ccctgaagag ccagctcaca atctccaagg ataccttcag aaaccaggta    240
ttcctcaaga tcaccagtgt ggacactgca gatactgcca cttactactg tgctcgaaga    300
tcactatcca gggactactt tgactactgg ggccaaggca ccactctcac agtctcctca    360

<210> SEQ ID NO 570
<211> LENGTH: 120
<212> TYPE: PRT
<213> ORGANISM: Mus musculus

<400> SEQUENCE: 570

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ser Leu Ser Arg Asp Tyr Phe Asp Tyr Trp Gly Gln
            100                 105                 110

Gly Thr Thr Leu Thr Val Ser Ser
        115                 120

<210> SEQ ID NO 571
<211> LENGTH: 336
<212> TYPE: DNA
<213> ORGANISM: Mus musculus

<400> SEQUENCE: 571
gatgttgtga tgacccaaac tccactctcc ctgcctgtca gtcttggaga tcaagcctcc     60

```
atctcttgca gatctagtca gagccttgta cacagtaatg aaacaccta tttacattgg    120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
ctcacgttcg gtgctgggac caagctggag ctgaaa                              336
```

<210> SEQ ID NO 572
<211> LENGTH: 112
<212> TYPE: PRT
<213> ORGANISM: Mus musculus

<400> SEQUENCE: 572

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 573
<211> LENGTH: 357
<212> TYPE: DNA
<213> ORGANISM: Mus musculus

<400> SEQUENCE: 573

```
caagttactc taaaagagtc tggccctggg atattgaagc cctcacagac cctcagtctg     60
acttgttctt tctctgggtt ttcactgagc acttctggta tgggtgtagg ctggattcgt    120
cagccttcag ggaagggtct ggagtggctg gcacacattt ggtgggatga tgataagtac    180
tataacccat ccctgaagag ccagctcaca atctccaagg atacctccag aaaccaggta    240
ttcctcaaga tcaccagtgt ggacactgca gatactgcca cttactactg tgctccatct    300
actatgatta caacctttgc ttactggggc caagggactc tggtcactgt ctctgca       357
```

<210> SEQ ID NO 574
<211> LENGTH: 119
<212> TYPE: PRT
<213> ORGANISM: Mus musculus

<400> SEQUENCE: 574

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

```
Leu Lys Ser Gln Leu Thr Ile Ser Lys Asp Thr Ser Arg Asn Gln Val
 65                  70                  75                  80

Phe Leu Lys Ile Thr Ser Val Asp Thr Ala Asp Thr Ala Thr Tyr Tyr
                 85                  90                  95

Cys Ala Pro Ser Thr Met Ile Thr Thr Phe Ala Tyr Trp Gly Gln Gly
            100                 105                 110

Thr Leu Val Thr Val Ser Ala
        115

<210> SEQ ID NO 575
<211> LENGTH: 336
<212> TYPE: DNA
<213> ORGANISM: Mus musculus

<400> SEQUENCE: 575
gatgttgtga tgacccaaac tccactctcc ctgcctgtca gtcttggaga tcaagcctcc      60
atctcttgca gatctagtca gagccttgta cacagtaatg aaacaccta tttacattgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttcct     300
ctcacgttcg gtgctgggac caagctggag ctgaaa                              336

<210> SEQ ID NO 576
<211> LENGTH: 112
<212> TYPE: PRT
<213> ORGANISM: Mus musculus

<400> SEQUENCE: 576

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Leu Lys
            100                 105                 110

<210> SEQ ID NO 577
<211> LENGTH: 363
<212> TYPE: DNA
<213> ORGANISM: Mus musculus

<400> SEQUENCE: 577
caggtgcagc tgaagcagtc aggacctggc ctagtgcagc cctcacagag cctgtccata      60
acctgcacag tctctggttt ctcattaact agctatggtg tacactgggt tcgccagtct     120
ccaggaaagg gtctggagtg gctgggagtg atatggagag gtggaagcac agactacaat     180
gcagctttca tgtccagact gagcatcacc aaggacaact ccaagagcca gttttctttt     240
aaaatgaaca gtctgcaagc tgatgacact gccatatact actgtgccaa caataggtac     300
```

```
gagagagggg gttactatgc tatggactac tggggtcaag gaacctcagt caccgtctcc    360
tca                                                                  363
```

<210> SEQ ID NO 578
<211> LENGTH: 121
<212> TYPE: PRT
<213> ORGANISM: Mus musculus

<400> SEQUENCE: 578

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Asn Asn Arg Tyr Glu Arg Gly Tyr Tyr Ala Met Asp Tyr Trp Gly
            100                 105                 110

Gln Gly Thr Ser Val Thr Val Ser Ser
        115                 120
```

<210> SEQ ID NO 579
<211> LENGTH: 336
<212> TYPE: DNA
<213> ORGANISM: Mus musculus

<400> SEQUENCE: 579

```
gatgttttga tgacccaaac tccactctcc ctgcctgtca gtcttggaga tcaagcctcc     60
atctcttgca gatctagtca gagcattgta catagtaatg aaacacccta tttagaatgg    120
tacctgcata accaggcca gtctccaaag ctcctgatct acaaagtttc caaccgattt     180
tctggggtcc cagacaggtt cagtggcagt ggatcaggga cagatttcac actcaagatc    240
agcagagtgg aggctgagga tctgggagtt tattactgct ttcaaggttc acatgttccg    300
ctcacgttcg gtgctgggac caagctggag ctgaaa                              336
```

<210> SEQ ID NO 580
<211> LENGTH: 112
<212> TYPE: PRT
<213> ORGANISM: Mus musculus

<400> SEQUENCE: 580

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu His Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Leu Gly Val Tyr Tyr Cys Phe Gln Gly
            85                  90                  95

Ser His Val Pro Leu Thr Phe Gly Ala Gly Thr Lys Leu Glu Leu Lys
            100                 105                 110

<210> SEQ ID NO 581
<211> LENGTH: 363
<212> TYPE: DNA
<213> ORGANISM: Mus musculus

<400> SEQUENCE: 581
caggtgcagc tgaagcagtc aggacctggc ctagtgcagc cctcacagag cctgtccata      60
acctgcacag tctctggttt ctcattaact agctatggtg tacactgggt tcgccagtct     120
ccaggaaagg gtctggagtg gctgggagtg atatggagag gtggaagcac agactacaat     180
gcagctttca tgtccagact gagcatcacc aaggacaact ccaagagcca gttttctttt     240
aaaatgaaca gtctgcaagc tgatgacact gccatatact actgtgccaa caataggtac     300
gagagagggg gttactatgc tatggactac tggggtcaag gaacctcagt caccgtctcc     360
tca                                                                    363

<210> SEQ ID NO 582
<211> LENGTH: 121
<212> TYPE: PRT
<213> ORGANISM: Mus musculus

<400> SEQUENCE: 582

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Asn Asn Arg Tyr Glu Arg Gly Gly Tyr Tyr Ala Met Asp Tyr Trp Gly
            100                 105                 110

Gln Gly Thr Ser Val Thr Val Ser Ser
        115                 120

<210> SEQ ID NO 583
<211> LENGTH: 336
<212> TYPE: DNA
<213> ORGANISM: Mus musculus

<400> SEQUENCE: 583
gatgttttga tgacccaaac tccactctcc ctgcctgtca gtcttggaga tcaagcctcc      60
atctcttgca gatctagtca gagcattgta catagtaatg aaacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctggggagtt tattactgct ttcaaggttc acatgttccg     300
ctcacgttcg gtgctgggac caagctggag ctgaaa 336

<210> SEQ ID NO 584
<211> LENGTH: 112
<212> TYPE: PRT
<213> ORGANISM: Mus musculus

<400> SEQUENCE: 584

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 585
<211> LENGTH: 351
<212> TYPE: DNA
<213> ORGANISM: Mus musculus

<400> SEQUENCE: 585
caggttactc tgaaagagtc tggccctggg atattgcagc cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180 tataaccat  ccctgaagag ccggctcaca atctccaagg atacctccag aaaccaggta     240
ttcctcaaga tcaccagtgt ggacactgca gatactgcca catactactg tgctcggtat     300
ggtaactcct ttgcttactg gggccaaggg actctggtca ctgtctctgc a              351

<210> SEQ ID NO 586
<211> LENGTH: 117
<212> TYPE: PRT
<213> ORGANISM: Mus musculus

<400> SEQUENCE: 586

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Tyr Gly Asn Ser Phe Ala Tyr Trp Gly Gln Gly Thr Leu
            100                 105                 110

Val Thr Val Ser Ala
        115

<210> SEQ ID NO 587
<211> LENGTH: 336
<212> TYPE: DNA
<213> ORGANISM: Mus musculus

<400> SEQUENCE: 587
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                               336

<210> SEQ ID NO 588
<211> LENGTH: 112
<212> TYPE: PRT
<213> ORGANISM: Mus musculus

<400> SEQUENCE: 588

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 589
<211> LENGTH: 354
<212> TYPE: DNA
<213> ORGANISM: Mus musculus

<400> SEQUENCE: 589
caggtccaac tgcagcagcc tggggctgaa ctggtgaagc tggggcttc agtgaagctg       60 tcctgcaagg cttctggcta caccttcacc agctactgga tgcactgggt gaagcagagg     120
cctggacaag ccttgagtg gattggagag attaatccta gcaacggtcg tactaactac      180
aatgagaagt tcaagagcaa ggccacactg actgtagaca atcctccag cacagcctac      240 atgcaactca gcagcctgac atctgaggac tctgcggtct attactgtgc aagagagcat     300
tactacggct acggtgctta ctggggccaa gggactctgg tcactgtctc tgca           354

<210> SEQ ID NO 590
<211> LENGTH: 118
<212> TYPE: PRT
<213> ORGANISM: Mus musculus

<400> SEQUENCE: 590

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu His Tyr Tyr Gly Tyr Gly Ala Tyr Trp Gly Gln Gly Thr
            100                 105                 110

Leu Val Thr Val Ser Ala
        115

<210> SEQ ID NO 591
<211> LENGTH: 336
<212> TYPE: DNA
<213> ORGANISM: Mus musculus

<400> SEQUENCE: 591
gatgttttga tgacccaaac tccactctcc ctgcctgtca gtcttggaga tcaagcctcc      60
atctcttgca gatctagtca gagcattgta catagtaatg aaacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                              336

<210> SEQ ID NO 592
<211> LENGTH: 112
<212> TYPE: PRT
<213> ORGANISM: Mus musculus

<400> SEQUENCE: 592

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 593
<211> LENGTH: 372
<212> TYPE: DNA

<213> ORGANISM: Mus musculus

<400> SEQUENCE: 593

```
caggttactc tgaaagagtc tggccctggg atattgcagc cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacccat ccctgaagag ccggctcaca atctccaagg atacctccag caaccaggta     240
ttcctcaaga tcaccagtgt ggacactgca gatactgcca catactactg tgctcgaagg     300
ggcccctcct actataggta cagggactac tttgactact ggggccaagg caccactctc     360
acagtctcct ca                                                         372
```

<210> SEQ ID NO 594
<211> LENGTH: 124
<212> TYPE: PRT
<213> ORGANISM: Mus musculus

<400> SEQUENCE: 594

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Pro Ser Tyr Tyr Arg Tyr Arg Asp Tyr Phe Asp
            100                 105                 110

Tyr Trp Gly Gln Gly Thr Thr Leu Thr Val Ser Ser
        115                 120
```

<210> SEQ ID NO 595
<211> LENGTH: 336
<212> TYPE: DNA
<213> ORGANISM: Mus musculus

<400> SEQUENCE: 595

```
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagtttcac actcaagatc     240
agcagagtgg aggctgagga tctgggagtt tattactgct tcaaggttc acatgttccg     300
ctcacgttcg gtgctgggac caagctggag ctgaaa                               336
```

<210> SEQ ID NO 596
<211> LENGTH: 112
<212> TYPE: PRT
<213> ORGANISM: Mus musculus

<400> SEQUENCE: 596

```
Asp Val Leu Met Thr Gln Thr Pro Leu Ser Leu Pro Val Ser Leu Gly
```

```
1               5                   10                  15
Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 597
<211> LENGTH: 363
<212> TYPE: DNA
<213> ORGANISM: Mus musculus

<400> SEQUENCE: 597

```
caagttactc taaaagagtc tggccctggg atattgaagc cctcacagac cctcagtctg      60
acttgttctt tctctgggtt ttcactgagc acttctggta tgggtgtagg ctggattcgt     120
cagccttcag ggaagggtct ggagtggctg gcacacattt ggtgggatga tgataagtac     180
tataacccat ccctgaagag ccagctcaca atctccaagg atacctccag aaaccaggta     240
ttcctcaaga tcaccagtgt ggacactgca gatactgcca cttactactg tgctcgaaga     300
gccctctatg gttacgacgc tatggactac tggggtcaag aacctcagt caccgtctcc     360
tca                                                                    363
```

<210> SEQ ID NO 598
<211> LENGTH: 121
<212> TYPE: PRT
<213> ORGANISM: Mus musculus

<400> SEQUENCE: 598

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Leu Tyr Gly Tyr Asp Ala Met Asp Tyr Trp Gly
            100                 105                 110

Gln Gly Thr Ser Val Thr Val Ser Ser
            115                 120
```

<210> SEQ ID NO 599
<211> LENGTH: 336
<212> TYPE: DNA
<213> ORGANISM: Mus musculus

<400> SEQUENCE: 599

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcct   300
ctcacgttcg gtgctgggac caagctggag ctgaaa                             336
```

<210> SEQ ID NO 600
<211> LENGTH: 112
<212> TYPE: PRT
<213> ORGANISM: Mus musculus

<400> SEQUENCE: 600

```
Asp Val Leu Met Thr Gln Thr Pro Leu Ser Leu Pro Val Ser Leu Gly
1               5                  10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
            100                 105                 110
```

<210> SEQ ID NO 601
<211> LENGTH: 351
<212> TYPE: DNA
<213> ORGANISM: Mus musculus

<400> SEQUENCE: 601

```
caggttactc tgaaagagtc tggccctggg atattgcagc cctcccagac cctcagtctg    60
acttgttctt tctctgggtt ttcactgagc acttctggta tgggtgtgag ctggattcgt   120
cagccttcag gaaagggtct ggagtggctg gcacacattt actgggatga tgacaagcgc   180
tataacccat ccctgaagag ccggctcaca atctccaagg atacctccag caaccaggta   240
ttcctcaaga tcaccagtgt ggacactgca gatactgcca catactactg tgcctactat   300
aggtccggtt ttgcttactg gggccaaggg actctggtca ctgtctctgc a            351
```

<210> SEQ ID NO 602
<211> LENGTH: 117
<212> TYPE: PRT
<213> ORGANISM: Mus musculus

<400> SEQUENCE: 602

```
Gln Val Thr Leu Lys Glu Ser Gly Pro Gly Ile Leu Gln Pro Ser Gln
1               5                  10                  15
Thr Leu Ser Leu Thr Cys Ser Phe Ser Gly Phe Ser Leu Ser Thr Ser
            20                  25                  30
Gly Met Gly Val Ser Trp Ile Arg Gln Pro Ser Gly Lys Gly Leu Glu
```

```
              35                  40                  45
Trp Leu Ala His Ile Tyr Trp Asp Asp Lys Arg Tyr Asn Pro Ser
 50                  55                  60
Leu Lys Ser Arg Leu Thr Ile Ser Lys Asp Thr Ser Asn Gln Val
 65                  70                  75                  80
Phe Leu Lys Ile Thr Ser Val Asp Thr Ala Asp Thr Ala Thr Tyr Tyr
                 85                  90                  95
Cys Ala Tyr Tyr Arg Ser Gly Phe Ala Tyr Trp Gly Gln Gly Thr Leu
                100                 105                 110
Val Thr Val Ser Ala
        115

<210> SEQ ID NO 603
<211> LENGTH: 336
<212> TYPE: DNA
<213> ORGANISM: Mus musculus

<400> SEQUENCE: 603
gatgttttga tgacccaaac tccactctcc ctgcctgtca gtcttggaga tcaagcctcc      60
atctcttgca gatctagtca gagcattgta catagtaatg caacaccta tttagaatgg     120 tacctgcaga accaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                               336

<210> SEQ ID NO 604
<211> LENGTH: 112
<212> TYPE: PRT
<213> ORGANISM: Mus musculus

<400> SEQUENCE: 604

Asp Val Leu Met Thr Gln Thr Pro Leu Ser Leu Pro Val Ser Leu Gly
  1               5                  10                  15
Asp Gln Ala Ser Ile Ser Cys Arg Ser Ser Gln Ser Ile Val His Ser
             20                  25                  30
Asn Gly Asn Thr Tyr Leu Glu Trp Tyr Leu Gln Lys Pro Gly Gln Ser
         35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Leu Thr Phe Gly Ala Gly Thr Lys Leu Glu Leu Lys
                100                 105                 110

<210> SEQ ID NO 605
<211> LENGTH: 354
<212> TYPE: DNA
<213> ORGANISM: Mus musculus

<400> SEQUENCE: 605
caggtccaac tgcagcagcc tggggctgaa ctggtgaagc ctggggcttc agtgaagctg      60
tcctgcaagg cttctggcta caccttcacc agctactgga tgcactgggt gaagcagagg     120
cctggacaag gccttgagtg gattggagag attaatccta gcaacggtcg tactaactac     180
```

```
aatgagaagt tcaagagcaa ggccacactg actgtagaca aatcctccag cacagcctac    240
atgcaactca gcagcctgac atctgaggac tctgcggtct attactgtgc aagagagcat    300
tactacggct acggtgctta ctggggccaa gggactctgg tcactgtctc tgca          354
```

<210> SEQ ID NO 606
<211> LENGTH: 118
<212> TYPE: PRT
<213> ORGANISM: Mus musculus

<400> SEQUENCE: 606

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu His Tyr Tyr Gly Tyr Gly Ala Tyr Trp Gly Gln Gly Thr
            100                 105                 110

Leu Val Thr Val Ser Ala
        115
```

<210> SEQ ID NO 607
<211> LENGTH: 336
<212> TYPE: DNA
<213> ORGANISM: Mus musculus

<400> SEQUENCE: 607

```
gatgttttga tgacccaaac tccactctcc ctgcctgtca gtcttggaga tcaagcctcc    60
atctcttgca gatctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tacacgttcg gaggggggac caagctggaa ataaaa                              336
```

<210> SEQ ID NO 608
<211> LENGTH: 112
<212> TYPE: PRT
<213> ORGANISM: Mus musculus

<400> SEQUENCE: 608

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

<210> SEQ ID NO 609
<211> LENGTH: 360
<212> TYPE: DNA
<213> ORGANISM: Mus musculus

<400> SEQUENCE: 609
caagttactc taaaagagtc tggccctggg atattgaagc cctcacagac cctcagtctg     60
acttgttctt tctctgggtt ttcactgagc acttctggta tgggtgtagg ctggattcgt    120
cagccttcag ggaagggtct ggagtggctg gcacacattt ggtgggatga tgataagtac    180
tataacccat ccctgaagag ccagctcaca atctccaagg ataccttcag aaaccaggta    240
ttcctcaaga tcaccagtgt ggacactgca gatactgcca cttactactg tgctcgaaga    300
tcactatcca gggactactt tgactactgg ggccaaggca ccactctcac agtctcctca    360

<210> SEQ ID NO 610
<211> LENGTH: 120
<212> TYPE: PRT
<213> ORGANISM: Mus musculus

<400> SEQUENCE: 610

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
                20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ser Leu Ser Arg Asp Tyr Phe Asp Tyr Trp Gly Gln
                100                 105                 110

Gly Thr Thr Leu Thr Val Ser Ser
            115                 120

<210> SEQ ID NO 611
<211> LENGTH: 336
<212> TYPE: DNA
<213> ORGANISM: Mus musculus

<400> SEQUENCE: 611
gatgttttga tgacccaaac tccactctcc ctgcctgtca gtcttggaga tcaagcctcc     60
atctcttgca gatctagtca gagcattgta catagtaatg aaacacccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
ctcacgttcg gtgctgggac caagctggag ctgaaa                                          336

<210> SEQ ID NO 612
<211> LENGTH: 112
<212> TYPE: PRT
<213> ORGANISM: Mus musculus

<400> SEQUENCE: 612

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 613
<211> LENGTH: 369
<212> TYPE: DNA
<213> ORGANISM: Mus musculus

<400> SEQUENCE: 613
caagttactc taaaagagtc tggccctggg atattgaagc cctcacagac cctcagtctg      60
acttgttctt tctctggggtt ttcactgagc actgctggta tgggtgtagg ctggattcgt     120
cagccttcag ggaagggtct ggagtggctg gcacacattt ggtgggatga tgataagtac     180
tataatccat ccctgaagag ccagctcaca atctccaagg atacctccag aaaccaggta     240
ttcctcaaga tcaccagtgt ggacactgca gatactgcca cttactctg tgctcgaaga     300 ggtctctact atggtaacta cgatgctatg gactactggg gtcaaggaac ctcagtcacc     360
gtctcctca                                                            369

<210> SEQ ID NO 614
<211> LENGTH: 123
<212> TYPE: PRT
<213> ORGANISM: Mus musculus

<400> SEQUENCE: 614

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ala
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Leu Tyr Tyr Gly Asn Tyr Asp Ala Met Asp Tyr
                100                 105                 110

Trp Gly Gln Gly Thr Ser Val Thr Val Ser Ser
        115                 120

<210> SEQ ID NO 615
<211> LENGTH: 336
<212> TYPE: DNA
<213> ORGANISM: Mus musculus

<400> SEQUENCE: 615
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc cacccgattt     180
tctggggtcc cagacaggtt cagtggcagt ggatcaggga cagatttcac actcaagatc     240
agcagagtgg aggctgagga tctgggagtt tattactgct ttcaaggttc acgtgttccg     300
ctcacgttcg gtgctgggac caagctggag ctgaaa                               336

<210> SEQ ID NO 616
<211> LENGTH: 112
<212> TYPE: PRT
<213> ORGANISM: Mus musculus

<400> SEQUENCE: 616

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Arg Val Pro Leu Thr Phe Gly Ala Gly Thr Lys Leu Glu Leu Lys
            100                 105                 110

<210> SEQ ID NO 617
<211> LENGTH: 366
<212> TYPE: DNA
<213> ORGANISM: Mus musculus

<400> SEQUENCE: 617
caagttactc taaaagagtc tggccctggg atattgaagc cctcacagac cctcagtctg      60
acttgttctt tctctgggtt ttcactgagc acttctggta tgggtgtagg ctggattcgt     120
cagccttcag ggaagggtct ggagtggctg gcacacattt ggtgggatga tgataagtac     180
tataacccat ccctgaagag ccagctcaca atctccaagg atacctccag aaaccaggta     240
ttcctcaaga tcaccagtgt ggacactgca gatactgcca cttactactg tgctcgaaga     300
gctttgatta cgacgagaga ctactttgac tactggggcc aaggcaccac tctcacagtc     360
tcctca                                                                366

<210> SEQ ID NO 618

```
<211> LENGTH: 122
<212> TYPE: PRT
<213> ORGANISM: Mus musculus

<400> SEQUENCE: 618

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Thr Tyr Tyr
                85                  90                  95

Cys Ala Arg Arg Ala Leu Ile Thr Thr Arg Asp Tyr Phe Asp Tyr Trp
            100                 105                 110

Gly Gln Gly Thr Thr Leu Thr Val Ser Ser
        115                 120

<210> SEQ ID NO 619
<211> LENGTH: 336
<212> TYPE: DNA
<213> ORGANISM: Mus musculus

<400> SEQUENCE: 619
gatgttttga tgacccaaac tccactctcc ctgcctgtca gtcttggaga tcaagcctcc      60
atctcttgca gatctagtca gagcattgta catagtaatg aaacacctta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                                336

<210> SEQ ID NO 620
<211> LENGTH: 112
<212> TYPE: PRT
<213> ORGANISM: Mus musculus

<400> SEQUENCE: 620

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 621
<211> LENGTH: 351
<212> TYPE: DNA
<213> ORGANISM: Mus musculus

<400> SEQUENCE: 621

```
gatgtgcagc tggtggagtc tgggggaggc ttagtgcagc ctggagggtc ccggaaactc    60
tcctgtgcag cctctggatt cactttcagt agctttggaa tgcactgggt tcgtcaggct   120
ccagagaagg ggctggagtg ggtcgcatac attagtagtg gcagtagtac catctactat   180
gcagacacag tgaagggccg attcaccatc tccagagaca atcccaagaa caccctgttc   240
ctgcaaatga ccagtctaag gtctgaggac acggccatgt attactgtgc aagatatggt   300
aactacgcta tggactactg gggtcaagga acctcagtca ccgtctcctc a            351
```

<210> SEQ ID NO 622
<211> LENGTH: 117
<212> TYPE: PRT
<213> ORGANISM: Mus musculus

<400> SEQUENCE: 622

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Tyr Gly Asn Tyr Ala Met Asp Tyr Trp Gly Gln Gly Thr Ser
            100                 105                 110

Val Thr Val Ser Ser
        115

<210> SEQ ID NO 623
<211> LENGTH: 336
<212> TYPE: DNA
<213> ORGANISM: Mus musculus

<400> SEQUENCE: 623

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
ggcagagtgg aggctgagga tctgggagtt tattactgct ttcaaggttc acatgttcct   300
ccgacgttcg gtggaggcac cgagctggaa atcaaa                             336
```

<210> SEQ ID NO 624
<211> LENGTH: 112
<212> TYPE: PRT
<213> ORGANISM: Mus musculus

<400> SEQUENCE: 624

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Gly Arg Val Glu Ala Glu Asp Leu Gly Val Tyr Tyr Cys Phe Gln Gly
                85                  90                  95

Ser His Val Pro Pro Thr Phe Gly Gly Gly Thr Glu Leu Glu Ile Lys
            100                 105                 110
```

<210> SEQ ID NO 625
<211> LENGTH: 363
<212> TYPE: DNA
<213> ORGANISM: Mus musculus

<400> SEQUENCE: 625

```
caagttactc taaaagagtc tggccctggg atattgaagc cctcacagac cctcagtctg    60
acttgttctt tctctgggtt ttcactgagc acttctggta tgggtgtagg ctggattcgt   120
cagccttcag ggaagggtct ggagtggctg gcacacattt ggtgggatga tgataagtac   180
tataacccat ccctgaagag ccagctcaca atctccaagg atacctccag aaaccaggta   240
ttcctcaaga tcaccagtgt ggacactgca gatactgcca cttactactg tgctcgaagg   300
ggattgatac ggcaagacta ctttgactac tggggccaag gcaccactct cacagtctcc   360
tca                                                                 363
```

<210> SEQ ID NO 626
<211> LENGTH: 121
<212> TYPE: PRT
<213> ORGANISM: Mus musculus

<400> SEQUENCE: 626

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Leu Ile Arg Gln Asp Tyr Phe Asp Tyr Trp Gly
            100                 105                 110

Gln Gly Thr Thr Leu Thr Val Ser Ser
            115                 120
```

<210> SEQ ID NO 627
<211> LENGTH: 336

```
<212> TYPE: DNA
<213> ORGANISM: Mus musculus

<400> SEQUENCE: 627
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ctcacgttcg gtgctgggac caagctggag ctgaaa                               336

<210> SEQ ID NO 628
<211> LENGTH: 112
<212> TYPE: PRT
<213> ORGANISM: Mus musculus

<400> SEQUENCE: 628

Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
            100                 105                 110

<210> SEQ ID NO 629
<211> LENGTH: 357
<212> TYPE: DNA
<213> ORGANISM: Mus musculus

<400> SEQUENCE: 629
caggttactc tgaaagagtc tggccctggg atattgcagc cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacccat ccctgaagag ccggctcaca atctccaagg atacctccag caaccaggta     240
ttcctcaaga tcaccagtgt ggacactgca gatactgcca catactactg tgctcgaggg     300
gactataggt acgacggggc ttactggggc caagggactc tggtcactgt ctctgca        357

<210> SEQ ID NO 630
<211> LENGTH: 119
<212> TYPE: PRT
<213> ORGANISM: Mus musculus

<400> SEQUENCE: 630

Gln Val Thr Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Ser Thr Ser
            20                  25                  30
```

```
Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Gly Asp Tyr Arg Tyr Asp Gly Ala Tyr Trp Gly Gln Gly
                100                 105                 110

Thr Leu Val Thr Val Ser Ala
        115

<210> SEQ ID NO 631
<211> LENGTH: 336
<212> TYPE: DNA
<213> ORGANISM: Mus musculus

<400> SEQUENCE: 631
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
ctcacgttcg gtgctgggac caagctggag ctgaaa                              336

<210> SEQ ID NO 632
<211> LENGTH: 112
<212> TYPE: PRT
<213> ORGANISM: Mus musculus

<400> SEQUENCE: 632

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 633
<211> LENGTH: 360
<212> TYPE: DNA
<213> ORGANISM: Mus musculus

<400> SEQUENCE: 633
caggttactc tgaaagagtc tggccctggg atattgcagc cctcccagac cctcagtctg      60
acttgttctt tctctgggtt ttcactgagc acttctggta tgggtgtgag ctggattcgt     120
```

```
cagccttcag gaaagggtct ggagtggctg gcacacattt actgggatga tgacaagcgc    180
tataacccat ccctgaagag ccggctcaca atctccaagg atacctccag aaaccaggta    240
ttcctcaaga tcaccagtgt ggacactgca gatactgcca catactactg tgctcgatgc    300
tatggtaact acggagctat ggactactgg ggtcaaggaa cctcagtcac cgtctcctca    360
```

<210> SEQ ID NO 634
<211> LENGTH: 120
<212> TYPE: PRT
<213> ORGANISM: Mus musculus

<400> SEQUENCE: 634

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Cys Tyr Gly Asn Tyr Gly Ala Met Asp Tyr Trp Gly Gln
            100                 105                 110

Gly Thr Ser Val Thr Val Ser Ser
        115                 120
```

<210> SEQ ID NO 635
<211> LENGTH: 336
<212> TYPE: DNA
<213> ORGANISM: Mus musculus

<400> SEQUENCE: 635

```
gatgttgtga tgacccaaac tccactctcc ctgcctgtca gtcttggaga tcaagcctcc    60
atctcttgca gatctagtca gagccttgta cacagtaatg aaacacccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtga aggctgagga tctgggagtt tatttctgct ctcaaagtac acatgttccg    300
ctcacgttcg gtgctgggac caagctggag ctgaaa                              336
```

<210> SEQ ID NO 636
<211> LENGTH: 112
<212> TYPE: PRT
<213> ORGANISM: Mus musculus

<400> SEQUENCE: 636

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 637
<211> LENGTH: 369
<212> TYPE: DNA
<213> ORGANISM: Mus musculus

<400> SEQUENCE: 637
caagttactc taaaagagtc tggccctggg atattgaagc cctcacagac cctcagtctg      60
acttgttctt tctctgggtt ttcactgagc acttctggta tgggtgtagg ctggattcgt     120
cagccttcag ggaagggtct ggagtggctg gcacacattt ggtgggatga tgataagtac     180
tataacccat ccctgaagag ccggctcact atctccaagg atacctccag aaaccaggta     240
ttcctcaaga tcaccagtgt ggacactgca gatactgcca cttactactg tactcgaaga     300
gctttactac ggctacaagg ggactacttt gactactggg gccaaggcac cactctcaca     360
gtctcctca                                                             369

<210> SEQ ID NO 638
<211> LENGTH: 123
<212> TYPE: PRT
<213> ORGANISM: Mus musculus

<400> SEQUENCE: 638

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Thr Arg Arg Ala Leu Leu Arg Leu Gln Gly Asp Tyr Phe Asp Tyr
            100                 105                 110

Trp Gly Gln Gly Thr Thr Leu Thr Val Ser Ser
        115                 120

<210> SEQ ID NO 639
<211> LENGTH: 336
<212> TYPE: DNA
<213> ORGANISM: Mus musculus

<400> SEQUENCE: 639
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180

```
tctggggtcc cagacaggtt cagtggcagt ggatcaggga cagatttcac actcaagatc      240
agcagagtgg aggctgagga tctgggagtt tattactgct ttcaaggttc acatgttccg      300
ctcacgttcg gtgctgggac caagctggag ctgaaa                                336
```

<210> SEQ ID NO 640
<211> LENGTH: 112
<212> TYPE: PRT
<213> ORGANISM: Mus musculus

<400> SEQUENCE: 640

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110
```

<210> SEQ ID NO 641
<211> LENGTH: 348
<212> TYPE: DNA
<213> ORGANISM: Mus musculus

<400> SEQUENCE: 641

```
caggttactc tgaaagagtc tggccctggg atattgcagc cctcccagac cctcagtctg       60
acttgttctt tctctgggtt ttcactgagc acttctggta tgggtgtgag ctggattcgt      120
cagccttcag gaaagggtct ggagtggctg gcacacattt actgggatga tgacaagcgc      180
tataacccat ccctgaagag ccggctcaca atctccaagg atacctccag aaaccaggta      240
ttcctcaaga tcaccagtgt ggacactgca gatactgcca catactactg tgctcgaagg      300
ggggactttg actactgggg ccaaggcacc actctcacag tctcctca                    348
```

<210> SEQ ID NO 642
<211> LENGTH: 116
<212> TYPE: PRT
<213> ORGANISM: Mus musculus

<400> SEQUENCE: 642

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
```

```
                    85                  90                  95
Cys Ala Arg Arg Gly Asp Phe Asp Tyr Trp Gly Gln Gly Thr Thr Leu
            100                 105                 110
Thr Val Ser Ser
        115

<210> SEQ ID NO 643
<211> LENGTH: 336
<212> TYPE: DNA
<213> ORGANISM: Mus musculus

<400> SEQUENCE: 643
gatgttgtga tgacccaaac tccactctcc ctgcctgtca gtcttggaga tcaagcctcc      60
atctcttgca gatctagtca gagccttgta cacagtaatg aaacaccta tttacattgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttcct     300
ccgacgttcg gtggaggcac caagctggaa atcaaa                              336

<210> SEQ ID NO 644
<211> LENGTH: 112
<212> TYPE: PRT
<213> ORGANISM: Mus musculus

<400> SEQUENCE: 644

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 645
<211> LENGTH: 348
<212> TYPE: DNA
<213> ORGANISM: Mus musculus

<400> SEQUENCE: 645
caggttactc tgaaagagtc tggccctggg atattgcagc cctcccagac cctcagtctg      60
acttgttctt tctctgggtt ttcactgagc acttctggta tgggtgtgag ctggattcgt     120 cagccttcag␣aaagggtct ggagtggctg gcacacattt actgggatga tgacaagcgc     180
tataacccat ccctgaagag ccggctcaca atctccaagg atacctccag caaccaggta     240
ttcctcaaga tcaccagtgt ggacactgca gatactgcca catactactg tgctctttat     300
tactacggtc tctactgggg ccaagggact ctggtcactg tctctgca                 348

<210> SEQ ID NO 646
```

<211> LENGTH: 116
<212> TYPE: PRT
<213> ORGANISM: Mus musculus

<400> SEQUENCE: 646

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Leu Tyr Tyr Tyr Gly Leu Tyr Trp Gly Gln Gly Thr Leu Val
            100                 105                 110

Thr Val Ser Ala
        115

<210> SEQ ID NO 647
<211> LENGTH: 336
<212> TYPE: DNA
<213> ORGANISM: Mus musculus

<400> SEQUENCE: 647
gatgttttga tgacccaaac tccactctcc ctgcctgtca gtcttggaga tcaagcctcc      60
atctcttgca gatctagtca gagcattgta catagtaatg aaacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                               336

<210> SEQ ID NO 648
<211> LENGTH: 112
<212> TYPE: PRT
<213> ORGANISM: Mus musculus

<400> SEQUENCE: 648

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 649
<211> LENGTH: 360
<212> TYPE: DNA
<213> ORGANISM: Mus musculus

<400> SEQUENCE: 649

```
caagttactc taaaagagtc tggccctggg atattgaagc cctcacagac cctcagtctg    60
acttgttctt tctctgggtt ttcactgagc acttctggta tgggtgtagg ctggattcgt   120
cagccttcag ggaagggtct ggagtggctg gcacacattt ggtgggatga tgataagtac   180
tataacccat ccctgaagag ccagctcaca atctccaagg atacctccag aaaccaggta   240
ttcctcaaga tcaccagtgt ggacactgca gatactgcca cttactactg tgctcgaaga   300
gccctcaact gggacgtatt tgactactgg ggccaaggca ccactctcac agtctcctca   360
```

<210> SEQ ID NO 650
<211> LENGTH: 120
<212> TYPE: PRT
<213> ORGANISM: Mus musculus

<400> SEQUENCE: 650

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Leu Asn Trp Asp Val Phe Asp Tyr Trp Gly Gln
            100                 105                 110

Gly Thr Thr Leu Thr Val Ser Ser
        115                 120
```

<210> SEQ ID NO 651
<211> LENGTH: 336
<212> TYPE: DNA
<213> ORGANISM: Mus musculus

<400> SEQUENCE: 651

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
ctcacgttcg gtgctgggac caagctggag ctgaaa                             336
```

<210> SEQ ID NO 652
<211> LENGTH: 112
<212> TYPE: PRT
<213> ORGANISM: Mus musculus

<400> SEQUENCE: 652

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 653
<211> LENGTH: 363
<212> TYPE: DNA
<213> ORGANISM: Mus musculus

<400> SEQUENCE: 653
caagttactc taaaagagtc tggccctggg atattgaagc cctcacagac cctcagtctg     60
acttgttctt tctctgggtt ttcactgagc acttctggta tgggtgtagg ctggattcgt    120
cagccttcag ggaagggtct ggagtggctg gcacacattt ggtgggatga tgataagtac    180
tataacccat ccctgaagag ccagctcaca atctccaagg atacctccag aaaccaggta    240
ttcctcaaga tcaccagtgt ggacactgca gatactgcca cttactactg tactcgaaga    300
gccctctatg attacgacgc tatggactac tggggtcaag gaacctcagt caccgtctcc    360
tca                                                                  363

<210> SEQ ID NO 654
<211> LENGTH: 121
<212> TYPE: PRT
<213> ORGANISM: Mus musculus

<400> SEQUENCE: 654

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Thr Arg Arg Ala Leu Tyr Asp Tyr Asp Ala Met Asp Tyr Trp Gly
            100                 105                 110

Gln Gly Thr Ser Val Thr Val Ser Ser
        115                 120

<210> SEQ ID NO 655
<211> LENGTH: 336

<212> TYPE: DNA
<213> ORGANISM: Mus musculus

<400> SEQUENCE: 655

```
gatgttttga tgacccaaac tccactctcc ctgcctgtca gtcttggaga tcaagcctcc      60
atctcttgca gatctagtca gagcattgta catagtaatg aaacaccta  tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
ctcacgttcg gtcctgggac caagctggag ctgaaa                              336
```

<210> SEQ ID NO 656
<211> LENGTH: 112
<212> TYPE: PRT
<213> ORGANISM: Mus musculus

<400> SEQUENCE: 656

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Pro Gly Thr Lys Leu Glu Leu Lys
            100                 105                 110
```

<210> SEQ ID NO 657
<211> LENGTH: 363
<212> TYPE: DNA
<213> ORGANISM: Mus musculus

<400> SEQUENCE: 657

```
gatgtgcagc ttcaggagtc aggacctgac ctggtgaaac cttctcagtc actttcactc      60
acctgcactg tcactggcta ctccatcacc agtggttata ctggcactg gatccggcag     120
tttccaggaa acaaactgga atggatgggc tacatacact acagtggtag cactaactac    180
aacccatctc tcaaaagtcg aatctctatc actcgagaca catccaagaa ccagttcttc    240
ctgcagttga attctgtgac tactgaggac acagccacat attactgtgc aagaaggggc    300
tatgatggtt actactcctg gtttgcttac tggggccaag gactctggt  cactgtctct    360
gca                                                                  363
```

<210> SEQ ID NO 658
<211> LENGTH: 121
<212> TYPE: PRT
<213> ORGANISM: Mus musculus

<400> SEQUENCE: 658

```
Asp Val Gln Leu Gln Glu Ser Gly Pro Asp Leu Val Lys Pro Ser Gln
 1               5                  10                  15
```

```
Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65              70                  75                  80

Leu Gln Leu Asn Ser Val Thr Thr Glu Asp Thr Ala Thr Tyr Tyr Cys
                85                  90                  95

Ala Arg Arg Gly Tyr Asp Gly Tyr Tyr Ser Trp Phe Ala Tyr Trp Gly
            100                 105                 110

Gln Gly Thr Leu Val Thr Val Ser Ala
            115                 120
```

<210> SEQ ID NO 659
<211> LENGTH: 333
<212> TYPE: DNA
<213> ORGANISM: Mus musculus

<400> SEQUENCE: 659

```
tcccaggctg ttgtgactca ggaatctgca ctcaccacat cacctggtga acagtcaca      60
ctcacttgtc gctcaagtac tggggctgtt acaactagta actatgccaa ctgggtccaa    120
gaaaaaccag atcatttatt cactggtcta ataggtggta ccaacaaccg agctccaggt    180
gttcctgcca gattctcagg ctccctgatt ggagacaagg ctgccctcac catcacaggg    240
gcacagactg aggatgaggc aatatatttc tgtgctctat ggtacagcaa ccattgggtg    300
ttcggtggag ggaccaaact gactgtccta ggc                                 333
```

<210> SEQ ID NO 660
<211> LENGTH: 111
<212> TYPE: PRT
<213> ORGANISM: Mus musculus

<400> SEQUENCE: 660

```
Ser Gln Ala Val Val Thr Gln Glu Ser Ala Leu Thr Thr Ser Pro Gly
1               5                   10                  15

Glu Thr Val Thr Leu Thr Cys Arg Ser Ser Thr Gly Ala Val Thr Thr
            20                  25                  30

Ser Asn Tyr Ala Asn Trp Val Gln Glu Lys Pro Asp His Leu Phe Thr
        35                  40                  45

Gly Leu Ile Gly Gly Thr Asn Asn Arg Ala Pro Gly Val Pro Ala Arg
    50                  55                  60

Phe Ser Gly Ser Leu Ile Gly Asp Lys Ala Ala Leu Thr Ile Thr Gly
65              70                  75                  80

Ala Gln Thr Glu Asp Glu Ala Ile Tyr Phe Cys Ala Leu Trp Tyr Ser
                85                  90                  95

Asn His Trp Val Phe Gly Gly Gly Thr Lys Leu Thr Val Leu Gly
            100                 105                 110
```

<210> SEQ ID NO 661
<211> LENGTH: 57
<212> TYPE: DNA
<213> ORGANISM: Mus musculus

<400> SEQUENCE: 661

```
atggctgtcc tggtgctgct cctctgcctg gtgacattcc caagctgtgt cctgtcc        57
```

<210> SEQ ID NO 662
<211> LENGTH: 19
<212> TYPE: PRT
<213> ORGANISM: Mus musculus

<400> SEQUENCE: 662

Met Ala Val Leu Val Leu Leu Leu Cys Leu Val Thr Phe Pro Ser Cys
1               5                   10                  15

Val Leu Ser

<210> SEQ ID NO 663
<211> LENGTH: 57
<212> TYPE: DNA
<213> ORGANISM: Mus musculus

<400> SEQUENCE: 663
atggacaggc ttacttcttc attcctgctg ctgattgtcc ctgcatatgt cttgccc         57

<210> SEQ ID NO 664
<211> LENGTH: 19
<212> TYPE: PRT
<213> ORGANISM: Mus musculus

<400> SEQUENCE: 664

Met Asp Arg Leu Thr Ser Ser Phe Leu Leu Leu Ile Val Pro Ala Tyr
1               5                   10                  15

Val Leu Pro

<210> SEQ ID NO 665
<211> LENGTH: 57
<212> TYPE: DNA
<213> ORGANISM: Mus musculus

<400> SEQUENCE: 665
atggacaggc ttacttcctc attcctgctg ctgattgtcc ctgcatatgt cctttcc         57

<210> SEQ ID NO 666
<211> LENGTH: 57
<212> TYPE: DNA
<213> ORGANISM: Mus musculus

<400> SEQUENCE: 666
atggacaggc ttacttcttc attcctgctg ctgattgtcc ctgcatatgt cttgtcc         57

<210> SEQ ID NO 667
<211> LENGTH: 19
<212> TYPE: PRT
<213> ORGANISM: Mus musculus

<400> SEQUENCE: 667

Met Asp Arg Leu Thr Ser Ser Phe Leu Leu Leu Ile Val Pro Ala Tyr
1               5                   10                  15

Val Leu Ser

<210> SEQ ID NO 668
<211> LENGTH: 57
<212> TYPE: DNA
<213> ORGANISM: Mus musculus

<400> SEQUENCE: 668
atggacaggc ttacttcctc attgctgctg ctgattgtct ctgcatatgt cctgtcc         57

<210> SEQ ID NO 669
<211> LENGTH: 19
<212> TYPE: PRT
<213> ORGANISM: Mus musculus

<400> SEQUENCE: 669

Met Asp Arg Leu Thr Ser Ser Leu Leu Leu Ile Val Ser Ala Tyr
1               5                   10                  15

Val Leu Ser

<210> SEQ ID NO 670
<211> LENGTH: 57
<212> TYPE: DNA
<213> ORGANISM: Mus musculus

<400> SEQUENCE: 670
atggactcca ggctcaattt agttttcctt gtccttattt taaaaggtgt ccagtgt      57

<210> SEQ ID NO 671
<211> LENGTH: 19
<212> TYPE: PRT
<213> ORGANISM: Mus musculus

<400> SEQUENCE: 671

Met Asp Ser Arg Leu Asn Leu Val Phe Leu Val Leu Ile Leu Lys Gly
1               5                   10                  15

Val Gln Cys

<210> SEQ ID NO 672
<211> LENGTH: 57
<212> TYPE: DNA
<213> ORGANISM: Mus musculus

<400> SEQUENCE: 672
atgggatgga gctatatcat cctctttttg gtagcaacag ctacagatgt ccactcc      57

<210> SEQ ID NO 673
<211> LENGTH: 19
<212> TYPE: PRT
<213> ORGANISM: Mus musculus

<400> SEQUENCE: 673

Met Gly Trp Ser Tyr Ile Ile Leu Phe Leu Val Ala Thr Ala Thr Asp
1               5                   10                  15

Val His Ser

<210> SEQ ID NO 674
<211> LENGTH: 57
<212> TYPE: DNA
<213> ORGANISM: Mus musculus

<400> SEQUENCE: 674
atgaacttcg gactcagctt gattttcctt gccctcattt taaaaggtgt ccagtgt      57

<210> SEQ ID NO 675
<211> LENGTH: 19
<212> TYPE: PRT
<213> ORGANISM: Mus musculus

<400> SEQUENCE: 675

Met Asn Phe Gly Leu Ser Leu Ile Phe Leu Ala Leu Ile Leu Lys Gly

<210> SEQ ID NO 676
<211> LENGTH: 57
<212> TYPE: DNA
<213> ORGANISM: Mus musculus

<400> SEQUENCE: 676
atgaacttcg ggctcagctt gattttcctt gtccttgttt taaaaggtgt ccagtgt        57

<210> SEQ ID NO 677
<211> LENGTH: 19
<212> TYPE: PRT
<213> ORGANISM: Mus musculus

<400> SEQUENCE: 677

Met Asn Phe Gly Leu Ser Leu Ile Phe Leu Val Leu Val Leu Lys Gly
1               5                   10                  15
Val Gln Cys

<210> SEQ ID NO 678
<211> LENGTH: 57
<212> TYPE: DNA
<213> ORGANISM: Mus musculus

<400> SEQUENCE: 678
atgaacaggc ttacttcctc attgctgctg ctgattgtcc ctgcatatgt cctgtcc        57

<210> SEQ ID NO 679
<211> LENGTH: 19
<212> TYPE: PRT
<213> ORGANISM: Mus musculus

<400> SEQUENCE: 679

Met Asn Arg Leu Thr Ser Ser Leu Leu Leu Leu Ile Val Pro Ala Tyr
1               5                   10                  15
Val Leu Ser

<210> SEQ ID NO 680
<211> LENGTH: 54
<212> TYPE: DNA
<213> ORGANISM: Mus musculus

<400> SEQUENCE: 680
atgagagtgc tgattctttt gtgcctgttc acagcctttc ctggtatcct gtct        54

<210> SEQ ID NO 681
<211> LENGTH: 18
<212> TYPE: PRT
<213> ORGANISM: Mus musculus

<400> SEQUENCE: 681

Met Arg Val Leu Ile Leu Leu Cys Leu Phe Thr Ala Phe Pro Gly Ile
1               5                   10                  15
Leu Ser

<210> SEQ ID NO 682
<211> LENGTH: 54
<212> TYPE: DNA
<213> ORGANISM: Mus musculus

<400> SEQUENCE: 682
atgagagtgc tgattctttt gtggctgttc acagcctttc ctggtatcct gtcc            54

<210> SEQ ID NO 683
<211> LENGTH: 18
<212> TYPE: PRT
<213> ORGANISM: Mus musculus

<400> SEQUENCE: 683

Met Arg Val Leu Ile Leu Leu Trp Leu Phe Thr Ala Phe Pro Gly Ile
1               5                   10                  15

Leu Ser

<210> SEQ ID NO 684
<211> LENGTH: 57
<212> TYPE: DNA
<213> ORGANISM: Mus musculus

<400> SEQUENCE: 684
atgtacttgg gactgaactg tgtattcata gtttgtctct taaaagggt ccagagt          57

<210> SEQ ID NO 685
<211> LENGTH: 19
<212> TYPE: PRT
<213> ORGANISM: Mus musculus

<400> SEQUENCE: 685

Met Tyr Leu Gly Leu Asn Cys Val Phe Ile Val Cys Leu Leu Lys Gly
1               5                   10                  15

Val Gln Ser

<210> SEQ ID NO 686
<211> LENGTH: 54
<212> TYPE: DNA
<213> ORGANISM: Mus musculus

<400> SEQUENCE: 686
atggcctgga tttcacttat actctctctc ctggctctca gctcaggggc catt            54

<210> SEQ ID NO 687
<211> LENGTH: 18
<212> TYPE: PRT
<213> ORGANISM: Mus musculus

<400> SEQUENCE: 687

Met Ala Trp Ile Ser Leu Ile Leu Ser Leu Leu Ala Leu Ser Ser Gly
1               5                   10                  15

Ala Ile

<210> SEQ ID NO 688
<211> LENGTH: 66
<212> TYPE: DNA
<213> ORGANISM: Mus musculus

<400> SEQUENCE: 688
atggattttc aggtgcagat tttcagcttc ctgctaatca gtgcctcagt cataatgtcc      60
agagga                                                                 66

<210> SEQ ID NO 689
<211> LENGTH: 22
<212> TYPE: PRT

<213> ORGANISM: Mus musculus

<400> SEQUENCE: 689

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 690
<211> LENGTH: 60
<212> TYPE: DNA
<213> ORGANISM: Mus musculus

<400> SEQUENCE: 690
atggagaaag acacactcct gctatgggtc ctgcttctct gggttccagg ttccacaggt     60

<210> SEQ ID NO 691
<211> LENGTH: 20
<212> TYPE: PRT
<213> ORGANISM: Mus musculus

<400> SEQUENCE: 691

Met Glu Lys Asp Thr Leu Leu Leu Trp Val Leu Leu Trp Val Pro
1               5                   10                  15

Gly Ser Thr Gly
            20

<210> SEQ ID NO 692
<211> LENGTH: 60
<212> TYPE: DNA
<213> ORGANISM: Mus musculus

<400> SEQUENCE: 692
atggaatcac agacacaggt cttcctctcc ctgctgctct gggtatctgg tacctgtggg     60

<210> SEQ ID NO 693
<211> LENGTH: 60
<212> TYPE: DNA
<213> ORGANISM: Mus musculus

<400> SEQUENCE: 693
atggaatcac agactcaggt cttcctctcc ctgctgctct gggtatctgg tacctgtggg     60

<210> SEQ ID NO 694
<211> LENGTH: 20
<212> TYPE: PRT
<213> ORGANISM: Mus musculus

<400> SEQUENCE: 694

Met Glu Ser Gln Thr Gln Val Phe Leu Ser Leu Leu Leu Trp Val Ser
1               5                   10                  15

Gly Thr Cys Gly
            20

<210> SEQ ID NO 695
<211> LENGTH: 27
<212> TYPE: DNA
<213> ORGANISM: Mus musculus

<400> SEQUENCE: 695
atgttctgga ttcctgcttc cagcagt                                         27

```
<210> SEQ ID NO 696
<211> LENGTH: 9
<212> TYPE: PRT
<213> ORGANISM: Mus musculus

<400> SEQUENCE: 696

Met Phe Trp Ile Pro Ala Ser Ser Ser
1               5

<210> SEQ ID NO 697
<211> LENGTH: 57
<212> TYPE: DNA
<213> ORGANISM: Mus musculus

<400> SEQUENCE: 697
atgaagttgc ctgttaggct gttggtgctg atgttctgga ttcctgcttc caacagt      57

<210> SEQ ID NO 698
<211> LENGTH: 19
<212> TYPE: PRT
<213> ORGANISM: Mus musculus

<400> SEQUENCE: 698

Met Lys Leu Pro Val Arg Leu Leu Val Leu Met Phe Trp Ile Pro Ala
1               5                   10                  15

Ser Asn Ser

<210> SEQ ID NO 699
<211> LENGTH: 57
<212> TYPE: DNA
<213> ORGANISM: Mus musculus

<400> SEQUENCE: 699
atgaagttgc ctgttaggct gttggtgctg atgttctgga ttcctgcttc cagcagt      57

<210> SEQ ID NO 700
<211> LENGTH: 19
<212> TYPE: PRT
<213> ORGANISM: Mus musculus

<400> SEQUENCE: 700

Met Lys Leu Pro Val Arg Leu Leu Val Leu Met Phe Trp Ile Pro Ala
1               5                   10                  15

Ser Ser Ser

<210> SEQ ID NO 701
<211> LENGTH: 60
<212> TYPE: DNA
<213> ORGANISM: Mus musculus

<400> SEQUENCE: 701
atgaagtcac agacccaggt cttcgtattt ctactgctct gtgtgtctgg tgctcatggg   60

<210> SEQ ID NO 702
<211> LENGTH: 20
<212> TYPE: PRT
<213> ORGANISM: Mus musculus

<400> SEQUENCE: 702

Met Lys Ser Gln Thr Gln Val Phe Val Phe Leu Leu Leu Cys Val Ser
1               5                   10                  15

Gly Ala His Gly
            20
```

```
<210> SEQ ID NO 703
<211> LENGTH: 60
<212> TYPE: DNA
<213> ORGANISM: Mus musculus

<400> SEQUENCE: 703
atgaggttcc aggttcaggt tctgggactc cttctgctct ggatatcagg tgcccagtgt    60

<210> SEQ ID NO 704
<211> LENGTH: 20
<212> TYPE: PRT
<213> ORGANISM: Mus musculus

<400> SEQUENCE: 704

Met Arg Phe Gln Val Gln Val Leu Gly Leu Leu Leu Leu Trp Ile Ser
1               5                   10                  15

Gly Ala Gln Cys
            20

<210> SEQ ID NO 705
<211> LENGTH: 60
<212> TYPE: DNA
<213> ORGANISM: Mus musculus

<400> SEQUENCE: 705
atgagaccgt ctattcagtt cctggggctc tcgttgttct ggcttcatgg tgctcagtgt    60

<210> SEQ ID NO 706
<211> LENGTH: 20
<212> TYPE: PRT
<213> ORGANISM: Mus musculus

<400> SEQUENCE: 706

Met Arg Pro Ser Ile Gln Phe Leu Gly Leu Ser Leu Phe Trp Leu His
1               5                   10                  15

Gly Ala Gln Cys
            20

<210> SEQ ID NO 707
<211> LENGTH: 22
<212> TYPE: DNA
<213> ORGANISM: Artificial
<220> FEATURE:
<223> OTHER INFORMATION: a primer sequence

<400> SEQUENCE: 707
aaggcttaca accacaatcc ct                                              22

<210> SEQ ID NO 708
<211> LENGTH: 19
<212> TYPE: DNA
<213> ORGANISM: Artificial
<220> FEATURE:
<223> OTHER INFORMATION: a primer sequence

<400> SEQUENCE: 708
tgctgggcat ttgcatgga                                                  19

<210> SEQ ID NO 709
<211> LENGTH: 19
<212> TYPE: DNA
<213> ORGANISM: Artificial
<220> FEATURE:
```

```
<223> OTHER INFORMATION: a primer sequence

<400> SEQUENCE: 709
tgggcatttg tgacactcc                                              19

<210> SEQ ID NO 710
<211> LENGTH: 21
<212> TYPE: DNA
<213> ORGANISM: Artificial
<220> FEATURE:
<223> OTHER INFORMATION: a primer sequence

<400> SEQUENCE: 710
actgggcttg ggtattctag g                                           21

<210> SEQ ID NO 711
<211> LENGTH: 31
<212> TYPE: DNA
<213> ORGANISM: Artificial
<220> FEATURE:
<223> OTHER INFORMATION: a primer sequence

<400> SEQUENCE: 711
gtccaactgt tcaggacgcc attttgtcgt t                                31

<210> SEQ ID NO 712
<211> LENGTH: 27
<212> TYPE: DNA
<213> ORGANISM: Artificial
<220> FEATURE:
<223> OTHER INFORMATION: a primer sequence

<400> SEQUENCE: 712
tccacagtgt gaccttcatg agtgacc                                     27

<210> SEQ ID NO 713
<211> LENGTH: 19
<212> TYPE: DNA
<213> ORGANISM: Artificial
<220> FEATURE:
<223> OTHER INFORMATION: a primer sequence

<400> SEQUENCE: 713
acagggatcc agagttcca                                              19

<210> SEQ ID NO 714
<211> LENGTH: 18
<212> TYPE: DNA
<213> ORGANISM: Artificial
<220> FEATURE:
<223> OTHER INFORMATION: a primer sequence

<400> SEQUENCE: 714
taactgctca ctggatgg                                               18

<210> SEQ ID NO 715
<211> LENGTH: 24
<212> TYPE: DNA
<213> ORGANISM: Artificial
<220> FEATURE:
<223> OTHER INFORMATION: a primer sequence

<400> SEQUENCE: 715
agtgtggcct tgttagtctc gagc                                        24
```

```
<210> SEQ ID NO 716
<211> LENGTH: 30
<212> TYPE: DNA
<213> ORGANISM: Artificial
<220> FEATURE:
<223> OTHER INFORMATION: a primer sequence

<400> SEQUENCE: 716
ggccacgcgt cgactagtac gggggggggg                                      30

<210> SEQ ID NO 717
<211> LENGTH: 20
<212> TYPE: DNA
<213> ORGANISM: Artificial
<220> FEATURE:
<223> OTHER INFORMATION: a primer sequence

<400> SEQUENCE: 717
ggccacgcgt cgactagtac                                                 20

<210> SEQ ID NO 718
<211> LENGTH: 24
<212> TYPE: DNA
<213> ORGANISM: Artificial
<220> FEATURE:
<223> OTHER INFORMATION: a primer sequence

<400> SEQUENCE: 718
cgccagggtt ttcccagtca cgac                                            24

<210> SEQ ID NO 719
<211> LENGTH: 22
<212> TYPE: DNA
<213> ORGANISM: Artificial
<220> FEATURE:
<223> OTHER INFORMATION: a primer sequence

<400> SEQUENCE: 719
tcacacagga aacagctatg ac                                              22
```